United States Patent
Barouch et al.

(10) Patent No.: US 9,017,691 B2
(45) Date of Patent: Apr. 28, 2015

(54) ANTIVIRAL VACCINES WITH IMPROVED CELLULAR IMMUNOGENICITY

(75) Inventors: Dan H. Barouch, Brookline, MA (US); Bette T. Korber, Los Alamos, NM (US); William M. Fischer, Los Alamos, NM (US)

(73) Assignees: Beth Israel Deaconess Medical Center, Boston, MA (US); Los Alamos National Security, LLC, Los Alamos, NM (US)

( * ) Notice: Subject to any disclaimer, the term of this patent is extended or adjusted under 35 U.S.C. 154(b) by 575 days.

(21) Appl. No.: 13/130,018

(22) PCT Filed: Nov. 18, 2009

(86) PCT No.: PCT/US2009/064999
§ 371 (c)(1),
(2), (4) Date: Dec. 8, 2011

(87) PCT Pub. No.: WO2010/059732
PCT Pub. Date: May 27, 2010

(65) Prior Publication Data
US 2012/0076812 A1    Mar. 29, 2012

Related U.S. Application Data

(60) Provisional application No. 61/115,703, filed on Nov. 18, 2008, provisional application No. 61/152,184, filed on Feb. 12, 2009, provisional application No. 61/248,188, filed on Oct. 2, 2009.

(51) Int. Cl.
*A61K 39/21* (2006.01)
*A61K 39/00* (2006.01)
*C07K 14/005* (2006.01)

(52) U.S. Cl.
CPC ............... *A61K 39/21* (2013.01); *C07K 14/005* (2013.01); *C12N 2710/10343* (2013.01); *C12N 2740/16122* (2013.01); *C12N 2740/16134* (2013.01); *C12N 2740/16171* (2013.01); *C12N 2740/16222* (2013.01); *C12N 2740/16234* (2013.01);
(Continued)

(58) Field of Classification Search
None
See application file for complete search history.

(56) References Cited

U.S. PATENT DOCUMENTS

2003/0207287 A1    11/2003  Short
2008/0199939 A1     8/2008  Havenga et al.
2008/0279879 A1    11/2008  Zolla-Pazner

FOREIGN PATENT DOCUMENTS

WO    WO-2007/024941 A2    3/2007
WO    WO-2010/042817 A1    4/2010
WO    WO-2010/096561 A1    8/2010

OTHER PUBLICATIONS

Blondelle, et al. Immunogenically Optimized Peptides Derived from Natural Mutants of HIV CTL Epitopes and Peptide Combinatorial Libraries. Peptide Science, 2008; 90(5): 683-694.*
(Continued)

*Primary Examiner* — Zachariah Lucas
*Assistant Examiner* — Stuart W Snyder
(74) *Attorney, Agent, or Firm* — Clark & Elbing LLP; Kristina Bieker-Brady; Todd Armstrong

(57) ABSTRACT

The invention provides compositions, methods, and kits for the treatment or prevention of viral infections. The polyvalent (e.g., 2-valent) vaccines described herein incorporate computationally-optimized viral polypeptides that can increase the diversity or breadth and depth of cellular immune response in vaccinated subjects.

23 Claims, 54 Drawing Sheets

(52) U.S. Cl.
CPC ............... *C12N2740/16271* (2013.01); *C12N 2740/16322* (2013.01); *C12N 2740/16334* (2013.01)

(56) References Cited

OTHER PUBLICATIONS

Gotch, et al. Candidate vaccines for immunotherapy in HIV. HIV Medicine (2001) 2, 260-265.*
Girard, et al. A review of vaccine research and development: The human immunodeficiency virus (HIV). Vaccine 24 (2006) 4062-4081.*
Barouch, D.H. Challenges in the development of an HIV-1 vaccine. Nature. 2008; 455(2): 613-619.*
Cohen, J. Did Merck's Failed HIV Vaccine Cause Harm? Science. 2007; 318: 1048-1049.*
Blondelle et al., "Immunogenically optimized peptides derived from natural mutants of HIV CTL epitopes and peptide combinatorial libraries," Biopolymers. 90(5):683-694 (2008).
Fischer et al., "Coping with viral diversity in HIV vaccine design: A response to Nickle et al.," PLoS Comput Biol. 4(1):175-179 (2008).
Fischer et al., "Polyvalent vaccines for optimal coverage of potential T-cell epitopes in global HIV-1 variants," Nat Med. 13(1):100-106 (2007).
Kong et al., "Expanded breadth of the T-cell response to mosaic human immunodeficiency virus type 1 envelope DNA vaccination," J Virol. 83(5):2201-2215 (2009).
Korber et al., "T-Cell vaccine strategies for human immunodeficiency virus, the virus with a thousand faces," J Virol. 83(17):8300-8314 (2009).
NCBI Blast for GenBank AAY23526.1. "Envelope glycoprotein [Human immunodeficiency virus 1]," <http://www.ncbi.nlm.nih.gov/protein/62956393>, retrieved on Feb. 13, 2010 (2 pages).
Thurmond et al., "Web-based design and evaluation of T-cell vaccine candidates," Bioinformatics. 24(14):1639-1640 (2008).
Communication Pursuant to Rules 161(2) and 162 EPC for European Patent Application No. 09828172.8, dated Jul. 4, 2011 (2 pages).
Extended European Search Report for European Patent Application No. 09828172.8, dated Jul. 1, 2013 (16 pages).
First Examination Report for New Zealand Patent Application No. 593598, dated Jul. 7, 2011 (3 pages).
First Examination Report for New Zealand Patent Application No. 602504, dated Sep. 24, 2012 (4 pages).
Second Examination Report for New Zealand Patent Application No. 593598, dated Oct. 9, 2012 (3 pages).
Third Examination Report for New Zealand Patent Application No. 593598, dated Dec. 21, 2012 (1 page).
English Translation of the Notification of the First Office Action for Chinese Patent Application No. 200980154787.4, issued Mar. 7, 2013 (4 pages).
International Search Report for International Application No. PCT/US2009/064999, mailed Mar. 5, 2010 (4 pages).
International Preliminary Report on Patentability and Written Opinion of the International Searching Authority for International Application No. PCT/US2009/064999, issued May 24, 2011 (9 pages).
Office Action in Japanese Patent Application No. 2011-537586 mailed May 27, 2014 (with English Translation) (4 pages).
Examination Report for Singapore Patent Application No. 201103573-0, mailed Sep. 8, 2014 (13 pages).
Third Office Action for Chinese Patent Application No. 200980154787.4, dated Sep. 30, 2014 (4 pages) (Chinese language only).
Chinese Office Action in Chinese Application No. 200980154787.4 mailed Feb. 7, 2014 (with English Translation) (9 pages).

\* cited by examiner

Fig. 6

- CD8 T cells: median (range)
  - 2 Mosaic: 16 (12-29)
  - Mcon: 6 (0-7)
  - OptC: 3 (0-7)
- CD4 T cells:
  - 2 Mosaic: 4 (2-6)
  - Mcon: 1 (0-2)
  - OptC: 0.5 (0-2)

Fig. 9

OptC 366-07:

5 CD8 responses:

| | | | | |
|---|---|---|---|---|
| OptC | IVQQQSNLLRAIEAQQ | Env | 548 | 562 |
| E54 | VVQQQSNLLRAIEAQ | Env | 549 | 563 |
| E72 | -VQQQNLLRAIEAQH | | | |
| OptC | AVFIHNFKRKGGIGGY | Pol | 894 | 908 |
| P22 | AVFIHNFKRKGGIGG | Pol | 895 | 909 |
| P236 | -VLIHNFKRKGGIGGY | | | |
| OptC | MAICEEMEKEGKITK | Pol | 190 | 204 |
| P224 | TAICEEMEKEGKITK | | | |
| OptC | CTHGIKPVVSTQLLL | Env | 247 | 261 |
| E15 | CTHGIKPVVSTQLLL | | | |
| OptC | GGPSHKARVLAEAMS | Gag | 354 | 368 |
| G76 | GGPSHKARVLAEAMG | | | |

1 CD4 response:

| | | | | |
|---|---|---|---|---|
| OptC | IIGQVRDQAEHLKTA | Pol | 876 | 890 |
| P86 | LIGQVRDQAEHLKTA | | | |

Fig. 10

```
Mos1   ICTTTVPWNASWSNKSL
Mos2   ICTTAVPWNTSWSNKSQ   T...A
E334   ICTTTVPWNASWSNR     T...S
E214   -CTTTVPWNSSWSNKT    A...A
E158   --TTAVPWNASWSNKSL   A...T
E290   --TTAVPWNTSWSNKSL
```

Fig. 11

8 CD8 responses:

| | | | | |
|---|---|---|---|---|
| Mos1 | EQLIKKERVYLSWVPAHKGIG | | | |
| Mos2 | EQLIKKEKVYLAWVPAHKGIG | | | |
| P221 | EELIKKEKVYLAWVP | Pol | 678 | 692 |
| P250 | EPLIKKEKVYLSWVP | Pol | 678 | 692 |
| P316 | -KLIEKDKVYLSWVPA | Pol | 679 | 693 |
| P223 | --LIKKERVYLSWVPAH | Pol | 680 | 694 |
| P169 | ------EKVYLAWVPAHKGIG | Pol | 684 | 698 |
| P83 | ------EKVYLSWVPAHKGIG | Pol | 684 | 698 |
| | | | | |
| Mos1 | CTHGIRPVVSTQLLL | | | |
| Mos2 | CTHGIKPVVSTQLLL | | | |
| E15 | CTHGIKPVVSTQLLL | Env | 247 | 261 |
| E47 | CTHGIRPVVSTQLLL | Env | 247 | 261 |
| | | | | |
| Mos1 | ICTTTVPWNASWSNKSL | | | |
| Mos2 | ICTTAVPWNTSWSNKSQ | | | |
| E334 | ICTTTVPWNASWSNR | Env | 603 | 617 |
| E214 | -CTTTVPWNSSWSNKT | Env | 604 | 618 |
| E158 | --TTAVPWNASWSNKSL | Env | 605 | 619 |
| E290 | --TTAVPWNTSWSNKSL | Env | 605 | 619 |
| | | | | |
| Mos1 | ACQGVGGPGHKARVLAEAMS | | | |
| Mos2 | ACQGVGGPSHKARVLAEAMS | | | |
| G166 | ACQEVGGPGHKARVL | Gag | 349 | 363 |
| G76 | -----GGPSHKARVLAEAMG | Gag | 354 | 368 |
| | | | | |
| Mos1 | AAEWDRVHPVHAGPIAPGQ | | | |
| Mos2 | AAEWDRLHPVHAGPVAPGQ | | | |
| G319 | AAE-DRLHPVHAGPIP | Gag | 209 | 225 |
| G242 | -ADWDRLHPVHAGPVA | Gag | 210 | 224 |
| G44 | -AEWDRLHPVHAGPIA | Gag | 210 | 224 |
| G277 | ---WDRVHPVHAGPNPPG | Gag | 212 | 226 |
| G102 | ----DRVHPVHAGPIPPGQ | Gag | 212 | 226 |
| | | | | |
| Mos1 | HSNWRAMASDFNLPP | | | |
| Mos2 | HSNWRAMASEFNLPP | | | |
| P93 | HSNWRAMASDFNLPP | Pol | 731 | 745 |
| | | | | |
| Mos1 | KGRPGNFLQNRPEPT | | | |
| Mos2 | KGRPGNFLQSRPEPT | | | |
| G86 | KGRPGNFLQNRPEPT | Gag | 442 | 456 |
| | | | | |
| Mos1 | SRELERFAVNPGLLE | | | |
| Mos2 | SRELERFALNPGLLE | | | |
| G39 | SRELERFALNPGLLE | Gag | 38 | 52 |

Fig. 11 cont.

5 CD4 responses:

| | | | | |
|---|---|---|---|---|
| Mos1 | RSLYNTVATLYCVHQR | | | |
| Mos2 | RSLFNTVATLYCVHAE | | | |
| G289 | KSLFNTVATLYCVHA | Gag | 76 | 90 |
| G54 | -SLYNTVATLYCVHQR | Gag | 77 | 91 |
| Mos1 | YVTDRGRQKIVSLTE | | | |
| Mos2 | YVTDRGRQKVVSLTD | | | |
| P134 | YVTDRGRQKVVSLIE | Pol | 612 | 626 |
| Mos1 | CTTTVPWNASWSNKS | | | |
| Mos2 | CTTAVPWNTSWSNKS | | | |
| E53 | CTTNVPWNSSWSNKS | Env | 604 | 618 |
| Mos1 | WWAGIQQEFGIPYNP | | | |
| Mos2 | WWAGIKQEFGIPYNP | | | |
| P135 | WWAGIQQEFGIPYNP | Pol | 846 | 860 |
| Mos1 | GPGHKARVLAEAMSQ | | | |
| Mos2 | GPSHKARVLAEAMSQ | | | |
| G15 | GPGHKARVLAEAMSQ | Gag | 355 | 369 |

Fig. 14

- CD8 T cells: median (range)
  - 2 Mosaic: 8 (7-14)
  - Mcon: 3 (0-6)
  - OptC: 1.5 (0-5)
- CD4 T cells:
  - 2 Mosaic: 3 (2-5)
  - Mcon: 1 (0-2)
  - OptC: 0.5 (0-2)

Fig. 20A

CD8 Pol

CD8 Env

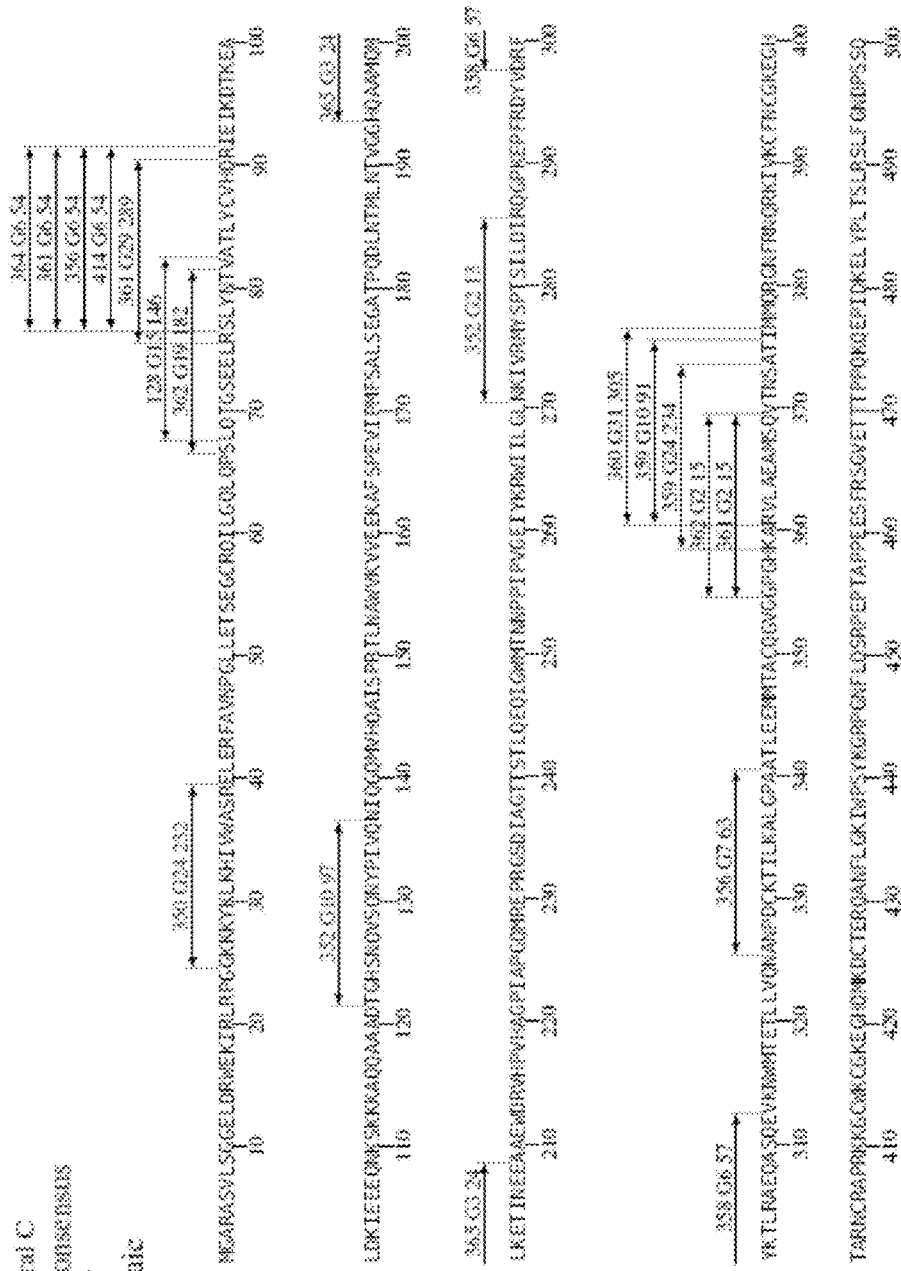
Fig. 21A CD4 Gag

Fig. 21B

CD4 Pol

[Figure showing protein sequence with position markers from 10 to 1000, with annotated regions/epitopes marked by horizontal bars labeled with identifiers such as 358 P28 204, 359 P15 141, 358 P15 141, 355 P15 141, 354 P15 141, 358 P26 352, 354 P26 352, 362 P14 136, 297 P14 13x, 362 P27 266, 357 P48 474, 361 P14 134, 368 P1 25, 358 P3 25, 361 P14 135, 266 P5 26, 362 P3 28, 357 P18 173, 360 P18 173]

SEQ 1003

Fig. 21C

CD4 Env

Fig. 22

Reactive peptides and breadth and depth of responses: Clade B+C Vaccine

```
Clade B+C 287-95:
3 CD8 PTE+, 1 CD4 PTE+
3 CD8+ regions, 1 CD4+ region
Number of overlapping peptides per region: CD8: 1 2 2 CD4: 1

3 CD8 responses:
C      AAEWDRLHPVHAGPIA
B      AAEWDRLHPVHAGPIA
G319   AAE-DRLHPVHAGPIP Gag   209   225

C      EQMHEDIISLWDQSLK
B      EQMHEDIISLWDQSLK
E26    EQMHEDIISLWDQSL  Env   102   116
E282   MHEDIISLWDESLK   Env   103   117

1 CD4 response:
C      KLNWASQIYSGIKVR
B      KLNWASQIYPGIKVR
P136   KLNWASQIYAGIKVK  Pol   418   432

Clade B+C 128-92:
5 CD8 PTE+, 2 CD4 PTE+
5 CD8+ regions, 2 CD4+ regions
Number of overlapping peptides per region: CD8: 1 1 1 1 1 CD4: 1 1

5 CD8 responses:
C      KHLVWASRELERFAL
B      KHIVWASRELERFAV
G20    KHLVWASRELERFAL  Gag   32   46

C      LQEQIAWMTNNPPVP
B      LQEQIGWMTNNPPIP
G174   LAEQIAWMTSNPPIP  Gag   243   257

C      QMHEDIISLWDQSLK
B      QMHEDIISLWDQSLK
E282   MHEDIISLWDESLK   Env   103   117

C      DIWDNMTWMQWDREI
B      DIWDNMTWMEWEREI
E297   DIWNNMTWMEWEKEI  Env   621   635

C      WPVKVIHTANGSNFT
B      WPVKTIHTANGSNFT
P214   WPVKVVHTDNGSNFT  Pol   623   637

2 CD4 responses:
C      AQTGTEELRSLYNTV
B      LQTGSEELRSLYNTV
G146   LQTGSEELRSLFNTV  Gag   69   82

C      YFMMWKNDMVDQMHE
B      NFMMWKNDMVEQMHE
E544   NFMMWKNDMVEQMHE  Env   92   106
```

Fig. 22 cont.

```
Clade B+C 263-00:
3 CD8 PTE+, 1 CD4 PTE+
3 CD8+ regions, 1 CD4+ region
Number of overlapping peptides per region: CD8: 1 1 1 CD4: 1

3 CD8 responses:
C     GRPGNFLQSRPEPT
B     GRPGNFLQSRPEPT
G86   GRPGNFLQNRPEPT   Gag   442   456

C     PVHAGPIAPGQMREP
B     PVHAGPIAPGQMREP
G213  PVQAGPIAPGQMREP  Gag   217   231

C     VQQQSNLLRAIEAQQ
B     VQQQNNLLRAIEAQQ
E73   VQQQNNLLRAIEAQH  Env   549   563

1 CD4 response:
C     LIEESQNQQEKNEKD
B     LIEESQNQQEKNEQE
E49   LIEESQNQQEKNEQD  Env   645   659
```

```
Clade B+C 311-00:
5 CD8 PTE+, 0 CD4 PTE+
5 CD8+ regions, 0 CD4+ region
Number of overlapping peptides per region: CD8: 1 1 1 1 1 CD4: 0

5 CD8 responses:
C     DRLHPVHAGPIAPGQ
B     DRLHPVHAGPIAPGQ
G102  DRVHPVHAGPIPPGQ  Gag   213   227

C     GDIIGDIRQAHCNIS
B     GEIIGDIRQAHCNIS
E64   GDIIGDIRQAHCNIS  Env   321   334

C     TGMLRNCQPWWIWGI
B     KGIRKNYQHLWRWGT
E459  KEIRKNYQHLWRWGT  Env   4     18

C     MTKILEPFRAKNPEI
B     MTKILEPFRKQNPDI
P144  MTKILEPFRKQNPDI  Pol   319   333

C     RAMASEFNLPPVVAK
B     RAMASDFNLPPVVAK
P193  KAMASDFNLPPIVAK  Pol   735   749
```

Fig. 22 cont.

```
Clade B+C 335-96:
6 CD8 PTE+, 0 CD4 PTE+
2 CD8+ regions, 0 CD4+ region

Number of overlapping peptides per region: CD8: 3 3 CD4: 0

6 CD8 responses:
C      AAEWDRLHPVHAGPIAPGQ
B      AAEWDRLHPVHAGPIAPGQ
G319   AAE-DRLHPVHAGPIP       Gag    209    225
G44     AEWDRLHPVHAGPIA       Gag    210    224
G102       DRVHPVHAGPIPPGQ    Gag    213    227

C      QLIKKERVYLSWVPAHKGIG
B      QLIKKEKVYLAWVPAHKGIG
P316   KLIKKEKVYLSWVPA         Pol    679    693
P213   LIKKERVYLSWVPAH         Pol    680    694
P83        EKVYLSWVPAHKGIG     Pol    684    698

Clade B+C 414-95:
0 CD8 PTE+, 1 CD4 PTE+
0 CD8+ regions, 1 CD4+ region
Number of overlapping peptides per region: CD8: 0 CD4: 1

1 CD4 responses:
C      SLYNTVATLYCVHAG
B      SLYNTVATLYCVHQK
G54    SLYNTVATLYCVHQR   Gag    77     91

Clade B+C 431-01:
3 CD8 PTE+, 1 CD4 PTE+
2 CD8+ regions, 1 CD4+ region
Number of overlapping peptides per region: CD8: 2 1 CD4: 1

3 CD8 responses:
C      HQAAMQMLKDTINEE
B      HQAAMQMLKETINEE
G24    HQAAMQMLKDTINEE   Gag    194    208
G51    HQAAMQMLKETINEE   Gag    194    208

C      AVFIHNFKRKGGIGG
B      AVFIHNFKRKGGIGG
P22    AVFIHNFKRKGGIGG   Pol    894    908

1 CD4 response:
C      YFKMWKNDMVDQMHE
B      NFKMWKNNMVEQMHE
E44    NFKMWKNNMVEQMHE   Env    92     106
```

Fig. 22 cont.

Reactive peptides and breadth and depth of responses: M Consensus Vaccine

M consensus 349-07:
7 CD8 PTE+, 2 CD4 PTE+
3 CD8+ regions, 2 CD4+ regions
Number of overlapping peptides per region: CD8: 3 2 2 CD4: 1 1

3 CD8 responses:
```
Mcon   EQATQEVKNWMTDTLLVQNANP
G197   EQATQEVKNWMTDTL         Gag   307   321
G128   ---TQDVKNWMTPTLLIQ      Gag   310   324
G55    --------KNWMTDTLLVQNANP Gag   314   328

Mcon   IVQQQSNLLRAIEAQQ
E54    VVQQQSNLLRAIEAQ         Env   548   562
E72    -VQQQNSLLRAIEAQH        Env   549   563

Mcon   AVFIHNFKRKGGIGGY
P22    AVFIHNFKRKGGIGG         Pol   894   908
P336   -VIHNFKRKGGIGGY         Pol   895   909
```

2 CD4 responses:
```
Mcon   SELYKYKVVKIEPLG
E42    SELYKYKVVKIEPLG         Env   481   495

Mcon   NFNMWKNNMVEQMHE
E44    NFNMWKNNMVEQMHE         Env   92    106
```

M consensus 350-07:
0 CD8 PTE+, 2 CD4 PTE+
0 CD8+ regions, 2 CD4+ regions
Number of overlapping peptides per region: CD8: none CD4: 1 1

2 CD4 responses:
```
Mcon   GKKKYRLKHLVWASR
G232   GKKKYRLKHIVWASR         Gag   25    39

Mcon   DIKVVPRRKAKIIRD
P173   DIKVVPRRKVKIIRD         Pol   971   985
```

M consensus 351-07:
7 CD8 PTE+, 1 CD4 PTE+
4 CD8+ regions, 1 CD4+ regions
Number of overlapping peptides per region: CD8: 2 2 2 1 CD4: 1

Fig. 22 cont.

```
4 CD8 responses:
Mcon  KHLVWASRELERFALNPGLL
G20   KHLVWASRELERFAL        Gag    32    46
G68   -----ASRELERFAVNPGLL   Gag    37     5

Mcon  IVQQQSNLLRAIEAQQ
E4    VVQQQSNLLRAIEAQ        Env   548   562
E8    -VQQQSNLLRAIEAQH       Env   549   563

Mcon  AVFIHNFKRKGGIGGY
P22   AVFIHNFKRKGGIGS        Pol   894   908
P236  -VLIHNFKRKGGIGGY       Pol   895   909

Mcon  KNWMTDTLLVQNANP
G55   KNWMTDTLLVQNANP        Gag   314   328

1 CD4 response:
Mcon  WKGSPAIFQSSMTKI
P352  WKGSPAIFQASMTKI        Pol   308   322
------------------------------------------------
M consensus 352-07:
6 CD8 PTE+, 2 CD4 PTE+
6 CD8+ regions, 2 CD4+ regions
Number of overlapping peptides per region: CD8: 1 1 1 1 1 1  CD4: 1

6 CD8 responses:
Mcon  QPALQTGSEELRSLY
G268  LPALNTGSEELRSLY        Gag    65    79

Mcon  IVQQQSNLLRAIEAQ
E54   VVQQQSNLLRAIEAQ        Env   548   562

Mcon  CSGKLICTTTVPWNS
E73   CSGKLICTTAVPWNS        Env   598   612

Mcon  AKAYDTEVHNVWATH
E215  AKAYEKEVHNVWATH        Env    58    72

Mcon  KKDSTKWRKLVDFRE
P23   KKDSTKWRKLVDFRE        Pol   220   234

Mcon  VFIHNFKRKGGIGGY
P236  VLIHNFKRKGGIGGY        Pol   895   909

2 CD4 responses:
Mcon  NKIVRMYSPVSILDI
G13   NKIVRMYSPVSILDI        Gag   271   285

Mcon  RGNSSKVSQNYPIVQ
G97   TGNSSQVSQNYPIVQ        Gag   122   136
```

Fig. 22 cont.

```
M consensus 353-07:
2 CD8 PTE+, 0 CD4 PTE+
2 CD8+ regions, 0 CD4+ regions
Number of overlapping peptides per region: CD8: 1 1  CD4: none 2 CD8 responses:
Mcon  GCKQIIGQLQPALQT
G151  GCRQILGQLQPSLQT       Gag    56    70

Mcon  PVHAGPIPPGQMREP
G213  PVQAGPIAPSQMREP       Gag   217   231

M consensus 354-07:
5 CD8 PTE+, 1 CD4 PTE+
3 CD8+ regions, 1 CD4+ regions
Number of overlapping peptides per region: CD8: 2 2 1  CD4: 1

3 CD8 responses:
Mcon  EQATQDVKNWMTDTLLVQNANP
G197  EQSTQEVKNWMTDTL       Gag   307   321
G55   -------KNWMTDTLLVQNANP Gag   314   328

Mcon  IVQQQSNLLRAIEAQQ
E54   VVQQQSNLLRAIEAQ       Env   549   562
E72   -VQQNNLLRAIEAQR       Env   549   563

Mcon  HSNWRAMASDFNLPP
P93   HSNWRAMASDFNLPP       Pol   731   745

1 CD4 response:
Mcon  GSPAIFQSSMTKILE
P141  GSPAIFQSSMTKILD       Pol   310   324

M consensus 355-07:
3 CD8 PTE+, 1 CD4 PTE+
2 CD8+ regions, 1 CD4+ regions
Number of overlapping peptides per region: CD8: 1 3  CD4: 1

2 CD8 responses:
Mcon  IIGDIRQAHCNISGT
E325  ITGDIRQAHCNVSRS       Env   322   336

Mcon  SNWRAMASDFNLPPIVAK
P93   SNWRAMASDFNLPP        Pol   731   745
P149  ----RTMASDFNLPPVVAK   Pol   735   749
P153  ----KAMASDFNLPPIVAK   Pol   735   749

1 CD4 response:
Mcon  GSPAIFQSSMTKILE
P141  GSPAIFQSSMTKILD       Pol   310   324
```

Fig. 22 cont.

Reactive peptides and breadth and depth of responses: Mosaic Vaccine

```
Mosaic 356-07:
15 CD8 PTE+, 2 CD4 PTE+
8 CD4+ regions, 2 CD4+ regions
Number of overlapping peptides per region: CD8: 5 3 1 2 1 1 1 2   CD4: 1 1

8 CD8 responses:
Mos1   AAEKDRVHPVHAGPIAPGQ
Mos2   AAEKDRLHPVHAGPVAPGQ
G319   AAE-DRLHPVHAGPIP        Gag    309    325
G44    -AEKDRLHPVHAGPIA        Gag    310    324
G243   -AEKDRLHPVHAGPVA        Gag    310    324
G277   ---VHPVHPVHAGPNPG       Gag    312    326
G102   ----DRVHPVHAGPIPPGQ     Gag    313    327

Mos1   IVQQQNNLLRAIEAQ
Mos2   IVQQQSNLLRAIEAQ
E54    VVQQQSNLLRAIEAQ         Env    549    562
E72    -VQQQNNLLRAIEAQR        Env    549    563
E191   -VQQQSNLLRAIEAQQ        Env    549    563

Mos1   ASQDVKNWMTETLLV
Mos2   ATQDVKNWMTETLLV
G66    ASQEVKNWMTETLLI         Gag    309    323

Mos1   RVFIHNFKRKGGIGGY
Mos2   RVFIHNFKRKGGIGGY
P22    RVFIHNFKRKGGIGG         Pol    694    908
P236   -VLIHNFKRKGGIGGY        Pol    895    909

Mos1   PLVKLWYQLEKDPIA
Mos2   PLVKLWYQLEKEPIV

P73    PLVKLWYQLEKEPIV         Pol    576    590

Mos1   TIPSTNNETPGIRYQ
Mos2   TIPSINNETPGIRYQ
P79    TIPSINNETPGIRYQ         Pol    286    300

Mos1   YPGIKVRQLCKLLRG
Mos2   YPGIKVRQLCKLLRG
P156   YPGIKVRQLCKLLRG         Pol    426    440

Mos1   LIKKERVYLSWVPAHKGIG
Mos2   LIKKERVYLAWVPAHRGIG
P223   LIKKERVYLSWVPAH         Pol    680    694
P83    ----ERVYLSWVPAHRGIG     Pol    684    698

2 CD4 responses:
Mos1   SLYNTVATLYCVHQR
Mos2   SLYNTVATLYCVHAR
G54    SLYNTVATLYCVHQR         Gag     77     91

Mos1   ANPDCKTILKALGPA
Mos2   ANPDCKTILKALGPG
G63    ANPDCKTILRALGPG         Gag    326    340
```

Fig. 22 cont.

```
Mosaic 357-07:
29 CD8 PTE+, 4 CD4 PTE+
14 CD8+ regions, 4 CD4+ regions
Number of overlapping peptides per region: CD8: 5 5 2 5 5 1 1 1 1 1 1 1 1 1 CD4: 1 1 1 1

14 CD8 responses:
Mos1  EPLIPKEKVILSWVPAKKHIS
Mos2  EPLIPKEKVILSWVPAKKHIS
P250  EPLIPKEKVILSWVP          Pol    678    692
P318  -PLIPKDKVILSWVPA         Pol    679    693
P263  --LIPKEKVILSWVPAK        Pol    680    694
P189  -------EKVILSWVPAKKHIS   Pol    684    698
P83   -------EKVILSWVPAKKHIS   Pol    684    698

Mos1  IVQQQNNLLRAIEAQQ
Mos2  IVQQQNNLLRAIEAQQ
E58   VVQQQNLLRAIEAQ           Env    548    562
E70   -VQQNNLLRAIEAQR          Env    549    563

Mos1  EQASQDVKNWMTETLLVQNANP
Mos2  EQASQDVKNWMTDTLLVQNANP
G187  EQASQDVKNWMTDTPL         Gag    307    321
G55   -------PNWMTDTLLVQNANP   Gag    314    328

Mos1  RSNNRAMASDFNLPPVVAK
Mos2  RSNNRAMASDFNLPPIVAK
P83   RSNNRAMASDFNLPP          Pol    731    745
P262  -SNNRAMASDFNLPPI         Pol    732    746
P473  --NNRTMASDFNLPPVI        Pol    733    747
P149  ----RTMASDFNLPPVVAK      Pol    735    749
P193  ----RTMASDFNLPPIVAK      Pol    735    749

Mos1  AEWDRVHPVHAGPIAPGQ
Mos2  AEWDRLHPVHAGPVAPGQ
G319  AAFPRLHPVHAGPIE          Gag    209    223
G242  AEWDRLHPVHAGPVA          Gag    210    224
G44   AEWDRLHPVHAGPIA          Gag    210    224
G277  --WDRVHPVHAGPVPPG        Gag    212    226
G192  ----DRVHPVHAGPIPPGQ      Gag    213    227

Mos1  RVFIHNFKRKGGIGGY
Mos2  RVFIHNFKRKGGIGSY
P60   RVFIHNFKRKGGIGG          Pol    894    908
P038  -VFIHNFKRKGGIGGY         Pol    895    909

Mos1  PLDEDFRKYTAFTIP
Mos2  PLDEDFRKYTAFTIP
P242  PLDEDFRKYTAFTIP          Pol    274    288

Mos1  TRILEPFRAKNPEIV
Mos2  TNILEPFRKQNPEIV
P394  TNILEPFRAQNPEIV          Pol    320    334

Mos1  ICTEMEKEGKITKIG
Mos2  ICTEMEKEGKISKIG
P193  ICTEMEKEGKISKIG          Pol    192    206

Mos1  VKLWYQLEKDPIAGV
Mos2  VKLWYQLEKEPIVGA
P226  VKLWYQLEKDPIVGA          Pol    579    593

Mos1  GDIIGDIRQAHCNIS
Mos2  GDIIGDIRQAHCNLS
E764  GDIIGDIRQAHCNIS          Env    521    534

Mos1  ICTTTVPWNASWSNK
Mos2  ICTTAVPWNSSWSNK
E334  ICTTTVPWNASWSNK          Env    603    617
```

Fig. 22 cont.

```
Mos1  IGQVRDQAEHLKTAV
Mos2  IGQVRDQAEHLKTAV
P174  IGQVRDQAEHLKTAV        Pol   677   691

Mos1  GKQMAGADCVAGRQD
Mos2  GKQMAGDDCVASRQD
P95   GKQMAGDDCVAGRQD        Pol   987   1001

4 CD4 responses:
Mos1  KYAKMRTAHTNDVKQ
Mos2  KYASMRGAHTNDVKQ
P474  KYAKMRTAHTNDVRQ        Pol   508   522

Mos1  AGDIIGDIRQAHCNI
Mos2  TGDIIGDIRQAHCNL
E412  TGEIIGDIRQAHCNL        Env   320   333

Mos1  NQQEKNEKDLLALDS
Mos2  NQQEKNEQELLELDK
E68   NQQEKNEQDLLALDK        Env   651   665

Mos1  DIKVVPRRKVKIIKD
Mos2  DIKVVPRRKAKIIKD
P173  DIKVVPRRKVKIIKD        Pol   971   985
```

---

```
Mosaic 358-07:
19 CD8 PTE+, 3 CD4 PTE+
7 CD8+ regions, 3 CD4+ regions
Number of overlapping peptides per region: CD8: 2 4 2 6 3 1 1  CD4: 1 1 1

7 CD8 responses:
Mos1  LIKKERVYLSWVPAHKGIG
Mos2  LIKKESVYLAWVPAHKGIG
P213  LIKKERVYLSWVPAH        Pol   680   694
P93   -----ERVYLSWVPAHKGIG   Pol   684   698

Mos1  IVQQQNNLLRAIEAQQHLLQL
Mos2  IVQQQSNLLRAIEAQQHMLQL
E54   VVQQQSNLLRAIEAQ        Env   549   562
E191  -VQQQSNLLRAIEAQQ       Env   549   563
E70   -VQQNNLLRAIEAQQH       Env   549   563
E19   ------NLLRAIEAQQHLLQL  Env   554   568

Mos1  AVFIHNFKRKGGIGGY
Mos2  AVFIHNFKRKGGIGEY
```

Fig. 22 cont.

```
P222  AVFHNFKRKGGIGG              Pol    894    908
P236  -VLHNFKRKGGIGGY             Pol    895    909

Mos1  EQASQDVKNWMTETLLVQNANP
Mos2  EQAQQDVKNWMTDTLLVQNANP
G122  EQASQEVKNWMTETL             Gag    307    321
G197  EQPSQEVKNWMTDTL             Gag    307    321
G66   --ASQEVKNWMTETLLI           Gag    309    323
G108  ---SQDVKNWMTDTLLIQ          Gag    310    324
G30   --------KNWMTETLLVQNANP     Gag    314    328
G55   --------KNWMTDTLLVQNANP     Gag    314    328

Mos1  AEWDRVHPVHAGPIAPGQ
Mos2  AEWDRLHPVHAGPVAPGQ
G319  AEWDRLHPVHAGPIP             Gag    209    225
G44   AEWDRLHPVHAGPIA             Gag    210    224
G11   ---DRVHPVHAGPIPPGQ          Gag    213    227

Mos1  WKGSPAIFQCSMTRI
Mos2  WKGSPAIFQSSMTKI
P238  WKGSPAIFQCSMTKI             Pol    306    322

Mos1  MTRILEPFRAKNPEI
Mos2  MTKILEPFRKQNPDI
P144  MTKILEPFRKQNPDI             Pol    319    333

3 CD4 responses:
Mos1  GSPAIFQCSMTRILE
Mos2  GSPAIFQSSMTKILE
P141  GSPAIFQSSMTKILD             Pol    310    324

Mos1  HGQVDCSPGIWQLAC
Mos2  HGQVDCSPGIWQLAC
P25   HGQVDCSPGIWQLDC             Pol    766    780

Mos1  DRFYKTLRAEQASQD
Mos2  DRFYKTLRAEQATQD
G57   DRFYKTLRAEQASQE             Gag    298    312
```

```
Mosaic 359-07:
12 CD8 PTE+, 5 CD4 PTE+
10 CD8+ regions, 2 CD4+ regions
Number of overlapping peptides per region: CD8: 2 2 1 1 1 1 1 1 1 1  CD4: 3 2

10 CD8 responses:
Mos1  LIKKERVYLSWVPAHKGIG
```

Fig. 22 cont.

```
Mos2  LKKEKVYLAWVPAHKGIG
P203  LKKEKVYLSWVPAH          Pol    680    694
P03   ----EKVYLSWVPAHKGIG     Pol    684    698

Mos1  AEWDRVHPVHAGPIAPGQ
Mos2  AEWDRLHPVHAGPVAPGQ
G44   AEWDRLHPVHAGPIA         Gag    210    224
G102  ----DRVHPVHAGPIAPGQ     Gag    213    227

Mos1  AIFQCSMTKILEPFR
Mos2  AIFQSSMTKILEPFR
P359  AIFQSSMTKILEPFR         Pol    313    327

Mos1  ASQIYPGIKVRQLCK
Mos2  ASQIYAGIKVRQLCK
P365  WSQIYAGIKVRQLCK         Pol    421    436

Mos1  RELNKRTQDFWEVQL
Mos2  RELNKRTQDFWEVQL
P132  RELNKRTQDFWEVQL         Pol    233    247

Mos1  LLRAIEAQQHLLQLT
Mos2  LLRAIEAQQHMLQLT
E227  LLMAIEAQQHLLQLT         Env    555    569

Mos1  LICTTTVPWNASWSN
Mos2  LICTTAVPWNTSWSN
E432  RICTTNVPWNASWSN         Env    602    616

Mos1  KHIVWASRELERFAV
Mos2  KHLVWASRELERFAL
G10   KHLVWASRELERFAL         Gag    32     46

Mos1  RSLYNTVATLYCVHQ
Mos2  RSLFNTVATLYCVHA
G20   KSLYNTVAVLYCVHQ         Gag    76     90

Mos1  EEKAFSPEVIPMFSA
Mos2  EEKAFSPEVIPMFTA
G14   EEKAFSPEVIPMFSA         Gag    160    174

2 CD4 responses:
Mos1  WKGSPAIFQCSMTRILEPFRA
Mos2  WKGSPAIFQSSMTKILEPFRX
P352  WKGSPAIFQASMTKI         Pol    308    322
P141  ---GSPAIFQSSMTKILQ      Pol    310    324
```

Fig. 22 cont.

```
P284  ------IFQCSMTKILEPFRA      Pol   314

Mos1  KARVLAEAMSQVTNSAT
Mos2  KARVLAEAMSQTNSTIL
G234  KAKVLAEAMSQVQQT            Gag   359   373
G91   --RVLAEAMSQVTNSAT          Gag   361   375
```

Mosaic 360-07:
16 CD8 PTE+, 2 CD4 PTE+
13 CD8+ regions, 2 CD4+ regions
Number of overlapping peptides per region: CD8: 2 2 3 1 1 1 1 1 1 1 1 1 1 CD4: 1 1

12 CD8 responses:
```
Mos1  SDLEIGQHRAKIEELR
Mos2  SDLEIGQHRSKIEELR
P385  SDLEIGQHRIKIEEL            Pol   346   360
P133  -DLEIGQHRAKIEELR           Pol   347   361

Mos1  QMHEDIISLWDQSLKP
Mos2  QMHEDIIPLWDQSLKP
E382  RMHEDIISLWDESLK            Env   103   117
E392  --MHEDVISLWDQSLKP          Env   104   119

Mos1  EEKAFSPEVIPMFSAL
Mos2  EEKAFSPEVIPMFTAL
G14   EEKAFSPEVIPMFSA            Gag   160   174
G192  EEKGFNPEVIPMFSA            Gag   160   174
G111  -EKGFSPEVIPMFTAL           Gag   161   175

Mos1  KYTAFTIPSTNNETP
Mos2  KYTAFTIPSINNETP
P286  KYTAFTIPSTNNETP            Pol   281   295

Mos1  EKIKALTAICEEMEK
Mos2  EKIKALVEICTEMEK
P439  EKIEALTAICEEMEK            Pol   184   198

Mos1  GKYAKMRTAHTNDVK
Mos2  GKYAKMRGAHTNDVK
P444  GKYAKMRGAHTNDVK            Pol   507   521

Mos1  LPIQKETWETWWTDY
Mos2  LPIQKETWEAWWTSY
P358  LPIQKETWEAWWTSY            Pol   546   560

Mos1  WYQLEKDPIAGVETF
```

Fig. 22 cont.

```
Mos2   WYQLEKEPIVGAETF
P370   WYQLEKDPIAGAETF        Pol    581    595

Mos1   ENVTENFNMWKNNMV
Mos2   ENVTENFNMWKNDMV
E273   ENVTEEFNMKNNMV          Env     87    101

Mos1   VIQDNSDIKVVPRRK
Mos2   VIQDNSDIKVVPRRK
P765   VIQDNSDIKVVPRRK         Pol    965    979

Mos1   VSQNYPIVQNIQGQM
Mos2   VSQNYPIVQNLQGQM
G39    VSQNYPIVQNLQGQR         Gag    128    142

Mos1   VLAEAMSQVTNSATIM
Mos2   VLAEAMSQ-TNSTILN
G307   VLAEAMSQ-AQQTNIM        Gag    362    377

2 CD4 responses:
Mos1   RGQVDCSPGIWQLAC
Mos2   RGQVDCSPGIWQLAC
P25    RGQVDCSPGIWQLDC         Pol    766    780

Mos1   RVLAEAMSQVTNSAT
Mos2   RVLAEAMSQTNSTIL
G305   RVLAEAMSQTNSAIL         Gag    361    376
----------------------------------------------
Mosaic 361-07:
21 CD8 PTE+, 6 CD4 PTE+
7 CD8+ regions, 5 CD4+ regions
Number of overlapping peptides per region: CD8: 6 2 4 2 5 1 1 CD4: 2 1 1 1 1

7 CD8 responses:
Mos1   EQLIKKERVYLSWVPAHKGIG
Mos2   EQLIKKEKVYLAWVPAHKGIG
P221   EELIKKEKVYLAWVP         Pol    678    692
P250   EELIKKEKVYLSWVP         Pol    678    692
P316   -KLIEKDKVYLSWVPA        Pol    679    693
P223   --LIKKERVYLSWVPAH       Pol    680    694
P169   ------EKVYLAWVPAHKGIG   Pol    684    698
P83    ------EKVYLSWVPAHKGIG   Pol    684    698

Mos1   CTHGIRPVVSTQLLL
Mos2   CTHGIKPVVSTQLLL
E15    CTHGIKPVVSTQLLL         Env    247    261
```

Fig. 22 cont.

```
E47   CTHGIRPVVSTQLLL          Env    247    261

Mos1  ICTTTVPWNASWSNKSL
Mos2  ICTTAVPWNTSWSNKSQ
E334  ICTTTVPWNASWSNR          Env    603    617
E214  -CTTTVPWNSSWSNKT         Env    604    618
E158  --TTAVPWNASWSNKSL        Env    605    619
E190  --TTAVPWNTSWSNKSL        Env    605    619

Mos1  ACQGVGGPGHKARVLAEAMS
Mos2  ACQGVGGPSHKARVLAEAMS
G166  ACQEVGGPGHKARVL          Gag    349    363
G76   -----GGPSHKARVLAEAMG     Gag    354    368

Mos1  AAEWDRVHPVHAGPIAPGQ
Mos2  AAEWDRLHPVHAGPVAPGQ
G319  AAE-DRLHPVHAGPIP         Gag    209    225
G242  -AEWDRLHPVHAGPVA         Gag    210    224
G44   -AEWDRLHPVHAGPIA         Gag    210    224
G277  ---WDRVHPVHAGPIPG        Gag    212    226
G102  ----DRVHPVHAGPIPGQ       Gag    212    226

Mos1  HSNWRAMASDFNLPP
Mos2  HSNWRAMASEFNLPP
P93   HSNWRAMASDFNLPP          Pol    731    745

Mos1  KGRPGNFLQNRPEPT
Mos2  KGRPGNFLQSRPEPT
G96   KGRPGNFLQNRPEPT          Gag    442    456

5 CD4 responses:
Mos1  RSLYNTVATLYCVHQR
Mos2  RSLFNTVATLYCVHAS
G289  KSLFNTVATLYCVHA          Gag    76     90
G54   -SLYNTVATLYCVHQR         Gag    77     91

Mos1  YVTDRGRQKIVSLTE
Mos2  YVTDRGRQKVVSLTD
P134  YVTDRGRQKVVSLTE          Pol    612    626

Mos1  CTTTVPWNASWSNKS
Mos2  CTTAVPWNTSWSNKS
E53   CTTNVPWNSSWSNKS          Env    604    618

Mos1  WWAGIQQEFGIPYNP
Mos2  WWAGIKQEFGIPYNP
```

Fig. 22 cont.

```
P135   WWAGIQQEFGIPYNP              Pol   846   860

Mos1   GPGHKARVLAEAMSQ
Mos2   GPSHKARVLAEAMSQ
G15    GPGHKARVLAEAMSQ              Gag   355   369
```

---

Mosaic 362-07:
13 CD8 PTE+, 5 CD4 PTE+
7 CD8+ regions, 5 CD4+ regions
Number of overlapping peptides per region: CD8: 2 2 4 2 1 1 1  CD4: 1 1 1 1 1

7 CD8 responses:

```
Mos1   CTHGIRPVVSTQLLL
Mos2   CTHGIKPVVSTQLLL
E15    CTHGIKPVVSTQLLI              Env   247   261
E47    CTHGIRPVVSTQLLI              Env   247   261

Mos1   KHIVWASRELERFAVNPGLL
Mos2   KHLVWASRELERFALNPGLL
G29    KHLVWASRELERFAL              Gag   32    46
G68    -----ASRELERFAVNPGLL         Gag   37    51

Mos1   QPSLQTGSEELRSLYNTVATL
Mos2   QPALQTGTEELRSLYNTVATL
G268   LPALKTGSEELRSLY              Gag   65    79
G249   --ALQTGSEELRSLYNT            Gag   67    81
G132   ----LQTGTEELRSLYNTV          Gag   68    82
G129   ------GSEELRSLYNTVATL        Gag   71    85

Mos1   ACQEVGGPGHKARVLAEAMS
Mos2   ACQGVGGPSHKARVLAEAMS
G166   ACQEVGGPGHKARVL              Gag   349   363
G76    -----GGPSHKARVLAEAMG         Gag   354   368

Mos1   RELNKRTQDFWEVQL
Mos2   RELNKRTQDFWEVQL
P233   RELNKRTQDFWEVQL              Pol   233   247

Mos1   LLRAIEAQQHLLQLT
Mos2   LLRAIEAQQHMLQLT
E227   LLMAIEAQQHLLQLT              Env   555   569

Mos1   KTAVQMAVFIHNFKR
Mos2   KTAVQMAVFIHNFKR
P5     KTAVQMAVFIHNFKR              Pol   888   902
```

Fig. 22 cont.

```
5 CD4 responses:
Mos1  KLNWASQIYPGIKVR
Mos2  KLNWASQIYAGIKVK
P136  KLNWASQIYAGIKVK           Pol   418   432

Mos1  YARMRTAHTNDVKQL
Mos2  YASMRGAHTNDVKQL
P266  YARKRSAHTNDVKQL           Pol   509   523

Mos1  DQAEHLKTAVQMAVF
Mos2  DQAEHLKTAVQMAVF
P29   DQAEHLKTAVQMAVF           Pol   882   896

Mos1  SLQTGSEELRSLYNT
Mos2  ALQTGTEELRSLYNT
G182  RLKTGTEELRSLYNT           Gag    67    81

Mos1  GPGHKARVLAEAMSQ
Mos2  GPSHKARVLAEAMSQ
G15   GPGHKARVLAEAMSQ           Gag   355   369
```

Reactive peptides and breadth and depth of responses: Optimal Natural Clade C Vaccine

Natural Clade C 363-07:
2 CD8 PTE+, 0 CD4 PTE+
1 CD8+ regions, 0 CD4+ regions
Number of overlapping peptides per region: CD8: 2 CD4: none

```
1 CD8 responses:
C     QPALQTGTEELRSLYNTVATL
G168  LPALKTGSEELRSLY
G125  -----GSEELRSLYNTVATL
```

Natural Clade C 364-07:
5 CD8 PTE+, 2 CD4 PTE+
5 CD8+ regions, 2 CD4+ regions
Number of overlapping peptides per region: CD8: 1 1 1 1 1 CD4: 1 1

```
5 CD8 responses:
C     AHTNDVKQLTEAVQK
P30   AHTNDVKQLTEAVQK  Pol   515   529

C     GDIIGDIRQAHCNIS
E64   GDIIGDIRQAHCNIS  Env   321   334
```

Fig. 22 cont.

```
C       SEKSAVGIGAVFLGF
E192    SEKRAVGLGAVFLGF    Env    508    522

C       RASILRGGKLDKWEK
G283    SASILRGGKLDKWEK    Gag    4      18

C       TNNPPVPVGDIYKRW
G195    TSNPPVPVGDIYKRW    Gag    251    265

2 CD4 responses:
C       CKSNITGLLLTRDGG
E316    CTSNITGLLLVRDGG    Env    445    459

C       SLYNTVATLYCVHAG
G54     SLYNTVATLYCVHQR    Gag    77     91
```

---
Natural Clade C 365-07:
2 CD8 PTE+, 1 CD4 PTE+
2 CD8+ regions, 1 CD4+ regions
Number of overlapping peptides per region: CD8: 1 1 CD4: 1

```
2 CD8 responses:
C       SQLINKERVYLSWVP
P350    SPLIKKEKVYLSWVP    Pol    678    692

C       AEWDRLHPVHAGPIA
G44     AEWDRLHPVHAGPIA    Gag    210    224

1 CD4 response:
C       HQAAMQMLKDTINEE
G24     RQAAMQMLKDTINEE    Gag    194    208
```

---
Natural Clade C 366-07:
6 CD8 PTE+, 1 CD4 PTE+
4 CD8+ regions, 1 CD4+ regions
Number of overlapping peptides per region: CD8: 2 2 1 1 CD4: 1

```
4 CD8 responses:
C       IVQQQSNLLRAIEAQ
E54     VVQQQSNLLPAIEAQ    Env    548    562
E72     -VQQQNLLRAIEAQR   Env    549    563

C       AVFIHNFKRKGGIGGY
P22     AVFIHNFKRKGGIGG    Pol    894    908
P136    -VLIHNFKRKGGIGGY  Pol    895    909
```

Fig. 22 cont.

```
C       MAICEEMEKEGKITK
P224    TRICEEMEKEGKITK      Pol    190    204

C       GGPSHKARVLAEAMS
G76     GGPSHKAPVLAEAMS      Gag    354    368

1 CD4 response:
C       IIGQVRDQAEHLKTA
P86     LIGQVRDQAEHLKTA      Pol    876    890
```

---
Natural Clade C 367-07:
0 CD8 PTE+, 0 CD4 PTE+
0 CD8+ regions, 0 CD4+ regions
Number of overlapping peptides per region: none 0 CD8 responses 0 CD4 responses ---
Natural Clade C 368-07:
2 CD8 PTE+, 0 CD4 PTE+
1 CD8+ regions, 0 CD4+ regions
Number of overlapping peptides per region: CD8: 2 CD4: 0

```
1 CD8 response
C       AVFIHNFKRKGGIGGY
P23     AVFIHNFKRKGGIGG      Pol    894    908
P236    -VIHNFKRKGGIGGY      Pol    895    909
```

Fig. 24

A  Monkey 366 (Natural C)

OptC    IVQQSNLLRAIEAQQ
E54     VVQQSNLLRAIEAQ
E70     -VQQNNLLRAIEAQH

OptC    AVFIHNFKRKGGIGGY
P22     AVFIHNFKRKGGIGG
P236    -VLIHNFKRKGGIGGY

OptC    MAICEEMEKEGKITK
P324    YAICEEMEKEGKITK

OptC    GGPSHKARVLAEAMS
G76     GGPSHKARVLAEAMG

B  Monkey 361 (Mosaic)

Mos1    EQLIKKERVYLSWVPAHKGIG
Mos2    EQLIKKEKVYLAWVPAHKGIG
P201    EELIKKEKVYLAWVP
P250    EQLIKKEKVYLSWVP
P316    -KLIKKDKVYLSWVPA
P223    --LIKKERVYLSWVPAH
P169    ------EKVYLAWVPAHKGIG
P33     ------EKVYLSWVPAHKGIG

Mos1    CTHGIRPVVSTQLLL
Mos2    CTHGIKPVVSTQLLL
E15     CTHGIKPVVSTQLLL
E47     CTHGIRPVVSTQLLL

Mos1    ICTTTVPWNASWSNKSL
Mos2    ICTTAVPWNISWSNKSQ
E334    ICTTTVPWNASWSNK
E314    -CTTTVPWNSSWSNKY
E158    --TTAVPWNASWSNKSL
E290    --TTAVPWNISWSNKSL

Mos1    ACQGVGGPGHKARVLAEAMS
Mos2    ACQGVGGPSHKARVLAEAMS
G166    ACQEVGGPGHKARVL
G76     -----GGPSHKARVLAEAMG

Mos1    AAEWDRVHPVHAGPIAPGQ
Mos2    AAEWDRLHPVHAGPVAPGQ
G319    AAE-DRLHPVHAGPIP
G242    -ADWDRLHPVHAGPVA
G44     -AEWDRLHPVHAGPIA
G277    ---WDRVHPVHAGPIPPG
G102    ----DRVHPVHAGPIPPGQ

Mos1    HSNWRAMASDFNLPP
Mos2    HSNWRAMASEFNLPP
P93     HSNWRAMASDFNLPP

Mos1    KGRPGNFLQNRPEPT
Mos2    KGRPGNFLQSRPEPT
G86     KGRPGNFLQNRPEPT

SEQUENCE LISTING

<160> NUMBER OF SEQ ID NOS: 685

<210> SEQ ID NO 1
<211> LENGTH: 857
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

-continued

```
Leu Gly Lys Gln Phe Gly Asn Asn Lys Thr Ile Val Phe Asn His Ser
            355                 360                 365
Ser Gly Gly Asp Pro Glu Ile Val Met His Ser Phe Asn Cys Gly Gly
        370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Thr Lys Arg Ser Asn Asp Thr Glu
                405                 410                 415
Glu His Ile Thr Leu Pro Cys Arg Ile Lys Gln Ile Ile Asn Met Trp
                420                 425                 430
Gln Glu Val Gly Lys Ala Met Tyr Ala Pro Pro Ile Arg Gly Gln Ile
            435                 440                 445
Arg Cys Ser Ser Asn Ile Thr Gly Leu Leu Leu Thr Arg Asp Gly Gly
        450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Gln
            500                 505                 510
Arg Glu Lys Arg Ala Val Gly Ile Gly Ala Val Phe Leu Gly Phe Leu
        515                 520                 525
Gly Ala Ala Gly Ser Thr Met Gly Ala Ala Ser Met Thr Leu Thr Val
        530                 535                 540
Gln Ala Arg Leu Leu Leu Ser Gly Ile Val Gln Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
        595                 600                 605
Cys Thr Thr Thr Val Pro Trp Asn Ala Ser Trp Ser Asn Lys Ser Leu
        610                 615                 620
Asp Lys Ile Trp Asn Asn Met Thr Trp Met Glu Trp Glu Arg Glu Ile
625                 630                 635                 640
Asn Asn Tyr Thr Ser Leu Ile Tyr Thr Leu Ile Glu Glu Ser Gln Asn
                645                 650                 655
Gln Gln Glu Lys Asn Glu Gln Glu Leu Leu Glu Leu Asp Lys Trp Ala
            660                 665                 670
Ser Leu Trp Asn Trp Phe Asp Ile Ser Asn Trp Leu Trp Tyr Ile Lys
        675                 680                 685
Ile Phe Ile Met Ile Val Gly Gly Leu Val Gly Leu Arg Ile Val Phe
        690                 695                 700
Ala Val Leu Ser Ile Val Asn Arg Val Arg Gln Gly Tyr Ser Pro Leu
705                 710                 715                 720
Ser Phe Gln Thr Arg Leu Pro Ala Pro Arg Gly Pro Asp Arg Pro Glu
                725                 730                 735
Gly Ile Glu Glu Glu Gly Gly Glu Arg Asp Arg Asp Arg Ser Val Arg
            740                 745                 750
Leu Val Asp Gly Phe Leu Val Leu Ile Trp Asp Asp Leu Gln Ser Leu
        755                 760                 765
Cys Leu Phe Ser Tyr His Arg Leu Arg Asp Leu Leu Leu Ile Val Glu
```

```
                    770                 775                 780
Leu Leu Gly Arg Arg Gly Trp Glu Ala Leu Lys Tyr Trp Trp Asn Leu
785                 790                 795                 800

Leu Gln Tyr Trp Ser Gln Glu Leu Lys Asn Ser Ala Ile Ser Leu Leu
                805                 810                 815

Asn Ala Thr Ala Val Ala Val Ala Glu Gly Thr Asp Arg Val Ile Glu
                820                 825                 830

Ala Leu Gln Arg Ala Cys Arg Ala Ile Leu His Ile Pro Arg Arg Ile
                835                 840                 845

Arg Gln Gly Leu Glu Arg Leu Leu Leu
    850                 855

<210> SEQ ID NO 2
<211> LENGTH: 867
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
                20                  25                  30

Leu Trp Val Thr Val Tyr Tyr Gly Val Pro Val Trp Lys Glu Ala Lys
                35                  40                  45

Thr Thr Leu Phe Cys Ala Ser Asp Ala Lys Ala Tyr Glu Lys Glu Val
                50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
                100                 105                 110

Gln Ser Leu Lys Pro Cys Val Lys Leu Thr Pro Leu Cys Val Thr Leu
                115                 120                 125

Glu Cys Arg Asn Val Arg Asn Val Ser Ser Asn Gly Thr Tyr Asn Ile
                130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
                180                 185                 190

Ser Glu Asn Ser Ser Glu Tyr Tyr Arg Leu Ile Asn Cys Asn Thr Ser
                195                 200                 205

Ala Ile Thr Gln Ala Cys Pro Lys Val Ser Phe Asp Pro Ile Pro Ile
                210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
                260                 265                 270
```

```
Ser Leu Ala Glu Glu Ile Ile Ile Arg Ser Glu Asn Leu Thr Asn
            275                 280                 285

Asn Ala Lys Thr Ile Ile Val His Leu Asn Glu Thr Val Asn Ile Thr
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
                340                 345                 350

Val Lys Lys Lys Leu Ala Glu His Phe Pro Asn Lys Thr Ile Asn Phe
            355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
                420                 425                 430

Arg Ala Met Tyr Ala Pro Pro Ile Ala Gly Asn Ile Thr Cys Arg Ser
            435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Arg
                500                 505                 510

Glu Lys Arg Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
    595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp Tyr Ile Lys Ile
    675                 680                 685

Phe Ile Met Ile Val Gly Gly Leu Ile Gly Leu Arg Ile Ile Leu Gly
```

690                 695                 700
Val Leu Ser Ile Val Arg Arg Val Arg Gln Gly Tyr Ser Pro Leu Ser
705                 710                 715                 720

Phe Gln Thr Leu Thr Pro Asn Pro Arg Gly Leu Asp Arg Leu Gly Arg
                725                 730                 735

Ile Glu Glu Gly Gly Glu Gln Asp Arg Asp Arg Ser Ile Arg Leu
            740                 745                 750

Val Asn Gly Phe Leu Ala Leu Ala Trp Asp Asp Leu Arg Ser Leu Cys
            755                 760                 765

Leu Phe Ser Tyr His Gln Leu Arg Asp Phe Ile Leu Ile Val Ala Arg
        770                 775                 780

Ala Val Glu Leu Leu Gly Arg Ser Ser Leu Arg Gly Leu Gln Arg Gly
785                 790                 795                 800

Trp Glu Ala Leu Lys Tyr Leu Gly Asn Leu Val Gln Tyr Trp Gly Leu
                805                 810                 815

Glu Leu Lys Lys Gly Ala Ile Ser Leu Leu Asp Thr Ile Ala Ile Ala
            820                 825                 830

Val Ala Glu Gly Thr Asp Arg Ile Ile Glu Leu Ile Gln Ser Ile Cys
            835                 840                 845

Arg Ala Ile Arg Asn Ile Pro Arg Arg Ile Arg Gln Gly Phe Glu Ala
        850                 855                 860

Ser Leu Leu
865

<210> SEQ ID NO 3
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

```
Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln
            500

<210> SEQ ID NO 4
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30
```

His Leu Val Trp Ala Ser Arg Glu Leu Glu Arg Phe Ala Leu Asn Pro
                35                  40                  45

Gly Leu Leu Glu Thr Ser Glu Gly Cys Lys Gln Ile Ile Lys Gln Leu
 50                  55                  60

Gln Pro Ala Leu Gln Thr Gly Thr Glu Leu Arg Ser Leu Phe Asn
 65                  70                  75                  80

Thr Val Ala Thr Leu Tyr Cys Val His Ala Glu Ile Glu Val Arg Asp
                 85                  90                  95

Thr Lys Glu Ala Leu Asp Lys Ile Glu Glu Gln Asn Lys Ser Gln
                100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
                180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
        210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
                260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
        290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
        370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
        420                 425                 430

Trp Pro Ser His Lys Gly Arg Pro Gly Asn Phe Leu Gln Ser Arg Pro
        435                 440                 445

```
Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 5
<211> LENGTH: 999
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Phe Phe Arg Glu Asn Leu Ala Phe Gln Gln Gly Glu Ala Arg Glu Phe
1               5                   10                  15

Pro Ser Glu Gln Thr Arg Ala Asn Ser Pro Thr Ser Arg Glu Leu Gln
                20                  25                  30

Val Arg Gly Asp Asn Pro His Ser Glu Ala Gly Ala Glu Arg Gln Gly
            35                  40                  45

Thr Leu Asn Phe Pro Gln Ile Thr Leu Trp Gln Arg Pro Leu Val Ser
    50                  55                  60

Ile Lys Val Gly Gly Gln Ile Arg Glu Ala Leu Leu Asp Thr Gly Ala
65                  70                  75                  80

Asp Asp Thr Val Leu Glu Asp Ile Asn Leu Pro Gly Lys Trp Lys Pro
                85                  90                  95

Lys Met Ile Gly Gly Ile Gly Gly Phe Ile Lys Val Arg Gln Tyr Asp
            100                 105                 110

Gln Ile Leu Ile Glu Ile Cys Gly Lys Lys Ala Ile Gly Thr Val Leu
        115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
145                 150                 155                 160

Val Lys Leu Lys Pro Gly Met Asp Gly Pro Arg Val Lys Gln Trp Pro
                165                 170                 175

Leu Thr Glu Glu Lys Ile Lys Ala Leu Thr Ala Ile Cys Glu Glu Met
            180                 185                 190

Glu Lys Glu Gly Lys Ile Thr Lys Ile Gly Pro Glu Asn Pro Tyr Asn
        195                 200                 205

Thr Pro Val Phe Ala Ile Lys Lys Lys Asp Ser Thr Lys Trp Arg Lys
    210                 215                 220

Leu Val Asp Phe Arg Glu Leu Asn Lys Arg Thr Gln Asp Phe Trp Glu
225                 230                 235                 240

Val Gln Leu Gly Ile Pro His Pro Ala Gly Leu Lys Lys Lys Lys Ser
                245                 250                 255

Val Thr Val Leu Asp Val Gly Asp Ala Tyr Phe Ser Val Pro Leu Asp
            260                 265                 270

Glu Gly Phe Arg Lys Tyr Thr Ala Phe Thr Ile Pro Ser Thr Asn Asn
        275                 280                 285

Glu Thr Pro Gly Ile Arg Tyr Gln Tyr Asn Val Leu Pro Gln Gly Trp
    290                 295                 300

Lys Gly Ser Pro Ala Ile Phe Gln Cys Ser Met Thr Arg Ile Leu Glu
305                 310                 315                 320
```

```
Pro Phe Arg Ala Lys Asn Pro Glu Ile Val Ile Tyr Gln Tyr Met Asp
            325                 330                 335

Asp Leu Tyr Val Gly Ser Asp Leu Glu Ile Gly Gln His Arg Ala Lys
            340                 345                 350

Ile Glu Glu Leu Arg Glu His Leu Leu Lys Trp Gly Phe Thr Thr Pro
            355                 360                 365

Asp Lys Lys His Gln Lys Glu Pro Pro Phe Leu Trp Met Gly Tyr Glu
            370                 375                 380

Leu His Pro Asp Lys Trp Thr Val Gln Pro Ile Gln Leu Pro Glu Lys
385                 390                 395                 400

Asp Ser Trp Thr Val Asn Asp Ile Gln Lys Leu Val Gly Lys Leu Asn
            405                 410                 415

Trp Ala Ser Gln Ile Tyr Pro Gly Ile Lys Val Arg Gln Leu Cys Lys
            420                 425                 430

Leu Leu Arg Gly Ala Lys Ala Leu Thr Asp Ile Val Pro Leu Thr Glu
            435                 440                 445

Glu Ala Glu Leu Glu Leu Ala Glu Asn Arg Glu Ile Leu Lys Glu Pro
            450                 455                 460

Val His Gly Val Tyr Tyr Asp Pro Ser Lys Asp Leu Ile Ala Glu Ile
465                 470                 475                 480

Gln Lys Gln Gly His Asp Gln Trp Thr Tyr Gln Ile Tyr Gln Glu Pro
            485                 490                 495

Phe Lys Asn Leu Lys Thr Gly Lys Tyr Ala Lys Met Arg Thr Ala His
            500                 505                 510

Thr Asn Asp Val Lys Gln Leu Thr Glu Ala Val Gln Lys Ile Ala Met
            515                 520                 525

Glu Ser Ile Val Ile Trp Gly Lys Thr Pro Lys Phe Arg Leu Pro Ile
530                 535                 540

Gln Lys Glu Thr Trp Glu Thr Trp Trp Thr Asp Tyr Trp Gln Ala Thr
545                 550                 555                 560

Trp Ile Pro Glu Trp Glu Phe Val Asn Thr Pro Pro Leu Val Lys Leu
            565                 570                 575

Trp Tyr Gln Leu Glu Lys Asp Pro Ile Ala Gly Val Glu Thr Phe Tyr
            580                 585                 590

Val Asp Gly Ala Ala Asn Arg Glu Thr Lys Leu Gly Lys Ala Gly Tyr
            595                 600                 605

Val Thr Asp Arg Gly Arg Gln Lys Ile Val Ser Leu Thr Glu Thr Thr
610                 615                 620

Asn Gln Lys Thr Glu Leu Gln Ala Ile Tyr Leu Ala Leu Gln Asp Ser
625                 630                 635                 640

Gly Ser Glu Val Asn Ile Val Thr Asp Ser Gln Tyr Ala Leu Gly Ile
            645                 650                 655

Ile Gln Ala Gln Pro Asp Lys Ser Glu Ser Glu Leu Val Asn Gln Ile
            660                 665                 670

Ile Glu Gln Leu Ile Lys Lys Glu Arg Val Tyr Leu Ser Trp Val Pro
            675                 680                 685

Ala His Lys Gly Ile Gly Gly Asn Glu Gln Val Asp Lys Leu Val Ser
            690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Asp
            725                 730                 735
```

```
Phe Asn Leu Pro Pro Val Ala Lys Glu Ile Val Ala Ser Cys Asp
                740                 745                 750

Gln Cys Gln Leu Lys Gly Glu Ala Met His Gly Gln Val Asp Cys Ser
        755                 760                 765

Pro Gly Ile Trp Gln Leu Asp Cys Thr His Leu Glu Gly Lys Ile Ile
    770                 775                 780

Leu Val Ala Val His Val Ala Ser Gly Tyr Ile Glu Ala Glu Val Ile
785                 790                 795                 800

Pro Ala Glu Thr Gly Gln Glu Thr Ala Tyr Phe Ile Leu Lys Leu Ala
                805                 810                 815

Gly Arg Trp Pro Val Lys Val Ile His Thr Asp Asn Gly Ser Asn Phe
        820                 825                 830

Thr Ser Ala Ala Val Lys Ala Ala Cys Trp Trp Ala Gly Ile Gln Gln
    835                 840                 845

Glu Phe Gly Ile Pro Tyr Asn Pro Gln Ser Gln Gly Val Val Glu Ser
850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
        900                 905                 910

Asp Ile Ile Ala Thr Asp Ile Gln Thr Lys Glu Leu Gln Lys Gln Ile
    915                 920                 925

Ile Lys Ile Gln Asn Phe Arg Val Tyr Tyr Arg Asp Ser Arg Asp Pro
930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Val
                965                 970                 975

Lys Ile Ile Lys Asp Tyr Gly Lys Gln Met Ala Gly Ala Asp Cys Val
        980                 985                 990

Ala Gly Arg Gln Asp Glu Asp
        995

<210> SEQ ID NO 6
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Phe Arg Glu Asn Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
                20                  25                  30

Val Trp Gly Arg Asp Asn Asn Ser Leu Ser Glu Ala Gly Ala Asp Arg
            35                  40                  45

Gln Gly Thr Val Ser Phe Ser Phe Pro Gln Ile Thr Leu Trp Gln Arg
        50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95
```

-continued

```
Arg Trp Lys Pro Lys Met Ile Gly Gly Ile Gly Phe Ile Lys Val
            100                 105                 110
Arg Gln Tyr Asp Gln Ile Pro Ile Glu Ile Cys Gly His Lys Ala Ile
            115                 120                 125
Gly Thr Val Leu Val Gly Pro Thr Pro Val Asn Ile Ile Gly Arg Asn
            130                 135                 140
Leu Leu Thr Gln Ile Gly Cys Thr Leu Asn Phe Pro Ile Ser Pro Ile
145                 150                 155                 160
Glu Thr Val Pro Val Lys Leu Lys Pro Gly Met Asp Gly Pro Lys Val
                    165                 170                 175
Lys Gln Trp Pro Leu Thr Glu Glu Lys Ile Lys Ala Leu Val Glu Ile
                180                 185                 190
Cys Thr Glu Met Glu Lys Glu Gly Lys Ile Ser Lys Ile Gly Pro Glu
            195                 200                 205
Asn Pro Tyr Asn Thr Pro Ile Phe Ala Ile Lys Lys Lys Asp Ser Thr
            210                 215                 220
Lys Trp Arg Lys Leu Val Asp Phe Arg Glu Leu Asn Lys Arg Thr Gln
225                 230                 235                 240
Asp Phe Trp Glu Val Gln Leu Gly Ile Pro His Pro Ala Gly Leu Lys
                    245                 250                 255
Lys Lys Lys Ser Val Thr Val Leu Asp Val Gly Asp Ala Tyr Phe Ser
                260                 265                 270
Val Pro Leu Asp Glu Asp Phe Arg Lys Tyr Thr Ala Phe Thr Ile Pro
            275                 280                 285
Ser Ile Asn Asn Glu Thr Pro Gly Ile Arg Tyr Gln Tyr Asn Val Leu
            290                 295                 300
Pro Gln Gly Trp Lys Gly Ser Pro Ala Ile Phe Gln Ser Ser Met Thr
305                 310                 315                 320
Lys Ile Leu Glu Pro Phe Arg Lys Gln Asn Pro Asp Ile Val Ile Tyr
                    325                 330                 335
Gln Tyr Met Asp Asp Leu Tyr Val Gly Ser Asp Leu Glu Ile Gly Gln
                340                 345                 350
His Arg Thr Lys Ile Glu Glu Leu Arg Gln His Leu Leu Arg Trp Gly
            355                 360                 365
Phe Thr Thr Pro Asp Lys Lys His Gln Lys Glu Pro Pro Phe Leu Trp
            370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                    405                 410                 415
Gly Lys Leu Asn Trp Ala Ser Gln Ile Tyr Ala Gly Ile Lys Val Lys
                420                 425                 430
Gln Leu Cys Lys Leu Leu Arg Gly Thr Lys Ala Leu Thr Glu Val Val
            435                 440                 445
Pro Leu Thr Glu Glu Ala Glu Leu Glu Leu Ala Glu Asn Arg Glu Ile
            450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                    485                 490                 495
Tyr Gln Glu Pro Phe Lys Asn Leu Lys Thr Gly Lys Tyr Ala Arg Met
                500                 505                 510
```

Arg Gly Ala His Thr Asn Asp Val Lys Gln Leu Thr Glu Ala Val Gln
            515                 520                 525

Lys Ile Ala Thr Glu Ser Ile Val Ile Trp Gly Lys Thr Pro Lys Phe
        530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Ser Leu
610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
690                 695                 700

Lys Leu Val Ser Arg Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Glu Phe Asn Leu Pro Pro Ile Val Ala Lys Glu Ile Val
            740                 745                 750

Ala Ser Cys Asp Lys Cys Gln Leu Lys Gly Glu Ala Ile His Gly Gln
        755                 760                 765

Val Asp Cys Ser Pro Gly Ile Trp Gln Leu Asp Cys Thr His Leu Glu
770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
            820                 825                 830

Gly Ser Asn Phe Thr Ser Ala Thr Val Lys Ala Ala Cys Trp Trp Ala
        835                 840                 845

Gly Ile Lys Gln Glu Phe Gly Ile Pro Tyr Asn Pro Gln Ser Gln Gly
850                 855                 860

Val Val Glu Ser Ile Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Glu Tyr Ser Ala Gly
            900                 905                 910

Glu Arg Ile Val Asp Ile Ile Ala Ser Asp Ile Gln Thr Lys Glu Leu
        915                 920                 925

Gln Lys Gln Ile Thr Lys Ile Gln Asn Phe Arg Val Tyr Tyr Arg Asp

```
Ser Arg Asp Pro Leu Trp Lys Gly Pro Ala Lys Leu Trp Lys Gly
945                 950                 955                 960

Glu Gly Ala Val Val Ile Gln Asp Asn Ser Asp Ile Lys Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln  Asp Glu Asp
        995                 1000
```

<210> SEQ ID NO 7
<211> LENGTH: 206
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 7

```
Met Gly Gly Lys Trp Ser Lys Ser Ser Val Gly Trp Pro Ala Ile
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
            115                 120                 125

Pro Gly Pro Gly Ile Arg Tyr Pro Leu Thr Phe Gly Trp Cys Phe Lys
        130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
                180                 185                 190

His Met Ala Arg Glu Leu His Pro Glu Tyr Tyr Lys Asp Cys
            195                 200                 205
```

<210> SEQ ID NO 8
<211> LENGTH: 206
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

```
Met Gly Gly Lys Trp Ser Lys Ser Ser Ile Gly Trp Pro Ala Val
1               5                   10                  15

Arg Glu Arg Ile Arg Arg Ala Glu Pro Ala Ala Glu Gly Val Gly Ala
```

```
                    20                  25                  30
Ala Ser Gln Asp Leu Asp Lys Tyr Gly Ala Leu Thr Ser Ser Asn Thr
            35                  40                  45

Ala Ala Thr Asn Ala Asp Cys Ala Trp Leu Glu Ala Gln Glu Asp Glu
        50                  55                  60

Glu Val Gly Phe Pro Val Lys Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110

Trp Val Tyr Asn Thr Gln Gly Phe Phe Pro Asp Trp Gln Asn Tyr Thr
        115                 120                 125

Pro Gly Pro Gly Val Arg Tyr Pro Leu Thr Phe Gly Trp Cys Phe Lys
    130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
                165                 170                 175

Glu Arg Glu Val Leu Val Trp Arg Phe Asp Ser Arg Leu Ala Phe His
            180                 185                 190

His Met Ala Arg Glu Lys His Pro Glu Tyr Tyr Lys Asn Cys
        195                 200                 205

<210> SEQ ID NO 9
<211> LENGTH: 685
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175
```

```
Ala Leu Phe Tyr Lys Leu Asp Val Val Pro Ile Asp Asn Asp Ser Asn
                180                 185                 190

Asn Thr Asn Tyr Arg Leu Ile Ser Cys Asn Thr Ser Val Ile Thr Gln
            195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
        355                 360                 365

Ser Gly Gly Asp Pro Glu Ile Val Met His Ser Phe Asn Cys Gly Gly
    370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Leu Leu Thr Arg Asp Gly Gly
    450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Ser Glu Lys Ser Ala Val Gly Ile Gly Ala Val Phe Leu Gly Phe Leu
        515                 520                 525

Gly Ala Ala Gly Ser Thr Met Gly Ala Ala Ser Met Thr Leu Thr Val
    530                 535                 540

Gln Ala Arg Leu Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
```

```
            595                 600                 605
Cys Thr Thr Thr Val Pro Trp Asn Ala Ser Trp Ser Asn Lys Ser Leu
    610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp
        675                 680                 685

<210> SEQ ID NO 10
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110

Gln Ser Leu Lys Pro Cys Val Lys Leu Thr Pro Leu Cys Val Thr Leu
        115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270
```

```
Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
275             290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
                340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
                420                 425                 430

Arg Ala Met Tyr Ala Pro Pro Ile Ala Gly Asn Ile Thr Cys Arg Ser
            435                 440                 445

Asn Ile Thr Gly Leu Leu Leu Thr Arg Asp Gly Gly Ser Asn Asn Gly
        450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
                500                 505                 510

Glu Lys Ser Ala Val Gly Ile Gly Ala Val Phe Leu Gly Ile Leu Gly
        515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
        595                 600                 605

Thr Thr Ala Val Pro Trp Asn Thr Ser Trp Ser Asn Lys Ser Gln Thr
    610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
                660                 665                 670

Leu Trp Asn Trp Phe Asp Ile Thr Asn Trp Leu Trp
                675                 680
```

-continued

```
<210> SEQ ID NO 11
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Arg Val Lys Gly Ile Arg Lys Asn Tyr Gln His Leu Trp Lys Trp
1               5                   10                  15

Gly Thr Met Leu Leu Gly Met Leu Met Ile Cys Ser Ala Ala Glu Gln
                20                  25                  30

Leu Trp Val Thr Val Tyr Tyr Gly Val Pro Val Trp Arg Asp Ala Glu
            35                  40                  45

Thr Thr Leu Phe Cys Ala Ser Asp Ala Lys Ala Tyr Glu Arg Glu Val
        50                  55                  60

His Asn Ile Trp Ala Thr His Ala Cys Val Pro Thr Asp Pro Asn Pro
65                  70                  75                  80

Gln Glu Ile Val Leu Glu Asn Val Thr Glu Glu Phe Asn Met Trp Lys
                85                  90                  95

Asn Asp Met Val Glu Gln Met His Thr Asp Ile Ile Ser Leu Trp Asp
            100                 105                 110

Glu Ser Leu Lys Pro Cys Val Lys Leu Ala Pro Leu Cys Val Thr Leu
        115                 120                 125

Asn Cys Thr Asn Ala Asn Leu Asn Cys Thr Asn Asp Asn Cys Asn Arg
130                 135                 140

Thr Val Asp Lys Met Arg Glu Glu Ile Lys Asn Cys Ser Phe Asn Met
145                 150                 155                 160

Thr Thr Glu Leu Arg Asp Lys Lys Gln Lys Val Tyr Ala Leu Phe Tyr
                165                 170                 175

Lys Leu Asp Ile Val Pro Ile Glu Lys Asn Ser Ser Glu Tyr Arg Leu
            180                 185                 190

Ile Asn Cys Asn Thr Ser Thr Ile Thr Gln Ala Cys Pro Lys Val Thr
        195                 200                 205

Phe Glu Pro Ile Pro Ile His Tyr Cys Thr Pro Ala Gly Phe Ala Ile
    210                 215                 220

Leu Lys Cys Lys Asp Lys Lys Phe Asn Gly Thr Gly Pro Cys Lys Asn
225                 230                 235                 240

Val Ser Thr Val Gln Cys Thr His Gly Ile Lys Pro Val Ile Ser Thr
                245                 250                 255

Gln Leu Leu Leu Asn Gly Ser Leu Ala Glu Gly Glu Ile Ile Ile Arg
            260                 265                 270

Ser Glu Asn Ile Thr Asn Asn Ala Lys Thr Ile Ile Val Gln Leu Asn
        275                 280                 285

Glu Ser Val Val Ile Asn Cys Thr Arg Pro Gly Asn Asn Thr Arg Lys
    290                 295                 300

Ser Val Arg Ile Gly Pro Gly Gln Ala Phe Tyr Ala Thr Gly Glu Ile
305                 310                 315                 320

Ile Gly Asp Ile Arg Gln Ala Tyr Cys Asn Ile Ser Arg Ala Lys Trp
                325                 330                 335

Asn Asn Thr Leu Lys Gln Ile Val Thr Lys Leu Lys Glu Gln Phe Lys
            340                 345                 350

Asn Lys Thr Ile Val Phe Asn Gln Ser Ser Gly Gly Asp Pro Glu Ile
        355                 360                 365
```

Thr Thr His Ser Phe Asn Cys Gly Gly Glu Phe Phe Tyr Cys Asn Thr
370                 375                 380

Thr Gln Leu Phe Asn Ser Thr Trp Asn Ser Asn Ser Thr Trp Asn Asp
385                 390                 395                 400

Thr Thr Gly Ser Val Thr Glu Gly Asn Asp Thr Ile Thr Leu Pro Cys
            405                 410                 415

Arg Ile Lys Gln Ile Val Asn Met Trp Gln Arg Val Gly Gln Ala Met
            420                 425                 430

Tyr Ala Pro Pro Ile Glu Gly Asn Ile Thr Cys Lys Ser Asn Ile Thr
            435                 440                 445

Gly Leu Leu Leu Val Arg Asp Gly Gly Asn Ile Asn Arg Thr Asn Glu
450                 455                 460

Thr Phe Arg Pro Gly Gly Gly Asn Met Lys Asp Asn Trp Arg Ser Glu
465                 470                 475                 480

Leu Tyr Lys Tyr Lys Val Glu Ile Lys Pro Leu Gly Val Ala Pro
            485                 490                 495

Thr Arg Ala Lys Arg Arg Val Val Glu Ser Glu Lys Ser Ala Val Gly
            500                 505                 510

Leu Gly Ala Val Phe Leu Gly Phe Leu Gly Thr Ala Gly Ser Thr Met
            515                 520                 525

Gly Ala Ala Ser Leu Thr Leu Thr Val Gln Ala Arg Gln Val Leu Ser
530                 535                 540

Gly Ile Val Gln Gln Gln Ser Asn Leu Leu Lys Ala Ile Glu Ala Gln
545                 550                 555                 560

Gln His Leu Leu Lys Leu Thr Val Trp Gly Ile Lys Gln Leu Gln Ala
            565                 570                 575

Arg Ile Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
            595                 600                 605

Asn Ser Ser Trp Ser Asn Lys Ser Gln Glu Glu Ile Trp Asn Asn Met
610                 615                 620

Thr Trp Met Gln Trp Asp Arg Glu Ile Ser Asn Tyr Thr Asp Thr Ile
625                 630                 635                 640

Tyr Arg Leu Leu Glu Asp Ser Gln Asn Gln Gln Glu Lys Asn Glu Gln
            645                 650                 655

Asp Leu Leu Ala Leu Asp Lys Trp Ala Ser Leu Trp Asn Trp Phe Ser
            660                 665                 670

Ile Thr Asn Trp Leu Trp
            675

<210> SEQ ID NO 12
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
            20                  25                  30

Ile Lys Ala Leu Thr Ala Ile Cys Glu Glu Met Glu Lys Glu Gly Lys
            35                  40                  45

```
Ile Thr Lys Ile Gly Pro Glu Asn Pro Tyr Asn Thr Pro Val Phe Ala
 50                  55                  60

Ile Lys Lys Asp Ser Thr Lys Trp Arg Lys Leu Val Asp Phe Arg
 65                  70                  75                  80

Glu Leu Asn Lys Arg Thr Gln Asp Phe Trp Glu Val Gln Leu Gly Ile
                     85                  90                  95

Pro His Pro Ala Gly Leu Lys Lys Lys Ser Val Thr Val Leu Ala
                100                 105                 110

Val Gly Asp Ala Tyr Phe Ser Val Pro Leu Asp Glu Gly Phe Arg Lys
                115                 120                 125

Tyr Thr Ala Phe Thr Ile Pro Ser Thr Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
                180                 185                 190

Ser Asp Leu Glu Ile Gly Gln His Arg Ala Lys Ile Glu Glu Leu Arg
                195                 200                 205

Glu His Leu Leu Lys Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
                260                 265                 270

Tyr Pro Gly Ile Lys Val Arg Gln Leu Cys Lys Leu Leu Arg Gly Ala
                275                 280                 285

Lys Ala Leu Thr Asp Ile Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly His
                325                 330                 335

Asp Gln Trp Thr Tyr Gln Ile Tyr Gln Glu Pro Phe Lys Asn Leu Lys
                340                 345                 350

Thr Gly Lys Tyr Ala Lys Met Arg Thr Ala His Thr Asn Asp Val Lys
    355                 360                 365

Gln Leu Thr Glu Ala Val Gln Lys Ile Ala Met Glu Ser Ile Val Ile
    370                 375                 380

Trp Gly Lys Thr Pro Lys Phe Arg Leu Pro Ile Gln Lys Glu Thr Trp
385                 390                 395                 400

Glu Thr Trp Trp Thr Asp Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Asp Pro Ile Ala Gly Val Glu Thr Phe Tyr Val Ala Gly Ala Ala
                435                 440                 445

Asn Arg Glu Thr Lys Leu Gly Lys Ala Gly Tyr Val Thr Asp Arg Gly
    450                 455                 460
```

```
Arg Gln Lys Ile Val Ser Leu Thr Glu Thr Thr Asn Gln Lys Thr Ala
465                 470                 475                 480

Leu Gln Ala Ile Tyr Leu Ala Leu Gln Asp Ser Gly Ser Glu Val Asn
            485                 490                 495

Ile Val Thr Ala Ser Gln Tyr Ala Leu Gly Ile Ile Gln Ala Gln Pro
        500                 505                 510

Asp Lys Ser Glu Ser Glu Leu Val Asn Gln Ile Ile Glu Gln Leu Ile
    515                 520                 525

Lys Lys Glu Arg Val Tyr Leu Ser Trp Val Pro Ala His Lys Gly Ile
530                 535                 540

Gly Gly Asn Glu Gln Val Asp Lys Leu Val Ser Ser Gly Ile Arg Lys
545                 550                 555                 560

Val Leu Phe Leu Asp Gly Ile Asp Lys Ala Gln Glu Glu His Glu Lys
            565                 570                 575

Tyr His Ser Asn Trp Arg Ala Met Ala Ser Asp Phe Asn Leu Pro Pro
        580                 585                 590

Val Val Ala Lys Glu Ile Val Ala Ser Cys Asp Gln Cys Gln Leu Lys
    595                 600                 605

Gly Glu Ala Met His Gly Gln Val Asp Cys Ser Pro Gly Ile Trp Gln
610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
            645                 650                 655

Gln Glu Thr Ala Tyr Phe Ile Leu Lys Leu Ala Gly Arg Trp Pro Val
        660                 665                 670

Lys Val Ile His Thr Ala Asn Gly Ser Asn Phe Thr Ser Ala Ala Val
    675                 680                 685

Lys Ala Ala Cys Trp Trp Ala Gly Ile Gln Gln Glu Phe Gly Ile Pro
690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
            725                 730                 735

Ala Val Gln Met Ala Val Phe Ile His Asn Phe Lys Arg Lys Gly Gly
        740                 745                 750

Ile Gly Gly Tyr Ser Ala Gly Glu Arg Ile Ile Asp Ile Ile Ala Thr
    755                 760                 765

Asp Ile Gln Thr Lys Glu Leu Gln Lys Gln Ile Lys Ile Gln Asn
770                 775                 780

Phe Arg Val Tyr Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
            805                 810                 815

Ser Asp Ile Lys Val Val Pro Arg Arg Lys Val Lys Ile Ile Lys Asp
        820                 825                 830

Tyr Gly Lys Gln Met Ala Gly Ala Asp Cys Val Ala Gly Arg Gln Asp
    835                 840                 845

Glu Asp
    850

<210> SEQ ID NO 13
<211> LENGTH: 850
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 13

```
Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Ala Gly Ile Lys Val Lys Gln Leu Cys Lys Leu Leu Arg Gly Thr
        275                 280                 285

Lys Ala Leu Thr Glu Val Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Ala Thr Glu Ser Ile Val Ile
    370                 375                 380
```

```
Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
            405                 410                 415

Glu Phe Val Asn Thr Pro Pro Leu Val Lys Leu Trp Tyr Gln Leu Glu
        420                 425                 430

Lys Glu Pro Ile Val Gly Ala Glu Thr Phe Tyr Val Ala Gly Ala Ala
    435                 440                 445

Asn Arg Glu Thr Lys Leu Gly Lys Ala Gly Tyr Val Thr Asp Arg Gly
450                 455                 460

Arg Gln Lys Val Val Ser Leu Thr Asp Thr Thr Asn Gln Lys Thr Ala
465                 470                 475                 480

Leu Gln Ala Ile His Leu Ala Leu Gln Asp Ser Gly Leu Glu Val Asn
                485                 490                 495

Ile Val Thr Ala Ser Gln Tyr Ala Leu Gly Ile Ile Gln Ala Gln Pro
            500                 505                 510

Asp Lys Ser Glu Ser Glu Leu Val Ser Gln Ile Ile Glu Gln Leu Ile
        515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Arg Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Glu Phe Asn Leu Pro Pro
            580                 585                 590

Ile Val Ala Lys Glu Ile Val Ala Ser Cys Asp Lys Cys Gln Leu Lys
        595                 600                 605

Gly Glu Ala Ile His Gly Gln Val Asp Cys Ser Pro Gly Ile Trp Gln
610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Ala Asn Gly Ser Asn Phe Thr Ser Ala Thr Val
        675                 680                 685

Lys Ala Ala Cys Trp Trp Ala Gly Ile Lys Gln Glu Phe Gly Ile Pro
690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
        755                 760                 765

Asp Ile Gln Thr Lys Glu Leu Gln Lys Gln Ile Thr Lys Ile Gln Asn
770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
```

```
                        805                 810                 815
Ser Asp Ile Lys Val Pro Arg Arg Lys Ala Lys Ile Ile Arg Asp
                820                 825                 830

Tyr Gly Lys Gln Met Ala Gly Asp Asp Cys Val Ala Ser Arg Gln Asp
            835                 840                 845

Glu Asp
    850

<210> SEQ ID NO 14
<211> LENGTH: 851
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Pro Ile Ser Pro Ile Asp Thr Val Pro Val Thr Leu Lys Pro
1               5                   10                  15

Gly Met Asp Gly Pro Lys Ile Lys Gln Trp Pro Leu Thr Glu Glu Lys
            20                  25                  30

Ile Lys Ala Leu Thr Glu Ile Cys Thr Glu Met Glu Lys Glu Gly Lys
        35                  40                  45

Ile Ser Arg Ile Gly Pro Glu Asn Pro Tyr Asn Thr Pro Val Phe Ala
    50                  55                  60

Ile Lys Lys Lys Asn Ser Thr Arg Trp Arg Lys Leu Val Asp Phe Arg
65                  70                  75                  80

Glu Leu Asn Lys Lys Thr Gln Asp Phe Trp Glu Val Gln Leu Gly Ile
                85                  90                  95

Pro His Pro Ala Gly Leu Lys Lys Lys Arg Ser Val Thr Val Leu Ala
            100                 105                 110

Val Gly Asp Ala Tyr Phe Ser Val Pro Leu Asp Lys Asp Phe Arg Lys
        115                 120                 125

Tyr Thr Ala Phe Thr Ile Pro Ser Val Asn Asn Glu Thr Pro Gly Val
    130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Lys Ile Leu Glu Pro Phe Arg Ala Gln
                165                 170                 175

Asn Pro Glu Ile Val Ile Tyr Gln Tyr Val Ala Ala Leu Tyr Val Gly
            180                 185                 190

Ser Asp Leu Glu Ile Glu Gln His Arg Thr Lys Ile Glu Glu Leu Arg
        195                 200                 205

Ala His Leu Leu Ser Trp Gly Phe Thr Thr Pro Asp Lys Lys His Gln
    210                 215                 220

Arg Glu Pro Pro Phe Leu Trp Met Gly Tyr Glu Leu His Pro Asp Arg
225                 230                 235                 240

Trp Thr Val Gln Pro Ile Glu Leu Pro Glu Lys Glu Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Lys Gln Leu Cys Arg Leu Leu Arg Gly Ala
        275                 280                 285

Lys Ala Leu Thr Glu Val Ile Pro Leu Thr Lys Glu Ala Glu Leu Glu
    290                 295                 300
```

-continued

Leu Ala Glu Asn Arg Glu Ile Leu Arg Glu Pro Val His Gly Val Tyr
305                 310                 315                 320

Tyr Asp Pro Ser Lys Asp Leu Val Ala Glu Ile Gln Lys Gln Gly Gln
            325                 330                 335

Asp Gln Trp Thr Tyr Gln Ile Tyr Gln Glu Pro Tyr Lys Asn Leu Lys
        340                 345                 350

Thr Gly Lys Tyr Ala Arg Lys Arg Ser Ala His Thr Asn Asp Val Arg
    355                 360                 365

Gln Leu Thr Glu Ala Val Gln Lys Ile Ala Leu Glu Ser Ile Val Ile
370                 375                 380

Trp Gly Lys Ile Pro Lys Phe Arg Leu Pro Ile Gln Arg Glu Thr Trp
385                 390                 395                 400

Glu Thr Trp Trp Thr Glu Tyr Trp Gln Ala Thr Trp Ile Pro Asp Trp
            405                 410                 415

Glu Phe Val Asn Thr Pro Pro Leu Val Lys Leu Trp Tyr Gln Leu Glu
        420                 425                 430

Lys Glu Pro Ile Ala Gly Ala Glu Thr Phe Tyr Val Ala Gly Ala Ser
    435                 440                 445

Asn Arg Glu Thr Lys Ile Gly Lys Ala Gly Tyr Val Thr Asp Lys Gly
450                 455                 460

Arg Gln Lys Val Val Ser Leu Thr Glu Thr Thr Asn Gln Lys Ala Ala
465                 470                 475                 480

Leu Gln Ala Ile Gln Leu Ala Leu Gln Asp Ser Gly Pro Glu Val Asn
            485                 490                 495

Ile Val Thr Ala Ser Gln Tyr Val Leu Gly Ile Gln Ala Gln Pro
        500                 505                 510

Asp Arg Ser Glu Ser Glu Leu Val Asn Gln Ile Ile Glu Glu Leu Ile
    515                 520                 525

Lys Lys Glu Lys Val Tyr Leu Ser Trp Val Pro Ala His Lys Gly Ile
530                 535                 540

Gly Gly Asn Glu Gln Val Asp Lys Leu Val Ser Ala Gly Ile Arg Lys
545                 550                 555                 560

Ile Leu Phe Leu Asp Gly Ile Asp Lys Ala Gln Glu Glu His Glu Arg
            565                 570                 575

Tyr His Ser Asn Trp Arg Thr Met Ala Ser Asp Phe Asn Leu Pro Pro
        580                 585                 590

Ile Val Ala Lys Glu Ile Val Ala Asn Cys Asp Lys Cys Gln Leu Lys
    595                 600                 605

Gly Glu Ala Met His Gly Gln Val Asp Cys Ser Pro Gly Met Trp Gln
610                 615                 620

Leu Ala Cys Thr His Leu Glu Gly Lys Ile Ile Ile Val Ala Val His
625                 630                 635                 640

Val Ala Ser Gly Tyr Met Glu Ala Glu Val Ile Pro Ala Glu Thr Gly
            645                 650                 655

Gln Glu Thr Ala Tyr Tyr Ile Leu Lys Leu Ala Gly Arg Trp Pro Val
        660                 665                 670

Lys Val Val His Thr Ala Asn Gly Ser Asn Phe Thr Ser Thr Thr Val
    675                 680                 685

Lys Ala Ala Cys Trp Trp Ala Asn Val Thr Gln Glu Phe Gly Ile Pro
690                 695                 700

Tyr Asn Pro Gln Ser Gln Gly Val Ile Ala Ser Met Asn Lys Glu Leu
705                 710                 715                 720

Lys Lys Ile Ile Gly Gln Val Arg Glu Gln Ala Glu His Leu Lys Thr

```
                  725                 730                 735
Ala Val Gln Met Ala Val Leu Ile His Asn Phe Lys Arg Arg Gly Gly
                740                 745                 750

Ile Gly Gly Tyr Ser Ala Gly Glu Arg Ile Val Asp Ile Ile Ala Thr
            755                 760                 765

Asp Ile Gln Thr Arg Glu Leu Gln Lys Gln Ile Ile Lys Ile Gln Asn
        770                 775                 780

Phe Arg Val Tyr Phe Arg Asp Ser Arg Asp Pro Val Trp Lys Gly Pro
785                 790                 795                 800

Ala Lys Leu Leu Trp Lys Gly Glu Gly Ala Val Val Ile Gln Asp Asn
                805                 810                 815

Ser Glu Ile Lys Val Val Pro Arg Arg Lys Val Lys Ile Ile Arg Asp
                820                 825                 830

Tyr Gly Lys Gln Met Ala Gly Asp Asp Cys Val Ala Gly Arg Gln Asp
            835                 840                 845

Glu Asp Gln
    850

<210> SEQ ID NO 15
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Asp Arg Phe Ala Leu Asn Pro
        35                  40                  45

Gly Leu Leu Glu Thr Ala Glu Gly Cys Gln Gln Ile Ile Glu Gln Leu
    50                  55                  60

Gln Pro Ala Leu Gln Thr Gly Ser Glu Glu Leu Lys Ser Leu Tyr Asn
65                  70                  75                  80

Thr Val Ala Val Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Ser Ser Ser Lys Val
        115                 120                 125

Ser Gln Asn Tyr Pro Ile Val Gln Asn Ala Gln Gly Gln Met Val His
    130                 135                 140

Gln Ala Leu Ser Pro Arg Thr Leu Asn Ala Trp Val Lys Val Val Glu
145                 150                 155                 160

Glu Lys Gly Phe Asn Pro Glu Val Ile Pro Met Phe Ser Ala Leu Ala
                165                 170                 175

Glu Gly Ala Thr Pro Gln Asp Leu Asn Met Met Leu Asn Ile Val Gly
            180                 185                 190

Gly His Gln Ala Ala Met Gln Ile Leu Lys Asp Thr Ile Asn Glu Glu
        195                 200                 205

Ala Ala Asp Trp Asp Arg Leu His Pro Val His Ala Gly Pro Ile Pro
    210                 215                 220
```

```
Pro Gly Gln Met Arg Glu Pro Arg Gly Ser Asp Ile Ala Gly Thr Thr
225                 230                 235                 240

Ser Thr Pro Gln Glu Gln Ile Gly Trp Met Thr Ser Asn Pro Pro Val
                245                 250                 255

Pro Val Gly Glu Ile Tyr Lys Arg Trp Ile Ile Met Gly Leu Asn Lys
            260                 265                 270

Ile Val Arg Met Tyr Ser Pro Val Ser Ile Leu Asp Ile Lys Gln Gly
        275                 280                 285

Pro Lys Glu Ser Phe Arg Asp Tyr Val Asp Arg Phe Phe Lys Val Leu
    290                 295                 300

Arg Ala Glu Gln Ala Thr Gln Glu Val Lys Asn Trp Met Thr Glu Thr
305                 310                 315                 320

Leu Leu Ile Gln Asn Ala Asn Pro Asp Cys Lys Ser Ile Leu Arg Ala
                325                 330                 335

Leu Gly Pro Gly Ala Ser Leu Glu Glu Met Met Thr Ala Cys Gln Gly
                340                 345                 350

Val Gly Gly Pro Ser His Lys Ala Arg Ile Leu Ala Glu Ala Met Ser
            355                 360                 365

Gln Ala Asn Asn Thr Asn Ile Met Met Gln Arg Gly Asn Phe Lys Gly
370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Arg Gly Cys Trp Lys Cys Gly Arg
                405                 410                 415

Glu Gly His Gln Met Lys Asp Cys Asn Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Leu Glu Pro Thr Ala Pro Pro Ala
    450                 455                 460

Glu Pro Thr Ala Pro Pro Ala Glu Ser Phe Gly Phe Gly Glu Glu Ile
465                 470                 475                 480

Thr Pro Ser Pro Lys Gln Glu Gln Lys Asp Arg Glu Pro Leu Thr Ser
                485                 490                 495

Leu Lys Ser Leu Phe Gly Ser Asp Pro Leu Leu Gln
                500                 505

<210> SEQ ID NO 16
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Gly Lys Trp Ser Lys Ser Ser Val Val Gly Trp Pro Ala Ile
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80
```

Tyr Lys Gly Ala Leu Asp Leu Ser His Phe Leu Lys Glu Lys Gly Gly
                    85                  90                  95

Leu Glu Gly Leu Ile Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
        115                 120                 125

Pro Gly Pro Gly Ile Arg Tyr Pro Leu Thr Phe Gly Trp Cys Phe Lys
130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
            180                 185                 190

His Met Ala Arg Glu Leu His Pro Glu Tyr Tyr Lys Asp Cys
        195                 200                 205

<210> SEQ ID NO 17
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
            20                  25                  30

Ala Ser Gln Asp Leu Asp Lys Tyr Gly Ala Leu Thr Ser Ser Asn Thr
        35                  40                  45

Ala Ala Thr Asn Ala Asp Cys Ala Trp Leu Glu Ala Gln Glu Asp Glu
    50                  55                  60

Glu Val Gly Phe Pro Val Lys Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110

Trp Val Tyr Asn Thr Gln Gly Phe Phe Pro Asp Trp Gln Asn Tyr Thr
        115                 120                 125

Pro Gly Pro Gly Val Arg Tyr Pro Leu Thr Phe Gly Trp Cys Phe Lys
130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
                165                 170                 175

Glu Arg Glu Val Leu Val Trp Arg Phe Asp Ser Arg Leu Ala Phe His
            180                 185                 190

His Met Ala Arg Glu Lys His Pro Glu Tyr Tyr Lys Asn Cys
        195                 200                 205

<210> SEQ ID NO 18
<211> LENGTH: 208
<212> TYPE: PRT

-continued

<213> ORGANISM: Artificial Sequence
<220> FEATURE:
<223> OTHER INFORMATION: Description of Artificial Sequence: Synthetic
    polypeptide

<400> SEQUENCE: 18

Met Ala Gly Lys Trp Ser Lys Arg Ser Val Val Gly Trp Pro Ala Val
1               5                   10                  15

Arg Glu Arg Met Arg Arg Thr Glu Pro Ala Ala Glu Gly Val Gly Ala
            20                  25                  30

Val Ser Gln Asp Leu Asp Lys His Gly Ala Leu Thr Ser Ser Asn Thr
        35                  40                  45

Ala His Asn Asn Ala Asp Cys Ala Trp Leu Gln Ala Gln Glu Glu Glu
    50                  55                  60

Glu Glu Val Gly Phe Pro Val Arg Pro Gln Val Pro Val Arg Pro Met
65                  70                  75                  80

Thr Tyr Lys Ala Ala Val Asp Leu Ser His Phe Leu Lys Glu Lys Gly
                85                  90                  95

Gly Leu Glu Gly Leu Ile His Ser Gln Lys Arg Gln Glu Ile Leu Asp
            100                 105                 110

Leu Trp Val Tyr His Thr Gln Gly Phe Phe Pro Asp Trp His Asn Tyr
        115                 120                 125

Thr Pro Gly Pro Gly Thr Arg Phe Pro Leu Thr Phe Gly Trp Cys Tyr
    130                 135                 140

Lys Leu Val Pro Val Asp Pro Lys Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser Ser Leu Ala Arg
            180                 185                 190

Arg His Met Ala Arg Glu Leu His Pro Glu Phe Tyr Lys Asp Cys Leu
        195                 200                 205

<210> SEQ ID NO 19
<211> LENGTH: 705
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val

```
              115                 120                 125
Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Val Ser Ile Leu Asp Ile Arg Gln Gly
                275                 280                 285

Pro Lys Glu Pro Phe Arg Asp Tyr Val Asp Arg Phe Tyr Lys Thr Leu
290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Ser Ala Thr Ile Met Met Gln Arg Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Asn Lys Gly Arg Pro Gly Asn Phe
                435                 440                 445

Leu Gln Asn Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Ala Gly Lys Ser Lys Ser Ser Val Gly Trp
                500                 505                 510

Pro Ala Ile Arg Glu Arg Met Arg Arg Ala Glu Pro Ala Ala Asp Gly
                515                 520                 525

Val Gly Ala Val Ser Arg Asp Leu Glu Lys His Gly Ala Ile Thr Ser
530                 535                 540
```

```
Ser Asn Thr Ala Ala Asn Asn Ala Asp Cys Ala Trp Leu Glu Ala Gln
545                 550                 555                 560

Glu Glu Glu Glu Val Gly Phe Pro Val Arg Pro Gln Val Pro Leu Arg
            565                 570                 575

Pro Met Thr Tyr Lys Gly Ala Leu Asp Leu Ser His Phe Leu Lys Glu
            580                 585                 590

Lys Gly Gly Leu Glu Gly Leu Ile Tyr Ser Gln Lys Arg Gln Asp Ile
        595                 600                 605

Leu Asp Leu Trp Val Tyr His Thr Gln Gly Tyr Phe Pro Asp Trp Gln
    610                 615                 620

Asn Tyr Thr Pro Gly Pro Gly Ile Arg Tyr Pro Leu Thr Phe Gly Trp
625                 630                 635                 640

Cys Phe Lys Leu Val Pro Val Glu Pro Glu Lys Ile Glu Glu Ala Asn
            645                 650                 655

Glu Gly Glu Asn Asn Ser Leu Leu His Pro Met Ser Gln His Gly Met
            660                 665                 670

Asp Asp Pro Glu Lys Glu Val Leu Met Trp Lys Phe Asp Ser Arg Leu
            675                 680                 685

Ala Phe His His Met Ala Arg Glu Leu His Pro Glu Tyr Tyr Lys Asp
    690                 695                 700

Cys
705

<210> SEQ ID NO 20
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
```

-continued

```
                180                 185                 190
Ala Ala Met Gln Met Leu Lys Asp Thr Ile Asn Glu Glu Ala Ala Glu
            195                 200                 205
Trp Asp Arg Leu His Pro Val His Ala Gly Pro Val Ala Pro Gly Gln
        210                 215                 220
Met Arg Glu Pro Arg Gly Ser Asp Ile Ala Gly Thr Thr Ser Asn Leu
225                 230                 235                 240
Gln Glu Gln Ile Ala Trp Met Thr Ser Asn Pro Pro Ile Pro Val Gly
                245                 250                 255
Asp Ile Tyr Lys Arg Trp Ile Ile Leu Gly Leu Asn Lys Ile Val Arg
            260                 265                 270
Met Tyr Ser Pro Thr Ser Ile Leu Asp Ile Lys Gln Gly Pro Lys Glu
        275                 280                 285
Pro Phe Arg Asp Tyr Val Asp Arg Phe Phe Lys Thr Leu Arg Ala Glu
    290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
            340                 345                 350
Pro Ser His Lys Ala Arg Val Leu Ala Glu Ala Met Ser Gln Thr Asn
        355                 360                 365
Ser Thr Ile Leu Met Gln Arg Ser Asn Phe Lys Gly Ser Lys Arg Ile
    370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                405                 410                 415
Gln Met Lys Asp Cys Thr Glu Arg Gln Ala Asn Phe Leu Gly Lys Ile
            420                 425                 430
Trp Pro Ser His Lys Gly Arg Pro Gly Asn Phe Leu Gln Ser Arg Pro
        435                 440                 445
Glu Pro Thr Ala Pro Pro Ala Glu Ser Phe Arg Phe Glu Glu Thr Thr
    450                 455                 460
Pro Ala Pro Lys Gln Glu Pro Lys Asp Arg Glu Pro Leu Thr Ser Leu
465                 470                 475                 480
Arg Ser Leu Phe Gly Ser Asp Pro Leu Ser Gln Ala Gly Lys Trp Ser
                485                 490                 495
Lys Ser Ser Ile Val Gly Trp Pro Ala Val Arg Glu Arg Ile Arg Arg
            500                 505                 510
Ala Glu Pro Ala Ala Glu Gly Val Gly Ala Ala Ser Gln Asp Leu Asp
        515                 520                 525
Lys Tyr Gly Ala Leu Thr Ser Ser Asn Thr Ala Ala Thr Asn Ala Asp
    530                 535                 540
Cys Ala Trp Leu Glu Ala Gln Glu Asp Glu Glu Val Gly Phe Pro Val
545                 550                 555                 560
Lys Pro Gln Val Pro Leu Arg Pro Met Thr Tyr Lys Ala Ala Phe Asp
                565                 570                 575
Leu Ser Phe Phe Leu Lys Glu Lys Gly Gly Leu Asp Gly Leu Ile Tyr
            580                 585                 590
Ser Lys Lys Arg Gln Glu Ile Leu Asp Leu Trp Val Tyr Asn Thr Gln
        595                 600                 605
```

```
Gly Phe Phe Pro Asp Trp Gln Asn Tyr Thr Pro Gly Pro Gly Val Arg
        610                 615                 620

Tyr Pro Leu Thr Phe Gly Trp Cys Phe Lys Leu Val Pro Val Asp Pro
625                 630                 635                 640

Arg Glu Val Glu Ala Asn Lys Gly Glu Asn Asn Cys Leu Leu His
                645                 650                 655

Pro Met Asn Leu His Gly Met Asp Asp Pro Glu Arg Glu Val Leu Val
            660                 665                 670

Trp Arg Phe Asp Ser Arg Leu Ala Phe His His Met Ala Arg Glu Lys
            675                 680                 685

His Pro Glu Tyr Tyr Lys Asn Cys
            690                 695

<210> SEQ ID NO 21
<211> LENGTH: 1350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
```

-continued

```
                260                 265                 270
Ile Val Arg Met Tyr Ser Pro Val Ser Ile Leu Asp Ile Arg Gln Gly
            275                 280                 285
Pro Lys Glu Pro Phe Arg Asp Tyr Val Asp Arg Phe Tyr Lys Thr Leu
            290                 295                 300
Arg Ala Glu Gln Ala Ser Gln Asp Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
            355                 360                 365
Gln Val Thr Asn Ser Ala Thr Ile Met Met Gln Arg Gly Asn Phe Arg
        370                 375                 380
Asn Gln Arg Lys Thr Val Lys Cys Phe Asn Cys Gly Lys Glu Gly His
385                 390                 395                 400
Ile Ala Lys Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Asn Lys Gly Arg Pro Gly Asn Phe
            435                 440                 445
Leu Gln Asn Arg Pro Glu Pro Thr Ala Pro Pro Glu Glu Ser Phe Arg
        450                 455                 460
Phe Gly Glu Glu Thr Thr Thr Pro Ser Gln Lys Gln Glu Pro Ile Asp
465                 470                 475                 480
Lys Glu Met Tyr Pro Leu Ala Ser Leu Lys Ser Leu Phe Gly Asn Asp
                485                 490                 495
Pro Ser Ser Gln Met Ala Pro Ile Ser Pro Ile Glu Thr Val Pro Val
            500                 505                 510
Lys Leu Lys Pro Gly Met Asp Gly Pro Arg Val Lys Gln Trp Pro Leu
            515                 520                 525
Thr Glu Glu Lys Ile Lys Ala Leu Thr Ala Ile Cys Glu Glu Met Glu
        530                 535                 540
Lys Glu Gly Lys Ile Thr Lys Ile Gly Pro Glu Asn Pro Tyr Asn Thr
545                 550                 555                 560
Pro Val Phe Ala Ile Lys Lys Lys Asp Ser Thr Lys Trp Arg Lys Leu
                565                 570                 575
Val Asp Phe Arg Glu Leu Asn Lys Arg Thr Gln Asp Phe Trp Glu Val
            580                 585                 590
Gln Leu Gly Ile Pro His Pro Ala Gly Leu Lys Lys Lys Lys Ser Val
            595                 600                 605
Thr Val Leu Ala Val Gly Asp Ala Tyr Phe Ser Val Pro Leu Asp Glu
        610                 615                 620
Gly Phe Arg Lys Tyr Thr Ala Phe Thr Ile Pro Ser Thr Asn Asn Glu
625                 630                 635                 640
Thr Pro Gly Ile Arg Tyr Gln Tyr Asn Val Leu Pro Gln Gly Trp Lys
                645                 650                 655
Gly Ser Pro Ala Ile Phe Gln Cys Ser Met Thr Arg Ile Leu Glu Pro
            660                 665                 670
Phe Arg Ala Lys Asn Pro Glu Ile Val Ile Tyr Gln Tyr Met Ala Ala
            675                 680                 685
```

```
Leu Tyr Val Gly Ser Asp Leu Glu Ile Gly Gln His Arg Ala Lys Ile
    690             695                 700

Glu Glu Leu Arg Glu His Leu Leu Lys Trp Gly Phe Thr Thr Pro Asp
705             710                 715                 720

Lys Lys His Gln Lys Glu Pro Pro Phe Leu Trp Met Gly Tyr Glu Leu
                725             730                 735

His Pro Asp Lys Trp Thr Val Gln Pro Ile Gln Leu Pro Glu Lys Asp
            740             745                 750

Ser Trp Thr Val Asn Asp Ile Gln Lys Leu Val Gly Lys Leu Asn Trp
                755             760                 765

Ala Ser Gln Ile Tyr Pro Gly Ile Lys Val Arg Gln Leu Cys Lys Leu
770             775                 780

Leu Arg Gly Ala Lys Ala Leu Thr Asp Ile Val Pro Leu Thr Glu Glu
785             790                 795                 800

Ala Glu Leu Glu Leu Ala Glu Asn Arg Glu Ile Leu Lys Glu Pro Val
                805             810                 815

His Gly Val Tyr Tyr Asp Pro Ser Lys Asp Leu Ile Ala Glu Ile Gln
            820             825                 830

Lys Gln Gly His Asp Gln Trp Thr Tyr Gln Ile Tyr Gln Glu Pro Phe
            835             840                 845

Lys Asn Leu Lys Thr Gly Lys Tyr Ala Lys Met Arg Thr Ala His Thr
850             855                 860

Asn Asp Val Lys Gln Leu Thr Glu Ala Val Gln Lys Ile Ala Met Glu
865             870                 875                 880

Ser Ile Val Ile Trp Gly Lys Thr Pro Lys Phe Arg Leu Pro Ile Gln
                885             890                 895

Lys Glu Thr Trp Glu Thr Trp Trp Thr Asp Tyr Trp Gln Ala Thr Trp
                900             905                 910

Ile Pro Glu Trp Glu Phe Val Asn Thr Pro Pro Leu Val Lys Leu Trp
            915             920                 925

Tyr Gln Leu Glu Lys Asp Pro Ile Ala Gly Val Glu Thr Phe Tyr Val
930             935                 940

Ala Gly Ala Ala Asn Arg Glu Thr Lys Leu Gly Lys Ala Gly Tyr Val
945             950             955                 960

Thr Asp Arg Gly Arg Gln Lys Ile Val Ser Leu Thr Glu Thr Thr Asn
                965             970                 975

Gln Lys Thr Ala Leu Gln Ala Ile Tyr Leu Ala Leu Gln Asp Ser Gly
            980             985                 990

Ser Glu Val Asn Ile Val Thr Ala  Ser Gln Tyr Ala Leu  Gly Ile Ile
            995                 1000                1005

Gln Ala  Gln Pro Asp Lys Ser  Glu Ser Glu Leu Val  Asn Gln Ile
    1010                1015                1020

Ile Glu  Gln Leu Ile Lys Lys  Glu Arg Val Tyr Leu  Ser Trp Val
    1025                1030                1035

Pro Ala  His Lys Gly Ile Gly  Gly Asn Glu Gln Val  Asp Lys Leu
    1040                1045                1050

Val Ser  Ser Gly Ile Arg Lys  Val Leu Phe Leu Asp  Gly Ile Asp
    1055                1060                1065

Lys Ala  Gln Glu Glu His Glu  Lys Tyr His Ser Asn  Trp Arg Ala
    1070                1075                1080

Met Ala  Ser Asp Phe Asn Leu  Pro Pro Val Val Ala  Lys Glu Ile
    1085                1090                1095
```

-continued

Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Ala Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Ala Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 22
<211> LENGTH: 1341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

```
Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510
```

-continued

```
Lys Val Lys Gln Trp Pro Leu Thr Glu Glu Lys Ile Lys Ala Leu Val
            515                 520                 525
Glu Ile Cys Thr Glu Met Glu Lys Glu Gly Lys Ile Ser Lys Ile Gly
        530                 535                 540
Pro Glu Asn Pro Tyr Asn Thr Pro Ile Phe Ala Ile Lys Lys Lys Asp
545                 550                 555                 560
Ser Thr Lys Trp Arg Lys Leu Val Asp Phe Arg Glu Leu Asn Lys Arg
                565                 570                 575
Thr Gln Asp Phe Trp Glu Val Gln Leu Gly Ile Pro His Pro Ala Gly
            580                 585                 590
Leu Lys Lys Lys Lys Ser Val Thr Val Leu Ala Val Gly Asp Ala Tyr
        595                 600                 605
Phe Ser Val Pro Leu Asp Glu Asp Phe Arg Lys Tyr Thr Ala Phe Thr
610                 615                 620
Ile Pro Ser Ile Asn Asn Glu Thr Pro Gly Ile Arg Tyr Gln Tyr Asn
625                 630                 635                 640
Val Leu Pro Gln Gly Trp Lys Gly Ser Pro Ala Ile Phe Gln Ser Ser
                645                 650                 655
Met Thr Lys Ile Leu Glu Pro Phe Arg Lys Gln Asn Pro Asp Ile Val
            660                 665                 670
Ile Tyr Gln Tyr Met Ala Ala Leu Tyr Val Gly Ser Asp Leu Glu Ile
        675                 680                 685
Gly Gln His Arg Thr Lys Ile Glu Glu Leu Arg Gln His Leu Leu Arg
        690                 695                 700
Trp Gly Phe Thr Thr Pro Asp Lys Lys His Gln Lys Glu Pro Pro Phe
705                 710                 715                 720
Leu Trp Met Gly Tyr Glu Leu His Pro Asp Lys Trp Thr Val Gln Pro
                725                 730                 735
Ile Val Leu Pro Glu Lys Asp Ser Trp Thr Val Asn Asp Ile Gln Lys
            740                 745                 750
Leu Val Gly Lys Leu Asn Trp Ala Ser Gln Ile Tyr Ala Gly Ile Lys
        755                 760                 765
Val Lys Gln Leu Cys Lys Leu Leu Arg Gly Thr Lys Ala Leu Thr Glu
        770                 775                 780
Val Val Pro Leu Thr Glu Glu Ala Glu Leu Glu Leu Ala Glu Asn Arg
785                 790                 795                 800
Glu Ile Leu Lys Glu Pro Val His Gly Val Tyr Tyr Asp Pro Ser Lys
                805                 810                 815
Asp Leu Ile Ala Glu Ile Gln Lys Gln Gly Gln Gly Gln Trp Thr Tyr
            820                 825                 830
Gln Ile Tyr Gln Glu Pro Phe Lys Asn Leu Lys Thr Gly Lys Tyr Ala
        835                 840                 845
Arg Met Arg Gly Ala His Thr Asn Asp Val Lys Gln Leu Thr Glu Ala
    850                 855                 860
Val Gln Lys Ile Ala Thr Glu Ser Ile Val Ile Trp Gly Lys Thr Pro
865                 870                 875                 880
Lys Phe Lys Leu Pro Ile Gln Lys Glu Thr Trp Glu Ala Trp Trp Thr
                885                 890                 895
Glu Tyr Trp Gln Ala Thr Trp Ile Pro Glu Trp Glu Phe Val Asn Thr
            900                 905                 910
Pro Pro Leu Val Lys Leu Trp Tyr Gln Leu Glu Lys Glu Pro Ile Val
        915                 920                 925
Gly Ala Glu Thr Phe Tyr Val Ala Gly Ala Ala Asn Arg Glu Thr Lys
```

```
                930             935             940
Leu Gly Lys Ala Gly Tyr Val Thr Asp Arg Gly Arg Gln Lys Val Val
945             950             955             960
Ser Leu Thr Asp Thr Thr Asn Gln Lys Thr Ala Leu Gln Ala Ile His
                965             970             975
Leu Ala Leu Gln Asp Ser Gly Leu Glu Val Asn Ile Val Thr Ala Ser
            980             985             990
Gln Tyr Ala Leu Gly Ile Ile Gln Ala Gln Pro Asp Lys Ser Glu Ser
        995             1000            1005
Glu Leu Val Ser Gln Ile Ile Glu Gln Leu Ile Lys Lys Glu Lys
    1010            1015            1020
Val Tyr Leu Ala Trp Val Pro Ala His Lys Gly Ile Gly Gly Asn
    1025            1030            1035
Glu Gln Val Asp Lys Leu Val Ser Arg Gly Ile Arg Lys Val Leu
    1040            1045            1050
Phe Leu Asp Gly Ile Asp Lys Ala Gln Glu Glu His Glu Lys Tyr
    1055            1060            1065
His Ser Asn Trp Arg Ala Met Ala Ser Glu Phe Asn Leu Pro Pro
    1070            1075            1080
Ile Val Ala Lys Glu Ile Val Ala Ser Cys Asp Lys Cys Gln Leu
    1085            1090            1095
Lys Gly Glu Ala Ile His Gly Gln Val Asp Cys Ser Pro Gly Ile
    1100            1105            1110
Trp Gln Leu Ala Cys Thr His Leu Glu Gly Lys Val Ile Leu Val
    1115            1120            1125
Ala Val His Val Ala Ser Gly Tyr Ile Glu Ala Glu Val Ile Pro
    1130            1135            1140
Ala Glu Thr Gly Gln Glu Thr Ala Tyr Phe Leu Leu Lys Leu Ala
    1145            1150            1155
Gly Arg Trp Pro Val Lys Thr Ile His Thr Ala Asn Gly Ser Asn
    1160            1165            1170
Phe Thr Ser Ala Thr Val Lys Ala Ala Cys Trp Trp Ala Gly Ile
    1175            1180            1185
Lys Gln Glu Phe Gly Ile Pro Tyr Asn Pro Gln Ser Gln Gly Val
    1190            1195            1200
Val Ala Ser Ile Asn Lys Glu Leu Lys Lys Ile Gly Gln Val
    1205            1210            1215
Arg Asp Gln Ala Glu His Leu Lys Thr Ala Val Gln Met Ala Val
    1220            1225            1230
Phe Ile His Asn Phe Lys Arg Lys Gly Gly Ile Gly Glu Tyr Ser
    1235            1240            1245
Ala Gly Glu Arg Ile Val Asp Ile Ile Ala Ser Asp Ile Gln Thr
    1250            1255            1260
Lys Glu Leu Gln Lys Gln Ile Thr Lys Ile Gln Asn Phe Arg Val
    1265            1270            1275
Tyr Tyr Arg Asp Ser Arg Asp Pro Leu Trp Lys Gly Pro Ala Lys
    1280            1285            1290
Leu Leu Trp Lys Gly Glu Gly Ala Val Val Ile Gln Asp Asn Ser
    1295            1300            1305
Asp Ile Lys Val Val Pro Arg Arg Lys Ala Lys Ile Ile Arg Asp
    1310            1315            1320
Tyr Gly Lys Gln Met Ala Gly Asp Asp Cys Val Ala Ser Arg Gln
    1325            1330            1335
```

Asp Glu Asp
    1340

<210> SEQ ID NO 23
<211> LENGTH: 1359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Asp Arg Phe Ala Leu Asn Pro
        35                  40                  45

Gly Leu Leu Glu Thr Ala Glu Gly Cys Gln Gln Ile Ile Glu Gln Leu
    50                  55                  60

Gln Pro Ala Leu Gln Thr Gly Ser Glu Glu Leu Lys Ser Leu Tyr Asn
65                  70                  75                  80

Thr Val Ala Val Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Ser Ser Ser Lys Val
        115                 120                 125

Ser Gln Asn Tyr Pro Ile Val Gln Asn Ala Gln Gly Gln Met Val His
    130                 135                 140

Gln Ala Leu Ser Pro Arg Thr Leu Asn Ala Trp Val Lys Val Val Glu
145                 150                 155                 160

Glu Lys Gly Phe Asn Pro Glu Val Ile Pro Met Phe Ser Ala Leu Ala
                165                 170                 175

Glu Gly Ala Thr Pro Gln Asp Leu Asn Met Met Leu Asn Ile Val Gly
            180                 185                 190

Gly His Gln Ala Ala Met Gln Ile Leu Lys Asp Thr Ile Asn Glu Glu
        195                 200                 205

Ala Ala Asp Trp Asp Arg Leu His Pro Val His Ala Gly Pro Ile Pro
    210                 215                 220

Pro Gly Gln Met Arg Glu Pro Arg Gly Ser Asp Ile Ala Gly Thr Thr
225                 230                 235                 240

Ser Thr Pro Gln Glu Gln Ile Gly Trp Met Thr Ser Asn Pro Pro Val
                245                 250                 255

Pro Val Gly Glu Ile Tyr Lys Arg Trp Ile Ile Met Gly Leu Asn Lys
            260                 265                 270

Ile Val Arg Met Tyr Ser Pro Val Ser Ile Leu Asp Ile Lys Gln Gly
        275                 280                 285

Pro Lys Glu Ser Phe Arg Asp Tyr Val Asp Arg Phe Phe Lys Val Leu
    290                 295                 300

Arg Ala Glu Gln Ala Thr Gln Glu Val Lys Asn Trp Met Thr Glu Thr
305                 310                 315                 320

Leu Leu Ile Gln Asn Ala Asn Pro Asp Cys Lys Ser Ile Leu Arg Ala
                325                 330                 335

Leu Gly Pro Gly Ala Ser Leu Glu Glu Met Met Thr Ala Cys Gln Gly

```
                340             345             350
Val Gly Gly Pro Ser His Lys Ala Arg Ile Leu Ala Glu Ala Met Ser
            355                 360                 365
Gln Ala Asn Asn Thr Asn Ile Met Met Gln Arg Gly Asn Phe Lys Gly
        370                 375                 380
Gln Lys Arg Ile Lys Cys Phe Asn Cys Gly Lys Glu Gly His Leu Ala
385                 390                 395                 400
Arg Asn Cys Arg Ala Pro Arg Lys Arg Gly Cys Trp Lys Cys Gly Arg
                405                 410                 415
Glu Gly His Gln Met Lys Asp Cys Asn Glu Arg Gln Ala Asn Phe Leu
            420                 425                 430
Gly Lys Ile Trp Pro Ser Ser Lys Gly Arg Pro Gly Asn Phe Pro Gln
        435                 440                 445
Ser Arg Pro Glu Pro Thr Ala Pro Leu Glu Pro Thr Ala Pro Pro Ala
    450                 455                 460
Glu Pro Thr Ala Pro Pro Ala Glu Ser Phe Gly Phe Gly Glu Glu Ile
465                 470                 475                 480
Thr Pro Ser Pro Lys Gln Glu Gln Lys Asp Arg Glu Pro Leu Thr Ser
                485                 490                 495
Leu Lys Ser Leu Phe Gly Ser Asp Pro Leu Leu Gln Met Ala Pro Ile
            500                 505                 510
Ser Pro Ile Asp Thr Val Pro Val Thr Leu Lys Pro Gly Met Asp Gly
        515                 520                 525
Pro Lys Ile Lys Gln Trp Pro Leu Thr Glu Glu Lys Ile Lys Ala Leu
    530                 535                 540
Thr Glu Ile Cys Thr Glu Met Glu Lys Glu Gly Lys Ile Ser Arg Ile
545                 550                 555                 560
Gly Pro Glu Asn Pro Tyr Asn Thr Pro Val Phe Ala Ile Lys Lys Lys
                565                 570                 575
Asn Ser Thr Arg Trp Arg Lys Leu Val Asp Phe Arg Glu Leu Asn Lys
            580                 585                 590
Lys Thr Gln Asp Phe Trp Glu Val Gln Leu Gly Ile Pro His Pro Ala
        595                 600                 605
Gly Leu Lys Lys Lys Arg Ser Val Thr Val Leu Ala Val Gly Asp Ala
    610                 615                 620
Tyr Phe Ser Val Pro Leu Asp Lys Asp Phe Arg Lys Tyr Thr Ala Phe
625                 630                 635                 640
Thr Ile Pro Ser Val Asn Asn Glu Thr Pro Gly Val Arg Tyr Gln Tyr
                645                 650                 655
Asn Val Leu Pro Gln Gly Trp Lys Gly Ser Pro Ala Ile Phe Gln Cys
            660                 665                 670
Ser Met Thr Lys Ile Leu Glu Pro Phe Arg Ala Gln Asn Pro Glu Ile
        675                 680                 685
Val Ile Tyr Gln Tyr Val Ala Ala Leu Tyr Val Gly Ser Asp Leu Glu
    690                 695                 700
Ile Glu Gln His Arg Thr Lys Ile Glu Glu Leu Arg Ala His Leu Leu
705                 710                 715                 720
Ser Trp Gly Phe Thr Thr Pro Asp Lys Lys His Gln Arg Glu Pro Pro
                725                 730                 735
Phe Leu Trp Met Gly Tyr Glu Leu His Pro Asp Arg Trp Thr Val Gln
            740                 745                 750
Pro Ile Glu Leu Pro Glu Lys Glu Ser Trp Thr Val Asn Asp Ile Gln
        755                 760                 765
```

-continued

```
Lys Leu Val Gly Lys Leu Asn Trp Ala Ser Gln Ile Tyr Pro Gly Ile
770                 775                 780

Lys Val Lys Gln Leu Cys Arg Leu Leu Arg Gly Ala Lys Ala Leu Thr
785                 790                 795                 800

Glu Val Ile Pro Leu Thr Lys Glu Ala Glu Leu Glu Leu Ala Glu Asn
                805                 810                 815

Arg Glu Ile Leu Arg Glu Pro Val His Gly Val Tyr Tyr Asp Pro Ser
                820                 825                 830

Lys Asp Leu Val Ala Glu Ile Gln Lys Gln Gly Gln Asp Gln Trp Thr
                835                 840                 845

Tyr Gln Ile Tyr Gln Glu Pro Tyr Lys Asn Leu Lys Thr Gly Lys Tyr
850                 855                 860

Ala Arg Lys Arg Ser Ala His Thr Asn Asp Val Arg Gln Leu Thr Glu
865                 870                 875                 880

Ala Val Gln Lys Ile Ala Leu Glu Ser Ile Val Ile Trp Gly Lys Ile
                885                 890                 895

Pro Lys Phe Arg Leu Pro Ile Gln Arg Glu Thr Trp Glu Thr Trp Trp
                900                 905                 910

Thr Glu Tyr Trp Gln Ala Thr Trp Ile Pro Asp Trp Glu Phe Val Asn
                915                 920                 925

Thr Pro Pro Leu Val Lys Leu Trp Tyr Gln Leu Glu Lys Glu Pro Ile
                930                 935                 940

Ala Gly Ala Glu Thr Phe Tyr Val Ala Gly Ala Ser Asn Arg Glu Thr
945                 950                 955                 960

Lys Ile Gly Lys Ala Gly Tyr Val Thr Asp Lys Gly Arg Gln Lys Val
                965                 970                 975

Val Ser Leu Thr Glu Thr Thr Asn Gln Lys Ala Ala Leu Gln Ala Ile
                980                 985                 990

Gln Leu Ala Leu Gln Asp Ser Gly  Pro Glu Val Asn Ile  Val Thr Ala
                995                 1000                1005

Ser Gln  Tyr Val Leu Gly Ile  Ile Gln Ala Gln Pro  Asp Arg Ser
    1010                1015                1020

Glu Ser  Glu Leu Val Asn Gln  Ile Ile Glu Glu Leu  Ile Lys Lys
    1025                1030                1035

Glu Lys  Val Tyr Leu Ser Trp  Val Pro Ala His Lys  Gly Ile Gly
    1040                1045                1050

Gly Asn  Glu Gln Val Asp Lys  Leu Val Ser Ala Gly  Ile Arg Lys
    1055                1060                1065

Ile Leu  Phe Leu Asp Gly Ile  Asp Lys Ala Gln Glu  Glu His Glu
    1070                1075                1080

Arg Tyr  His Ser Asn Trp Arg  Thr Met Ala Ser Asp  Phe Asn Leu
    1085                1090                1095

Pro Pro  Ile Val Ala Lys Glu  Ile Val Ala Asn Cys  Asp Lys Cys
    1100                1105                1110

Gln Leu  Lys Gly Glu Ala Met  His Gly Gln Val Asp  Cys Ser Pro
    1115                1120                1125

Gly Met  Trp Gln Leu Ala Cys  Thr His Leu Glu Gly  Lys Ile Ile
    1130                1135                1140

Ile Val  Ala Val His Val Ala  Ser Gly Tyr Met Glu  Ala Glu Val
    1145                1150                1155

Ile Pro  Ala Glu Thr Gly Gln  Glu Thr Ala Tyr Tyr  Ile Leu Lys
    1160                1165                1170
```

```
Leu Ala Gly Arg Trp Pro Val Lys Val Val His Thr Ala Asn Gly
    1175                1180                1185

Ser Asn Phe Thr Ser Thr Thr Val Lys Ala Ala Cys Trp Trp Ala
    1190                1195                1200

Asn Val Thr Gln Glu Phe Gly Ile Pro Tyr Asn Pro Gln Ser Gln
    1205                1210                1215

Gly Val Ile Ala Ser Met Asn Lys Glu Leu Lys Lys Ile Ile Gly
    1220                1225                1230

Gln Val Arg Glu Gln Ala Glu His Leu Lys Thr Ala Val Gln Met
    1235                1240                1245

Ala Val Leu Ile His Asn Phe Lys Arg Arg Gly Gly Ile Gly Gly
    1250                1255                1260

Tyr Ser Ala Gly Glu Arg Ile Val Asp Ile Ile Ala Thr Asp Ile
    1265                1270                1275

Gln Thr Arg Glu Leu Gln Lys Gln Ile Ile Lys Ile Gln Asn Phe
    1280                1285                1290

Arg Val Tyr Phe Arg Asp Ser Arg Asp Pro Val Trp Lys Gly Pro
    1295                1300                1305

Ala Lys Leu Leu Trp Lys Gly Glu Gly Ala Val Val Ile Gln Asp
    1310                1315                1320

Asn Ser Glu Ile Lys Val Val Pro Arg Arg Lys Val Lys Ile Ile
    1325                1330                1335

Arg Asp Tyr Gly Lys Gln Met Ala Gly Asp Asp Cys Val Ala Gly
    1340                1345                1350

Arg Gln Asp Glu Asp Gln
    1355

<210> SEQ ID NO 24
<211> LENGTH: 1497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
                100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160
```

```
Glu Lys Ala Phe Ser Pro Glu Val Ile Pro Met Phe Ser Ala Leu Ser
            165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
            370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
            485                 490                 495

Pro Ser Ser Gln Arg Glu Asn Leu Ala Phe Gln Gln Gly Glu Ala Arg
            500                 505                 510

Glu Phe Pro Ser Glu Gln Thr Arg Ala Asn Ser Pro Thr Ser Arg Glu
            515                 520                 525

Leu Gln Val Arg Gly Asp Asn Pro His Ser Glu Ala Gly Ala Glu Arg
            530                 535                 540

Gln Gly Thr Leu Asn Phe Pro Gln Ile Thr Leu Trp Gln Arg Pro Leu
545                 550                 555                 560

Val Ser Ile Lys Val Gly Gly Gln Ile Arg Glu Ala Leu Leu Ala Thr
            565                 570                 575
```

```
Gly Ala Asp Asp Thr Val Leu Glu Asp Ile Asn Leu Pro Gly Lys Trp
                580                 585                 590

Lys Pro Lys Met Ile Gly Ile Gly Gly Phe Ile Lys Val Gly Gln
            595                 600                 605

Tyr Asp Gln Ile Leu Ile Glu Ile Cys Gly Lys Lys Ala Ile Gly Thr
        610                 615                 620

Val Leu Val Gly Pro Thr Pro Val Asn Ile Ile Gly Arg Asn Met Leu
625                 630                 635                 640

Thr Gln Leu Gly Cys Thr Leu Asn Phe Pro Ile Ser Pro Ile Glu Thr
                645                 650                 655

Val Pro Val Lys Leu Lys Pro Gly Met Asp Gly Pro Arg Val Lys Gln
            660                 665                 670

Trp Pro Leu Thr Glu Glu Lys Ile Lys Ala Leu Thr Ala Ile Cys Glu
        675                 680                 685

Glu Met Glu Lys Glu Gly Lys Ile Thr Lys Ile Gly Pro Glu Asn Pro
    690                 695                 700

Tyr Asn Thr Pro Val Phe Ala Ile Lys Lys Lys Asp Ser Thr Lys Trp
705                 710                 715                 720

Arg Lys Leu Val Asp Phe Arg Glu Leu Asn Lys Arg Thr Gln Asp Phe
                725                 730                 735

Trp Glu Val Gln Leu Gly Ile Pro His Pro Ala Gly Leu Lys Lys Lys
            740                 745                 750

Lys Ser Val Thr Val Leu Asp Val Gly Asp Ala Tyr Phe Ser Val Pro
        755                 760                 765

Leu Asp Glu Gly Phe Arg Lys Tyr Thr Ala Phe Thr Ile Pro Ser Thr
770                 775                 780

Asn Asn Glu Thr Pro Gly Ile Arg Tyr Gln Tyr Asn Val Leu Pro Gln
785                 790                 795                 800

Gly Trp Lys Gly Ser Pro Ala Ile Phe Gln Cys Ser Met Thr Arg Ile
                805                 810                 815

Leu Glu Pro Phe Arg Ala Lys Asn Pro Glu Ile Val Ile Tyr Gln Tyr
            820                 825                 830

Met Asp His Leu Tyr Val Gly Ser Asp Leu Glu Ile Gly Gln His Arg
        835                 840                 845

Ala Lys Ile Glu Glu Leu Arg Glu His Leu Leu Lys Trp Gly Phe Thr
850                 855                 860

Thr Pro Asp Lys Lys His Gln Lys Glu Pro Pro Phe Leu Trp Met Gly
865                 870                 875                 880

Tyr Glu Leu His Pro Asp Lys Trp Thr Val Gln Pro Ile Gln Leu Pro
                885                 890                 895

Glu Lys Asp Ser Trp Thr Val Asn Asp Ile Gln Lys Leu Val Gly Lys
            900                 905                 910

Leu Asn Trp Ala Ser Gln Ile Tyr Pro Gly Ile Lys Val Arg Gln Leu
        915                 920                 925

Cys Lys Leu Leu Arg Gly Ala Lys Ala Leu Thr Asp Ile Val Pro Leu
930                 935                 940

Thr Glu Glu Ala Glu Leu Glu Leu Ala Glu Asn Arg Glu Ile Leu Lys
945                 950                 955                 960

Glu Pro Val His Gly Val Tyr Tyr Asp Pro Ser Lys Asp Leu Ile Ala
                965                 970                 975

Glu Ile Gln Lys Gln Gly His Asp Gln Trp Thr Tyr Gln Ile Tyr Gln
            980                 985                 990

Glu Pro Phe Lys Asn Leu Lys Thr  Gly Lys Tyr Ala Lys  Met Arg Thr
```

```
                995              1000              1005
Ala His Thr Asn Asp Val Lys Gln Leu Thr Glu Ala Val Gln Lys
   1010             1015             1020

Ile Ala Met Glu Ser Ile Val Ile Trp Gly Lys Thr Pro Lys Phe
   1025             1030             1035

Arg Leu Pro Ile Gln Lys Glu Thr Trp Glu Thr Trp Trp Thr Asp
   1040             1045             1050

Tyr Trp Gln Ala Thr Trp Ile Pro Glu Trp Glu Phe Val Asn Thr
   1055             1060             1065

Pro Pro Leu Val Lys Leu Trp Tyr Gln Leu Glu Lys Asp Pro Ile
   1070             1075             1080

Ala Gly Val Glu Thr Phe Tyr Val Asp Gly Ala Ala Asn Arg Glu
   1085             1090             1095

Thr Lys Leu Gly Lys Ala Gly Tyr Val Thr Asp Arg Gly Arg Gln
   1100             1105             1110

Lys Ile Val Ser Leu Thr Glu Thr Thr Asn Gln Lys Thr Glu Leu
   1115             1120             1125

Gln Ala Ile Tyr Leu Ala Leu Gln Asp Ser Gly Ser Glu Val Asn
   1130             1135             1140

Ile Val Thr Asp Ser Gln Tyr Ala Leu Gly Ile Ile Gln Ala Gln
   1145             1150             1155

Pro Asp Lys Ser Glu Ser Glu Leu Val Asn Gln Ile Ile Glu Gln
   1160             1165             1170

Leu Ile Lys Lys Glu Arg Val Tyr Leu Ser Trp Val Pro Ala His
   1175             1180             1185

Lys Gly Ile Gly Gly Asn Glu Gln Val Asp Lys Leu Val Ser Ser
   1190             1195             1200

Gly Ile Arg Lys Val Leu Phe Leu Asp Gly Ile Asp Lys Ala Gln
   1205             1210             1215

Glu Glu His Glu Lys Tyr His Ser Asn Trp Arg Ala Met Ala Ser
   1220             1225             1230

Asp Phe Asn Leu Pro Pro Val Val Ala Lys Glu Ile Val Ala Ser
   1235             1240             1245

Cys Asp Gln Cys Gln Leu Lys Gly Glu Ala Met His Gly Gln Val
   1250             1255             1260

Asp Cys Ser Pro Gly Ile Trp Gln Leu Ala Cys Thr His Leu Glu
   1265             1270             1275

Gly Lys Ile Ile Leu Val Ala Val His Val Ala Ser Gly Tyr Ile
   1280             1285             1290

Glu Ala Glu Val Ile Pro Ala Glu Thr Gly Gln Glu Thr Ala Tyr
   1295             1300             1305

Phe Ile Leu Lys Leu Ala Gly Arg Trp Pro Val Lys Val Ile His
   1310             1315             1320

Thr Asp Asn Gly Ser Asn Phe Thr Ser Ala Ala Val Lys Ala Ala
   1325             1330             1335

Cys Trp Trp Ala Gly Ile Gln Gln Glu Phe Gly Ile Pro Tyr Asn
   1340             1345             1350

Pro Gln Ser Gln Gly Val Val Glu Ser Met Asn Lys Glu Leu Lys
   1355             1360             1365

Lys Ile Ile Gly Gln Val Arg Asp Gln Ala Glu His Leu Lys Thr
   1370             1375             1380

Ala Val Gln Met Ala Val Phe Ile His Asn Phe Lys Arg Lys Gly
   1385             1390             1395
```

```
Gly Ile Gly Gly Tyr Ser Ala Gly Glu Arg Ile Asp Ile Ile
            1400                1405                1410

Ala Thr Asp Ile Gln Thr Lys Glu Leu Gln Lys Gln Ile Ile Lys
        1415                1420                1425

Ile Gln Asn Phe Arg Val Tyr Tyr Arg Asp Ser Arg Asp Pro Ile
    1430                1435                1440

Trp Lys Gly Pro Ala Lys Leu Leu Trp Lys Gly Glu Gly Ala Val
1445                1450                1455

Val Ile Gln Asp Asn Ser Asp Ile Lys Val Val Pro Arg Arg Lys
    1460                1465                1470

Val Lys Ile Ile Lys Asp Tyr Gly Lys Gln Met Ala Gly Ala Asp
    1475                1480                1485

Cys Val Ala Gly Arg Gln Asp Glu Asp
    1490                1495

<210> SEQ ID NO 25
<211> LENGTH: 1492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
```

```
             245                 250                 255
Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
            290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                    325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
                355                 360                 365

Ser Thr Ile Leu Met Gln Arg Ser Asn Phe Lys Gly Ser Lys Arg Ile
            370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                    405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
                435                 440                 445

Glu Pro Thr Ala Pro Pro Ala Glu Ser Phe Arg Phe Glu Glu Thr Thr
            450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Arg Glu Asn Leu Ala
                    485                 490                 495

Phe Pro Gln Gly Lys Ala Arg Glu Phe Ser Ser Glu Gln Thr Arg Ala
                500                 505                 510

Asn Ser Pro Thr Arg Arg Glu Leu Gln Val Trp Gly Arg Asp Asn Asn
            515                 520                 525

Ser Leu Ser Glu Ala Gly Ala Asp Arg Gln Gly Thr Val Ser Phe Ser
530                 535                 540

Phe Pro Gln Ile Thr Leu Trp Gln Arg Pro Leu Val Thr Ile Lys Ile
545                 550                 555                 560

Gly Gly Gln Leu Lys Glu Ala Leu Leu Ala Thr Gly Ala Asp Asp Thr
                    565                 570                 575

Val Leu Glu Glu Met Asn Leu Pro Gly Arg Trp Lys Pro Lys Met Ile
                580                 585                 590

Gly Gly Ile Gly Gly Phe Ile Lys Val Gly Gln Tyr Asp Gln Ile Pro
            595                 600                 605

Ile Glu Ile Cys Gly His Lys Ala Ile Gly Thr Val Leu Val Gly Pro
            610                 615                 620

Thr Pro Val Asn Ile Ile Gly Arg Asn Leu Leu Thr Gln Ile Gly Cys
625                 630                 635                 640

Thr Leu Asn Phe Pro Ile Ser Pro Ile Glu Thr Val Pro Val Lys Leu
                    645                 650                 655

Lys Pro Gly Met Asp Gly Pro Lys Val Lys Gln Trp Pro Leu Thr Glu
                660                 665                 670
```

-continued

```
Glu Lys Ile Lys Ala Leu Val Glu Ile Cys Thr Glu Met Glu Lys Glu
            675                 680                 685

Gly Lys Ile Ser Lys Ile Gly Pro Glu Asn Pro Tyr Asn Thr Pro Ile
        690                 695                 700

Phe Ala Ile Lys Lys Lys Asp Ser Thr Lys Trp Arg Lys Leu Val Asp
705                 710                 715                 720

Phe Arg Glu Leu Asn Lys Arg Thr Gln Asp Phe Trp Glu Val Gln Leu
                725                 730                 735

Gly Ile Pro His Pro Ala Gly Leu Lys Lys Lys Ser Val Thr Val
            740                 745                 750

Leu Asp Val Gly Asp Ala Tyr Phe Ser Val Pro Leu Asp Glu Asp Phe
            755                 760                 765

Arg Lys Tyr Thr Ala Phe Thr Ile Pro Ser Ile Asn Asn Glu Thr Pro
770                 775                 780

Gly Ile Arg Tyr Gln Tyr Asn Val Leu Pro Gln Gly Trp Lys Gly Ser
785                 790                 795                 800

Pro Ala Ile Phe Gln Ser Ser Met Thr Lys Ile Leu Glu Pro Phe Arg
                805                 810                 815

Lys Gln Asn Pro Asp Ile Val Ile Tyr Gln Tyr Met Asp His Leu Tyr
            820                 825                 830

Val Gly Ser Asp Leu Glu Ile Gly Gln His Arg Thr Lys Ile Glu Glu
            835                 840                 845

Leu Arg Gln His Leu Leu Arg Trp Gly Phe Thr Thr Pro Asp Lys Lys
            850                 855                 860

His Gln Lys Glu Pro Pro Phe Leu Trp Met Gly Tyr Glu Leu His Pro
865                 870                 875                 880

Asp Lys Trp Thr Val Gln Pro Ile Val Leu Pro Glu Lys Asp Ser Trp
                885                 890                 895

Thr Val Asn Asp Ile Gln Lys Leu Val Gly Lys Leu Asn Trp Ala Ser
            900                 905                 910

Gln Ile Tyr Ala Gly Ile Lys Val Lys Gln Leu Cys Lys Leu Leu Arg
            915                 920                 925

Gly Thr Lys Ala Leu Thr Glu Val Val Pro Leu Thr Glu Glu Ala Glu
        930                 935                 940

Leu Glu Leu Ala Glu Asn Arg Glu Ile Leu Lys Glu Pro Val His Gly
945                 950                 955                 960

Val Tyr Tyr Asp Pro Ser Lys Asp Leu Ile Ala Glu Ile Gln Lys Gln
                965                 970                 975

Gly Gln Gly Gln Trp Thr Tyr Gln Ile Tyr Gln Glu Pro Phe Lys Asn
            980                 985                 990

Leu Lys Thr Gly Lys Tyr Ala Arg Met Arg Gly Ala His Thr Asn Asp
        995                 1000                1005

Val Lys Gln Leu Thr Glu Ala Val Gln Lys Ile Ala Thr Glu Ser
        1010                1015                1020

Ile Val Ile Trp Gly Lys Thr Pro Lys Phe Lys Leu Pro Ile Gln
        1025                1030                1035

Lys Glu Thr Trp Glu Ala Trp Trp Thr Glu Tyr Trp Gln Ala Thr
        1040                1045                1050

Trp Ile Pro Glu Trp Glu Phe Val Asn Thr Pro Leu Val Lys
        1055                1060                1065

Leu Trp Tyr Gln Leu Glu Lys Glu Pro Ile Val Gly Ala Glu Thr
        1070                1075                1080
```

```
Phe Tyr Val Asp Gly Ala Ala Asn Arg Glu Thr Lys Leu Gly Lys
    1085                1090                1095

Ala Gly Tyr Val Thr Asp Arg Gly Arg Gln Lys Val Val Ser Leu
    1100                1105                1110

Thr Asp Thr Thr Asn Gln Lys Thr Glu Leu Gln Ala Ile His Leu
    1115                1120                1125

Ala Leu Gln Asp Ser Gly Leu Glu Val Asn Ile Val Thr Asp Ser
    1130                1135                1140

Gln Tyr Ala Leu Gly Ile Ile Gln Ala Gln Pro Asp Lys Ser Glu
    1145                1150                1155

Ser Glu Leu Val Ser Gln Ile Ile Glu Gln Leu Ile Lys Lys Glu
    1160                1165                1170

Lys Val Tyr Leu Ala Trp Val Pro Ala His Lys Gly Ile Gly Gly
    1175                1180                1185

Asn Glu Gln Val Asp Lys Leu Val Ser Arg Gly Ile Arg Lys Val
    1190                1195                1200

Leu Phe Leu Asp Gly Ile Asp Lys Ala Gln Glu Glu His Glu Lys
    1205                1210                1215

Tyr His Ser Asn Trp Arg Ala Met Ala Ser Glu Phe Asn Leu Pro
    1220                1225                1230

Pro Ile Val Ala Lys Glu Ile Val Ala Ser Cys Asp Lys Cys Gln
    1235                1240                1245

Leu Lys Gly Glu Ala Ile His Gly Gln Val Asp Cys Ser Pro Gly
    1250                1255                1260

Ile Trp Gln Leu Ala Cys Thr His Leu Glu Gly Lys Val Ile Leu
    1265                1270                1275

Val Ala Val His Val Ala Ser Gly Tyr Ile Glu Ala Glu Val Ile
    1280                1285                1290

Pro Ala Glu Thr Gly Gln Glu Thr Ala Tyr Phe Leu Leu Lys Leu
    1295                1300                1305

Ala Gly Arg Trp Pro Val Lys Thr Ile His Thr Asp Asn Gly Ser
    1310                1315                1320

Asn Phe Thr Ser Ala Thr Val Lys Ala Ala Cys Trp Trp Ala Gly
    1325                1330                1335

Ile Lys Gln Glu Phe Gly Ile Pro Tyr Asn Pro Gln Ser Gln Gly
    1340                1345                1350

Val Val Glu Ser Ile Asn Lys Glu Leu Lys Lys Ile Ile Gly Gln
    1355                1360                1365

Val Arg Asp Gln Ala Glu His Leu Lys Thr Ala Val Gln Met Ala
    1370                1375                1380

Val Phe Ile His Asn Phe Lys Arg Lys Gly Gly Ile Gly Glu Tyr
    1385                1390                1395

Ser Ala Gly Glu Arg Ile Val Asp Ile Ile Ala Ser Asp Ile Gln
    1400                1405                1410

Thr Lys Glu Leu Gln Lys Gln Ile Thr Lys Ile Gln Asn Phe Arg
    1415                1420                1425

Val Tyr Tyr Arg Asp Ser Arg Asp Pro Leu Trp Lys Gly Pro Ala
    1430                1435                1440

Lys Leu Leu Trp Lys Gly Glu Gly Ala Val Val Ile Gln Asp Asn
    1445                1450                1455

Ser Asp Ile Lys Val Val Pro Arg Arg Lys Ala Lys Ile Ile Arg
    1460                1465                1470

Asp Tyr Gly Lys Gln Met Ala Gly Asp Asp Cys Val Ala Ser Arg
```

```
                    1475                1480                1485

Gln Asp  Glu Asp
    1490

<210> SEQ ID NO 26
<211> LENGTH: 1350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335
```

```
Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
        370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
        515                 520                 525

Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
        595                 600                 605

Thr Val Leu Asp Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Asp His
        675                 680                 685

Leu Tyr Val Gly Ser Asp Leu Glu Ile Gly Gln His Arg Ala Lys Ile
    690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
```

```
                755                 760                 765
Ala Ser Gln Ile Tyr Pro Gly Ile Lys Val Arg Gln Leu Cys Lys Leu
770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Pro Leu Val Lys Leu Trp
        915                 920                 925

Tyr Gln Leu Glu Lys Asp Pro Ile Ala Gly Val Glu Thr Phe Tyr Val
930                 935                 940

Asp Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Glu Leu Gln Ala Ile Tyr Leu Ala Leu Gln Asp Ser Gly
            980                 985                 990

Ser Glu Val Asn Ile Val Thr Asp  Ser Gln Tyr Ala Leu  Gly Ile Ile
        995                 1000                1005

Gln Ala  Gln Pro Asp Lys Ser  Glu Ser Glu Leu Val  Asn Gln Ile
1010                1015                1020

Ile Glu  Gln Leu Ile Lys Lys  Glu Arg Val Tyr Leu  Ser Trp Val
1025                1030                1035

Pro Ala  His Lys Gly Ile Gly  Gly Asn Glu Gln Val  Asp Lys Leu
1040                1045                1050

Val Ser  Ser Gly Ile Arg Lys  Val Leu Phe Leu Asp  Gly Ile Asp
1055                1060                1065

Lys Ala  Gln Glu Glu His Glu  Lys Tyr His Ser Asn  Trp Arg Ala
1070                1075                1080

Met Ala  Ser Asp Phe Asn Leu  Pro Pro Val Val Ala  Lys Glu Ile
1085                1090                1095

Val Ala  Ser Cys Asp Gln Cys  Gln Leu Lys Gly Glu  Ala Met His
1100                1105                1110

Gly Gln  Val Asp Cys Ser Pro  Gly Ile Trp Gln Leu  Ala Cys Thr
1115                1120                1125

His Leu  Glu Gly Lys Ile Ile  Leu Val Ala Val His  Val Ala Ser
1130                1135                1140

Gly Tyr  Ile Glu Ala Glu Val  Ile Pro Ala Glu Thr  Gly Gln Glu
1145                1150                1155

Thr Ala  Tyr Phe Ile Leu Lys  Leu Ala Gly Arg Trp  Pro Val Lys
1160                1165                1170
```

Val Ile His Thr Asp Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Glu Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 27
<211> LENGTH: 1341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala

```
                165                 170                 175
Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
            195                 200                 205

Trp Asp Arg Leu His Pro Val His Ala Gly Pro Val Ala Pro Gly Gln
            210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
                260                 265                 270

Met Tyr Ser Pro Thr Ser Ile Leu Asp Ile Lys Gln Gly Pro Lys Glu
                275                 280                 285

Pro Phe Arg Asp Tyr Val Asp Arg Phe Phe Lys Thr Leu Arg Ala Glu
            290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
            515                 520                 525

Glu Ile Cys Thr Glu Met Glu Lys Glu Gly Lys Ile Ser Lys Ile Gly
    530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
            580                 585                 590
```

```
Leu Lys Lys Lys Lys Ser Val Thr Val Leu Asp Val Gly Asp Ala Tyr
            595                 600                 605
Phe Ser Val Pro Leu Asp Glu Asp Phe Arg Lys Tyr Thr Ala Phe Thr
610                 615                 620
Ile Pro Ser Ile Asn Asn Glu Thr Pro Gly Ile Arg Tyr Gln Tyr Asn
625                 630                 635                 640
Val Leu Pro Gln Gly Trp Lys Gly Ser Pro Ala Ile Phe Gln Ser Ser
                645                 650                 655
Met Thr Lys Ile Leu Glu Pro Phe Arg Lys Gln Asn Pro Asp Ile Val
                660                 665                 670
Ile Tyr Gln Tyr Met Asp His Leu Tyr Val Gly Ser Asp Leu Glu Ile
                675                 680                 685
Gly Gln His Arg Thr Lys Ile Glu Glu Leu Arg Gln His Leu Leu Arg
            690                 695                 700
Trp Gly Phe Thr Thr Pro Asp Lys Lys His Gln Lys Glu Pro Pro Phe
705                 710                 715                 720
Leu Trp Met Gly Tyr Glu Leu His Pro Asp Lys Trp Thr Val Gln Pro
                725                 730                 735
Ile Val Leu Pro Glu Lys Asp Ser Trp Thr Val Asn Asp Ile Gln Lys
                740                 745                 750
Leu Val Gly Lys Leu Asn Trp Ala Ser Gln Ile Tyr Ala Gly Ile Lys
                755                 760                 765
Val Lys Gln Leu Cys Lys Leu Leu Arg Gly Thr Lys Ala Leu Thr Glu
            770                 775                 780
Val Val Pro Leu Thr Glu Glu Ala Glu Leu Glu Leu Ala Glu Asn Arg
785                 790                 795                 800
Glu Ile Leu Lys Glu Pro Val His Gly Val Tyr Tyr Asp Pro Ser Lys
                805                 810                 815
Asp Leu Ile Ala Glu Ile Gln Lys Gln Gly Gln Gly Gln Trp Thr Tyr
                820                 825                 830
Gln Ile Tyr Gln Glu Pro Phe Lys Asn Leu Lys Thr Gly Lys Tyr Ala
            835                 840                 845
Arg Met Arg Gly Ala His Thr Asn Asp Val Lys Gln Leu Thr Glu Ala
        850                 855                 860
Val Gln Lys Ile Ala Thr Glu Ser Ile Val Ile Trp Gly Lys Thr Pro
865                 870                 875                 880
Lys Phe Lys Leu Pro Ile Gln Lys Glu Thr Trp Glu Ala Trp Trp Thr
                885                 890                 895
Glu Tyr Trp Gln Ala Thr Trp Ile Pro Glu Trp Glu Phe Val Asn Thr
                900                 905                 910
Pro Pro Leu Val Lys Leu Trp Tyr Gln Leu Glu Lys Glu Pro Ile Val
            915                 920                 925
Gly Ala Glu Thr Phe Tyr Val Asp Gly Ala Ala Asn Arg Glu Thr Lys
        930                 935                 940
Leu Gly Lys Ala Gly Tyr Val Thr Asp Arg Gly Arg Gln Lys Val Val
945                 950                 955                 960
Ser Leu Thr Asp Thr Thr Asn Gln Lys Thr Glu Leu Gln Ala Ile His
                965                 970                 975
Leu Ala Leu Gln Asp Ser Gly Leu Glu Val Asn Ile Val Thr Asp Ser
            980                 985                 990
Gln Tyr Ala Leu Gly Ile Ile Gln  Ala Gln Pro Asp Lys  Ser Glu Ser
            995                 1000                1005
```

```
Glu Leu Val Ser Gln Ile Ile Glu Gln Leu Ile Lys Lys Glu Lys
1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Asp Asn Gly Ser Asn
1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
1190                1195                1200

Val Glu Ser Ile Asn Lys Glu Leu Lys Lys Ile Ile Gly Gln Val
    1205                1210                1215

Arg Asp Gln Ala Glu His Leu Lys Thr Ala Val Gln Met Ala Val
1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
1310                1315                1320

Tyr Gly Lys Gln Met Ala Gly Asp Asp Cys Val Ala Ser Arg Gln
    1325                1330                1335

Asp Glu Asp
1340

<210> SEQ ID NO 28
<211> LENGTH: 1556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

-continued

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
                100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415
```

```
Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
            450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
            485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
            515                 520                 525

Thr Glu Glu Lys Ile Lys Ala Leu Thr Ala Ile Cys Glu Glu Met Glu
            530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
            565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
            595                 600                 605

Thr Val Leu Ala Val Gly Asp Ala Tyr Phe Ser Val Pro Leu Asp Glu
            610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
            645                 650                 655

Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Ala Ala
            675                 680                 685

Leu Tyr Val Gly Ser Asp Leu Glu Ile Gly Gln His Arg Ala Lys Ile
            690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
            725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
            755                 760                 765

Ala Ser Gln Ile Tyr Pro Gly Ile Lys Val Arg Gln Leu Cys Lys Leu
            770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
            805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
```

-continued

```
            835                 840                 845
Lys Asn Leu Lys Thr Gly Lys Tyr Ala Lys Met Arg Thr Ala His Thr
    850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
                900                 905                 910

Ile Pro Glu Trp Glu Phe Val Asn Thr Pro Pro Leu Val Lys Leu Trp
                915                 920                 925

Tyr Gln Leu Glu Lys Asp Pro Ile Ala Gly Val Glu Thr Phe Tyr Val
    930                 935                 940

Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
            995                 1000                1005

Gln Ala Gln Pro Asp Lys Ser Glu Ser Glu Leu Val Asn Gln Ile
    1010                1015                1020

Ile Glu Gln Leu Ile Lys Lys Glu Arg Val Tyr Leu Ser Trp Val
    1025                1030                1035

Pro Ala His Lys Gly Ile Gly Gly Asn Glu Gln Val Asp Lys Leu
    1040                1045                1050

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
    1070                1075                1080

Met Ala Ser Asp Phe Asn Leu Pro Pro Val Val Ala Lys Glu Ile
    1085                1090                1095

Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Ala Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Ala Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245
```

```
Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp Met Ala Gly
    1340                1345                1350

Lys Trp Ser Lys Ser Ser Val Val Gly Trp Pro Ala Ile Arg Glu
    1355                1360                1365

Arg Met Arg Arg Ala Glu Pro Ala Ala Asp Gly Val Gly Ala Val
    1370                1375                1380

Ser Arg Asp Leu Glu Lys His Gly Ala Ile Thr Ser Ser Asn Thr
    1385                1390                1395

Ala Ala Asn Asn Ala Asp Cys Ala Trp Leu Glu Ala Gln Glu Glu
    1400                1405                1410

Glu Glu Val Gly Phe Pro Val Arg Pro Gln Val Pro Leu Arg Pro
    1415                1420                1425

Met Thr Tyr Lys Gly Ala Leu Asp Leu Ser His Phe Leu Lys Glu
    1430                1435                1440

Lys Gly Gly Leu Glu Gly Leu Ile Tyr Ser Gln Lys Arg Gln Asp
    1445                1450                1455

Ile Leu Asp Leu Trp Val Tyr His Thr Gln Gly Tyr Phe Pro Asp
    1460                1465                1470

Trp Gln Asn Tyr Thr Pro Gly Pro Gly Ile Arg Tyr Pro Leu Thr
    1475                1480                1485

Phe Gly Trp Cys Phe Lys Leu Val Pro Val Glu Pro Glu Lys Ile
    1490                1495                1500

Glu Glu Ala Asn Glu Gly Glu Asn Asn Ser Leu Leu His Pro Met
    1505                1510                1515

Ser Gln His Gly Met Asp Asp Pro Glu Lys Glu Val Leu Met Trp
    1520                1525                1530

Lys Phe Asp Ser Arg Leu Ala Phe His His Met Ala Arg Glu Leu
    1535                1540                1545

His Pro Glu Tyr Tyr Lys Asp Cys
    1550                1555

<210> SEQ ID NO 29
<211> LENGTH: 1547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
```

```
                20                  25                  30
His Leu Val Trp Ala Ser Arg Glu Leu Glu Arg Phe Ala Leu Asn Pro
             35                  40                  45
Gly Leu Leu Glu Thr Ser Glu Gly Cys Lys Gln Ile Ile Lys Gln Leu
 50                  55                  60
Gln Pro Ala Leu Gln Thr Gly Thr Glu Glu Leu Arg Ser Leu Phe Asn
 65                  70                  75                  80
Thr Val Ala Thr Leu Tyr Cys Val His Ala Glu Ile Glu Val Arg Asp
             85                  90                  95
Thr Lys Glu Ala Leu Asp Lys Ile Glu Glu Glu Gln Asn Lys Ser Gln
            100                 105                 110
Gln Lys Thr Gln Gln Ala Lys Glu Ala Asp Gly Lys Val Ser Gln Asn
            115                 120                 125
Tyr Pro Ile Val Gln Asn Leu Gln Gly Gln Met Val His Gln Pro Ile
            130                 135                 140
Ser Pro Arg Thr Leu Asn Ala Trp Val Lys Val Ile Glu Glu Lys Ala
145                 150                 155                 160
Phe Ser Pro Glu Val Ile Pro Met Phe Thr Ala Leu Ser Glu Gly Ala
                165                 170                 175
Thr Pro Gln Asp Leu Asn Thr Met Leu Asn Thr Val Gly Gly His Gln
            180                 185                 190
Ala Ala Met Gln Met Leu Lys Asp Thr Ile Asn Glu Glu Ala Ala Glu
            195                 200                 205
Trp Asp Arg Leu His Pro Val His Ala Gly Pro Val Ala Pro Gly Gln
            210                 215                 220
Met Arg Glu Pro Arg Gly Ser Asp Ile Ala Gly Thr Thr Ser Asn Leu
225                 230                 235                 240
Gln Glu Gln Ile Ala Trp Met Thr Ser Asn Pro Pro Ile Pro Val Gly
                245                 250                 255
Asp Ile Tyr Lys Arg Trp Ile Ile Leu Gly Leu Asn Lys Ile Val Arg
            260                 265                 270
Met Tyr Ser Pro Thr Ser Ile Leu Asp Ile Lys Gln Gly Pro Lys Glu
            275                 280                 285
Pro Phe Arg Asp Tyr Val Asp Arg Phe Phe Lys Thr Leu Arg Ala Glu
            290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
            340                 345                 350
Pro Ser His Lys Ala Arg Val Leu Ala Glu Ala Met Ser Gln Thr Asn
            355                 360                 365
Ser Thr Ile Leu Met Gln Arg Ser Asn Phe Lys Gly Ser Lys Arg Ile
            370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                405                 410                 415
Gln Met Lys Asp Cys Thr Glu Arg Gln Ala Asn Phe Leu Gly Lys Ile
            420                 425                 430
Trp Pro Ser His Lys Gly Arg Pro Gly Asn Phe Leu Gln Ser Arg Pro
            435                 440                 445
```

```
Glu Pro Thr Ala Pro Ala Glu Ser Phe Arg Phe Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
        515                 520                 525

Glu Ile Cys Thr Glu Met Glu Lys Glu Gly Lys Ile Ser Lys Ile Gly
    530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
            580                 585                 590

Leu Lys Lys Lys Ser Val Thr Val Leu Ala Val Gly Asp Ala Tyr
    595                 600                 605

Phe Ser Val Pro Leu Asp Glu Asp Phe Arg Lys Tyr Thr Ala Phe Thr
610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
            660                 665                 670

Ile Tyr Gln Tyr Met Ala Ala Leu Tyr Val Gly Ser Asp Leu Glu Ile
        675                 680                 685

Gly Gln His Arg Thr Lys Ile Glu Glu Leu Arg Gln His Leu Leu Arg
    690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                725                 730                 735

Ile Val Leu Pro Glu Lys Asp Ser Trp Thr Val Asn Asp Ile Gln Lys
            740                 745                 750

Leu Val Gly Lys Leu Asn Trp Ala Ser Gln Ile Tyr Ala Gly Ile Lys
        755                 760                 765

Val Lys Gln Leu Cys Lys Leu Leu Arg Gly Thr Lys Ala Leu Thr Glu
770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
        835                 840                 845

Arg Met Arg Gly Ala His Thr Asn Asp Val Lys Gln Leu Thr Glu Ala
850                 855                 860
```

```
Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
        915                 920                 925

Gly Ala Glu Thr Phe Tyr Val Ala Gly Ala Ala Asn Arg Glu Thr Lys
930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
        995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
```

```
              1265                1270                1275
Tyr Tyr Arg Asp Ser Arg Asp Pro Leu Trp Lys Gly Pro Ala Lys
         1280                1285                1290

Leu Leu Trp Lys Gly Glu Gly Ala Val Val Ile Gln Asp Asn Ser
     1295                1300                1305

Asp Ile Lys Val Val Pro Arg Arg Lys Ala Lys Ile Ile Arg Asp
         1310                1315                1320

Tyr Gly Lys Gln Met Ala Gly Asp Asp Cys Val Ala Ser Arg Gln
         1325                1330                1335

Asp Glu Asp Met Ala Gly Lys Trp Ser Lys Ser Ser Ile Val Gly
         1340                1345                1350

Trp Pro Ala Val Arg Glu Arg Ile Arg Arg Ala Glu Pro Ala Ala
         1355                1360                1365

Glu Gly Val Gly Ala Ala Ser Gln Asp Leu Asp Lys Tyr Gly Ala
         1370                1375                1380

Leu Thr Ser Ser Asn Thr Ala Ala Thr Asn Ala Asp Cys Ala Trp
         1385                1390                1395

Leu Glu Ala Gln Glu Asp Glu Glu Val Gly Phe Pro Val Lys Pro
         1400                1405                1410

Gln Val Pro Leu Arg Pro Met Thr Tyr Lys Ala Ala Phe Asp Leu
         1415                1420                1425

Ser Phe Phe Leu Lys Glu Lys Gly Gly Leu Asp Gly Leu Ile Tyr
         1430                1435                1440

Ser Lys Lys Arg Gln Glu Ile Leu Asp Leu Trp Val Tyr Asn Thr
         1445                1450                1455

Gln Gly Phe Phe Pro Asp Trp Gln Asn Tyr Thr Pro Gly Pro Gly
         1460                1465                1470

Val Arg Tyr Pro Leu Thr Phe Gly Trp Cys Phe Lys Leu Val Pro
         1475                1480                1485

Val Asp Pro Arg Glu Val Glu Glu Ala Asn Lys Gly Glu Asn Asn
         1490                1495                1500

Cys Leu Leu His Pro Met Asn Leu His Gly Met Asp Asp Pro Glu
         1505                1510                1515

Arg Glu Val Leu Val Trp Arg Phe Asp Ser Arg Leu Ala Phe His
         1520                1525                1530

His Met Ala Arg Glu Lys His Pro Glu Tyr Tyr Lys Asn Cys
         1535                1540                1545

<210> SEQ ID NO 30
<211> LENGTH: 841
<212> TYPE: PRT
<213> ORGANISM: Human immunodeficiency virus
<220> FEATURE:
<221> NAME/KEY: MOD_RES
<222> LOCATION: (785)..(785)
<223> OTHER INFORMATION: Any amino acid

<400> SEQUENCE: 30

Met Arg Val Thr Gly Met Leu Arg Asn Cys Gln Pro Trp Trp Ile Trp
1               5                   10                  15

Gly Ile Leu Gly Phe Trp Met Leu Leu Ile Tyr Asn Val Gly Gly Asn
                20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ala Tyr Glu Lys Glu Val
        50                  55                  60
```

```
His Asn Val Trp Ala Thr His Ala Cys Val Pro Thr Asp Pro Asn Pro
 65                  70                  75                  80

Gln Glu Met Val Leu Glu Asn Val Thr Glu Tyr Phe Asn Met Trp Lys
                 85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Arg Asn Val Thr Thr Ser Asn Asn Ala Thr Ser Asn Asp Asn
130                 135                 140

Pro Asn Gly Glu Ile Lys Asn Cys Ser Phe Asn Ile Thr Thr Glu Leu
145                 150                 155                 160

Arg Asp Lys Arg Arg Asn Glu Tyr Ala Leu Phe Tyr Arg Leu Asp Ile
                165                 170                 175

Val Pro Leu Ser Gly Ser Lys Asn Ser Ser Asn Ser Ser Glu Tyr Arg
            180                 185                 190

Leu Ile Asn Cys Asn Thr Ser Ala Ile Thr Gln Ala Cys Pro Lys Val
        195                 200                 205

Ser Phe Asp Pro Ile Pro Ile His Tyr Cys Ala Pro Ala Gly Tyr Ala
210                 215                 220

Ile Leu Lys Cys Asn Asn Lys Thr Phe Asn Gly Thr Gly Pro Cys Asn
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Ala Glu Gly Glu Ile Ile Ile
            260                 265                 270

Arg Ser Glu Asn Leu Thr Asn Asn Ala Lys Thr Ile Ile Val His Leu
        275                 280                 285

Asn Glu Ser Ile Glu Ile Val Cys Ala Arg Pro Asn Asn Asn Thr Arg
290                 295                 300

Lys Ser Met Arg Ile Gly Pro Gly Gln Thr Phe Tyr Ala Thr Gly Asp
305                 310                 315                 320

Ile Ile Gly Asp Ile Arg Gln Ala His Cys Asn Ile Ser Gly Asn Trp
                325                 330                 335

Asn Ala Thr Leu Glu Lys Val Lys Gly Lys Leu Gln Glu His Phe Pro
            340                 345                 350

Gly Lys Asn Ile Ser Phe Glu Pro Ser Ser Gly Gly Asp Leu Glu Ile
        355                 360                 365

Thr Thr His Ser Phe Asn Cys Arg Gly Glu Phe Phe Tyr Cys Asp Thr
370                 375                 380

Ser Lys Leu Phe Asn Gly Thr Thr His Thr Ala Asn Ser Ser Ile Thr
385                 390                 395                 400

Ile Gln Cys Arg Ile Lys Gln Ile Ile Asn Met Trp Gln Gly Val Gly
                405                 410                 415

Arg Ala Ile Tyr Ala Pro Pro Ile Ala Gly Asn Ile Thr Cys Lys Ser
            420                 425                 430

Asn Ile Thr Gly Leu Leu Leu Thr Arg Asp Gly Gly Thr Leu Asn Asn
        435                 440                 445

Asp Thr Glu Lys Phe Arg Pro Gly Gly Gly Asp Met Arg Asp Asn Trp
450                 455                 460

Arg Ser Glu Leu Tyr Lys Tyr Lys Val Val Glu Ile Lys Pro Leu Gly
465                 470                 475                 480
```

```
Ile Ala Pro Thr Lys Ala Lys Arg Arg Val Glu Arg Glu Lys Arg
                485                 490                 495

Ala Val Gly Ile Gly Ala Val Phe Leu Gly Phe Leu Gly Ala Ala Gly
            500                 505                 510

Ser Thr Met Gly Ala Ala Ser Ile Thr Leu Thr Val Gln Ala Arg Gln
            515                 520                 525

Leu Leu Ser Gly Ile Val Gln Gln Gln Ser Asn Leu Leu Arg Ala Ile
    530                 535                 540

Glu Ala Gln Gln His Met Leu Gln Leu Thr Val Trp Gly Ile Lys Gln
545                 550                 555                 560

Leu Gln Thr Arg Val Leu Ala Ile Glu Arg Tyr Leu Lys Asp Gln Gln
                565                 570                 575

Leu Leu Gly Ile Trp Gly Cys Ser Gly Lys Ile Ile Cys Thr Thr Ala
            580                 585                 590

Val Pro Trp Asn Thr Ser Trp Ser Asn Lys Ser Leu Glu Asp Ile Trp
            595                 600                 605

Asp Asn Met Thr Trp Met Gln Trp Asp Arg Glu Ile Asn Asn Tyr Thr
    610                 615                 620

Ser Ile Ile Tyr Ser Leu Leu Glu Glu Ser Gln Asn Gln Gln Glu Lys
625                 630                 635                 640

Asn Glu Lys Asp Leu Leu Ala Leu Asp Ser Trp Asn Asn Leu Trp Asn
                645                 650                 655

Trp Phe Asn Ile Thr Lys Trp Leu Trp Tyr Ile Lys Ile Phe Ile Met
            660                 665                 670

Ile Val Gly Gly Leu Ile Gly Leu Arg Ile Ile Phe Ala Val Leu Ser
            675                 680                 685

Ile Val Asn Arg Val Arg Gln Gly Tyr Ser Pro Leu Ser Phe Gln Thr
    690                 695                 700

Leu Ile Pro Asn Pro Arg Gly Pro Asp Arg Leu Gly Arg Ile Glu Glu
705                 710                 715                 720

Glu Gly Gly Glu Gln Asp Arg Asp Arg Ser Ile Arg Leu Val Asn Gly
                725                 730                 735

Phe Leu Ala Ile Ala Trp Asp Asp Leu Arg Ser Leu Cys Leu Phe Ser
            740                 745                 750

Tyr Arg Arg Leu Arg Asp Phe Ile Leu Ile Val Ala Arg Ala Val Glu
            755                 760                 765

Leu Leu Ile Gln Arg Gly Trp Glu Thr Leu Lys Tyr Leu Gly Ser Leu
    770                 775                 780

Xaa Gln Tyr Trp Gly Leu Glu Leu Lys Lys Ser Ala Ile Ser Leu Leu
785                 790                 795                 800

Asp Thr Ile Ala Ile Thr Val Ala Glu Gly Thr Asp Arg Ile Ile Glu
                805                 810                 815

Leu Val Gln Arg Ile Cys Arg Ala Ile Ser Asn Ile Pro Arg Arg Ile
            820                 825                 830

Arg Gln Gly Phe Glu Ala Ala Leu Gln
            835                 840

<210> SEQ ID NO 31
<211> LENGTH: 491
<212> TYPE: PRT
<213> ORGANISM: Human immunodeficiency virus

<400> SEQUENCE: 31

Met Gly Ala Arg Ala Ser Ile Leu Arg Gly Gly Lys Leu Asp Lys Trp
1               5                   10                  15
```

```
Glu Lys Ile Arg Leu Arg Pro Gly Gly Lys His Tyr Met Leu Lys
            20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Leu Lys Gln Leu
50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Gln Asn Lys Gly Gln
            100                 105                 110

Gln Lys Thr Gln Gln Ala Lys Gly Ala Asp Gly Lys Val Ser Gln Asn
            115                 120                 125

Tyr Pro Ile Val Gln Asn Leu Gln Gly Gln Met Val His Gln Ala Ile
130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
            195                 200                 205

Trp Asp Arg Leu His Pro Val His Ala Gly Pro Ile Ala Pro Gly Gln
210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Asn Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Gly
            355                 360                 365

Ser Thr Ile Met Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430
```

```
Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
450                 455                 460

Pro Ala Pro Lys Gln Glu Leu Lys Asp Arg Glu Pro Leu Thr Ser Leu
465                 470                 475                 480

Lys Ser Leu Phe Gly Ser Asp Pro Leu Ser Gln
            485                 490

<210> SEQ ID NO 32
<211> LENGTH: 999
<212> TYPE: PRT
<213> ORGANISM: Human immunodeficiency virus

<400> SEQUENCE: 32

Phe Phe Arg Glu Asn Leu Ala Phe Gln Gln Gly Glu Ala Arg Glu Phe
1               5                   10                  15

Pro Ser Glu Gln Ala Arg Ala Asn Ser Pro Thr Ser Arg Glu Phe Gln
            20                  25                  30

Val Arg Gly Asp Asn Pro Cys Ser Glu Ala Gly Val Lys Gly Gln Gly
        35                  40                  45

Thr Leu Asn Phe Pro Gln Ile Thr Leu Trp Gln Arg Pro Leu Val Ser
    50                  55                  60

Ile Lys Val Gly Gly Gln Val Lys Glu Ala Leu Leu Asp Thr Gly Ala
65                  70                  75                  80

Asp Asp Thr Val Leu Glu Glu Ile Asn Leu Pro Gly Lys Trp Lys Pro
                85                  90                  95

Lys Met Ile Gly Gly Ile Gly Gly Phe Ile Lys Val Arg Gln Tyr Asp
            100                 105                 110

Gln Ile Leu Ile Glu Ile Cys Gly Lys Lys Ala Ile Gly Thr Val Leu
        115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
145                 150                 155                 160

Val Lys Leu Lys Pro Gly Met Asp Gly Pro Lys Ile Lys Gln Trp Pro
                165                 170                 175

Leu Thr Glu Glu Lys Ile Lys Ala Leu Met Ala Ile Cys Glu Glu Met
            180                 185                 190

Glu Lys Glu Gly Lys Ile Thr Lys Ile Gly Pro Glu Asn Pro Tyr Asn
        195                 200                 205

Thr Pro Ile Phe Ala Ile Lys Lys Lys Asp Ser Thr Lys Trp Arg Lys
    210                 215                 220

Leu Val Asp Phe Arg Glu Leu Asn Lys Arg Thr Gln Asp Phe Trp Glu
225                 230                 235                 240

Val Gln Leu Gly Ile Pro His Pro Ala Gly Leu Lys Lys Lys Lys Ser
                245                 250                 255

Val Thr Val Leu Asp Val Gly Asp Ala Tyr Phe Ser Val Pro Leu Asp
            260                 265                 270

Glu Ser Phe Arg Lys Tyr Thr Ala Phe Thr Ile Pro Ser Ile Asn Asn
        275                 280                 285

Glu Thr Pro Gly Ile Arg Tyr Gln Tyr Asn Val Leu Pro Gln Gly Trp
    290                 295                 300

Lys Gly Ser Pro Ala Ile Phe Gln Ser Ser Met Thr Lys Ile Leu Glu
305                 310                 315                 320
```

-continued

```
Pro Phe Arg Ala Lys Asn Pro Glu Ile Val Ile Tyr Gln Tyr Met Asp
            325                 330                 335

Asp Leu Tyr Val Gly Ser Asp Leu Glu Ile Gly Gln His Arg Ala Lys
        340                 345                 350

Ile Glu Glu Leu Arg Glu His Leu Leu Arg Trp Gly Phe Thr Thr Pro
    355                 360                 365

Asp Lys Lys His Gln Lys Glu Pro Pro Phe Leu Trp Met Gly Tyr Glu
370                 375                 380

Leu His Pro Asp Lys Trp Thr Val Gln Pro Ile Gln Leu Pro Glu Lys
385                 390                 395                 400

Asp Ser Trp Thr Val Asn Asp Ile Gln Lys Leu Val Gly Lys Leu Asn
                405                 410                 415

Trp Ala Ser Gln Ile Tyr Ser Gly Ile Lys Val Arg Gln Leu Cys Lys
            420                 425                 430

Leu Leu Arg Gly Ala Lys Ala Leu Thr Asp Ile Val Pro Leu Thr Glu
        435                 440                 445

Glu Ala Glu Leu Glu Leu Ala Glu Asn Arg Glu Ile Leu Lys Glu Pro
    450                 455                 460

Val His Gly Val Tyr Tyr Asp Pro Ser Lys Asp Leu Ile Ala Glu Ile
465                 470                 475                 480

Gln Lys Gln Gly Tyr Asp Gln Trp Thr Tyr Gln Ile Tyr Gln Glu Pro
                485                 490                 495

Phe Lys Asn Leu Lys Thr Gly Lys Tyr Ala Lys Met Arg Thr Ala His
            500                 505                 510

Thr Asn Asp Val Lys Gln Leu Thr Glu Ala Val Gln Lys Ile Ala Leu
        515                 520                 525

Glu Ser Ile Val Ile Trp Gly Lys Thr Pro Lys Phe Arg Leu Pro Ile
    530                 535                 540

Gln Lys Glu Thr Trp Glu Ile Trp Trp Thr Asp Tyr Trp Gln Ala Thr
545                 550                 555                 560

Trp Ile Pro Glu Trp Glu Phe Val Asn Thr Pro Pro Leu Val Lys Leu
                565                 570                 575

Trp Tyr Gln Leu Glu Lys Glu Pro Ile Ala Gly Ala Glu Thr Phe Tyr
            580                 585                 590

Val Asp Gly Ala Ala Asn Arg Glu Thr Lys Ile Gly Lys Ala Gly Tyr
        595                 600                 605

Val Thr Asp Lys Gly Arg Gln Lys Ile Val Thr Leu Thr Glu Thr Thr
    610                 615                 620

Asn Gln Lys Thr Glu Leu Gln Ala Ile Gln Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
            660                 665                 670

Ile Glu Gln Leu Ile Asn Lys Glu Arg Val Tyr Leu Ser Trp Val Pro
        675                 680                 685

Ala His Lys Gly Ile Gly Gly Asn Glu Gln Val Asp Lys Leu Val Ser
    690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Glu
                725                 730                 735
```

```
Phe Asn Leu Pro Pro Val Val Ala Lys Glu Ile Val Ala Ser Cys Asp
                740                 745                 750

Lys Cys Gln Leu Lys Gly Glu Ala Ile His Gly Gln Val Asp Cys Ser
            755                 760                 765

Pro Gly Ile Trp Gln Leu Asp Cys Thr His Leu Glu Gly Lys Val Ile
        770                 775                 780

Leu Val Ala Val His Val Ala Ser Gly Tyr Met Glu Ala Glu Val Ile
785                 790                 795                 800

Pro Ala Glu Thr Gly Gln Glu Thr Ala Tyr Tyr Ile Leu Lys Leu Ala
                805                 810                 815

Gly Arg Trp Pro Val Lys Val Ile His Thr Asp Asn Gly Ser Asn Phe
            820                 825                 830

Thr Ser Ala Ala Val Lys Ala Ala Cys Trp Trp Ala Gly Ile Gln Gln
        835                 840                 845

Glu Phe Gly Ile Pro Tyr Asn Pro Gln Ser Gln Gly Val Val Glu Ser
850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
            900                 905                 910

Asp Ile Ile Ala Thr Asp Ile Gln Thr Lys Glu Leu Gln Lys Gln Ile
        915                 920                 925

Ile Lys Ile Gln Asn Phe Arg Val Tyr Tyr Arg Asp Ser Arg Asp Pro
930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Val
                965                 970                 975

Lys Ile Ile Lys Asp Tyr Gly Lys Gln Met Ala Gly Ala Asp Cys Val
            980                 985                 990

Ala Gly Arg Gln Asp Glu Asp
        995

<210> SEQ ID NO 33
<211> LENGTH: 206
<212> TYPE: PRT
<213> ORGANISM: Human immunodeficiency virus

<400> SEQUENCE: 33

Met Gly Gly Lys Trp Ser Lys Ser Ser Ile Val Gly Trp Pro Asp Val
1               5                   10                  15

Arg Glu Arg Met Arg Arg Thr Glu Pro Ala Ala Glu Gly Val Gly Ala
                20                  25                  30

Ala Ser Gln Asp Leu Asp Lys Tyr Gly Ala Leu Thr Ser Ser Asn Thr
            35                  40                  45

Thr His Asn Asn Ala Asp Cys Ala Trp Leu Glu Ala Gln Glu Glu Gly
        50                  55                  60

Glu Val Gly Phe Pro Val Arg Pro Gln Val Pro Leu Arg Pro Met Thr
65                  70                  75                  80

Tyr Lys Gly Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110
```

```
Trp Val Tyr His Thr Gln Gly Phe Phe Pro Asp Trp Gln Asn Tyr Thr
            115                 120                 125

Pro Gly Pro Gly Val Arg Tyr Pro Leu Thr Phe Gly Trp Cys Phe Lys
        130                 135                 140

Leu Val Pro Val Asp Pro Arg Glu Val Glu Glu Ala Asn Lys Gly Glu
145                 150                 155                 160

Asn Asn Cys Leu Leu His Pro Met Ser Leu His Gly Met Glu Asp Glu
                165                 170                 175

Glu Arg Glu Val Leu Lys Trp Glu Phe Asp Ser Ser Leu Ala Arg Arg
                180                 185                 190

His Leu Ala Arg Glu Leu His Pro Glu Tyr Tyr Lys Asp Cys
                195                 200                 205

<210> SEQ ID NO 34
<211> LENGTH: 665
<212> TYPE: PRT
<213> ORGANISM: Human immunodeficiency virus

<400> SEQUENCE: 34

Met Arg Val Thr Gly Met Leu Arg Asn Cys Gln Pro Trp Trp Ile Trp
1               5                   10                  15

Gly Ile Leu Gly Phe Trp Met Leu Leu Ile Tyr Asn Val Gly Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Tyr Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Arg Asn Val Thr Thr Ser Asn Asn Ala Thr Ser Asn Asp Asn
    130                 135                 140

Pro Asn Gly Glu Ile Lys Asn Cys Ser Phe Asn Ile Thr Thr Glu Leu
145                 150                 155                 160

Arg Asp Lys Arg Arg Asn Glu Tyr Ala Leu Phe Tyr Arg Leu Asp Ile
                165                 170                 175

Val Pro Leu Ser Gly Ser Lys Asn Ser Ser Asn Ser Ser Glu Tyr Arg
            180                 185                 190

Leu Ile Asn Cys Asn Thr Ser Ala Ile Thr Gln Ala Cys Pro Lys Val
        195                 200                 205

Ser Phe Asp Pro Ile Pro Ile His Tyr Cys Ala Pro Ala Gly Tyr Ala
    210                 215                 220

Ile Leu Lys Cys Asn Asn Lys Thr Phe Asn Gly Thr Gly Pro Cys Asn
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Ala Glu Gly Glu Ile Ile Ile
            260                 265                 270

Arg Ser Glu Asn Leu Thr Asn Asn Ala Lys Thr Ile Ile Val His Leu
```

```
            275                 280                 285
Asn Glu Ser Ile Glu Ile Val Cys Ala Arg Pro Asn Asn Asn Thr Arg
290                 295                 300

Lys Ser Met Arg Ile Gly Pro Gly Gln Thr Phe Tyr Ala Thr Gly Asp
305                 310                 315                 320

Ile Ile Gly Asp Ile Arg Gln Ala His Cys Asn Ile Ser Gly Asn Trp
                325                 330                 335

Asn Ala Thr Leu Glu Lys Val Lys Gly Lys Leu Gln Glu His Phe Pro
            340                 345                 350

Gly Lys Asn Ile Ser Phe Glu Pro Ser Ser Gly Gly Asp Leu Glu Ile
        355                 360                 365

Thr Thr His Ser Phe Asn Cys Arg Gly Glu Phe Phe Tyr Cys Asp Thr
    370                 375                 380

Ser Lys Leu Phe Asn Gly Thr Thr His Thr Ala Asn Ser Ser Ile Thr
385                 390                 395                 400

Ile Gln Cys Arg Ile Lys Gln Ile Ile Asn Met Trp Gln Gly Val Gly
                405                 410                 415

Arg Ala Ile Tyr Ala Pro Pro Ile Ala Gly Asn Ile Thr Cys Lys Ser
            420                 425                 430

Asn Ile Thr Gly Leu Leu Leu Thr Arg Asp Gly Gly Thr Leu Asn Asn
        435                 440                 445

Asp Thr Glu Lys Phe Arg Pro Gly Gly Gly Asp Met Arg Asp Asn Trp
    450                 455                 460

Arg Ser Glu Leu Tyr Lys Tyr Lys Val Val Glu Ile Lys Pro Leu Gly
465                 470                 475                 480

Ile Ala Pro Thr Lys Ala Lys Arg Arg Val Val Ser Glu Lys Ser
                485                 490                 495

Ala Val Gly Ile Gly Ala Val Phe Leu Gly Phe Leu Gly Ala Ala Gly
            500                 505                 510

Ser Thr Met Gly Ala Ala Ser Ile Thr Leu Thr Val Gln Ala Arg Gln
        515                 520                 525

Leu Leu Ser Gly Ile Val Gln Gln Gln Ser Asn Leu Leu Arg Ala Ile
    530                 535                 540

Glu Ala Gln Gln His Met Leu Gln Leu Thr Val Trp Gly Ile Lys Gln
545                 550                 555                 560

Leu Gln Thr Arg Val Leu Ala Ile Glu Arg Tyr Leu Lys Asp Gln Gln
                565                 570                 575

Leu Leu Gly Ile Trp Gly Cys Ser Gly Lys Ile Ile Cys Thr Thr Ala
            580                 585                 590

Val Pro Trp Asn Thr Ser Trp Ser Asn Lys Ser Leu Glu Asp Ile Trp
        595                 600                 605

Asp Asn Met Thr Trp Met Gln Trp Asp Arg Glu Ile Asn Asn Tyr Thr
    610                 615                 620

Ser Ile Ile Tyr Ser Leu Leu Glu Glu Ser Gln Asn Gln Gln Glu Lys
625                 630                 635                 640

Asn Glu Lys Asp Leu Leu Ala Leu Asp Ser Trp Asn Asn Leu Trp Asn
                645                 650                 655

Trp Phe Asn Ile Thr Lys Trp Leu Trp
            660                 665

<210> SEQ ID NO 35
<211> LENGTH: 850
<212> TYPE: PRT
<213> ORGANISM: Human immunodeficiency virus
```

<400> SEQUENCE: 35

```
Met Ala Pro Ile Ser Pro Ile Glu Thr Val Pro Val Lys Leu Lys Pro
1               5                   10                  15

Gly Met Asp Gly Pro Lys Ile Lys Gln Trp Pro Leu Thr Glu Glu Lys
                20                  25                  30

Ile Lys Ala Leu Met Ala Ile Cys Glu Glu Met Glu Lys Glu Gly Lys
            35                  40                  45

Ile Thr Lys Ile Gly Pro Glu Asn Pro Tyr Asn Thr Pro Ile Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Ala
            100                 105                 110

Val Gly Asp Ala Tyr Phe Ser Val Pro Leu Asp Glu Ser Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Ala Lys
                165                 170                 175

Asn Pro Glu Ile Val Ile Tyr Gln Tyr Met Ala Ala Leu Tyr Val Gly
            180                 185                 190

Ser Asp Leu Glu Ile Gly Gln His Arg Ala Lys Ile Glu Glu Leu Arg
        195                 200                 205

Glu His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Ser Gly Ile Lys Val Arg Gln Leu Cys Lys Leu Leu Arg Gly Ala
        275                 280                 285

Lys Ala Leu Thr Asp Ile Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Tyr
                325                 330                 335

Asp Gln Trp Thr Tyr Gln Ile Tyr Gln Glu Pro Phe Lys Asn Leu Lys
            340                 345                 350

Thr Gly Lys Tyr Ala Lys Met Arg Thr Ala His Thr Asn Asp Val Lys
        355                 360                 365

Gln Leu Thr Glu Ala Val Gln Lys Ile Ala Leu Glu Ser Ile Val Ile
    370                 375                 380

Trp Gly Lys Thr Pro Lys Phe Arg Leu Pro Ile Gln Lys Glu Thr Trp
385                 390                 395                 400

Glu Ile Trp Trp Thr Asp Tyr Trp Gln Ala Thr Trp Ile Pro Glu Trp
```

```
              405                 410                 415
Glu Phe Val Asn Thr Pro Pro Leu Val Lys Leu Trp Tyr Gln Leu Glu
                420                 425                 430
Lys Glu Pro Ile Ala Gly Ala Glu Thr Phe Tyr Val Ala Gly Ala Ala
            435                 440                 445
Asn Arg Glu Thr Lys Ile Gly Lys Ala Gly Tyr Val Thr Asp Lys Gly
450                 455                 460
Arg Gln Lys Ile Val Thr Leu Thr Glu Thr Thr Asn Gln Lys Thr Ala
465                 470                 475                 480
Leu Gln Ala Ile Gln Leu Ala Leu Gln Asp Ser Gly Ser Glu Val Asn
                485                 490                 495
Ile Val Thr Ala Ser Gln Tyr Ala Leu Gly Ile Ile Gln Ala Gln Pro
                500                 505                 510
Asp Lys Ser Glu Ser Glu Leu Val Asn Gln Ile Glu Gln Leu Ile
                515                 520                 525
Asn Lys Glu Arg Val Tyr Leu Ser Trp Val Pro Ala His Lys Gly Ile
                530                 535                 540
Gly Gly Asn Glu Gln Val Asp Lys Leu Val Ser Ser Gly Ile Arg Lys
545                 550                 555                 560
Val Leu Phe Leu Asp Gly Ile Asp Lys Ala Gln Glu Glu His Glu Lys
                565                 570                 575
Tyr His Ser Asn Trp Arg Ala Met Ala Ser Glu Phe Asn Leu Pro Pro
                580                 585                 590
Val Val Ala Lys Glu Ile Val Ala Ser Cys Asp Lys Cys Gln Leu Lys
                595                 600                 605
Gly Glu Ala Ile His Gly Gln Val Asp Cys Ser Pro Gly Ile Trp Gln
610                 615                 620
Leu Ala Cys Thr His Leu Glu Gly Lys Val Ile Leu Val Ala Val His
625                 630                 635                 640
Val Ala Ser Gly Tyr Met Glu Ala Glu Val Ile Pro Ala Glu Thr Gly
                645                 650                 655
Gln Glu Thr Ala Tyr Tyr Ile Leu Lys Leu Ala Gly Arg Trp Pro Val
                660                 665                 670
Lys Val Ile His Thr Ala Asn Gly Ser Asn Phe Thr Ser Ala Ala Val
                675                 680                 685
Lys Ala Ala Cys Trp Trp Ala Gly Ile Gln Gln Glu Phe Gly Ile Pro
                690                 695                 700
Tyr Asn Pro Gln Ser Gln Gly Val Val Ala Ser Met Asn Lys Glu Leu
705                 710                 715                 720
Lys Lys Ile Ile Gly Gln Val Arg Asp Gln Ala Glu His Leu Lys Thr
                725                 730                 735
Ala Val Gln Met Ala Val Phe Ile His Asn Phe Lys Arg Lys Gly Gly
                740                 745                 750
Ile Gly Gly Tyr Ser Ala Gly Glu Arg Ile Ile Asp Ile Ile Ala Thr
                755                 760                 765
Asp Ile Gln Thr Lys Glu Leu Gln Lys Gln Ile Ile Lys Ile Gln Asn
770                 775                 780
Phe Arg Val Tyr Tyr Arg Asp Ser Arg Asp Pro Ile Trp Lys Gly Pro
785                 790                 795                 800
Ala Lys Leu Leu Trp Lys Gly Glu Gly Ala Val Val Ile Gln Asp Asn
                805                 810                 815
Ser Asp Ile Lys Val Val Pro Arg Arg Lys Val Lys Ile Ile Lys Asp
                820                 825                 830
```

-continued

```
Tyr Gly Lys Gln Met Ala Gly Ala Asp Cys Val Ala Gly Arg Gln Asp
        835                 840                 845

Glu Asp
    850

<210> SEQ ID NO 36
<211> LENGTH: 696
<212> TYPE: PRT
<213> ORGANISM: Human immunodeficiency virus

<400> SEQUENCE: 36

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Leu Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Gln Asn Lys Gly Gln
            100                 105                 110

Gln Lys Thr Gln Gln Ala Lys Gly Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Asn Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
```

```
                    340                 345                 350
Pro Ser His Lys Ala Arg Val Leu Ala Glu Ala Met Ser Gln Thr Gly
            355                 360                 365
Ser Thr Ile Met Met Gln Arg Ser Asn Phe Lys Gly Ser Lys Arg Ile
        370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                405                 410                 415
Gln Met Lys Asp Cys Thr Glu Arg Gln Ala Asn Phe Leu Gly Lys Ile
            420                 425                 430
Trp Pro Ser His Lys Gly Arg Pro Gly Asn Phe Leu Gln Ser Arg Pro
        435                 440                 445
Glu Pro Thr Ala Pro Pro Ala Glu Ser Phe Arg Phe Gly Glu Thr Thr
    450                 455                 460
Pro Ala Pro Lys Gln Glu Leu Lys Asp Arg Glu Pro Leu Thr Ser Leu
465                 470                 475                 480
Lys Ser Leu Phe Gly Ser Asp Pro Leu Ser Gln Ala Gly Lys Trp Ser
                485                 490                 495
Lys Ser Ser Ile Val Gly Trp Pro Asp Val Arg Glu Arg Met Arg Arg
            500                 505                 510
Thr Glu Pro Ala Ala Glu Gly Val Gly Ala Ala Ser Gln Asp Leu Asp
        515                 520                 525
Lys Tyr Gly Ala Leu Thr Ser Ser Asn Thr Thr His Asn Asn Ala Asp
    530                 535                 540
Cys Ala Trp Leu Glu Ala Gln Glu Glu Gly Glu Val Gly Phe Pro Val
545                 550                 555                 560
Arg Pro Gln Val Pro Leu Arg Pro Met Thr Tyr Lys Gly Ala Phe Asp
                565                 570                 575
Leu Ser Phe Phe Leu Lys Glu Lys Gly Gly Leu Asp Gly Leu Ile Tyr
            580                 585                 590
Ser Lys Lys Arg Gln Glu Ile Leu Asp Leu Trp Val Tyr His Thr Gln
        595                 600                 605
Gly Phe Phe Pro Asp Trp Gln Asn Tyr Thr Pro Gly Pro Gly Val Arg
    610                 615                 620
Tyr Pro Leu Thr Phe Gly Trp Cys Phe Lys Leu Val Pro Val Asp Pro
625                 630                 635                 640
Arg Glu Val Glu Glu Ala Asn Lys Gly Glu Asn Asn Cys Leu Leu His
                645                 650                 655
Pro Met Ser Leu His Gly Met Glu Asp Glu Glu Arg Glu Val Leu Lys
            660                 665                 670
Trp Glu Phe Asp Ser Ser Leu Ala Arg Arg His Leu Ala Arg Glu Leu
        675                 680                 685
His Pro Glu Tyr Tyr Lys Asp Cys
    690                 695

<210> SEQ ID NO 37
<211> LENGTH: 672
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 37
```

-continued

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
                20                  25                  30

Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350

Thr Ile Ile Phe Lys Pro Ser Ser Gly Gly Asp Leu Glu Ile Thr Thr
        355                 360                 365

His Ser Phe Asn Cys Arg Gly Glu Phe Phe Tyr Cys Asn Thr Ser Gly
370                 375                 380

Leu Phe Asn Ser Thr Trp Ile Gly Asn Gly Thr Lys Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
```

```
                420             425             430
Lys Ile Thr Cys Lys Ser Asn Ile Thr Gly Leu Leu Leu Thr Arg Asp
            435                 440                 445

Gly Gly Asn Asn Thr Asn Glu Thr Glu Ile Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Glu Ser Glu Lys Ser Ala Val Gly Ile Gly Ala Val Phe Leu
                500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
            530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
                565                 570                 575

Arg Tyr Leu Lys Asp Gln Gln Leu Leu Gly Ile Trp Gly Cys Ser Gly
                580                 585                 590

Lys Leu Ile Cys Thr Thr Thr Val Pro Trp Asn Ser Ser Trp Ser Asn
            595                 600                 605

Lys Ser Gln Asp Glu Ile Trp Asp Asn Met Thr Trp Met Glu Trp Glu
            610                 615                 620

Arg Glu Ile Asn Asn Tyr Thr Asp Ile Ile Tyr Ser Leu Ile Glu Glu
625                 630                 635                 640

Ser Gln Asn Gln Gln Glu Lys Asn Glu Gln Glu Leu Leu Ala Leu Asp
                645                 650                 655

Lys Trp Ala Ser Leu Trp Asn Trp Phe Asp Ile Thr Asn Trp Leu Trp
            660                 665                 670

<210> SEQ ID NO 38
<211> LENGTH: 497
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 38

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Gly Gln Leu
        50                  55                  60

Gln Pro Ala Leu Gln Thr Gly Ser Glu Glu Leu Arg Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Glu Lys Ile Glu Glu Glu Gln Asn Lys Ser Gln
            100                 105                 110
```

```
Gln Lys Thr Gln Gln Ala Ala Asp Lys Gly Asn Ser Ser Lys Val
            115                 120                 125

Ser Gln Asn Tyr Pro Ile Val Gln Asn Leu Gln Gly Gln Met Val His
130                 135                 140

Gln Ala Ile Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Asp Thr Ile Asn Glu Glu
            195                 200                 205

Ala Ala Glu Trp Asp Arg Leu His Pro Val His Ala Gly Pro Ile Pro
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Ala Trp Met Thr Ser Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Lys Thr Leu
290                 295                 300

Arg Ala Glu Gln Ala Thr Gln Asp Val Lys Asn Trp Met Thr Asp Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ala Ala Ile Met Met Gln Arg Gly Asn Phe Lys Gly
370                 375                 380

Gln Arg Arg Ile Ile Lys Cys Phe Asn Cys Gly Lys Glu Gly His Ile
385                 390                 395                 400

Ala Arg Asn Cys Arg Ala Pro Arg Lys Lys Gly Cys Trp Lys Cys Gly
                405                 410                 415

Lys Glu Gly His Gln Met Lys Asp Cys Thr Glu Arg Gln Ala Asn Phe
            420                 425                 430

Leu Gly Lys Ile Trp Pro Ser Asn Lys Gly Arg Pro Gly Asn Phe Leu
            435                 440                 445

Gln Ser Arg Pro Glu Pro Thr Ala Pro Ala Glu Ser Phe Gly Phe
450                 455                 460

Gly Glu Glu Ile Thr Pro Ser Pro Lys Gln Glu Pro Lys Asp Lys Glu
465                 470                 475                 480

Pro Pro Leu Thr Ser Leu Lys Ser Leu Phe Gly Asn Asp Pro Leu Ser
                485                 490                 495

Gln

<210> SEQ ID NO 39
<211> LENGTH: 850
<212> TYPE: PRT
<213> ORGANISM: Artificial Sequence
```

<220> FEATURE:
<223> OTHER INFORMATION: Description of Artificial Sequence: Synthetic
      consensus sequence

<400> SEQUENCE: 39

```
Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Thr Glu Ile Cys Thr Glu Met Glu Lys Glu Gly Lys
        35                  40                  45

Ile Ser Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Asp
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Thr Gln
                165                 170                 175

Asn Pro Glu Ile Val Ile Tyr Gln Tyr Met Asp His Leu Tyr Val Gly
            180                 185                 190

Ser Asp Leu Glu Ile Gly Gln His Arg Ala Lys Ile Glu Glu Leu Arg
        195                 200                 205

Glu His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Lys Gln Leu Cys Lys Leu Leu Arg Gly Ala
        275                 280                 285

Lys Ala Leu Thr Asp Ile Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Asp Gln Trp Thr Tyr Gln Ile Tyr Gln Glu Pro Phe Lys Asn Leu Lys
            340                 345                 350

Thr Gly Lys Tyr Ala Lys Met Arg Ser Ala His Thr Asn Asp Val Lys
        355                 360                 365

Gln Leu Thr Glu Ala Val Gln Lys Ile Ala Thr Glu Ser Ile Val Ile
    370                 375                 380

Trp Gly Lys Thr Pro Lys Phe Arg Leu Pro Ile Gln Lys Glu Thr Trp
```

-continued

```
385                 390                 395                 400
Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Glu Pro Ile Ala Gly Ala Glu Thr Phe Tyr Val Asp Gly Ala Ala
                435                 440                 445

Asn Arg Glu Thr Lys Leu Gly Lys Ala Gly Tyr Val Thr Asp Arg Gly
450                 455                 460

Arg Gln Lys Val Val Ser Leu Thr Glu Thr Thr Asn Gln Lys Thr Glu
465                 470                 475                 480

Leu Gln Ala Ile His Leu Ala Leu Gln Asp Ser Gly Ser Glu Val Asn
                485                 490                 495

Ile Val Thr Asp Ser Gln Tyr Ala Leu Gly Ile Ile Gln Ala Gln Pro
                500                 505                 510

Asp Lys Ser Glu Ser Glu Leu Val Asn Gln Ile Ile Glu Gln Leu Ile
                515                 520                 525

Lys Lys Glu Lys Val Tyr Leu Ser Trp Val Pro Ala His Lys Gly Ile
530                 535                 540

Gly Gly Asn Glu Gln Val Asp Lys Leu Val Ser Thr Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
                580                 585                 590

Ile Val Ala Lys Glu Ile Val Ala Ser Cys Asp Lys Cys Gln Leu Lys
                595                 600                 605

Gly Glu Ala Met His Gly Gln Val Asp Cys Ser Pro Gly Ile Trp Gln
                610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Ile Leu Lys Leu Ala Gly Arg Trp Pro Val
                660                 665                 670

Lys Val Ile His Thr Asp Asn Gly Ser Asn Phe Thr Ser Ala Ala Val
                675                 680                 685

Lys Ala Ala Cys Trp Trp Ala Gly Ile Gln Gln Glu Phe Gly Ile Pro
                690                 695                 700

Tyr Asn Pro Gln Ser Gln Gly Val Val Glu Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
                740                 745                 750

Ile Gly Gly Tyr Ser Ala Gly Glu Arg Ile Ile Asp Ile Ile Ala Thr
                755                 760                 765

Asp Ile Gln Thr Lys Glu Leu Gln Lys Gln Ile Thr Lys Ile Gln Asn
                770                 775                 780

Phe Arg Val Tyr Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
                805                 810                 815
```

```
Ser Asp Ile Lys Val Pro Arg Arg Lys Ala Lys Ile Ile Arg Asp
            820                 825                 830

Tyr Gly Lys Gln Met Ala Gly Asp Asp Cys Val Ala Gly Arg Gln Asp
        835                 840                 845

Glu Asp
    850

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tctagagaat tcgccaccat g                                              21

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
taatgaggat ccgctagc                                                  18

<210> SEQ ID NO 42
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175
```

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
        260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
        340                 345                 350

Val Gly Gly Pro Gly His Lys Ala Arg Val Leu Ala Glu Ala Met Ser
    355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
        420                 425                 430

Phe Leu Gly Lys Ile Trp Pro Ser Tyr Lys Gly Arg Pro Gly Asn Phe
    435                 440                 445

Leu Gln Ser Arg Pro Glu Pro Thr Ala Pro Glu Glu Ser Phe Arg
450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
            485                 490                 495

Pro Ser Ser Gln
        500

<210> SEQ ID NO 43
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys

-continued

```
                20                  25                  30
His Ile Val Trp Ala Ser Arg Glu Leu Glu Arg Phe Ala Val Asn Pro
            35                  40                  45
Gly Leu Leu Glu Thr Ser Glu Cys Arg Gln Ile Leu Gly Gln Leu
50                  55                  60
Gln Pro Ser Leu Gln Thr Gly Ser Glu Glu Leu Arg Ser Leu Tyr Asn
65                  70                  75                  80
Thr Val Ala Thr Leu Tyr Cys Val His Gln Arg Ile Glu Ile Lys Asp
                85                  90                  95
Thr Lys Glu Ala Leu Asp Lys Ile Glu Glu Gln Asn Lys Ser Lys
            100                 105                 110
Lys Lys Ala Gln Gln Ala Ala Ala Asp Thr Gly His Ser Asn Gln Val
            115                 120                 125
Ser Gln Asn Tyr Pro Ile Val Gln Asn Ile Gln Gly Gln Met Val His
            130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
            195                 200                 205
Ala Ala Glu Trp Asp Arg Val His Pro Val His Ala Gly Pro Ile Ala
            210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
            275                 280                 285
Pro Lys Glu Pro Phe Arg Asp Tyr Val Asp Arg Phe Tyr Lys Thr Leu
            290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
            355                 360                 365
Gln Val Thr Asn Ser Ala Thr Ile Met Met Gln Arg Gly Asn Phe Arg
            370                 375                 380
Asn Gln Arg Lys Ile Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
            435                 440                 445
```

```
Leu Gln Ser Arg Pro Glu Pro Thr Ala Pro Pro Glu Glu Ser Phe Arg
        450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 44
<211> LENGTH: 16
<212> TYPE: PRT
<213> ORGANISM: Human immunodeficiency virus

<400> SEQUENCE: 44

Ile Val Gln Gln Gln Ser Asn Leu Leu Arg Ala Ile Glu Ala Gln Gln
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Val Gln Gln Gln Ser Asn Leu Leu Arg Ala Ile Glu Ala Gln
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Gln Gln Gln Asn Asn Leu Leu Arg Ala Ile Glu Ala Gln His
1               5                   10                  15

<210> SEQ ID NO 47
<211> LENGTH: 16
<212> TYPE: PRT
<213> ORGANISM: Human immunodeficiency virus

<400> SEQUENCE: 47

Ala Val Phe Ile His Asn Phe Lys Arg Lys Gly Gly Ile Gly Gly Tyr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Val Phe Ile His Asn Phe Lys Arg Lys Gly Gly Ile Gly Gly
1               5                   10                  15

<210> SEQ ID NO 49
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Leu Ile His Asn Phe Lys Arg Lys Gly Gly Ile Gly Gly Tyr
1               5                   10                  15

<210> SEQ ID NO 50
<211> LENGTH: 15
<212> TYPE: PRT
<213> ORGANISM: Human immunodeficiency virus

<400> SEQUENCE: 50

Met Ala Ile Cys Glu Glu Met Glu Lys Glu Gly Lys Ile Thr Lys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Ile Cys Glu Glu Met Glu Lys Glu Gly Lys Ile Thr Lys
1               5                   10                  15

<210> SEQ ID NO 52
<211> LENGTH: 15
<212> TYPE: PRT
<213> ORGANISM: Human immunodeficiency virus

<400> SEQUENCE: 52

Cys Thr His Gly Ile Lys Pro Val Val Ser Thr Gln Leu Leu Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Thr His Gly Ile Lys Pro Val Val Ser Thr Gln Leu Leu Leu
1               5                   10                  15

<210> SEQ ID NO 54
<211> LENGTH: 15
<212> TYPE: PRT
<213> ORGANISM: Human immunodeficiency virus

<400> SEQUENCE: 54

Gly Gly Pro Ser His Lys Ala Arg Val Leu Ala Glu Ala Met Ser
1               5                   10                  15

<210> SEQ ID NO 55
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 55

Gly Gly Pro Ser His Lys Ala Arg Val Leu Ala Glu Ala Met Gly
1               5                   10                  15

<210> SEQ ID NO 56
<211> LENGTH: 15
<212> TYPE: PRT
<213> ORGANISM: Human immunodeficiency virus

<400> SEQUENCE: 56

Ile Ile Gly Gln Val Arg Asp Gln Ala Glu His Leu Lys Thr Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Ile Gly Gln Val Arg Asp Gln Ala Glu His Leu Lys Thr Ala
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Cys Thr Thr Thr Val Pro Trp Asn Ala Ser Trp Ser Asn Lys Ser
1               5                   10                  15

Leu

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Cys Thr Thr Ala Val Pro Trp Asn Thr Ser Trp Ser Asn Lys Ser
1               5                   10                  15

Gln

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Cys Thr Thr Thr Val Pro Trp Asn Ala Ser Trp Ser Asn Arg
1               5                   10                  15
```

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Thr Thr Thr Val Pro Trp Asn Ser Ser Trp Ser Asn Lys Thr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Thr Ala Val Pro Trp Asn Ala Ser Trp Ser Asn Lys Ser Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Thr Ala Val Pro Trp Asn Thr Ser Trp Ser Asn Lys Ser Leu
1               5                   10                  15

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Gln Leu Ile Lys Lys Glu Arg Val Tyr Leu Ser Trp Val Pro Ala
1               5                   10                  15

His Lys Gly Ile Gly
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Gln Leu Ile Lys Lys Glu Lys Val Tyr Leu Ala Trp Val Pro Ala
1               5                   10                  15

His Lys Gly Ile Gly
            20

<210> SEQ ID NO 66
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Glu Leu Ile Lys Lys Glu Lys Val Tyr Leu Ala Trp Val Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Pro Leu Ile Lys Lys Glu Lys Val Tyr Leu Ser Trp Val Pro
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Leu Ile Glu Lys Asp Lys Val Tyr Leu Ser Trp Val Pro Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ile Lys Lys Glu Arg Val Tyr Leu Ser Trp Val Pro Ala His
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Lys Val Tyr Leu Ala Trp Val Pro Ala His Lys Gly Ile Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Lys Val Tyr Leu Ser Trp Val Pro Ala His Lys Gly Ile Gly
```

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Thr His Gly Ile Arg Pro Val Val Ser Thr Gln Leu Leu Leu
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr His Gly Ile Lys Pro Val Val Ser Thr Gln Leu Leu Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Thr His Gly Ile Lys Pro Val Val Ser Thr Gln Leu Leu Leu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Thr His Gly Ile Arg Pro Val Val Ser Thr Gln Leu Leu Leu
1               5                   10                  15

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Cys Thr Thr Thr Val Pro Trp Asn Ala Ser Trp Ser Asn Lys Ser
1               5                   10                  15

Leu

<210> SEQ ID NO 77
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 77

Ile Cys Thr Thr Ala Val Pro Trp Asn Thr Ser Trp Ser Asn Lys Ser
1               5                   10                  15

Gln

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Cys Thr Thr Thr Val Pro Trp Asn Ala Ser Trp Ser Asn Arg
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Thr Thr Thr Val Pro Trp Asn Ser Ser Trp Ser Asn Lys Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Thr Ala Val Pro Trp Asn Ala Ser Trp Ser Asn Lys Ser Leu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Thr Ala Val Pro Trp Asn Thr Ser Trp Ser Asn Lys Ser Leu
1               5                   10                  15

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Cys Gln Gly Val Gly Gly Pro Gly His Lys Ala Arg Val Leu Ala
```

```
1               5                   10                  15

Glu Ala Met Ser
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Cys Gln Gly Val Gly Gly Pro Ser His Lys Ala Arg Val Leu Ala
1               5                   10                  15

Glu Ala Met Ser
            20

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Cys Gln Glu Val Gly Gly Pro Gly His Lys Ala Arg Val Leu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Pro Ser His Lys Ala Arg Val Leu Ala Glu Ala Met Gly
1               5                   10                  15

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ala Glu Trp Asp Arg Val His Pro Val His Ala Gly Pro Ile Ala
1               5                   10                  15

Pro Gly Gln

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ala Glu Trp Asp Arg Leu His Pro Val His Ala Gly Pro Val Ala
1               5                   10                  15
```

Pro Gly Gln

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ala Glu Asp Arg Leu His Pro Val His Ala Gly Pro Ile Pro
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Asp Trp Asp Arg Leu His Pro Val His Ala Gly Pro Val Ala
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Glu Trp Asp Arg Leu His Pro Val His Ala Gly Pro Ile Ala
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Asp Arg Val His Pro Val His Ala Gly Pro Asn Pro Pro Gly
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Arg Val His Pro Val His Ala Gly Pro Ile Pro Pro Gly Gln
1               5                   10                  15

<210> SEQ ID NO 93
<211> LENGTH: 15
<212> TYPE: PRT
<213> ORGANISM: Artificial Sequence
<220> FEATURE:

<223> OTHER INFORMATION: Description of Artificial Sequence: Synthetic
     peptide

<400> SEQUENCE: 93

His Ser Asn Trp Arg Ala Met Ala Ser Asp Phe Asn Leu Pro Pro
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 94

His Ser Asn Trp Arg Ala Met Ala Ser Glu Phe Asn Leu Pro Pro
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 95

His Ser Asn Trp Arg Ala Met Ala Ser Asp Phe Asn Leu Pro Pro
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 96

Lys Gly Arg Pro Gly Asn Phe Leu Gln Asn Arg Pro Glu Pro Thr
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 97

Lys Gly Arg Pro Gly Asn Phe Leu Gln Ser Arg Pro Glu Pro Thr
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 98

Lys Gly Arg Pro Gly Asn Phe Leu Gln Asn Arg Pro Glu Pro Thr
1               5                   10                  15

```
<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Arg Glu Leu Glu Arg Phe Ala Val Asn Pro Gly Leu Leu Glu
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Arg Glu Leu Glu Arg Phe Ala Leu Asn Pro Gly Leu Leu Glu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Arg Glu Leu Glu Arg Phe Ala Leu Asn Pro Gly Leu Leu Glu
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ser Leu Tyr Asn Thr Val Ala Thr Leu Tyr Cys Val His Gln Arg
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ser Leu Phe Asn Thr Val Ala Thr Leu Tyr Cys Val His Ala Glu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

```
Lys Ser Leu Phe Asn Thr Val Ala Thr Leu Tyr Cys Val His Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Leu Tyr Asn Thr Val Ala Thr Leu Tyr Cys Val His Gln Arg
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Val Thr Asp Arg Gly Arg Gln Lys Ile Val Ser Leu Thr Glu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Val Thr Asp Arg Gly Arg Gln Lys Val Val Ser Leu Thr Asp
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Val Thr Asp Arg Gly Arg Gln Lys Val Val Ser Leu Thr Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Thr Thr Thr Val Pro Trp Asn Ala Ser Trp Ser Asn Lys Ser
1               5                   10                  15

<210> SEQ ID NO 110
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 110

Cys Thr Thr Ala Val Pro Trp Asn Thr Ser Trp Ser Asn Lys Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Thr Thr Asn Val Pro Trp Asn Ser Ser Trp Ser Asn Lys Ser
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Trp Ala Gly Ile Gln Gln Glu Phe Gly Ile Pro Tyr Asn Pro
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Trp Ala Gly Ile Lys Gln Glu Phe Gly Ile Pro Tyr Asn Pro
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Trp Ala Gly Ile Gln Gln Glu Phe Gly Ile Pro Tyr Asn Pro
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Pro Gly His Lys Ala Arg Val Leu Ala Glu Ala Met Ser Gln
1               5                   10                  15
```

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

```
Gly Pro Ser His Lys Ala Arg Val Leu Ala Glu Ala Met Ser Gln
1               5                   10                  15
```

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

```
Gly Pro Gly His Lys Ala Arg Val Leu Ala Glu Ala Met Ser Gln
1               5                   10                  15
```

<210> SEQ ID NO 118
<211> LENGTH: 500
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
```

```
              210                 215                 220
Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 119
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Pro Ser Glu Ala Gly Ala Asp Arg
        35                  40                  45

Gln Gly Thr Val Ser Phe Asn Phe Pro Gln Val Thr Leu Trp Gln Arg
    50                  55                  60
```

```
Pro Leu Val Thr Ile Lys Ile Gly Gly Gln Leu Lys Glu Ala Leu Leu
 65                  70                  75                  80

Asp Thr Gly Ala Asp Thr Val Leu Glu Glu Met Ser Leu Pro Gly
                 85                  90                  95

Arg Trp Lys Pro Lys Met Ile Gly Gly Ile Gly Gly Phe Ile Lys Val
                100                 105                 110

Arg Gln Tyr Asp Gln Ile Leu Ile Glu Ile Cys Gly His Lys Ala Ile
            115                 120                 125

Gly Thr Val Leu Val Gly Pro Thr Pro Val Asn Ile Ile Gly Arg Asn
        130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Leu Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Pro Gly Ile Lys Val Arg
            420                 425                 430

Gln Leu Cys Lys Leu Leu Arg Gly Thr Lys Ala Leu Thr Glu Val Ile
        435                 440                 445

Pro Leu Thr Glu Glu Ala Glu Leu Glu Leu Ala Glu Asn Arg Glu Ile
    450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
```

```
            485                 490                 495
Tyr Gln Glu Pro Phe Lys Asn Leu Lys Thr Gly Lys Tyr Ala Arg Met
                500                 505                 510

Arg Gly Ala His Thr Asn Asp Val Lys Gln Leu Thr Glu Ala Val Gln
                515                 520                 525

Lys Ile Thr Thr Glu Ser Ile Val Ile Trp Gly Lys Thr Pro Lys Phe
            530                 535                 540

Lys Leu Pro Ile Gln Lys Glu Thr Trp Glu Thr Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
                580                 585                 590

Glu Thr Phe Tyr Val Asp Gly Ala Ala Asn Arg Glu Thr Lys Leu Gly
                595                 600                 605

Lys Ala Gly Tyr Val Thr Asn Arg Gly Arg Gln Lys Val Val Thr Leu
            610                 615                 620

Thr Asp Thr Thr Asn Gln Lys Thr Glu Leu Gln Ala Ile Tyr Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Gln Ser Glu Ser Glu Leu
                660                 665                 670

Val Asn Gln Ile Ile Glu Gln Leu Ile Lys Lys Glu Lys Val Tyr Leu
            675                 680                 685

Ala Trp Val Pro Ala His Lys Gly Ile Gly Gly Asn Glu Gln Val Asp
            690                 695                 700

Lys Leu Val Ser Ala Gly Ile Arg Lys Val Leu Phe Leu Asp Gly Ile
705                 710                 715                 720

Asp Lys Ala Gln Asp Glu His Glu Lys Tyr His Ser Asn Trp Arg Ala
                725                 730                 735

Met Ala Ser Asp Phe Asn Leu Pro Pro Val Val Ala Lys Glu Ile Val
                740                 745                 750

Ala Ser Cys Asp Lys Cys Gln Leu Lys Gly Glu Ala Met His Gly Gln
            755                 760                 765

Val Asp Cys Ser Pro Gly Ile Trp Gln Leu Asp Cys Thr His Leu Glu
            770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
                820                 825                 830

Gly Ser Asn Phe Thr Gly Ala Thr Val Arg Ala Ala Cys Trp Trp Ala
            835                 840                 845

Gly Ile Lys Gln Glu Phe Gly Ile Pro Tyr Asn Pro Gln Ser Gln Gly
            850                 855                 860

Val Val Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
                900                 905                 910
```

-continued

Glu Arg Ile Val Asp Ile Ile Ala Thr Asp Ile Gln Thr Lys Glu Leu
            915                 920                 925

Gln Lys Gln Ile Thr Lys Ile Gln Asn Phe Arg Val Tyr Tyr Arg Asp
        930                 935                 940

Ser Arg Asn Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
        995                 1000

<210> SEQ ID NO 120
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile

```
            260                 265                 270
Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685
```

Val Gly Gly Leu Val Gly Leu Arg Ile Val Phe Ala Val Leu Ser Ile
            690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 121
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Gly Ala Arg Ala Ser Val Leu Ser Gly Glu Leu Asp Arg Trp
1               5                   10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly

```
            180                 185                 190
Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
        210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
        290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
        370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 122
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30
```

```
Val Trp Gly Arg Asp Asn Asn Ser Pro Ser Glu Ala Gly Ala Asp Arg
         35                  40                  45

Gln Gly Thr Val Ser Phe Asn Phe Pro Gln Val Thr Leu Trp Gln Arg
 50                  55                  60

Pro Leu Val Thr Ile Lys Ile Gly Gly Gln Leu Lys Glu Ala Leu Leu
 65                  70                  75                  80

Asp Thr Gly Ala Asp Asp Thr Val Leu Glu Glu Met Ser Leu Pro Gly
                 85                  90                  95

Arg Trp Lys Pro Lys Met Ile Gly Ile Gly Gly Phe Ile Lys Val
                100                 105                 110

Arg Gln Tyr Asp Gln Ile Leu Ile Glu Ile Cys Gly His Lys Ala Ile
                115                 120                 125

Gly Thr Val Leu Val Gly Pro Thr Pro Val Asn Ile Ile Gly Arg Asn
        130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
                180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
        210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
                260                 265                 270

Val Pro Leu Asp Glu Asp Phe Arg Lys Tyr Thr Ala Phe Thr Ile Pro
                275                 280                 285

Ser Ile Asn Asn Glu Thr Pro Gly Ile Arg Tyr Gln Tyr Asn Val Leu
290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
                340                 345                 350

His Arg Thr Lys Ile Glu Glu Leu Arg Gln His Leu Leu Arg Trp Gly
                355                 360                 365

Leu Thr Thr Pro Asp Lys Lys His Gln Lys Glu Pro Pro Phe Leu Trp
        370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Pro Gly Ile Lys Val Arg
                420                 425                 430

Gln Leu Cys Lys Leu Leu Arg Gly Thr Lys Ala Leu Thr Glu Val Ile
        435                 440                 445

Pro Leu Thr Glu Glu Ala Glu Leu Glu Leu Ala Glu Asn Arg Glu Ile
```

```
            450                 455                 460
Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                    485                 490                 495

Tyr Gln Glu Pro Phe Lys Asn Leu Lys Thr Gly Lys Tyr Ala Arg Met
                500                 505                 510

Arg Gly Ala His Thr Asn Asp Val Lys Gln Leu Thr Glu Ala Val Gln
                515                 520                 525

Lys Ile Thr Thr Glu Ser Ile Val Ile Trp Gly Lys Thr Pro Lys Phe
530                 535                 540

Lys Leu Pro Ile Gln Lys Glu Thr Trp Glu Thr Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
                580                 585                 590

Glu Thr Phe Tyr Val Asp Gly Ala Ala Asn Arg Glu Thr Lys Leu Gly
                595                 600                 605

Lys Ala Gly Tyr Val Thr Asn Arg Gly Arg Gln Lys Val Val Thr Leu
                610                 615                 620

Thr Asp Thr Thr Asn Gln Lys Thr Glu Leu Gln Ala Ile Tyr Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Gln Ser Glu Ser Glu Leu
                660                 665                 670

Val Asn Gln Ile Ile Glu Gln Leu Ile Lys Lys Glu Lys Val Tyr Leu
                675                 680                 685

Ala Trp Val Pro Ala His Lys Gly Ile Gly Gly Asn Glu Gln Val Asp
                690                 695                 700

Lys Leu Val Ser Ala Gly Ile Arg Lys Val Leu Phe Leu Asp Gly Ile
705                 710                 715                 720

Asp Lys Ala Gln Asp Glu His Glu Lys Tyr His Ser Asn Trp Arg Ala
                725                 730                 735

Met Ala Ser Asp Phe Asn Leu Pro Pro Val Val Ala Lys Glu Ile Val
                740                 745                 750

Ala Ser Cys Asp Lys Cys Gln Leu Lys Gly Glu Ala Met His Gly Gln
                755                 760                 765

Val Asp Cys Ser Pro Gly Ile Trp Gln Leu Asp Cys Thr His Leu Glu
                770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
                820                 825                 830

Gly Ser Asn Phe Thr Gly Ala Thr Val Arg Ala Ala Cys Trp Trp Ala
                835                 840                 845

Gly Ile Lys Gln Glu Phe Gly Ile Pro Tyr Asn Pro Gln Ser Gln Gly
                850                 855                 860

Val Val Glu Ser Met Asn Lys Glu Leu Lys Lys Ile Ile Gly Gln Val
865                 870                 875                 880
```

```
Arg Asp Gln Ala Glu His Leu Lys Thr Ala Val Gln Met Ala Val Phe
            885                 890                 895

Ile His Asn Phe Lys Arg Lys Gly Gly Ile Gly Gly Tyr Ser Ala Gly
        900                 905                 910

Glu Arg Ile Val Asp Ile Ile Ala Thr Asp Ile Gln Thr Lys Glu Leu
            915                 920                 925

Gln Lys Gln Ile Thr Lys Ile Gln Asn Phe Arg Val Tyr Tyr Arg Asp
    930                 935                 940

Ser Arg Asn Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln  Asp Glu Asp
            995                 1000

<210> SEQ ID NO 123
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
```

```
            225                 230                 235                 240

Asn Val Ser Thr Val Gln Cys Thr His Gly Ile Arg Pro Val Val Ser
                        245                 250                 255

Thr Gln Leu Leu Leu Asn Gly Ser Leu Ala Glu Glu Val Val Ile
                    260                 265                 270

Arg Ser Val Asn Phe Thr Asp Asn Ala Lys Thr Ile Ile Val Gln Leu
                        275                 280                 285

Asn Thr Ser Val Glu Ile Asn Cys Thr Arg Pro Asn Asn Asn Thr Arg
                    290                 295                 300

Lys Arg Ile Arg Ile Gln Arg Gly Pro Gly Arg Ala Phe Val Thr Ile
        305                 310                 315                 320

Gly Lys Ile Gly Asn Met Arg Gln Ala His Cys Asn Ile Ser Arg Ala
                                325                 330                 335

Lys Trp Asn Asn Thr Leu Lys Gln Ile Ala Ser Lys Leu Arg Glu Gln
                        340                 345                 350

Phe Gly Asn Asn Lys Thr Ile Ile Phe Lys Gln Ser Ser Gly Gly Asp
                    355                 360                 365

Pro Glu Ile Val Thr His Ser Phe Asn Cys Gly Gly Glu Phe Phe Tyr
                    370                 375                 380

Cys Asn Ser Thr Gln Leu Phe Asn Ser Thr Trp Phe Asn Ser Thr Trp
        385                 390                 395                 400

Ser Thr Glu Gly Ser Asn Asn Thr Glu Gly Ser Asp Thr Ile Thr Leu
                        405                 410                 415

Pro Cys Arg Ile Lys Gln Ile Ile Asn Met Trp Gln Lys Val Gly Lys
                    420                 425                 430

Ala Met Tyr Ala Pro Pro Ile Ser Gly Gln Ile Arg Cys Ser Ser Asn
                    435                 440                 445

Ile Thr Gly Leu Leu Leu Thr Arg Asp Gly Gly Asn Ser Asn Asn Glu
                    450                 455                 460

Ser Glu Ile Phe Arg Pro Gly Gly Gly Asp Met Arg Asp Asn Trp Arg
        465                 470                 475                 480

Ser Glu Leu Tyr Lys Tyr Lys Val Val Lys Ile Glu Pro Leu Gly Val
                        485                 490                 495

Ala Pro Thr Lys Ala Lys Arg Arg Val Val Gln Arg Glu Lys Arg Ala
                    500                 505                 510

Val Gly Ile Gly Ala Leu Phe Leu Gly Phe Leu Gly Ala Ala Gly Ser
                    515                 520                 525

Thr Met Gly Ala Ala Ser Met Thr Leu Thr Val Gln Ala Arg Gln Leu
                    530                 535                 540

Leu Ser Gly Ile Val Gln Gln Gln Asn Asn Leu Leu Arg Ala Ile Glu
        545                 550                 555                 560

Ala Gln Gln His Leu Leu Gln Leu Thr Val Trp Gly Ile Lys Gln Leu
                            565                 570                 575

Gln Ala Arg Ile Leu Ala Val Glu Arg Tyr Leu Lys Asp Gln Gln Leu
                        580                 585                 590

Leu Gly Ile Trp Gly Cys Ser Gly Lys Leu Ile Cys Thr Thr Ala Val
                    595                 600                 605

Pro Trp Asn Ala Ser Trp Ser Asn Lys Ser Leu Glu Gln Ile Trp Asn
                    610                 615                 620

His Thr Thr Trp Met Glu Trp Asp Arg Glu Ile Asn Asn Tyr Thr Ser
        625                 630                 635                 640

Leu Ile His Ser Leu Ile Glu Glu Ser Gln Asn Gln Gln Glu Lys Asn
                            645                 650                 655
```

-continued

```
Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Ala Glu Trp Asp Arg Leu His Pro Val His Ala Gly Pro Ile Ala
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ala Glu Trp Asp Arg Leu His Pro Val His Ala Gly Pro Ile Ala
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126
```

```
Ala Ala Glu Asp Arg Leu His Pro Val His Ala Gly Pro Ile Pro
1               5                   10                  15
```

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Asp Gln Met His Glu Asp Ile Ile Ser Leu Trp Asp Gln Ser Leu Lys
1               5                   10                  15
```

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Glu Gln Met His Glu Asp Ile Ile Ser Leu Trp Asp Gln Ser Leu Lys
1               5                   10                  15
```

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Glu Gln Met His Glu Asp Ile Ile Ser Leu Trp Asp Gln Ser Leu
1               5                   10                  15
```

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
His Met His Glu Asp Ile Ile Ser Leu Trp Asp Glu Ser Leu Lys
1               5                   10                  15
```

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Lys Leu Asn Trp Ala Ser Gln Ile Tyr Ser Gly Ile Lys Val Arg
1               5                   10                  15
```

<210> SEQ ID NO 132
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 132

Lys Leu Asn Trp Ala Ser Gln Ile Tyr Pro Gly Ile Lys Val Arg
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Leu Asn Trp Ala Ser Gln Ile Tyr Ala Gly Ile Lys Val Lys
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys His Leu Val Trp Ala Ser Arg Glu Leu Glu Arg Phe Ala Leu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys His Ile Val Trp Ala Ser Arg Glu Leu Glu Arg Phe Ala Val
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys His Leu Val Trp Ala Ser Arg Glu Leu Glu Arg Phe Ala Leu
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Leu Gln Glu Gln Ile Ala Trp Met Thr Asn Asn Pro Pro Val Pro
1               5                   10                  15

```
<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Gln Glu Gln Ile Gly Trp Met Thr Asn Asn Pro Pro Ile Pro
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Ala Glu Gln Ile Ala Trp Met Thr Ser Asn Pro Pro Ile Pro
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Met His Glu Asp Ile Ile Ser Leu Trp Asp Gln Ser Leu Lys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Met His Glu Asp Ile Ile Ser Leu Trp Asp Gln Ser Leu Lys
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

His Met His Glu Asp Ile Ile Ser Leu Trp Asp Glu Ser Leu Lys
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143
```

```
Asp Ile Trp Asp Asn Met Thr Trp Met Gln Trp Asp Arg Glu Ile
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Ile Trp Asp Asn Met Thr Trp Met Glu Trp Glu Arg Glu Ile
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Glu Ile Trp Asn Asn Met Thr Trp Met Glu Trp Glu Lys Glu Ile
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Pro Val Lys Val Ile His Thr Ala Asn Gly Ser Asn Phe Thr
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Pro Val Lys Thr Ile His Thr Ala Asn Gly Ser Asn Phe Thr
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp Pro Val Lys Val Val His Thr Asp Asn Gly Ser Asn Phe Thr
1               5                   10                  15

<210> SEQ ID NO 149
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 149

Ala Gln Thr Gly Thr Glu Glu Leu Arg Ser Leu Tyr Asn Thr Val
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Leu Gln Thr Gly Ser Glu Glu Leu Arg Ser Leu Tyr Asn Thr Val
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Gln Thr Gly Ser Glu Glu Leu Lys Ser Leu Phe Asn Thr Val
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Phe Asn Met Trp Lys Asn Asp Met Val Asp Gln Met His Glu
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Phe Asn Met Trp Lys Asn Asn Met Val Glu Gln Met His Glu
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asn Phe Asn Met Trp Lys Asn Asn Met Val Glu Gln Met His Glu
1               5                   10                  15
```

```
<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Arg Pro Gly Asn Phe Leu Gln Ser Arg Pro Glu Pro Thr
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Arg Pro Gly Asn Phe Leu Gln Ser Arg Pro Glu Pro Thr
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Arg Pro Gly Asn Phe Leu Gln Asn Arg Pro Glu Pro Thr
1               5                   10

<210> SEQ ID NO 158
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

His Ala Gly Pro Ile Ala Pro Gly Gln Met Arg Glu Pro
1               5                   10

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Val His Ala Gly Pro Ile Ala Pro Gly Gln Met Arg Glu Pro
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 160

Pro Val Gln Ala Gly Pro Ile Ala Pro Gly Gln Met Arg Glu Pro
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Gln Gln Gln Ser Asn Leu Leu Arg Ala Ile Glu Ala Gln Gln
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Val Gln Gln Gln Asn Asn Leu Leu Arg Ala Ile Glu Ala Gln Gln
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Gln Gln Gln Asn Asn Leu Leu Arg Ala Ile Glu Ala Gln His
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Leu Glu Glu Ser Gln Asn Gln Gln Glu Lys Asn Glu Lys Asp
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Ile Glu Glu Ser Gln Asn Gln Gln Glu Lys Asn Glu Gln Glu
1               5                   10                  15

<210> SEQ ID NO 166
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 166

Leu Ile Glu Glu Ser Gln Asn Gln Gln Glu Lys Asn Glu Gln Asp
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Arg Leu His Pro Val His Ala Gly Pro Ile Ala Pro Gly Gln
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Arg Leu His Pro Val His Ala Gly Pro Ile Ala Pro Gly Gln
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Arg Val His Pro Val His Ala Gly Pro Ile Pro Pro Gly Gln
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Asp Ile Ile Gly Asp Ile Arg Gln Ala His Cys Asn Ile Ser
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Glu Ile Ile Gly Asp Ile Arg Gln Ala His Cys Asn Ile Ser
1               5                   10                  15
```

```
<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Asp Ile Ile Gly Asp Ile Arg Gln Ala His Cys Asn Ile Ser
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Gly Met Leu Arg Asn Cys Gln Pro Trp Trp Ile Trp Gly Ile
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Gly Ile Arg Lys Asn Tyr Gln His Leu Trp Arg Trp Gly Thr
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Glu Ile Arg Lys Asn Tyr Gln His Leu Trp Arg Trp Gly Thr
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Met Thr Lys Ile Leu Glu Pro Phe Arg Ala Lys Asn Pro Glu Ile
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 177

Met Thr Lys Ile Leu Glu Pro Phe Arg Lys Gln Asn Pro Asp Ile
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Met Thr Lys Ile Leu Glu Pro Phe Arg Lys Gln Asn Pro Asp Ile
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Ala Met Ala Ser Glu Phe Asn Leu Pro Pro Val Val Ala Lys
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Met Ala Ser Asp Phe Asn Leu Pro Pro Val Val Ala Lys
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Lys Ala Met Ala Ser Asp Phe Asn Leu Pro Pro Ile Val Ala Lys
1               5                   10                  15

<210> SEQ ID NO 182
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ala Glu Trp Asp Arg Leu His Pro Val His Ala Gly Pro Ile Ala
1               5                   10                  15

Pro Gly Gln

```
<210> SEQ ID NO 183
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ala Glu Trp Asp Arg Leu His Pro Val His Ala Gly Pro Ile Ala
1               5                   10                  15

Pro Gly Gln

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Glu Asp Arg Leu His Pro Val His Ala Gly Pro Ile Pro
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Glu Trp Asp Arg Leu His Pro Val His Ala Gly Pro Ile Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Arg Val His Pro Val His Ala Gly Pro Ile Pro Pro Gly Gln
1               5                   10                  15

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Leu Ile Asn Lys Glu Arg Val Tyr Leu Ser Trp Val Pro Ala His
1               5                   10                  15

Lys Gly Ile Gly
            20

<210> SEQ ID NO 188
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 188

Gln Leu Ile Lys Lys Glu Lys Val Tyr Leu Ala Trp Val Pro Ala His
1               5                   10                  15

Lys Gly Ile Gly
            20

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Lys Leu Ile Glu Lys Asp Lys Val Tyr Leu Ser Trp Val Pro Ala
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Ile Lys Lys Glu Arg Val Tyr Leu Ser Trp Val Pro Ala His
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Lys Val Tyr Leu Ser Trp Val Pro Ala His Lys Gly Ile Gly
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Leu Tyr Asn Thr Val Ala Thr Leu Tyr Cys Val His Ala Gly
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193
```

Ser Leu Tyr Asn Thr Val Ala Thr Leu Tyr Cys Val His Gln Lys
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Leu Tyr Asn Thr Val Ala Thr Leu Tyr Cys Val His Gln Arg
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Gln Ala Ala Met Gln Met Leu Lys Asp Thr Ile Asn Glu Glu
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

His Gln Ala Ala Met Gln Met Leu Lys Glu Thr Ile Asn Glu Glu
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

His Gln Ala Ala Met Gln Met Leu Lys Asp Thr Ile Asn Glu Glu
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

His Gln Ala Ala Met Gln Met Leu Lys Glu Thr Ile Asn Glu Glu
1               5                   10                  15

<210> SEQ ID NO 199
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 199

Ala Val Phe Ile His Asn Phe Lys Arg Lys Gly Gly Ile Gly Gly
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Val Phe Ile His Asn Phe Lys Arg Lys Gly Gly Ile Gly Gly
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Val Phe Ile His Asn Phe Lys Arg Lys Gly Gly Ile Gly Gly
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Phe Asn Met Trp Lys Asn Asp Met Val Asp Gln Met His Glu
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Phe Asn Met Trp Lys Asn Asn Met Val Glu Gln Met His Glu
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Phe Asn Met Trp Lys Asn Asn Met Val Glu Gln Met His Glu
1               5                   10                  15
```

```
<210> SEQ ID NO 205
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 205

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Glu Gln Ser Thr Gln Glu Val Lys Asn Trp Met Thr Asp Thr Leu
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Gln Asp Val Lys Asn Trp Met Thr Asp Thr Leu Leu Ile Gln
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Asn Trp Met Thr Asp Thr Leu Leu Val Gln Asn Ala Asn Pro
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 209

Ile Val Gln Gln Gln Ser Asn Leu Leu Arg Ala Ile Glu Ala Gln Gln
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 210

Val Val Gln Gln Gln Ser Asn Leu Leu Arg Ala Ile Glu Ala Gln
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Gln Gln Gln Asn Asn Leu Leu Arg Ala Ile Glu Ala Gln His
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 212

Ala Val Phe Ile His Asn Phe Lys Arg Lys Gly Gly Ile Gly Gly Tyr
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Val Phe Ile His Asn Phe Lys Arg Lys Gly Gly Ile Gly Gly
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Leu Ile His Asn Phe Lys Arg Lys Gly Gly Ile Gly Gly Tyr
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 215

Ser Glu Leu Tyr Lys Tyr Lys Val Val Lys Ile Glu Pro Leu Gly
1               5                   10                  15

<210> SEQ ID NO 216

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Glu Leu Tyr Lys Tyr Lys Val Val Lys Ile Glu Pro Leu Gly
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 217

Asn Phe Asn Met Trp Lys Asn Asn Met Val Glu Gln Met His Glu
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asn Phe Asn Met Trp Lys Asn Asn Met Val Glu Gln Met His Glu
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 219

Gly Lys Lys Lys Tyr Arg Leu Lys His Leu Val Trp Ala Ser Arg
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Arg Lys Lys Tyr Arg Leu Lys His Ile Val Trp Ala Ser Arg
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 221
```

```
Asp Ile Lys Val Val Pro Arg Arg Lys Ala Lys Ile Ile Arg Asp
1               5                   10                  15
```

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

```
Asp Ile Lys Val Val Pro Arg Arg Lys Val Lys Ile Ile Arg Asp
1               5                   10                  15
```

<210> SEQ ID NO 223
<211> LENGTH: 20
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 223

```
Lys His Leu Val Trp Ala Ser Arg Glu Leu Glu Arg Phe Ala Leu Asn
1               5                   10                  15
Pro Gly Leu Leu
            20
```

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

```
Lys His Leu Val Trp Ala Ser Arg Glu Leu Glu Arg Phe Ala Leu
1               5                   10                  15
```

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

```
Ala Ser Arg Glu Leu Glu Arg Phe Ala Val Asn Pro Gly Leu Leu
1               5                   10                  15
```

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 226

```
Ile Val Gln Gln Gln Ser Asn Leu Leu Arg Ala Ile Glu Ala Gln Gln
1               5                   10                  15
```

<210> SEQ ID NO 227
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Val Val Gln Gln Gln Ser Asn Leu Leu Arg Ala Ile Glu Ala Gln
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Val Gln Gln Gln Asn Asn Leu Leu Arg Ala Ile Glu Ala Gln His
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 229

Ala Val Phe Ile His Asn Phe Lys Arg Lys Gly Gly Ile Gly Gly Tyr
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Val Phe Ile His Asn Phe Lys Arg Lys Gly Gly Ile Gly Gly
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val Leu Ile His Asn Phe Lys Arg Lys Gly Gly Ile Gly Gly Tyr
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 232

Lys Asn Trp Met Thr Asp Thr Leu Leu Val Gln Asn Ala Asn Pro
```

```
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Lys Asn Trp Met Thr Asp Thr Leu Leu Val Gln Asn Ala Asn Pro
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 234

Trp Lys Gly Ser Pro Ala Ile Phe Gln Ser Ser Met Thr Lys Ile
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Trp Lys Gly Ser Pro Ala Ile Phe Gln Ala Ser Met Thr Lys Ile
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 236

Gln Pro Ala Leu Gln Thr Gly Ser Glu Glu Leu Arg Ser Leu Tyr
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Pro Ala Leu Lys Thr Gly Ser Glu Glu Leu Arg Ser Leu Tyr
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
``` consensus sequence

<400> SEQUENCE: 238

Ile Val Gln Gln Gln Ser Asn Leu Leu Arg Ala Ile Glu Ala Gln
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Val Val Gln Gln Gln Ser Asn Leu Leu Arg Ala Ile Glu Ala Gln
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 240

Cys Ser Gly Lys Leu Ile Cys Thr Thr Thr Val Pro Trp Asn Ser
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Ser Gly Lys Leu Ile Cys Thr Thr Ala Val Pro Trp Asn Ser
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 242

Ala Lys Ala Tyr Asp Thr Glu Val His Asn Val Trp Ala Thr His
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Lys Ala Tyr Glu Lys Glu Val His Asn Val Trp Ala Thr His
1               5                   10                  15

<210> SEQ ID NO 244

```
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 244

Lys Lys Asp Ser Thr Lys Trp Arg Lys Leu Val Asp Phe Arg Glu
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Lys Asp Ser Thr Lys Trp Arg Lys Leu Val Asp Phe Arg Glu
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 246

Val Phe Ile His Asn Phe Lys Arg Lys Gly Gly Ile Gly Gly Tyr
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Val Leu Ile His Asn Phe Lys Arg Lys Gly Gly Ile Gly Gly Tyr
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 248

Asn Lys Ile Val Arg Met Tyr Ser Pro Val Ser Ile Leu Asp Ile
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249
```

```
Asn Lys Ile Val Arg Met Tyr Ser Pro Val Ser Ile Leu Asp Ile
1               5                   10                  15
```

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 250

```
Lys Gly Asn Ser Ser Lys Val Ser Gln Asn Tyr Pro Ile Val Gln
1               5                   10                  15
```

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

```
Thr Gly Asn Ser Ser Gln Val Ser Gln Asn Tyr Pro Ile Val Gln
1               5                   10                  15
```

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 252

```
Gly Cys Lys Gln Ile Ile Gly Gln Leu Gln Pro Ala Leu Gln Thr
1               5                   10                  15
```

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Gly Cys Arg Gln Ile Leu Gly Gln Leu Gln Pro Ser Leu Gln Thr
1               5                   10                  15
```

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 254

```
Pro Val His Ala Gly Pro Ile Pro Pro Gly Gln Met Arg Glu Pro
1               5                   10                  15
```

<210> SEQ ID NO 255
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 255

Pro Val Gln Ala Gly Pro Ile Ala Pro Gly Gln Met Arg Glu Pro
1               5                   10                  15

<210> SEQ ID NO 256
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 256

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Gln Ser Thr Gln Glu Val Lys Asn Trp Met Thr Asp Thr Leu
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Lys Asn Trp Met Thr Asp Thr Leu Leu Val Gln Asn Ala Asn Pro
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 259

Ile Val Gln Gln Gln Ser Asn Leu Leu Arg Ala Ile Glu Ala Gln Gln
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Val Gln Gln Gln Ser Asn Leu Leu Arg Ala Ile Glu Ala Gln

```
                   1               5                  10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Val Gln Gln Gln Asn Asn Leu Leu Arg Ala Ile Glu Ala Gln His
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 262

His Ser Asn Trp Arg Ala Met Ala Ser Asp Phe Asn Leu Pro Pro
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Ser Asn Trp Arg Ala Met Ala Ser Asp Phe Asn Leu Pro Pro
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 264

Gly Ser Pro Ala Ile Phe Gln Ser Ser Met Thr Lys Ile Leu Glu
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Ser Pro Ala Ile Phe Gln Ser Ser Met Thr Lys Ile Leu Asp
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued consensus sequence

<400> SEQUENCE: 266

Ile Ile Gly Asp Ile Arg Gln Ala His Cys Asn Ile Ser Gly Thr
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ile Thr Gly Asp Ile Arg Gln Ala His Cys Asn Val Ser Arg Ser
1               5                   10                  15

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 268

Ser Asn Trp Arg Ala Met Ala Ser Asp Phe Asn Leu Pro Pro Ile Val
1               5                   10                  15

Ala Lys

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ser Asn Trp Arg Ala Met Ala Ser Asp Phe Asn Leu Pro Pro
1               5                   10

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Arg Thr Met Ala Ser Asp Phe Asn Leu Pro Pro Val Val Ala Lys
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Lys Ala Met Ala Ser Asp Phe Asn Leu Pro Pro Ile Val Ala Lys
1               5                   10                  15

```
<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 272

Gly Ser Pro Ala Ile Phe Gln Ser Ser Met Thr Lys Ile Leu Glu
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Ser Pro Ala Ile Phe Gln Ser Ser Met Thr Lys Ile Leu Asp
1               5                   10                  15

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ala Ala Glu Trp Asp Arg Val His Pro Val His Ala Gly Pro Ile Ala
1               5                   10                  15

Pro Gly Gln

<210> SEQ ID NO 275
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ala Ala Glu Trp Asp Arg Leu His Pro Val His Ala Gly Pro Val Ala
1               5                   10                  15

Pro Gly Gln

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Ala Glu Asp Arg Leu His Pro Val His Ala Gly Pro Ile Pro
1               5                   10                  15

<210> SEQ ID NO 277
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 277

Ala Glu Trp Asp Arg Leu His Pro Val His Ala Gly Pro Ile Ala
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Asp Trp Asp Arg Leu His Pro Val His Ala Gly Pro Val Ala
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Asp Arg Val His Pro Val His Ala Gly Pro Asn Pro Pro Gly
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asp Arg Val His Pro Val His Ala Gly Pro Ile Pro Pro Gly Gln
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ile Val Gln Gln Gln Asn Asn Leu Leu Arg Ala Ile Glu Ala Gln Gln
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ile Val Gln Gln Gln Ser Asn Leu Leu Arg Ala Ile Glu Ala Gln Gln
1               5                   10                  15
```

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Val Val Gln Gln Gln Ser Asn Leu Leu Arg Ala Ile Glu Ala Gln
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Val Gln Gln Gln Asn Asn Leu Leu Arg Ala Ile Glu Ala Gln His
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Gln Gln Gln Ser Asn Leu Leu Lys Ala Ile Glu Ala Gln Gln
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Ser Gln Asp Val Lys Asn Trp Met Thr Glu Thr Leu Leu Val
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Thr Gln Asp Val Lys Asn Trp Met Thr Asp Thr Leu Leu Val
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 288

Ala Ser Gln Glu Val Lys Asn Trp Met Thr Glu Thr Leu Leu Ile
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Val Phe Ile His Asn Phe Lys Arg Lys Gly Gly Ile Gly Gly Tyr
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Val Phe Ile His Asn Phe Lys Arg Lys Gly Gly Ile Gly Glu Tyr
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Val Phe Ile His Asn Phe Lys Arg Lys Gly Gly Ile Gly Gly
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Val Leu Ile His Asn Phe Lys Arg Lys Gly Gly Ile Gly Gly Tyr
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Pro Leu Val Lys Leu Trp Tyr Gln Leu Glu Lys Asp Pro Ile Ala
1               5                   10                  15

<210> SEQ ID NO 294
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 294

Pro Leu Val Lys Leu Trp Tyr Gln Leu Glu Lys Glu Pro Ile Val
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Pro Leu Val Lys Leu Trp Tyr Gln Leu Glu Lys Glu Pro Ile Val
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Ile Pro Ser Thr Asn Asn Glu Thr Pro Gly Ile Arg Tyr Gln
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Thr Ile Pro Ser Ile Asn Asn Glu Thr Pro Gly Ile Arg Tyr Gln
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Thr Ile Pro Ser Ile Asn Asn Glu Thr Pro Gly Ile Arg Tyr Gln
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Pro Gly Ile Lys Val Arg Gln Leu Cys Lys Leu Leu Arg Gly
1               5                   10                  15
```

```
<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Tyr Ala Gly Ile Lys Val Lys Gln Leu Cys Lys Leu Leu Arg Gly
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Pro Gly Ile Lys Val Arg Gln Leu Cys Lys Leu Leu Arg Gly
1               5                   10                  15

<210> SEQ ID NO 302
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Leu Ile Lys Lys Glu Arg Val Tyr Leu Ser Trp Val Pro Ala His Lys
1               5                   10                  15

Gly Ile Gly

<210> SEQ ID NO 303
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Leu Ile Lys Lys Glu Lys Val Tyr Leu Ala Trp Val Pro Ala His Lys
1               5                   10                  15

Gly Ile Gly

<210> SEQ ID NO 304
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Ile Lys Lys Glu Arg Val Tyr Leu Ser Trp Val Pro Ala His
1               5                   10                  15

<210> SEQ ID NO 305
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 305

Glu Lys Val Tyr Leu Ser Trp Val Pro Ala His Lys Gly Ile Gly
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Leu Tyr Asn Thr Val Ala Thr Leu Tyr Cys Val His Gln Arg
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Leu Phe Asn Thr Val Ala Thr Leu Tyr Cys Val His Ala Glu
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Leu Tyr Asn Thr Val Ala Thr Leu Tyr Cys Val His Gln Arg
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ala Asn Pro Asp Cys Lys Thr Ile Leu Lys Ala Leu Gly Pro Ala
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ala Asn Pro Asp Cys Lys Thr Ile Leu Arg Ala Leu Gly Pro Gly
1               5                   10                  15
```

```
<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Asn Pro Asp Cys Lys Thr Ile Leu Arg Ala Leu Gly Pro Gly
1               5                   10                  15

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Glu Gln Leu Ile Lys Lys Glu Arg Val Tyr Leu Ser Trp Val Pro Ala
1               5                   10                  15

His Lys Gly Ile Gly
            20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Glu Gln Leu Ile Lys Lys Glu Lys Val Tyr Leu Ala Trp Val Pro Ala
1               5                   10                  15

His Lys Gly Ile Gly
            20

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Glu Pro Leu Ile Lys Lys Glu Lys Val Tyr Leu Ser Trp Val Pro
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Lys Leu Ile Glu Lys Asp Lys Val Tyr Leu Ser Trp Val Pro Ala
1               5                   10                  15

<210> SEQ ID NO 316
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Leu Ile Lys Lys Glu Arg Val Tyr Leu Ser Trp Val Pro Ala His
1               5                   10                  15

<210> SEQ ID NO 317
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Glu Lys Val Tyr Leu Ala Trp Val Pro Ala His Lys Gly Ile Gly
1               5                   10                  15

<210> SEQ ID NO 318
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Lys Val Tyr Leu Ser Trp Val Pro Ala His Lys Gly Ile Gly
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ile Val Gln Gln Gln Asn Asn Leu Leu Arg Ala Ile Glu Ala Gln Gln
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ile Val Gln Gln Gln Ser Asn Leu Leu Arg Ala Ile Glu Ala Gln Gln
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321
```

```
Val Val Gln Gln Gln Ser Asn Leu Leu Arg Ala Ile Glu Ala Gln
1               5                  10                  15

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Gln Gln Gln Asn Asn Leu Leu Arg Ala Ile Glu Ala Gln His
1               5                  10                  15

<210> SEQ ID NO 323
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Gln Ala Ser Gln Asp Val Lys Asn Trp Met Thr Glu Thr Leu Leu
1               5                  10                  15

Val Gln Asn Ala Asn Pro
            20

<210> SEQ ID NO 324
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Glu Gln Ala Thr Gln Asp Val Lys Asn Trp Met Thr Asp Thr Leu Leu
1               5                  10                  15

Val Gln Asn Ala Asn Pro
            20

<210> SEQ ID NO 325
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Gln Ser Thr Gln Glu Val Lys Asn Trp Met Thr Asp Thr Leu
1               5                  10                  15

<210> SEQ ID NO 326
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Lys Asn Trp Met Thr Asp Thr Leu Leu Val Gln Asn Ala Asn Pro
1               5                  10                  15
```

<210> SEQ ID NO 327
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

His Ser Asn Trp Arg Ala Met Ala Ser Asp Phe Asn Leu Pro Pro Val
1               5                   10                  15

Val Ala Lys

<210> SEQ ID NO 328
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

His Ser Asn Trp Arg Ala Met Ala Ser Glu Phe Asn Leu Pro Pro Ile
1               5                   10                  15

Val Ala Lys

<210> SEQ ID NO 329
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

His Ser Asn Trp Arg Ala Met Ala Ser Asp Phe Asn Leu Pro Pro
1               5                   10                  15

<210> SEQ ID NO 330
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Asn Trp Arg Ala Met Ala Ser Glu Phe Asn Leu Pro Pro Ile
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asn Trp Arg Thr Met Ala Ser Asp Phe Asn Leu Pro Pro Val Ile
1               5                   10                  15

<210> SEQ ID NO 332
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 332

Arg Thr Met Ala Ser Asp Phe Asn Leu Pro Pro Val Val Ala Lys
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Lys Ala Met Ala Ser Asp Phe Asn Leu Pro Pro Ile Val Ala Lys
1               5                   10                  15

<210> SEQ ID NO 334
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ala Glu Trp Asp Arg Val His Pro Val His Ala Gly Pro Ile Ala Pro
1               5                   10                  15

Gly Gln

<210> SEQ ID NO 335
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Glu Trp Asp Arg Leu His Pro Val His Ala Gly Pro Val Ala Pro
1               5                   10                  15

Gly Gln

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Ala Glu Asp Arg Leu His Pro Val His Ala Gly Pro Ile Pro
1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337
```

Ala Asp Trp Asp Arg Leu His Pro Val His Ala Gly Pro Val Ala
1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ala Glu Trp Asp Arg Leu His Pro Val His Ala Gly Pro Ile Ala
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Trp Asp Arg Val His Pro Val His Ala Gly Pro Asn Pro Pro Gly
1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asp Arg Val His Pro Val His Ala Gly Pro Ile Pro Pro Gly Gln
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ala Val Phe Ile His Asn Phe Lys Arg Lys Gly Gly Ile Gly Gly Tyr
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Val Phe Ile His Asn Phe Lys Arg Lys Gly Gly Ile Gly Glu Tyr
1               5                   10                  15

<210> SEQ ID NO 343
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 343

Ala Val Phe Ile His Asn Phe Lys Arg Lys Gly Gly Ile Gly Gly
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Val Leu Ile His Asn Phe Lys Arg Lys Gly Gly Ile Gly Gly Tyr
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Pro Leu Asp Glu Gly Phe Arg Lys Tyr Thr Ala Phe Thr Ile Pro
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Pro Leu Asp Glu Asp Phe Arg Lys Tyr Thr Ala Phe Thr Ile Pro
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Pro Leu Asp Glu Ser Phe Arg Lys Tyr Thr Ala Phe Thr Ile Pro
1               5                   10                  15

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Thr Arg Ile Leu Glu Pro Phe Arg Ala Lys Asn Pro Glu Ile Val
1               5                   10                  15
```

<210> SEQ ID NO 349
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Thr Lys Ile Leu Glu Pro Phe Arg Lys Gln Asn Pro Asp Ile Val
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Thr Lys Ile Leu Glu Pro Phe Arg Ala Gln Asn Pro Glu Leu Val
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ile Cys Glu Glu Met Glu Lys Glu Gly Lys Ile Thr Lys Ile Gly
1               5                   10                  15

<210> SEQ ID NO 352
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ile Cys Thr Glu Met Glu Lys Glu Gly Lys Ile Ser Lys Ile Gly
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ile Cys Thr Glu Met Glu Lys Glu Gly Lys Ile Ser Lys Ile Gly
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Val Lys Leu Trp Tyr Gln Leu Glu Lys Asp Pro Ile Ala Gly Val
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Val Lys Leu Trp Tyr Gln Leu Glu Lys Glu Pro Ile Val Gly Ala
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Val Lys Leu Trp Tyr Gln Leu Glu Lys Asp Pro Ile Val Gly Ala
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Asp Ile Ile Gly Asp Ile Arg Gln Ala His Cys Asn Ile Ser
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Asp Ile Ile Gly Asp Ile Arg Gln Ala His Cys Asn Leu Ser
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gly Asp Ile Ile Gly Asp Ile Arg Gln Ala His Cys Asn Ile Ser
1               5                   10                  15

<210> SEQ ID NO 360
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 360

Ile Cys Thr Thr Thr Val Pro Trp Asn Ala Ser Trp Ser Asn Lys
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ile Cys Thr Thr Ala Val Pro Trp Asn Thr Ser Trp Ser Asn Lys
1               5                   10                  15

<210> SEQ ID NO 362
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ile Cys Thr Thr Thr Val Pro Trp Asn Ala Ser Trp Ser Asn Arg
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ile Gly Gln Val Arg Asp Gln Ala Glu His Leu Lys Thr Ala Val
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Gly Gln Val Arg Asp Gln Ala Glu His Leu Lys Thr Ala Val
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Gly Gln Val Arg Glu Gln Ala Glu His Leu Lys Thr Ala Val
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Lys Gln Met Ala Gly Ala Asp Cys Val Ala Gly Arg Gln Asp
1               5                   10                  15

<210> SEQ ID NO 367
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Lys Gln Met Ala Gly Asp Asp Cys Val Ala Ser Arg Gln Asp
1               5                   10                  15

<210> SEQ ID NO 368
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Lys Gln Met Ala Gly Asp Asp Cys Val Ala Gly Arg Gln Asp
1               5                   10                  15

<210> SEQ ID NO 369
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Lys Tyr Ala Lys Met Arg Thr Ala His Thr Asn Asp Val Lys Gln
1               5                   10                  15

<210> SEQ ID NO 370
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Lys Tyr Ala Arg Met Arg Gly Ala His Thr Asn Asp Val Lys Gln
1               5                   10                  15

<210> SEQ ID NO 371
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Lys Tyr Ala Lys Met Arg Thr Ala His Thr Asn Asp Val Arg Gln
1               5                   10                  15

<210> SEQ ID NO 372
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Gly Asp Ile Ile Gly Asp Ile Arg Gln Ala His Cys Asn Ile
1               5                   10                  15

<210> SEQ ID NO 373
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Thr Gly Asp Ile Ile Gly Asp Ile Arg Gln Ala His Cys Asn Leu
1               5                   10                  15

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Thr Gly Glu Ile Ile Gly Asp Ile Arg Gln Ala His Cys Asn Leu
1               5                   10                  15

<210> SEQ ID NO 375
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Asn Gln Gln Glu Lys Asn Glu Lys Asp Leu Leu Ala Leu Asp Ser
1               5                   10                  15

<210> SEQ ID NO 376
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Asn Gln Gln Glu Lys Asn Glu Gln Glu Leu Leu Glu Leu Asp Lys
1               5                   10                  15

<210> SEQ ID NO 377
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Asn Gln Gln Glu Lys Asn Glu Gln Asp Leu Leu Ala Leu Asp Lys
1               5                   10                  15

<210> SEQ ID NO 378
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Asp Ile Lys Val Val Pro Arg Arg Lys Val Lys Ile Ile Lys Asp
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Asp Ile Lys Val Val Pro Arg Arg Lys Ala Lys Ile Ile Arg Asp
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Asp Ile Lys Val Val Pro Arg Arg Lys Val Lys Ile Ile Arg Asp
1               5                   10                  15

<210> SEQ ID NO 381
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Leu Ile Lys Lys Glu Arg Val Tyr Leu Ser Trp Val Pro Ala His Lys
1               5                   10                  15

Gly Ile Gly

<210> SEQ ID NO 382
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382
```

```
Leu Ile Lys Lys Glu Lys Val Tyr Leu Ala Trp Val Pro Ala His Lys
1               5                   10                  15

Gly Ile Gly

<210> SEQ ID NO 383
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Leu Ile Lys Lys Glu Arg Val Tyr Leu Ser Trp Val Pro Ala His
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Glu Lys Val Tyr Leu Ser Trp Val Pro Ala His Lys Gly Ile Gly
1               5                   10                  15

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ile Val Gln Gln Gln Asn Asn Leu Leu Arg Ala Ile Glu Ala Gln Gln
1               5                   10                  15

His Leu Leu Gln Leu
            20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ile Val Gln Gln Gln Ser Asn Leu Leu Arg Ala Ile Glu Ala Gln Gln
1               5                   10                  15

His Met Leu Gln Leu
            20

<210> SEQ ID NO 387
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387
```

```
Val Val Gln Gln Gln Ser Asn Leu Leu Arg Ala Ile Glu Ala Gln
1               5                   10                  15
```

<210> SEQ ID NO 388
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

```
Val Gln Gln Gln Ser Asn Leu Leu Lys Ala Ile Glu Ala Gln Gln
1               5                   10                  15
```

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

```
Val Gln Gln Gln Asn Asn Leu Leu Arg Ala Ile Glu Ala Gln His
1               5                   10                  15
```

<210> SEQ ID NO 390
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

```
Asn Leu Leu Arg Ala Ile Glu Ala Gln Gln His Leu Leu Gln Leu
1               5                   10                  15
```

<210> SEQ ID NO 391
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

```
Ala Val Phe Ile His Asn Phe Lys Arg Lys Gly Gly Ile Gly Gly Tyr
1               5                   10                  15
```

<210> SEQ ID NO 392
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

```
Ala Val Phe Ile His Asn Phe Lys Arg Lys Gly Gly Ile Gly Glu Tyr
1               5                   10                  15
```

<210> SEQ ID NO 393
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 393

Ala Val Phe Ile His Asn Phe Lys Arg Lys Gly Gly Ile Gly Gly
1               5                   10                  15

<210> SEQ ID NO 394
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Val Leu Ile His Asn Phe Lys Arg Lys Gly Gly Ile Gly Gly Tyr
1               5                   10                  15

<210> SEQ ID NO 395
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Glu Gln Ala Ser Gln Asp Val Lys Asn Trp Met Thr Glu Thr Leu Leu
1               5                   10                  15

Val Gln Asn Ala Asn Pro
            20

<210> SEQ ID NO 396
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 397
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Glu Gln Ala Ser Gln Asp Val Lys Asn Trp Met Thr Glu Thr Leu
1               5                   10                  15

<210> SEQ ID NO 398
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Glu Gln Ser Thr Gln Glu Val Lys Asn Trp Met Thr Asp Thr Leu
1               5                   10                  15

<210> SEQ ID NO 399
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ala Ser Gln Glu Val Lys Asn Trp Met Thr Glu Thr Leu Leu Ile
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Thr Gln Asp Val Lys Asn Trp Met Thr Asp Thr Leu Leu Ile Gln
1               5                   10                  15

<210> SEQ ID NO 401
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Lys Asn Trp Met Thr Glu Thr Leu Leu Val Gln Asn Ala Asn Pro
1               5                   10                  15

<210> SEQ ID NO 402
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Lys Asn Trp Met Thr Asp Thr Leu Leu Val Gln Asn Ala Asn Pro
1               5                   10                  15

<210> SEQ ID NO 403
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ala Glu Trp Asp Arg Val His Pro Val His Ala Gly Pro Ile Ala Pro
1               5                   10                  15

Gly Gln

<210> SEQ ID NO 404

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ala Glu Trp Asp Arg Leu His Pro Val His Ala Gly Pro Val Ala Pro
1               5                   10                  15

Gly Gln

<210> SEQ ID NO 405
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Ala Glu Asp Arg Leu His Pro Val His Ala Gly Pro Ile Pro
1               5                   10                  15

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ala Glu Trp Asp Arg Leu His Pro Val His Ala Gly Pro Ile Ala
1               5                   10                  15

<210> SEQ ID NO 407
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Asp Arg Val His Pro Val His Ala Gly Pro Ile Pro Pro Gly Gln
1               5                   10                  15

<210> SEQ ID NO 408
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Trp Lys Gly Ser Pro Ala Ile Phe Gln Cys Ser Met Thr Arg Ile
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 409

Trp Lys Gly Ser Pro Ala Ile Phe Gln Ser Ser Met Thr Lys Ile
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Trp Lys Gly Ser Pro Ala Ile Phe Gln Cys Ser Met Thr Lys Ile
1               5                   10                  15

<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Met Thr Arg Ile Leu Glu Pro Phe Arg Ala Lys Asn Pro Glu Ile
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Met Thr Lys Ile Leu Glu Pro Phe Arg Lys Gln Asn Pro Asp Ile
1               5                   10                  15

<210> SEQ ID NO 413
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Met Thr Lys Ile Leu Glu Pro Phe Arg Lys Gln Asn Pro Asp Ile
1               5                   10                  15

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Ser Pro Ala Ile Phe Gln Cys Ser Met Thr Arg Ile Leu Glu
1               5                   10                  15

<210> SEQ ID NO 415
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 415

Gly Ser Pro Ala Ile Phe Gln Ser Ser Met Thr Lys Ile Leu Glu
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Ser Pro Ala Ile Phe Gln Ser Ser Met Thr Lys Ile Leu Asp
1               5                   10                  15

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

His Gly Gln Val Asp Cys Ser Pro Gly Ile Trp Gln Leu Ala Cys
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

His Gly Gln Val Asp Cys Ser Pro Gly Ile Trp Gln Leu Ala Cys
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

His Gly Gln Val Asp Cys Ser Pro Gly Ile Trp Gln Leu Asp Cys
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Asp Arg Phe Tyr Lys Thr Leu Arg Ala Glu Gln Ala Ser Gln Asp
1               5                   10                  15
```

```
<210> SEQ ID NO 421
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Asp Arg Phe Phe Lys Thr Leu Arg Ala Glu Gln Ala Thr Gln Asp
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Asp Arg Phe Tyr Lys Thr Leu Arg Ala Glu Gln Ala Ser Gln Glu
1               5                   10                  15

<210> SEQ ID NO 423
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Leu Ile Lys Lys Glu Arg Val Tyr Leu Ser Trp Val Pro Ala His Lys
1               5                   10                  15

Gly Ile Gly

<210> SEQ ID NO 424
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Leu Ile Lys Lys Glu Lys Val Tyr Leu Ala Trp Val Pro Ala His Lys
1               5                   10                  15

Gly Ile Gly

<210> SEQ ID NO 425
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Leu Ile Lys Lys Glu Arg Val Tyr Leu Ser Trp Val Pro Ala His
1               5                   10                  15

<210> SEQ ID NO 426
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 426

Glu Lys Val Tyr Leu Ser Trp Val Pro Ala His Lys Gly Ile Gly
1               5                   10                  15

<210> SEQ ID NO 427
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Glu Trp Asp Arg Val His Pro Val His Ala Gly Pro Ile Ala Pro
1               5                   10                  15

Gly Gln

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ala Glu Trp Asp Arg Leu His Pro Val His Ala Gly Pro Val Ala Pro
1               5                   10                  15

Gly Gln

<210> SEQ ID NO 429
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Ala Glu Trp Asp Arg Leu His Pro Val His Ala Gly Pro Ile Ala
1               5                   10                  15

<210> SEQ ID NO 430
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Asp Arg Val His Pro Val His Ala Gly Pro Ile Pro Pro Gly Gln
1               5                   10                  15

<210> SEQ ID NO 431
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 431

Ala Ile Phe Gln Cys Ser Met Thr Arg Ile Leu Glu Pro Phe Arg
1               5                   10                  15

<210> SEQ ID NO 432
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ile Phe Gln Ser Ser Met Thr Lys Ile Leu Glu Pro Phe Arg
1               5                   10                  15

<210> SEQ ID NO 433
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ala Ile Phe Gln Ser Ser Met Thr Arg Ile Leu Glu Pro Phe Arg
1               5                   10                  15

<210> SEQ ID NO 434
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ala Ser Gln Ile Tyr Pro Gly Ile Lys Val Arg Gln Leu Cys Lys
1               5                   10                  15

<210> SEQ ID NO 435
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Ala Ser Gln Ile Tyr Ala Gly Ile Lys Val Lys Gln Leu Cys Lys
1               5                   10                  15

<210> SEQ ID NO 436
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Trp Ser Gln Ile Tyr Ala Gly Ile Lys Val Arg Gln Leu Cys Lys
1               5                   10                  15

<210> SEQ ID NO 437
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 437

Arg Glu Leu Asn Lys Arg Thr Gln Asp Phe Trp Glu Val Gln Leu
1               5                   10                  15

<210> SEQ ID NO 438
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Arg Glu Leu Asn Lys Arg Thr Gln Asp Phe Trp Glu Val Gln Leu
1               5                   10                  15

<210> SEQ ID NO 439
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Arg Glu Leu Asn Arg Arg Thr Gln Asp Phe Trp Glu Val Gln Leu
1               5                   10                  15

<210> SEQ ID NO 440
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Leu Leu Arg Ala Ile Glu Ala Gln Gln His Leu Leu Gln Leu Thr
1               5                   10                  15

<210> SEQ ID NO 441
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Leu Leu Arg Ala Ile Glu Ala Gln Gln His Met Leu Gln Leu Thr
1               5                   10                  15

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Leu Leu Met Ala Ile Glu Ala Gln Gln His Leu Leu Gln Leu Thr
1               5                   10                  15
```

<210> SEQ ID NO 443
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Leu Ile Cys Thr Thr Thr Val Pro Trp Asn Ala Ser Trp Ser Asn
1               5                   10                  15

<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Ile Cys Thr Thr Ala Val Pro Trp Asn Thr Ser Trp Ser Asn
1               5                   10                  15

<210> SEQ ID NO 445
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

His Ile Cys Thr Thr Asn Val Pro Trp Asn Ala Ser Trp Ser Asn
1               5                   10                  15

<210> SEQ ID NO 446
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Lys His Ile Val Trp Ala Ser Arg Glu Leu Glu Arg Phe Ala Val
1               5                   10                  15

<210> SEQ ID NO 447
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Lys His Leu Val Trp Ala Ser Arg Glu Leu Glu Arg Phe Ala Leu
1               5                   10                  15

<210> SEQ ID NO 448
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 448

Lys His Leu Val Trp Ala Ser Arg Glu Leu Glu Arg Phe Ala Leu
1               5                   10                  15

<210> SEQ ID NO 449
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Arg Ser Leu Tyr Asn Thr Val Ala Thr Leu Tyr Cys Val His Gln
1               5                   10                  15

<210> SEQ ID NO 450
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Ser Leu Phe Asn Thr Val Ala Thr Leu Tyr Cys Val His Ala
1               5                   10                  15

<210> SEQ ID NO 451
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Lys Ser Leu Tyr Asn Thr Val Ala Val Leu Tyr Cys Val His Gln
1               5                   10                  15

<210> SEQ ID NO 452
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Glu Glu Lys Ala Phe Ser Pro Glu Val Ile Pro Met Phe Ser Ala
1               5                   10                  15

<210> SEQ ID NO 453
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Glu Glu Lys Ala Phe Ser Pro Glu Val Ile Pro Met Phe Thr Ala
1               5                   10                  15

<210> SEQ ID NO 454
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Glu Glu Lys Ala Phe Ser Pro Glu Val Ile Pro Met Phe Ser Ala
1               5                   10                  15

<210> SEQ ID NO 455
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Trp Lys Gly Ser Pro Ala Ile Phe Gln Cys Ser Met Thr Arg Ile Leu
1               5                   10                  15

Glu Pro Phe Arg Ala
            20

<210> SEQ ID NO 456
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Trp Lys Gly Ser Pro Ala Ile Phe Gln Ser Ser Met Thr Lys Ile Leu
1               5                   10                  15

Glu Pro Phe Arg Lys
            20

<210> SEQ ID NO 457
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Trp Lys Gly Ser Pro Ala Ile Phe Gln Ala Ser Met Thr Lys Ile
1               5                   10                  15

<210> SEQ ID NO 458
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Gly Ser Pro Ala Ile Phe Gln Ser Ser Met Thr Lys Ile Leu Asp
1               5                   10                  15

<210> SEQ ID NO 459
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 459

Ile Phe Gln Cys Ser Met Thr Lys Ile Leu Glu Pro Phe Arg Ala
1               5                   10                  15

<210> SEQ ID NO 460
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Lys Ala Arg Val Leu Ala Glu Ala Met Ser Gln Val Thr Asn Ser Ala
1               5                   10                  15

Thr

<210> SEQ ID NO 461
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Lys Ala Arg Val Leu Ala Glu Ala Met Ser Gln Thr Asn Ser Thr Ile
1               5                   10                  15

Leu

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Lys Ala Lys Val Leu Ala Glu Ala Met Ser Gln Val Gln Gln Thr
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Arg Val Leu Ala Glu Ala Met Ser Gln Val Thr Asn Ser Ala Thr
1               5                   10                  15

<210> SEQ ID NO 464
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

```
Ser Asp Leu Glu Ile Gly Gln His Arg Ala Lys Ile Glu Glu Leu Arg
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ser Asp Leu Glu Ile Gly Gln His Arg Thr Lys Ile Glu Glu Leu Arg
1               5                   10                  15

<210> SEQ ID NO 466
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ser Asp Leu Glu Ile Gly Gln His Arg Ile Lys Ile Glu Glu Leu
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Leu Glu Ile Gly Gln His Arg Ala Lys Ile Glu Glu Leu Arg
1               5                   10                  15

<210> SEQ ID NO 468
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gln Met His Glu Asp Ile Ile Ser Leu Trp Asp Gln Ser Leu Lys Pro
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gln Met His Glu Asp Ile Ile Arg Leu Trp Asp Gln Ser Leu Lys Pro
1               5                   10                  15

<210> SEQ ID NO 470
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 470

His Met His Glu Asp Ile Ile Ser Leu Trp Asp Glu Ser Leu Lys
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Met His Glu Asp Val Ile Ser Leu Trp Asp Gln Ser Leu Lys Pro
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Glu Glu Lys Ala Phe Ser Pro Glu Val Ile Pro Met Phe Ser Ala Leu
1               5                   10                  15

<210> SEQ ID NO 473
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Glu Glu Lys Ala Phe Ser Pro Glu Val Ile Pro Met Phe Thr Ala Leu
1               5                   10                  15

<210> SEQ ID NO 474
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Glu Glu Lys Ala Phe Ser Pro Glu Val Ile Pro Met Phe Ser Ala
1               5                   10                  15

<210> SEQ ID NO 475
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Glu Glu Lys Gly Phe Asn Pro Glu Val Ile Pro Met Phe Ser Ala
1               5                   10                  15
```

```
<210> SEQ ID NO 476
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Glu Lys Gly Phe Ser Pro Glu Val Ile Pro Met Phe Thr Ala Leu
1               5                   10                  15

<210> SEQ ID NO 477
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Lys Tyr Thr Ala Phe Thr Ile Pro Ser Thr Asn Asn Glu Thr Pro
1               5                   10                  15

<210> SEQ ID NO 478
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Lys Tyr Thr Ala Phe Thr Ile Pro Ser Ile Asn Asn Glu Thr Pro
1               5                   10                  15

<210> SEQ ID NO 479
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Lys Tyr Thr Ala Phe Thr Ile Pro Ser Thr Asn Asn Glu Thr Pro
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Glu Lys Ile Lys Ala Leu Thr Ala Ile Cys Glu Glu Met Glu Lys
1               5                   10                  15

<210> SEQ ID NO 481
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481
```

Glu Lys Ile Lys Ala Leu Val Glu Ile Cys Thr Glu Met Glu Lys
1               5                   10                  15

<210> SEQ ID NO 482
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Glu Lys Ile Glu Ala Leu Thr Ala Ile Cys Glu Glu Met Glu Lys
1               5                   10                  15

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Gly Lys Tyr Ala Lys Met Arg Thr Ala His Thr Asn Asp Val Lys
1               5                   10                  15

<210> SEQ ID NO 484
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Lys Tyr Ala Arg Met Arg Gly Ala His Thr Asn Asp Val Lys
1               5                   10                  15

<210> SEQ ID NO 485
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gly Lys Tyr Ala Arg Met Arg Gly Ala His Thr Asn Asp Val Arg
1               5                   10                  15

<210> SEQ ID NO 486
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Leu Pro Ile Gln Lys Glu Thr Trp Glu Thr Trp Trp Thr Asp Tyr
1               5                   10                  15

<210> SEQ ID NO 487
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 487

Leu Pro Ile Gln Lys Glu Thr Trp Glu Ala Trp Trp Thr Glu Tyr
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Leu Pro Ile Gln Lys Glu Thr Trp Glu Ala Trp Trp Thr Glu Tyr
1               5                   10                  15

<210> SEQ ID NO 489
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Trp Tyr Gln Leu Glu Lys Asp Pro Ile Ala Gly Val Glu Thr Phe
1               5                   10                  15

<210> SEQ ID NO 490
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Trp Tyr Gln Leu Glu Lys Glu Pro Ile Val Gly Ala Glu Thr Phe
1               5                   10                  15

<210> SEQ ID NO 491
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Trp Tyr Gln Leu Glu Lys Asp Pro Ile Ala Gly Ala Glu Thr Phe
1               5                   10                  15

<210> SEQ ID NO 492
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Glu Asn Val Thr Glu Asn Phe Asn Met Trp Lys Asn Asn Met Val
1               5                   10                  15
```

<210> SEQ ID NO 493
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Glu Asn Val Thr Glu Asn Phe Asn Met Trp Lys Asn Asp Met Val
1               5                   10                  15

<210> SEQ ID NO 494
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Glu Asn Val Thr Glu Glu Phe Asn Met Trp Lys Asn Asn Met Val
1               5                   10                  15

<210> SEQ ID NO 495
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Val Ile Gln Asp Asn Ser Asp Ile Lys Val Val Pro Arg Arg Lys
1               5                   10                  15

<210> SEQ ID NO 496
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Val Ile Gln Asp Asn Ser Asp Ile Lys Val Val Pro Arg Arg Lys
1               5                   10                  15

<210> SEQ ID NO 497
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Val Ile Gln Asp Asn Ser Asp Ile Lys Val Val Pro Arg Arg Lys
1               5                   10                  15

<210> SEQ ID NO 498
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 498

Val Ser Gln Asn Tyr Pro Ile Val Gln Asn Ile Gln Gly Gln Met
1               5                   10                  15

<210> SEQ ID NO 499
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Val Ser Gln Asn Tyr Pro Ile Val Gln Asn Leu Gln Gly Gln Met
1               5                   10                  15

<210> SEQ ID NO 500
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Val Ser Gln Asn Tyr Pro Ile Val Asn Leu Gln Gly Gln Met
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Val Leu Ala Glu Ala Met Ser Gln Val Thr Asn Ser Ala Thr Ile Met
1               5                   10                  15

<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Val Leu Ala Glu Ala Met Ser Gln Thr Asn Ser Thr Ile Leu Met
1               5                   10                  15

<210> SEQ ID NO 503
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Val Leu Ala Glu Ala Met Ser Gln Ala Gln Gln Thr Asn Ile Met
1               5                   10                  15

<210> SEQ ID NO 504
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 504

His Gly Gln Val Asp Cys Ser Pro Gly Ile Trp Gln Leu Ala Cys
1               5                   10                  15

<210> SEQ ID NO 505
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

His Gly Gln Val Asp Cys Ser Pro Gly Ile Trp Gln Leu Ala Cys
1               5                   10                  15

<210> SEQ ID NO 506
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

His Gly Gln Val Asp Cys Ser Pro Gly Ile Trp Gln Leu Asp Cys
1               5                   10                  15

<210> SEQ ID NO 507
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Arg Val Leu Ala Glu Ala Met Ser Gln Val Thr Asn Ser Ala Thr
1               5                   10                  15

<210> SEQ ID NO 508
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Arg Val Leu Ala Glu Ala Met Ser Gln Thr Asn Ser Thr Ile Leu
1               5                   10                  15

<210> SEQ ID NO 509
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Arg Val Leu Ala Glu Ala Met Ser Gln Thr Asn Ser Ala Ile Leu
1               5                   10                  15
```

<210> SEQ ID NO 510
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Glu Gln Leu Ile Lys Lys Glu Arg Val Tyr Leu Ser Trp Val Pro Ala
1               5                   10                  15

His Lys Gly Ile Gly
            20

<210> SEQ ID NO 511
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Glu Gln Leu Ile Lys Lys Glu Lys Val Tyr Leu Ala Trp Val Pro Ala
1               5                   10                  15

His Lys Gly Ile Gly
            20

<210> SEQ ID NO 512
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Glu Glu Leu Ile Lys Lys Glu Lys Val Tyr Leu Ala Trp Val Pro
1               5                   10                  15

<210> SEQ ID NO 513
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Glu Pro Leu Ile Lys Lys Glu Lys Val Tyr Leu Ser Trp Val Pro
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Lys Leu Ile Glu Lys Asp Lys Val Tyr Leu Ser Trp Val Pro Ala
1               5                   10                  15

<210> SEQ ID NO 515

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Leu Ile Lys Lys Glu Arg Val Tyr Leu Ser Trp Val Pro Ala His
1               5                   10                  15

<210> SEQ ID NO 516
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Glu Lys Val Tyr Leu Ala Trp Val Pro Ala His Lys Gly Ile Gly
1               5                   10                  15

<210> SEQ ID NO 517
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Glu Lys Val Tyr Leu Ser Trp Val Pro Ala His Lys Gly Ile Gly
1               5                   10                  15

<210> SEQ ID NO 518
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Cys Thr His Gly Ile Arg Pro Val Val Ser Thr Gln Leu Leu Leu
1               5                   10                  15

<210> SEQ ID NO 519
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Cys Thr His Gly Ile Lys Pro Val Val Ser Thr Gln Leu Leu Leu
1               5                   10                  15

<210> SEQ ID NO 520
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520
```

```
Cys Thr His Gly Ile Lys Pro Val Val Ser Thr Gln Leu Leu Leu
1               5                   10                  15
```

<210> SEQ ID NO 521
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

```
Cys Thr His Gly Ile Arg Pro Val Val Ser Thr Gln Leu Leu Leu
1               5                   10                  15
```

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

```
Ile Cys Thr Thr Thr Val Pro Trp Asn Ala Ser Trp Ser Asn Lys Ser
1               5                   10                  15

Leu
```

<210> SEQ ID NO 523
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

```
Ile Cys Thr Thr Ala Val Pro Trp Asn Thr Ser Trp Ser Asn Lys Ser
1               5                   10                  15

Gln
```

<210> SEQ ID NO 524
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

```
Ile Cys Thr Thr Thr Val Pro Trp Asn Ala Ser Trp Ser Asn Arg
1               5                   10                  15
```

<210> SEQ ID NO 525
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

```
Cys Thr Thr Thr Val Pro Trp Asn Ser Ser Trp Ser Asn Lys Thr
1               5                   10                  15
```

<210> SEQ ID NO 526

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Thr Thr Ala Val Pro Trp Asn Ala Ser Trp Ser Asn Lys Ser Leu
1               5                   10                  15

<210> SEQ ID NO 527
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Thr Thr Ala Val Pro Trp Asn Thr Ser Trp Ser Asn Lys Ser Leu
1               5                   10                  15

<210> SEQ ID NO 528
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ala Cys Gln Gly Val Gly Gly Pro Gly His Lys Ala Arg Val Leu Ala
1               5                   10                  15

Glu Ala Met Ser
            20

<210> SEQ ID NO 529
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Ala Cys Gln Gly Val Gly Gly Pro Ser His Lys Ala Arg Val Leu Ala
1               5                   10                  15

Glu Ala Met Ser
            20

<210> SEQ ID NO 530
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Ala Cys Gln Glu Val Gly Gly Pro Gly His Lys Ala Arg Val Leu
1               5                   10                  15

<210> SEQ ID NO 531
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 531

Gly Gly Pro Ser His Lys Ala Arg Val Leu Ala Glu Ala Met Gly
1               5                   10                  15

<210> SEQ ID NO 532
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ala Ala Glu Trp Asp Arg Val His Pro Val His Ala Gly Pro Ile Ala
1               5                   10                  15

Pro Gly Gln

<210> SEQ ID NO 533
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ala Ala Glu Trp Asp Arg Leu His Pro Val His Ala Gly Pro Val Ala
1               5                   10                  15

Pro Gly Gln

<210> SEQ ID NO 534
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Ala Ala Glu Asp Arg Leu His Pro Val His Ala Gly Pro Ile Pro
1               5                   10                  15

<210> SEQ ID NO 535
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Ala Asp Trp Asp Arg Leu His Pro Val His Ala Gly Pro Val Ala
1               5                   10                  15

<210> SEQ ID NO 536
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536
```

```
Ala Glu Trp Asp Arg Leu His Pro Val His Ala Gly Pro Ile Ala
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Trp Asp Arg Val His Pro Val His Ala Gly Pro Asn Pro Pro Gly
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Asp Arg Val His Pro Val His Ala Gly Pro Ile Pro Pro Gly Gln
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

His Ser Asn Trp Arg Ala Met Ala Ser Asp Phe Asn Leu Pro Pro
1               5                   10                  15

<210> SEQ ID NO 540
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

His Ser Asn Trp Arg Ala Met Ala Ser Glu Phe Asn Leu Pro Pro
1               5                   10                  15

<210> SEQ ID NO 541
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

His Ser Asn Trp Arg Ala Met Ala Ser Asp Phe Asn Leu Pro Pro
1               5                   10                  15

<210> SEQ ID NO 542
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 542

Lys Gly Arg Pro Gly Asn Phe Leu Gln Asn Arg Pro Glu Pro Thr
1               5                   10                  15

<210> SEQ ID NO 543
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Lys Gly Arg Pro Gly Asn Phe Leu Gln Ser Arg Pro Glu Pro Thr
1               5                   10                  15

<210> SEQ ID NO 544
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Lys Gly Arg Pro Gly Asn Phe Leu Gln Asn Arg Pro Glu Pro Thr
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Arg Ser Leu Tyr Asn Thr Val Ala Thr Leu Tyr Cys Val His Gln Arg
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Arg Ser Leu Phe Asn Thr Val Ala Thr Leu Tyr Cys Val His Ala Glu
1               5                   10                  15

<210> SEQ ID NO 547
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Lys Ser Leu Phe Asn Thr Val Ala Thr Leu Tyr Cys Val His Ala
1               5                   10                  15
```

```
<210> SEQ ID NO 548
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Ser Leu Tyr Asn Thr Val Ala Thr Leu Tyr Cys Val His Gln Arg
1               5                   10                  15

<210> SEQ ID NO 549
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Tyr Val Thr Asp Arg Gly Arg Gln Lys Ile Val Ser Leu Thr Glu
1               5                   10                  15

<210> SEQ ID NO 550
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Tyr Val Thr Asp Arg Gly Arg Gln Lys Val Val Ser Leu Thr Asp
1               5                   10                  15

<210> SEQ ID NO 551
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Tyr Val Thr Asp Arg Gly Arg Gln Lys Val Val Ser Leu Thr Glu
1               5                   10                  15

<210> SEQ ID NO 552
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Cys Thr Thr Thr Val Pro Trp Asn Ala Ser Trp Ser Asn Lys Ser
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 553

Cys Thr Thr Ala Val Pro Trp Asn Thr Ser Trp Ser Asn Lys Ser
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Cys Thr Thr Asn Val Pro Trp Asn Ser Ser Trp Ser Asn Lys Ser
1               5                   10                  15

<210> SEQ ID NO 555
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Trp Trp Ala Gly Ile Gln Gln Glu Phe Gly Ile Pro Tyr Asn Pro
1               5                   10                  15

<210> SEQ ID NO 556
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Trp Trp Ala Gly Ile Lys Gln Glu Phe Gly Ile Pro Tyr Asn Pro
1               5                   10                  15

<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Trp Trp Ala Gly Ile Gln Gln Glu Phe Gly Ile Pro Tyr Asn Pro
1               5                   10                  15

<210> SEQ ID NO 558
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gly Pro Gly His Lys Ala Arg Val Leu Ala Glu Ala Met Ser Gln
1               5                   10                  15

<210> SEQ ID NO 559
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 559

Gly Pro Ser His Lys Ala Arg Val Leu Ala Glu Ala Met Ser Gln
1               5                   10                  15

<210> SEQ ID NO 560
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gly Pro Gly His Lys Ala Arg Val Leu Ala Glu Ala Met Ser Gln
1               5                   10                  15

<210> SEQ ID NO 561
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Cys Thr His Gly Ile Arg Pro Val Val Ser Thr Gln Leu Leu Leu
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Cys Thr His Gly Ile Lys Pro Val Val Ser Thr Gln Leu Leu Leu
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Cys Thr His Gly Ile Lys Pro Val Val Ser Thr Gln Leu Leu Leu
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Cys Thr His Gly Ile Arg Pro Val Val Ser Thr Gln Leu Leu Leu
1               5                   10                  15
```

<210> SEQ ID NO 565
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Lys His Ile Val Trp Ala Ser Arg Glu Leu Glu Arg Phe Ala Val Asn
1               5                   10                  15

Pro Gly Leu Leu
            20

<210> SEQ ID NO 566
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Lys His Leu Val Trp Ala Ser Arg Glu Leu Glu Arg Phe Ala Leu Asn
1               5                   10                  15

Pro Gly Leu Leu
            20

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Lys His Leu Val Trp Ala Ser Arg Glu Leu Glu Arg Phe Ala Leu
1               5                   10                  15

<210> SEQ ID NO 568
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ala Ser Arg Glu Leu Glu Arg Phe Ala Val Asn Pro Gly Leu Leu
1               5                   10                  15

<210> SEQ ID NO 569
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Gln Pro Ser Leu Gln Thr Gly Ser Glu Glu Leu Arg Ser Leu Tyr Asn
1               5                   10                  15

Thr Val Ala Thr Leu
            20

```
<210> SEQ ID NO 570
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gln Pro Ala Leu Gln Thr Gly Thr Glu Glu Leu Arg Ser Leu Phe Asn
1               5                   10                  15

Thr Val Ala Thr Leu
            20

<210> SEQ ID NO 571
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Leu Pro Ala Leu Lys Thr Gly Ser Glu Glu Leu Arg Ser Leu Tyr
1               5                   10                  15

<210> SEQ ID NO 572
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Ala Leu Gln Thr Gly Ser Glu Glu Leu Arg Ser Leu Phe Asn Thr
1               5                   10                  15

<210> SEQ ID NO 573
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Leu Gln Thr Gly Thr Glu Glu Leu Arg Ser Leu Phe Asn Thr Val
1               5                   10                  15

<210> SEQ ID NO 574
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Ser Glu Glu Leu Arg Ser Leu Tyr Asn Thr Val Ala Thr Leu
1               5                   10                  15

<210> SEQ ID NO 575
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 575

Ala Cys Gln Gly Val Gly Gly Pro Gly His Lys Ala Arg Val Leu Ala
1               5                   10                  15

Glu Ala Met Ser
            20

<210> SEQ ID NO 576
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ala Cys Gln Gly Val Gly Gly Pro Ser His Lys Ala Arg Val Leu Ala
1               5                   10                  15

Glu Ala Met Ser
            20

<210> SEQ ID NO 577
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Ala Cys Gln Glu Val Gly Gly Pro Gly His Lys Ala Arg Val Leu
1               5                   10                  15

<210> SEQ ID NO 578
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gly Gly Pro Ser His Lys Ala Arg Val Leu Ala Glu Ala Met Gly
1               5                   10                  15

<210> SEQ ID NO 579
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Arg Glu Leu Asn Lys Arg Thr Gln Asp Phe Trp Glu Val Gln Leu
1               5                   10                  15

<210> SEQ ID NO 580
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 580

Arg Glu Leu Asn Lys Arg Thr Gln Asp Phe Trp Glu Val Gln Leu
1               5                   10                  15

<210> SEQ ID NO 581
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Arg Glu Leu Asn Arg Arg Thr Gln Asp Phe Trp Glu Val Gln Leu
1               5                   10                  15

<210> SEQ ID NO 582
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Leu Leu Arg Ala Ile Glu Ala Gln Gln His Leu Leu Gln Leu Thr
1               5                   10                  15

<210> SEQ ID NO 583
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Leu Leu Arg Ala Ile Glu Ala Gln Gln His Met Leu Gln Leu Thr
1               5                   10                  15

<210> SEQ ID NO 584
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Leu Leu Met Ala Ile Glu Ala Gln Gln His Leu Leu Gln Leu Thr
1               5                   10                  15

<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Lys Thr Ala Val Gln Met Ala Val Phe Ile His Asn Phe Lys Arg
1               5                   10                  15

<210> SEQ ID NO 586
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Lys Thr Ala Val Gln Met Ala Val Phe Ile His Asn Phe Lys Arg
1               5                   10                  15

<210> SEQ ID NO 587
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Lys Thr Ala Val Gln Met Ala Val Phe Ile His Asn Phe Lys Arg
1               5                   10                  15

<210> SEQ ID NO 588
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Lys Leu Asn Trp Ala Ser Gln Ile Tyr Pro Gly Ile Lys Val Arg
1               5                   10                  15

<210> SEQ ID NO 589
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Lys Leu Asn Trp Ala Ser Gln Ile Tyr Ala Gly Ile Lys Val Lys
1               5                   10                  15

<210> SEQ ID NO 590
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Lys Leu Asn Trp Ala Ser Gln Ile Tyr Ala Gly Ile Lys Val Lys
1               5                   10                  15

<210> SEQ ID NO 591
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Tyr Ala Lys Met Arg Thr Ala His Thr Asn Asp Val Lys Gln Leu
```

```
1               5                   10                  15

<210> SEQ ID NO 592
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Tyr Ala Arg Met Arg Gly Ala His Thr Asn Asp Val Lys Gln Leu
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Tyr Ala Arg Lys Arg Ser Ala His Thr Asn Asp Val Lys Gln Leu
1               5                   10                  15

<210> SEQ ID NO 594
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Asp Gln Ala Glu His Leu Lys Thr Ala Val Gln Met Ala Val Phe
1               5                   10                  15

<210> SEQ ID NO 595
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Asp Gln Ala Glu His Leu Lys Thr Ala Val Gln Met Ala Val Phe
1               5                   10                  15

<210> SEQ ID NO 596
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Asp Gln Ala Glu His Leu Lys Thr Ala Val Gln Met Ala Val Phe
1               5                   10                  15

<210> SEQ ID NO 597
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                             peptide

<400> SEQUENCE: 597

Ser Leu Gln Thr Gly Ser Glu Glu Leu Arg Ser Leu Tyr Asn Thr
1               5                   10                  15

<210> SEQ ID NO 598
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Ala Leu Gln Thr Gly Thr Glu Glu Leu Arg Ser Leu Phe Asn Thr
1               5                   10                  15

<210> SEQ ID NO 599
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Ala Leu Lys Thr Gly Thr Glu Glu Leu Arg Ser Leu Tyr Asn Thr
1               5                   10                  15

<210> SEQ ID NO 600
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gly Pro Gly His Lys Ala Arg Val Leu Ala Glu Ala Met Ser Gln
1               5                   10                  15

<210> SEQ ID NO 601
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Gly Pro Ser His Lys Ala Arg Val Leu Ala Glu Ala Met Ser Gln
1               5                   10                  15

<210> SEQ ID NO 602
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Gly Pro Gly His Lys Ala Arg Val Leu Ala Glu Ala Met Ser Gln
1               5                   10                  15

<210> SEQ ID NO 603
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gln Pro Ala Leu Gln Thr Gly Thr Glu Glu Leu Arg Ser Leu Tyr Asn
1               5                   10                  15

Thr Val Ala Thr Leu
            20

<210> SEQ ID NO 604
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Leu Pro Ala Leu Lys Thr Gly Ser Glu Glu Leu Arg Ser Leu Tyr
1               5                   10                  15

<210> SEQ ID NO 605
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gly Ser Glu Glu Leu Arg Ser Leu Tyr Asn Thr Val Ala Thr Leu
1               5                   10                  15

<210> SEQ ID NO 606
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Ala His Thr Asn Asp Val Lys Gln Leu Thr Glu Ala Val Gln Lys
1               5                   10                  15

<210> SEQ ID NO 607
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Ala His Thr Asn Asp Val Lys Gln Leu Thr Glu Ala Val Gln Lys
1               5                   10                  15

<210> SEQ ID NO 608
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 608

Gly Asp Ile Ile Gly Asp Ile Arg Gln Ala His Cys Asn Ile Ser
1               5                   10                  15

<210> SEQ ID NO 609
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Gly Asp Ile Ile Gly Asp Ile Arg Gln Ala His Cys Asn Ile Ser
1               5                   10                  15

<210> SEQ ID NO 610
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Ser Glu Lys Ser Ala Val Gly Ile Gly Ala Val Phe Leu Gly Phe
1               5                   10                  15

<210> SEQ ID NO 611
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Arg Glu Lys Arg Ala Val Gly Leu Gly Ala Val Phe Leu Gly Phe
1               5                   10                  15

<210> SEQ ID NO 612
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Arg Ala Ser Ile Leu Arg Gly Gly Lys Leu Asp Lys Trp Glu Lys
1               5                   10                  15

<210> SEQ ID NO 613
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Ser Ala Ser Ile Leu Arg Gly Gly Lys Leu Asp Lys Trp Glu Lys
1               5                   10                  15

<210> SEQ ID NO 614
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Thr Asn Asn Pro Pro Val Pro Val Gly Asp Ile Tyr Lys Arg Trp
1               5                   10                  15

<210> SEQ ID NO 615
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Thr Ser Asn Pro Pro Val Pro Val Gly Asp Ile Tyr Lys Arg Trp
1               5                   10                  15

<210> SEQ ID NO 616
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Cys Lys Ser Asn Ile Thr Gly Leu Leu Leu Thr Arg Asp Gly Gly
1               5                   10                  15

<210> SEQ ID NO 617
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Cys Thr Ser Asn Ile Thr Gly Leu Leu Leu Val Arg Asp Gly Gly
1               5                   10                  15

<210> SEQ ID NO 618
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Ser Leu Tyr Asn Thr Val Ala Thr Leu Tyr Cys Val His Ala Gly
1               5                   10                  15

<210> SEQ ID NO 619
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Ser Leu Tyr Asn Thr Val Ala Thr Leu Tyr Cys Val His Gln Arg
```

<210> SEQ ID NO 620
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Glu Gln Leu Ile Asn Lys Glu Arg Val Tyr Leu Ser Trp Val Pro
1               5                   10                  15

<210> SEQ ID NO 621
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Glu Pro Leu Ile Lys Lys Glu Lys Val Tyr Leu Ser Trp Val Pro
1               5                   10                  15

<210> SEQ ID NO 622
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Ala Glu Trp Asp Arg Leu His Pro Val His Ala Gly Pro Ile Ala
1               5                   10                  15

<210> SEQ ID NO 623
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Ala Glu Trp Asp Arg Leu His Pro Val His Ala Gly Pro Ile Ala
1               5                   10                  15

<210> SEQ ID NO 624
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

His Gln Ala Ala Met Gln Met Leu Lys Asp Thr Ile Asn Glu Glu
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 625

His Gln Ala Ala Met Gln Met Leu Lys Asp Thr Ile Asn Glu Glu
1               5                   10                  15

<210> SEQ ID NO 626
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Ile Val Gln Gln Gln Ser Asn Leu Leu Arg Ala Ile Glu Ala Gln Gln
1               5                   10                  15

<210> SEQ ID NO 627
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Val Val Gln Gln Gln Ser Asn Leu Leu Arg Ala Ile Glu Ala Gln
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Val Gln Gln Gln Asn Asn Leu Leu Arg Ala Ile Glu Ala Gln His
1               5                   10                  15

<210> SEQ ID NO 629
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Ala Val Phe Ile His Asn Phe Lys Arg Lys Gly Gly Ile Gly Gly Tyr
1               5                   10                  15

<210> SEQ ID NO 630
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Ala Val Phe Ile His Asn Phe Lys Arg Lys Gly Gly Ile Gly Gly
1               5                   10                  15

<210> SEQ ID NO 631

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Val Leu Ile His Asn Phe Lys Arg Lys Gly Gly Ile Gly Gly Tyr
1               5                   10                  15

<210> SEQ ID NO 632
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Met Ala Ile Cys Glu Glu Met Glu Lys Glu Gly Lys Ile Thr Lys
1               5                   10                  15

<210> SEQ ID NO 633
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Thr Ala Ile Cys Glu Glu Met Glu Lys Glu Gly Lys Ile Thr Lys
1               5                   10                  15

<210> SEQ ID NO 634
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Gly Gly Pro Ser His Lys Ala Arg Val Leu Ala Glu Ala Met Ser
1               5                   10                  15

<210> SEQ ID NO 635
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Gly Gly Pro Ser His Lys Ala Arg Val Leu Ala Glu Ala Met Gly
1               5                   10                  15

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636
```

```
Ile Ile Gly Gln Val Arg Asp Gln Ala Glu His Leu Lys Thr Ala
1               5                   10                  15

<210> SEQ ID NO 637
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Leu Ile Gly Gln Val Arg Asp Gln Ala Glu His Leu Lys Thr Ala
1               5                   10                  15

<210> SEQ ID NO 638
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Ala Val Phe Ile His Asn Phe Lys Arg Lys Gly Gly Ile Gly Gly Tyr
1               5                   10                  15

<210> SEQ ID NO 639
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Ala Val Phe Ile His Asn Phe Lys Arg Lys Gly Gly Ile Gly Gly
1               5                   10                  15

<210> SEQ ID NO 640
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Val Leu Ile His Asn Phe Lys Arg Lys Gly Gly Ile Gly Gly Tyr
1               5                   10                  15

<210> SEQ ID NO 641
<211> LENGTH: 16
<212> TYPE: PRT
<213> ORGANISM: Human immunodeficiency virus

<400> SEQUENCE: 641

Ile Val Gln Gln Gln Ser Asn Leu Leu Arg Ala Ile Glu Ala Gln Gln
1               5                   10                  15

<210> SEQ ID NO 642
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 642

Val Val Gln Gln Gln Ser Asn Leu Leu Arg Ala Ile Glu Ala Gln
1               5                   10                  15

<210> SEQ ID NO 643
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Val Gln Gln Gln Asn Asn Leu Leu Arg Ala Ile Glu Ala Gln His
1               5                   10                  15

<210> SEQ ID NO 644
<211> LENGTH: 16
<212> TYPE: PRT
<213> ORGANISM: Human immunodeficiency virus

<400> SEQUENCE: 644

Ala Val Phe Ile His Asn Phe Lys Arg Lys Gly Gly Ile Gly Gly Tyr
1               5                   10                  15

<210> SEQ ID NO 645
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Ala Val Phe Ile His Asn Phe Lys Arg Lys Gly Gly Ile Gly Gly
1               5                   10                  15

<210> SEQ ID NO 646
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Val Leu Ile His Asn Phe Lys Arg Lys Gly Gly Ile Gly Gly Tyr
1               5                   10                  15

<210> SEQ ID NO 647
<211> LENGTH: 15
<212> TYPE: PRT
<213> ORGANISM: Human immunodeficiency virus

<400> SEQUENCE: 647

Met Ala Ile Cys Glu Glu Met Glu Lys Glu Gly Lys Ile Thr Lys
1               5                   10                  15

<210> SEQ ID NO 648
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

```
Thr Ala Ile Cys Glu Glu Met Glu Lys Glu Gly Lys Ile Thr Lys
1               5                   10                  15

<210> SEQ ID NO 649
<211> LENGTH: 15
<212> TYPE: PRT
<213> ORGANISM: Human immunodeficiency virus

<400> SEQUENCE: 649

Gly Gly Pro Ser His Lys Ala Arg Val Leu Ala Glu Ala Met Ser
1               5                   10                  15

<210> SEQ ID NO 650
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Gly Gly Pro Ser His Lys Ala Arg Val Leu Ala Glu Ala Met Gly
1               5                   10                  15

<210> SEQ ID NO 651
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Glu Gln Leu Ile Lys Lys Glu Arg Val Tyr Leu Ser Trp Val Pro Ala
1               5                   10                  15

His Lys Gly Ile Gly
            20

<210> SEQ ID NO 652
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Glu Gln Leu Ile Lys Lys Glu Lys Val Tyr Leu Ala Trp Val Pro Ala
1               5                   10                  15

His Lys Gly Ile Gly
            20

<210> SEQ ID NO 653
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Glu Glu Leu Ile Lys Lys Glu Lys Val Tyr Leu Ala Trp Val Pro
1               5                   10                  15

<210> SEQ ID NO 654
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Glu Pro Leu Ile Lys Lys Glu Lys Val Tyr Leu Ser Trp Val Pro
1               5                   10                  15

<210> SEQ ID NO 655
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Lys Leu Ile Glu Lys Asp Lys Val Tyr Leu Ser Trp Val Pro Ala
1               5                   10                  15

<210> SEQ ID NO 656
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Leu Ile Lys Lys Glu Arg Val Tyr Leu Ser Trp Val Pro Ala His
1               5                   10                  15

<210> SEQ ID NO 657
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Glu Lys Val Tyr Leu Ala Trp Val Pro Ala His Lys Gly Ile Gly
1               5                   10                  15

<210> SEQ ID NO 658
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Glu Lys Val Tyr Leu Ser Trp Val Pro Ala His Lys Gly Ile Gly
1               5                   10                  15

<210> SEQ ID NO 659
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659
```

```
Cys Thr His Gly Ile Arg Pro Val Val Ser Thr Gln Leu Leu Leu
1               5                   10                  15

<210> SEQ ID NO 660
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Cys Thr His Gly Ile Lys Pro Val Val Ser Thr Gln Leu Leu Leu
1               5                   10                  15

<210> SEQ ID NO 661
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Cys Thr His Gly Ile Lys Pro Val Val Ser Thr Gln Leu Leu Leu
1               5                   10                  15

<210> SEQ ID NO 662
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Cys Thr His Gly Ile Arg Pro Val Val Ser Thr Gln Leu Leu Leu
1               5                   10                  15

<210> SEQ ID NO 663
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Ile Cys Thr Thr Thr Val Pro Trp Asn Ala Ser Trp Ser Asn Lys Ser
1               5                   10                  15

Leu

<210> SEQ ID NO 664
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Ile Cys Thr Thr Ala Val Pro Trp Asn Thr Ser Trp Ser Asn Lys Ser
1               5                   10                  15

Gln

<210> SEQ ID NO 665
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Ile Cys Thr Thr Thr Val Pro Trp Asn Ala Ser Trp Ser Asn Arg
1               5                   10                  15

<210> SEQ ID NO 666
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Cys Thr Thr Thr Val Pro Trp Asn Ser Ser Trp Ser Asn Lys Thr
1               5                   10                  15

<210> SEQ ID NO 667
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Thr Thr Ala Val Pro Trp Asn Ala Ser Trp Ser Asn Lys Ser Leu
1               5                   10                  15

<210> SEQ ID NO 668
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Thr Thr Ala Val Pro Trp Asn Thr Ser Trp Ser Asn Lys Ser Leu
1               5                   10                  15

<210> SEQ ID NO 669
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Ala Cys Gln Gly Val Gly Gly Pro Gly His Lys Ala Arg Val Leu Ala
1               5                   10                  15

Glu Ala Met Ser
            20

<210> SEQ ID NO 670
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 670

Ala Cys Gln Gly Val Gly Gly Pro Ser His Lys Ala Arg Val Leu Ala
1               5                   10                  15

Glu Ala Met Ser
            20

<210> SEQ ID NO 671
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Ala Cys Gln Glu Val Gly Gly Pro Gly His Lys Ala Arg Val Leu
1               5                   10                  15

<210> SEQ ID NO 672
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Gly Pro Ser His Lys Ala Arg Val Leu Ala Glu Ala Met Gly
1               5                   10                  15

<210> SEQ ID NO 673
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ala Ala Glu Trp Asp Arg Val His Pro Val His Ala Gly Pro Ile Ala
1               5                   10                  15

Pro Gly Gln

<210> SEQ ID NO 674
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Ala Ala Glu Trp Asp Arg Leu His Pro Val His Ala Gly Pro Val Ala
1               5                   10                  15

Pro Gly Gln

<210> SEQ ID NO 675
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675
```

```
Ala Ala Glu Asp Arg Leu His Pro Val His Ala Gly Pro Ile Pro
1               5                   10                  15

<210> SEQ ID NO 676
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Ala Asp Trp Asp Arg Leu His Pro Val His Ala Gly Pro Val Ala
1               5                   10                  15

<210> SEQ ID NO 677
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Ala Glu Trp Asp Arg Leu His Pro Val His Ala Gly Pro Ile Ala
1               5                   10                  15

<210> SEQ ID NO 678
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Trp Asp Arg Val His Pro Val His Ala Gly Pro Asn Pro Pro Gly
1               5                   10                  15

<210> SEQ ID NO 679
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Asp Arg Val His Pro Val His Ala Gly Pro Ile Pro Pro Gly Gln
1               5                   10                  15

<210> SEQ ID NO 680
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

His Ser Asn Trp Arg Ala Met Ala Ser Asp Phe Asn Leu Pro Pro
1               5                   10                  15

<210> SEQ ID NO 681
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 681

His Ser Asn Trp Arg Ala Met Ala Ser Glu Phe Asn Leu Pro Pro
1               5                   10                  15

<210> SEQ ID NO 682
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

His Ser Asn Trp Arg Ala Met Ala Ser Asp Phe Asn Leu Pro Pro
1               5                   10                  15

<210> SEQ ID NO 683
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Lys Gly Arg Pro Gly Asn Phe Leu Gln Asn Arg Pro Glu Pro Thr
1               5                   10                  15

<210> SEQ ID NO 684
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Lys Gly Arg Pro Gly Asn Phe Leu Gln Ser Arg Pro Glu Pro Thr
1               5                   10                  15

<210> SEQ ID NO 685
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Lys Gly Arg Pro Gly Asn Phe Leu Gln Asn Arg Pro Glu Pro Thr
1               5                   10                  15
```

ANTIVIRAL VACCINES WITH IMPROVED CELLULAR IMMUNOGENICITY

CROSS-REFERENCE TO RELATED APPLICATIONS

This application is a National Stage Application of PCT/US2009/064999, filed Nov. 18, 2009, which claims the benefit of the filing date of U.S. provisional patent application No. 61/115,703, filed Nov. 18, 2008; U.S. provisional application No. 61/152,184, filed Feb. 12, 2009; and U.S. provisional application No. 61/248,188, filed on Oct. 2, 2009, each of which is hereby incorporated by reference.

STATEMENT OF FEDERALLY FUNDED RESEARCH

This research has been sponsored in part by NIH grant numbers U19-AI066305 and U19-AI078526. The government has certain rights to the invention.

FIELD OF THE INVENTION

The invention provides compositions, methods, and kits for the treatment or prevention of viral infections. The polyvalent (e.g., 2-valent) vaccines described herein incorporate computationally-optimized viral polypeptides that can increase the diversity or breadth and depth of cellular immune response in vaccinated subjects.

BACKGROUND OF THE INVENTION

Vaccines that elicit cellular immune responses against viruses must reflect global viral diversity in order to effectively treat or prevent viral infection. For example, the initiation of intense and diverse HIV-1-specific T cell responses is likely crucial for an effective HIV-1 vaccine. Cytotoxic T lymphocyte (CTL) responses are correlated with slow disease progression in humans, and the importance of CTL responses in non-human primate vaccination models is well established. While the highly variable Envelope (Env) is the primary target for neutralizing antibodies against HIV, and vaccine antigens will also need to be tailored to elicit these antibody responses, T cell vaccine components can target more conserved proteins to trigger responses that are more likely to cross-react. But even the most conserved HIV-1 proteins are diverse enough that variation will be an issue. Artificial central-sequence vaccine approaches, such as consensus and ancestral HIV-1 sequences, essentially "split the differences" between strains, can stimulate responses with enhanced cross-reactivity compared to natural strain vaccines. Consensus antigens represent synthetic antigen sequences that are the single best "average" of all circulating strains. While these antigens can elicit directed cellular immune responses, the breadth and intensity of these responses are not substantially improved over previous vaccine strategies. The development of next-generation vaccines to treat or prevent viral infection must elicit an increased breadth of cellular immunity in order to allow for successful vaccination outcomes. The need for such vaccines is particularly urgent for the treatment or prevention of HIV-1.

SUMMARY OF THE INVENTION

In a first aspect, the invention features a vaccine for treating or reducing the risk of a viral infection in a mammal, such as a human, that includes at least two distinct optimized viral polypeptides (e.g., 2, 3, 4, 5, or more distinct optimized viral polypeptides), wherein the optimized viral polypeptides correspond to the same viral gene product. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In other embodiments, the retrovirus is human immunodeficiency virus type 1 (HIV-1), and the viral gene products include Gag, Pol, Env, Nef, Tat, Rev, Vif, Vpr, or Vpu. In a further embodiment, the vaccine includes no more than two optimized viral polypeptides corresponding to one of the Gag, Pol, Env, Nef, Tat, Rev, Vif, Vpr, or Vpu viral gene products. In another embodiment, the vaccine does not include optimized viral polypeptides corresponding to Gag and Nef. In yet another embodiment, the vaccine includes at least two distinct optimized viral polypeptides (e.g., 2, 3, 4, 5, or more distinct optimized viral polypeptides) for a first viral gene product selected from Gag, Pol, Env, Nef, Tat, Rev, Vif, Vpr, and Vpu and one or more distinct optimized viral polypeptides (e.g., 2, 3, 4, 5, or more distinct optimized viral polypeptides) for a second viral gene product different from the first viral gene product selected from Gag, Pol, Env, Nef, Tat, Rev, Vif, Vpr, and Vpu.

In a second aspect, the invention features a vaccine for treating or reducing the risk of human immunodeficiency virus type 1 (HIV-1) infection in a mammal, such as a human, that includes an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having amino acid sequence identity to any one of the sequences set forth in SEQ ID NOS:1-29. In another embodiment, the optimized viral polypeptide has the amino acid sequence of any one of the sequences set forth in SEQ NOS:1-29. In a further embodiment, the vaccine includes at least two optimized viral polypeptides selected from any one or more of groups a)-k): a) SEQ ID NOS:1 and 2; b) SEQ ID NOS:3, 4, and 5; c) SEQ ID NOS:6 and 7; d) SEQ ID NOS:8-12; e) SEQ ID NOS:13, 14, and 15; SEQ ID NOS:16, 17, and 18; g) SEQ ID NOS:19 and 20; h) SEQ ID NOS:21, 22, and 23; i) SEQ ID NOS:24 and 25; j) SEQ ID NOS:26 and 27; k) and SEQ ID NOS:21-22. In another embodiment, the vaccine can include a pair of optimized viral polypeptides selected from any one of groups a)-k) above and one or more different optimized viral polypeptides from the same or a different group a)-k). In other embodiments, the vaccine can include at least three or four or more optimized viral polypeptides from one or more of groups a)-k).

In a third aspect, the invention features a vaccine for treating or reducing the risk of a viral infection in a mammal, such as a human, that includes at least two pairs of distinct optimized viral polypeptides, wherein each pair of optimized viral polypeptides corresponds to the same viral gene product, and wherein no more than two optimized viral polypeptides incorporated in the vaccine correspond to the same viral gene product. In one embodiment, the vaccine includes at least three pairs of distinct optimized viral polypeptides. In another embodiment, the vaccine includes at least four pairs of distinct optimized viral polypeptides. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In other embodiments, the retrovirus is human immunodeficiency virus type 1 (HIV-1), and the viral gene products include Gag, Pol, Env, Nef, Tat, Rev, Vif, Vpr, or Vpu. In a further embodiment, the vaccine includes no more than two optimized viral polypeptides corresponding to one of the Gag, Pol, Env, Nef, Tat, Rev, Vif, Vpr, or Vpu viral gene products. In another embodiment, the vaccine does not include optimized viral polypeptides corresponding to Gag and Nef. In a further embodiment, the vaccine includes at least three pairs of distinct optimized viral polypeptides corresponding to any three of the Gag, Pol, Env, Nef, Tat, Rev, Vif, Vpr, or Vpu viral gene products. In another embodiment, the vaccine includes at least four pairs of distinct optimized viral polypeptides corresponding to any four of the Gag, Pol, Env, Nef, Tat, Rev, Vif, Vpr, or Vpu viral gene products.

In one embodiment of any of the first three aspects of the invention, the vaccine elicits a cellular immune response against a viral gene product. In another embodiment, the vaccine elicits a cellular immune response against HIV-1. In a further embodiment, the nucleotide sequence of at least one distinct optimized viral polypeptide is encoded by a nucleic acid or vector. In one embodiment, the vector is a recombinant adenovirus, such as adenovirus serotype 26 (Ad26), adenovirus serotype 34 (Ad34), adenovirus serotype 35 (Ad35), adenovirus serotype 48 (Ad48), or adenovirus serotype 5 HVR48 (Ad5HVR48). In a further embodiment, the vaccine is in combination with a pharmaceutically acceptable carrier, excipient, or diluent.

In a fourth aspect, the invention features a nucleic acid that includes the nucleotide sequence of an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the amino acid sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having sequence identity to any one of the amino acid sequences set forth in SEQ ID NOS:1-29. In another embodiment, the optimized viral polypeptide has any one of the amino acid sequences set forth in SEQ ID NOS:1-29. In a further embodiment, the nucleic acid includes a vector. In one embodiment, the vector is a recombinant adenovirus, such as adenovirus serotype 26 (Ad26), adenovirus serotype 34 (Ad34), adenovirus serotype 35 (Ad35), adenovirus serotype 48 (Ad48), or adenovirus serotype 5 HVR48 (Ad5HVR48).

In a fifth aspect, the invention features an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the amino acid sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having sequence identity to any one of the amino acid sequences set forth in SEQ ID NOS:1-29. In another embodiment, the optimized viral polypeptide has any one of the amino acid sequences set forth in SEQ ID NOS:1-29.

In a sixth aspect, the invention features a method for treating or reducing the risk of a viral infection in a mammal, such as a human, by administering a vaccine or nucleic acid of the invention. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In further embodiments, the retrovirus is human immunodeficiency virus type 1 (HIV-1), and the viral gene products include Gag, Pol, Env, Nef, Tat, Rev, Vif, Vpr, or Vpu. In one embodiment, the vaccine or nucleic acid elicits a cellular immune response against a viral gene product.

In a seventh aspect, the invention features a method of manufacturing a vaccine for treating or reducing the risk of a viral infection in a mammal, such as a human, by synthesizing a vaccine of the invention.

In an eighth aspect, the invention features a method of manufacturing a vaccine for treating or reducing the risk of a viral infection in a mammal, such as a human, by contacting a nucleic acid of the invention with a cell and isolating a optimized viral polypeptide.

In one embodiment of the seventh or eighth aspects of the invention, the optimized viral polypeptide elicits a cellular immune response when administered to a mammal. The cellular immune response can be against a viral gene product. In another embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In further embodiments, the retrovirus is human immunodeficiency virus type 1 (HIV-1), and the viral gene products include Gag, Pol, Env, Nef, Tat, Rev, Vif, Vpr, or Vpu.

In a ninth aspect, the invention features a kit that includes a vaccine of the invention, a pharmaceutically acceptable carrier, excipient, or diluent, and instructions for the use thereof. In one embodiment, the kit also includes an adjuvant.

In a final aspect, the invention features a kit that includes a nucleic acid of the invention, a pharmaceutically acceptable carrier, excipient, or diluent, and instructions for the use thereof. In one embodiment, the kit also includes an adjuvant.

In an embodiment of all aspects of the invention, the optimized viral polypeptide is encoded by a nucleic acid sequence that is optimized for expression in humans (e.g., any one of SEQ ID NOS:5, 10, 11, 12, 15, 18, and 23).

DEFINITIONS

By "optimized viral polypeptide" or "computationally-optimized viral polypeptide" is meant an immunogenic polypeptide that is not a naturally-occurring viral peptide, polypeptide, or protein. Optimized viral polypeptide sequences are initially generated by modifying the amino acid sequence of one or more naturally-occurring viral gene products (e.g., peptides, polypeptides, and proteins) to increase the breadth, intensity, depth, or longevity of the antiviral immune response (e.g., cellular or humoral immune responses) generated upon immunization (e.g., when incorporated into a vaccine of the invention) of a mammal (e.g., a human). Thus, the optimized viral polypeptide may correspond to a "parent" viral gene sequence; alternatively, the optimized viral polypeptide may not correspond to a specific "parent" viral gene sequence but may correspond to analogous sequences from various strains or quasispecies of a virus. Modifications to the viral gene sequence that can be included in an optimized viral polypeptide include amino acid additions, substitutions, and deletions. In one embodiment of the invention, the optimized viral polypeptide is the composite or merged amino acid sequence of two or more naturally-occurring viral gene products (e.g., natural or clinical viral isolates) in which each potential epitope (e.g., each contiguous or overlapping amino acid sequence of 5, 6, 7, 8, 9, 10, 11, 12, 13, 14, 15, 16, 17, 18, 19, 20, 21, 22, 23, 24, 25, 26, 27, 28, 29, or more amino acids in length) is analyzed and modified to improve the immunogenicity of the resulting optimized viral polypeptide. Optimized viral polypeptides that correspond to different viral gene products can also be fused to facilitate incorporation in a vaccine of the invention. Methods of generating an optimized viral polypeptides are described in, e.g., Fisher et al. "Polyvalent Vaccine for Optimal Coverage of Potential T-Cell Epitopes in Global HIV-1 Variants," *Nat. Med.* 13(1):100-106 (2007) and International Patent Application Publication WO 2007/024941, herein incorporated by reference. Once the optimized viral polypeptide sequence is generated, the corresponding polypeptide can be produced or administered by standard techniques (e.g., recombinant viral vectors, such as the adenoviral vectors disclosed in International Patent Application Publications WO 2006/040330 and WO 2007/104792, herein incorporated by reference).

By "pharmaceutically acceptable carrier" is meant a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, e.g., in *Remington's Pharmaceutical Sciences* (18$^{th}$ edition, ed. A. Gennaro, 1990, Mack Publishing Company, Easton, Pa.), incorporated herein by reference.

By "vector" is meant a DNA construct that contains a promoter operably linked to a downstream gene or coding region (e.g., a cDNA or genomic DNA fragment, which encodes a polypeptide or polypeptide fragment). Introduction of the vector into a recipient cell (e.g., a prokaryotic or eukaryotic cell, e.g., a bacterium, yeast, insect cell, or mammalian cell, depending upon the promoter within the expression vector) or organism (including, e.g., a human) allows the cell to express mRNA encoded by the vector, which is then translated into the encoded optimized viral polypeptide of the invention. Vectors for in vitro transcription/translation are also well known in the art and are described further herein. A vector may be a genetically engineered plasmid, virus, or artificial chromosome derived from, e.g., a bacteriophage, adenovirus, retrovirus, poxvirus, or herpesvirus.

By "viral gene product" is meant any naturally-occurring viral peptide, polypeptide, or protein, or fragment thereof. In one embodiment of the invention, the viral gene product is derived from the human immunodeficiency virus type 1 (HIV-1). HIV-1 viral gene products include the Gag, Pol, Env, Nef, Tat, Rev, Vif, Vpr, and Vpu polypeptides.

BRIEF DESCRIPTION OF THE DRAWINGS

FIG. 8 discloses SEQ ID NO: 43.

FIG. 9 is a chart illustrating typical patterns of PTE responses to the ConM vaccine or to the optimal natural vaccine, aligning peptides that elicit a response with the relevant region of the vaccine. Good matches with solid stretches of identity between vaccine and target PTE peptide are necessary to achieve a reaction to these vaccines. FIG. 9 discloses SEQ ID NOS 44-57, respectively, in order of appearance.

FIG. 10 is a chart illustrating that mosaic vaccines generated many responses that recognized multiple variant overlapping peptides with no apparent antigenic competition and with broad local responses. In particular, four variable PTE peptides were recognized. Moreover, in the region of overlap both mosaic forms were recognized, as well a combination of the two. Finally, a new form (S) was recognized. FIG. 10 discloses SEQ ID NOS 58-63, respectively, in order of appearance.

FIG. 11 is a chart illustrating a typical pattern of CD8+ PTE peptide responses in mosaic vaccinated animal (361-07). 22 PTE peptides were tested and 8 CD8 responsive regions were identified; 5 regions included variable peptides that match amino acids in one or the other of the mosaics. 5 CD4 responsive regions were identified. Thus, T cell responses to Mosaics see more variable peptides in a given region. This seemed to be true of CD8 T cell responses in particular. This could be the result of triggering multiple T cell clones that recognize variants of epitopes, and these may block fit escape routes. Not only are there more responses, they are deeper and cover more variants. FIG. 11 discloses CD8 responses as SEQ ID NOS 64-101, respectively, in order of appearance. CD4 responses disclosed as SEQ ID NOS 102-117, respectively, in order of appearance.

FIG. 13 is similar to FIG. 5, monkeys shown in the same order from right to left, but with the scale changed to reflect number of responses to regions that contain one or more overlapping PTE peptides rather than single peptides.

FIG. 14 is a chart showing the number of T cell responses in animals following administration of 2 valent mosaic (Mos2), Mcon, and OptC vaccines. The 2 valent mosaic (Mos2) vaccine triggers a median number of 8 responses in CD8+ T cells, while only a median number of 3 (range: 0-6) and 1.5 peptides (range: 0-5) CD8+ T cell responses are triggered by Mcon and OptC vaccines, respectively. The 2 valent mosaic (Mos2) vaccine triggers a median number of 3 (range; 2-5) responses in CD4+ T cells, while only a median number of 1 (range: 0-2) and 0.5 (range: 0-2) CD4+ T cell response are triggered by Mcon and OptC vaccines, respectively. Thus, the trend for responses is Mos2>Mcon>OptC.

FIG. 19A is a graph showing the numbers of epitope-specific CD4+ (top) and CD8+ (bottom) T lymphocyte responses to individual PTE peptides following a single immunization of rAd26 vectors expressing mosaic (blue), M consensus (green), clade B+clade C (purple), or optimal natural clade C (red) HIV-1 Gag, Pol, and Env antigens. Individual monkeys are depicted on the x-axis. The different shades of each color reflect responses to the different antigens (Gag, Pol, Env). FIG. 19B is a graph showing the numbers of CD4+ (top) and CD8+ (bottom) T lymphocyte response regions.

Figure 21C:
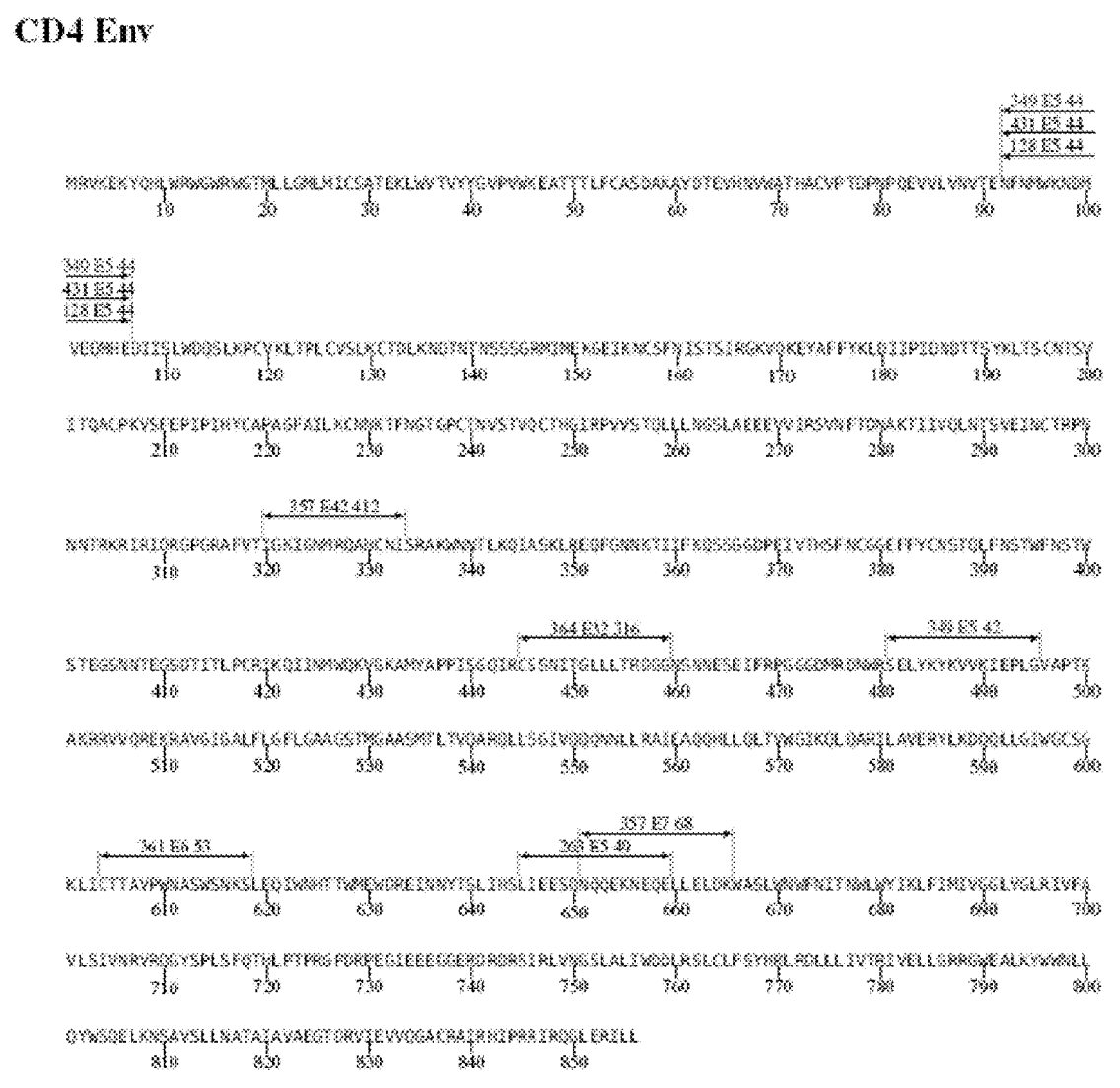

FIGS. 21A-21C show a schematic showing CD4+ T lymphocyte responses to PTE peptides at week 4 following immunization mapped on HIV-1 Gag (FIG. 21A) (SEQ ID NO: 121), Pol (FIG. 21B) (SEQ ID NO: 122), and Env (FIG. 21C) (SEQ ID NO: 123) protein sequences. Colors denote monkeys that received the mosaic (blue), M consensus (green), clade B+clade C (purple), or optimal natural clade C (red) HIV-1 Gag, Pol, and Env antigens. For each epitope, the monkey number, antigen (G, Gag; P, Pol; E, Env), subpool number, and individual PTE peptide number are indicated.

FIG. 22 is a schematic showing the alignment of vaccine sequences with reactive PTE peptides in all monkeys at week 4 following immunization with rAd26 vectors expressing mosaic, M consensus, clade B+clade C, or optimal natural Blade C HIV-1 Gag, Pol, and Env antigens. For each monkey, vaccine sequences are shown on the top, and reactive PTE peptides are shown beneath the vaccine sequences denoted by the antigen (G, Gag; P, Pol; E, Env) and PTE peptide numbers. The minimal overlap region is shown in bold. Sequence polymorphisms between the two mosaic or the two clade B+clade C antigens are shown in blue. Differences between the vaccine sequences and the reactive PTE peptides are shown in red. FIG. 22 discloses SEQ ID NOS124-640, respectively, in order of appearance.

Minimal regions within the peptides that are likely to contain the immune response epitope, based on overlap between reactive peptides when it occurs, are in bold in the vaccines. If there is no overlapping peptide, we assume the epitope can be anywhere in the peptide, so the whole region is bold. We cannot differentiate between different T cell responses targeting epitopes with different boundaries within a peptide, or more promiscuous clonal T cell responses that can tolerate variation when variants are present; either scenario could be advantageous in a vaccine immune response. The number of targeted regions corresponds to the minimum number of T cell responses required to account for the data.

Amino acids where the vaccine and the peptides don't match are written in red; if they fall within the region likely to carry the epitope, they are bold red. Amino acid differences outside of the overlapping regions when multiple peptides overlap are marked in red, but not bold.

The vaccines are always at the top. The letter for each protein (Gag is G, Pol is P, Envelope is E) and the peptide number are used to label for each reactive PTE peptide. The protein and HXB2 numbers follow each peptide.

For the mosaic and clade B+C vaccines, there are 2 antigens each and both are included in the alignment; amino acid differences in the vaccines are noted in blue, and if the reactive peptide carries the variant amino acid in the second mosaic, it is also in blue. In each of the positions where the two vaccine antigens differ, the reactive peptides are also marked in bold to indicate the positions where including two variants may have impacted the vaccine immune response and allowed greater breadth and depth.

For example, the first vaccine summarized is the clade B+C vaccine, and animal 287-95 is the first animal for which responses are listed. There were 3 CD8 responses to PTE peptides, 1 to CD4. Two of the CD8 peptides show substantial overlap, E26 and E282, so both may be targets for the same CTL response; thus we also note there are only 2 CD8 responsive regions, and 1 CD4 responsive region. For each responsive region, we write out the number of overlapping peptides per region (e.g., CD8:1 2CD4:1) to assess depth of responses; the two is red to indicate that the region of overlap is variable in the reactive peptides. If the vaccine differs, like the D/E in the second reactive region, it is marked in blue. Only the region of overlap is bold. The H in E282 was not found in either vaccine so it is marked with red; it is within the region of overlap so it is bold. Each reactive peptide has its protein and corresponding HXB2 numbering noted on the right.

Figure 23:
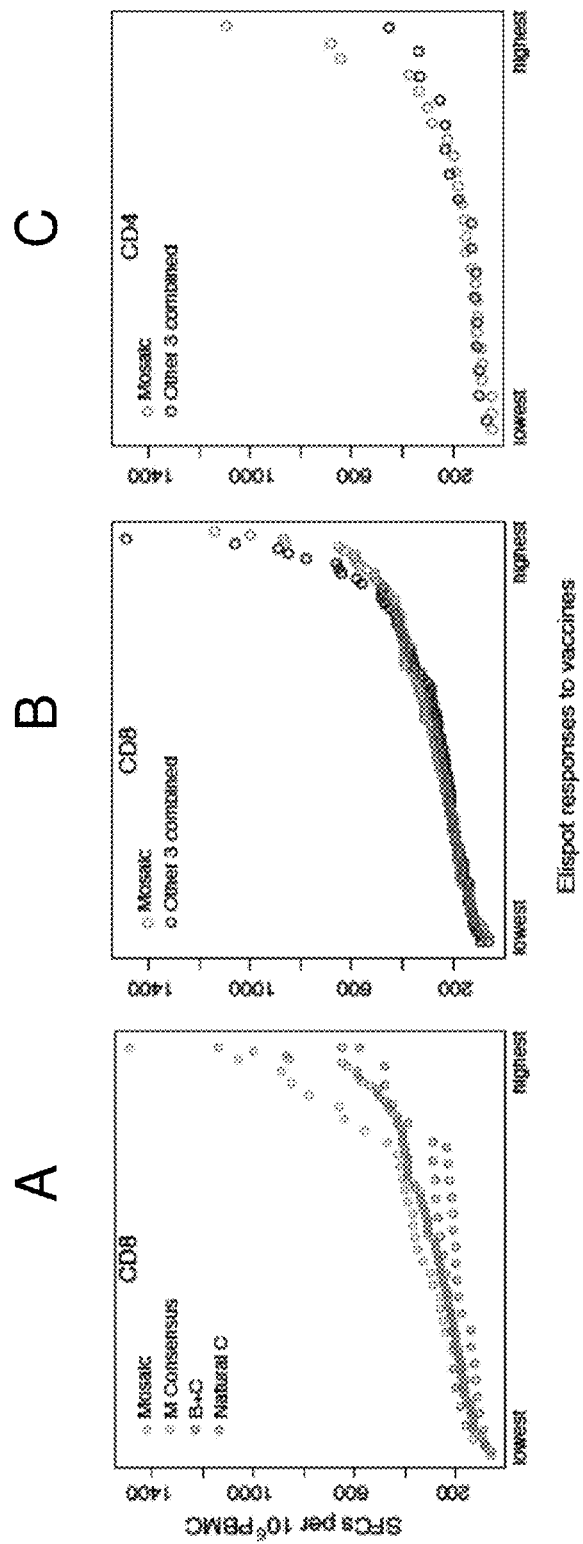

FIGS. 23A-23C are graphs showing the magnitude of all Gag-, Pol-, and Env-specific CD8+ (FIGS. 23A and 23B) and CD4+ (FIG. 23C) T lymphocyte responses arranged from lowest to highest.

Figure 24:
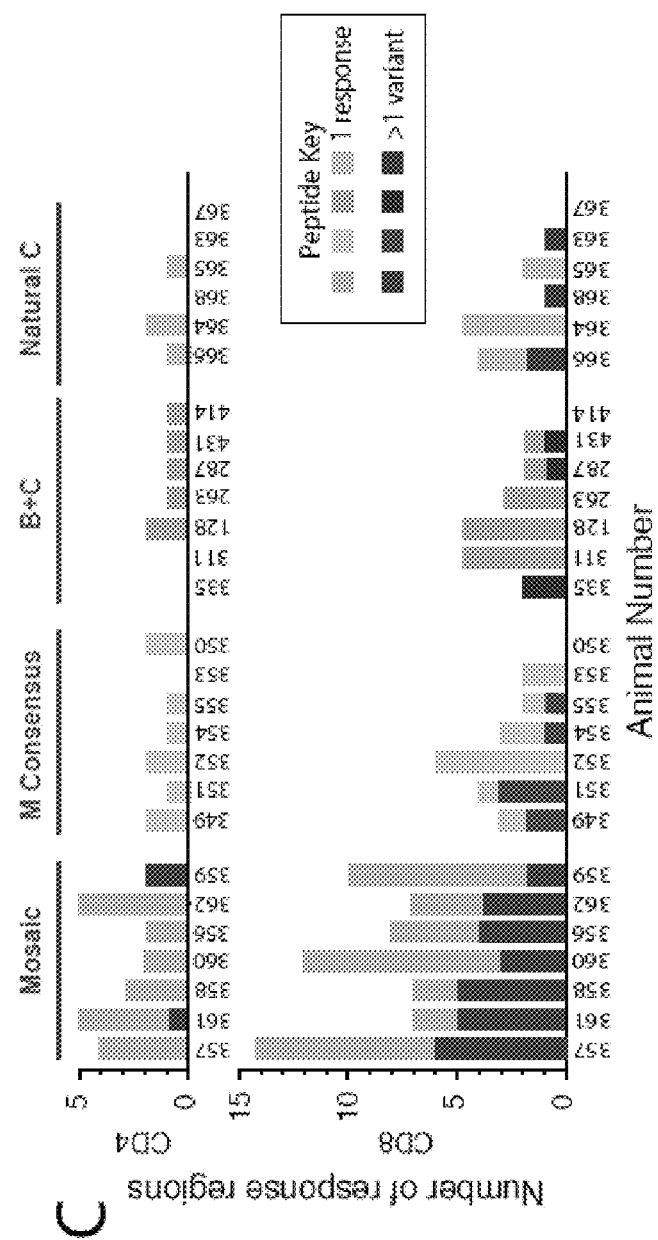

FIGS. 24A-C show the depth of epitope-specific T lymphocyte responses to PTE peptides. FIG. 24A is a schematic showing an example of mapped T lymphocyte responses in monkey 366 that received the optimal natural clade C antigens. FIG. 24B is a schematic showing an example of mapped T lymphocyte responses in monkey 361 that received the 2-valent mosaic antigens. In FIGS. 24A and 24B, vaccine sequences are shown on the top (OptC; Mos1, Mos2), and reactive PTE peptides are shown beneath the vaccine sequences denoted by the antigen (G, Gag; P, Pol; E, Env) and the PTE peptide numbers. The minimal overlap region is shown in bold. Sequence polymorphisms between the two mosaic antigens are shown in blue. Differences between the vaccine sequences and the reactive PTE peptides are shown in red. Complete alignments of all positive peptides organized by response regions are shown in FIG. 22. FIG. 24C is a graph showing the depth of CD4+ (top) and CD8+ (bottom) T lymphocyte responses following immunization with rAd26 vectors expressing mosaic, M consensus, clade B+clade C, or optimal natural clade C antigens. Individual monkeys are depicted on the x-axis. One response variant (light shade) or >1 response variants (dark shade) are shown for each epitopic region. FIG. 24A discloses SEQ ID NOS 641-650, respectively, in order of appearance. FIG. 24B discloses SEQ ID NOS 651-685, respectively, in order of appearance.

Figure 25:
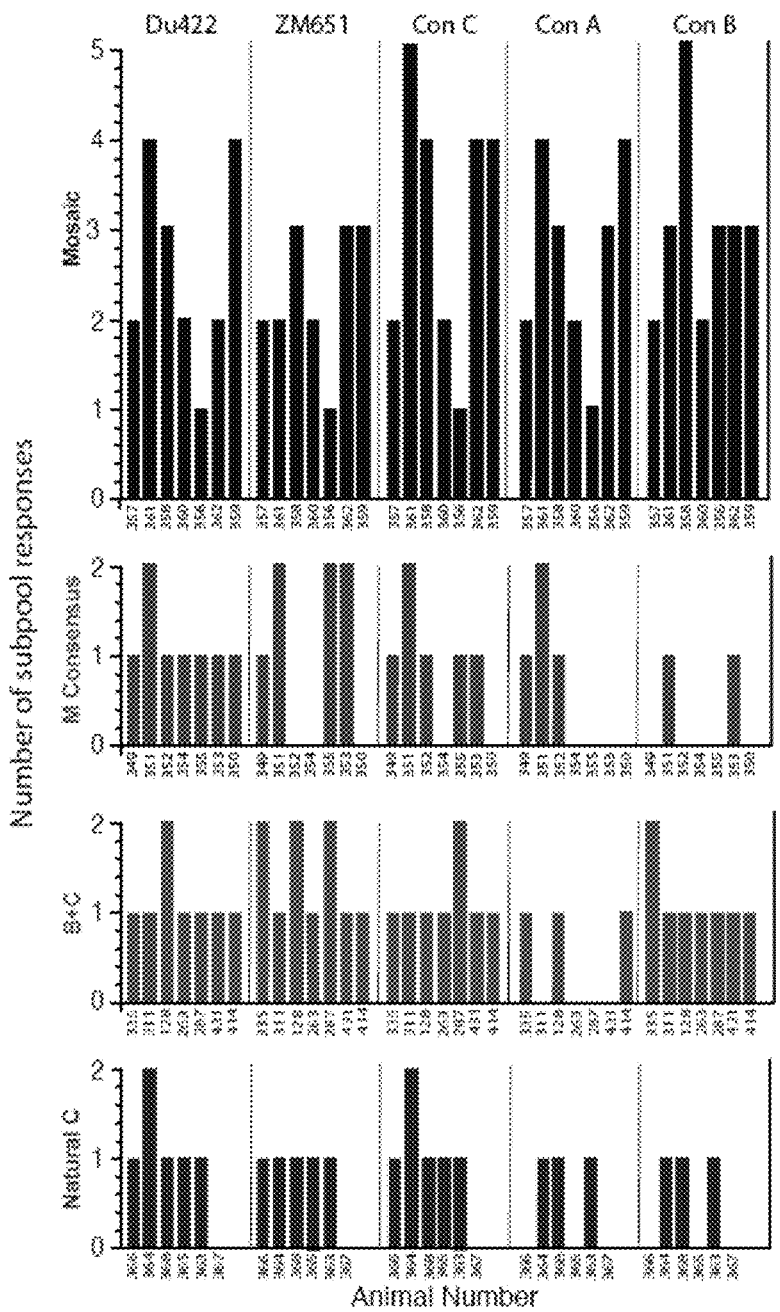

FIG. 25 is a graph showing the breadth of epitope-specific T lymphocyte responses to HIV-1 Gag peptides from clades A, B, and C. Breadth of cellular immune responses was assessed utilizing subpools of overlapping peptides from the following strains of HIV-1 Gag: clade C DU422, clade C ZM651, consensus C, consensus A, and consensus B. Numbers of positive subpools are shown following a single immunization of rAd26 vectors expressing mosaic (blue), M consensus (green), clade B+clade C (purple), or optimal natural clade C (red) HIV-1 Gag, Pol, and Env antigens. Individual monkeys are depicted on the x-axis.

Figure 26:
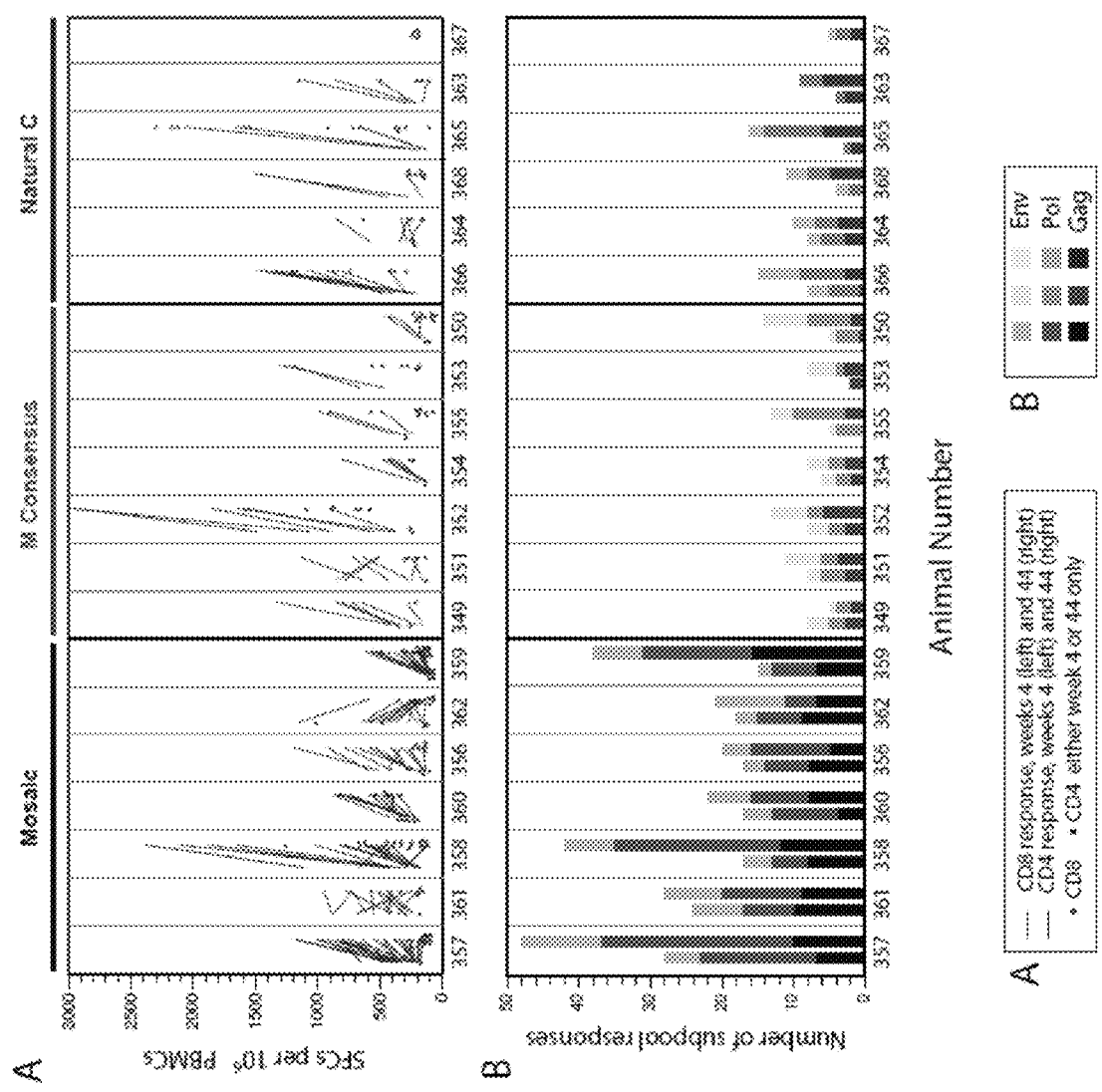
Figure 26:
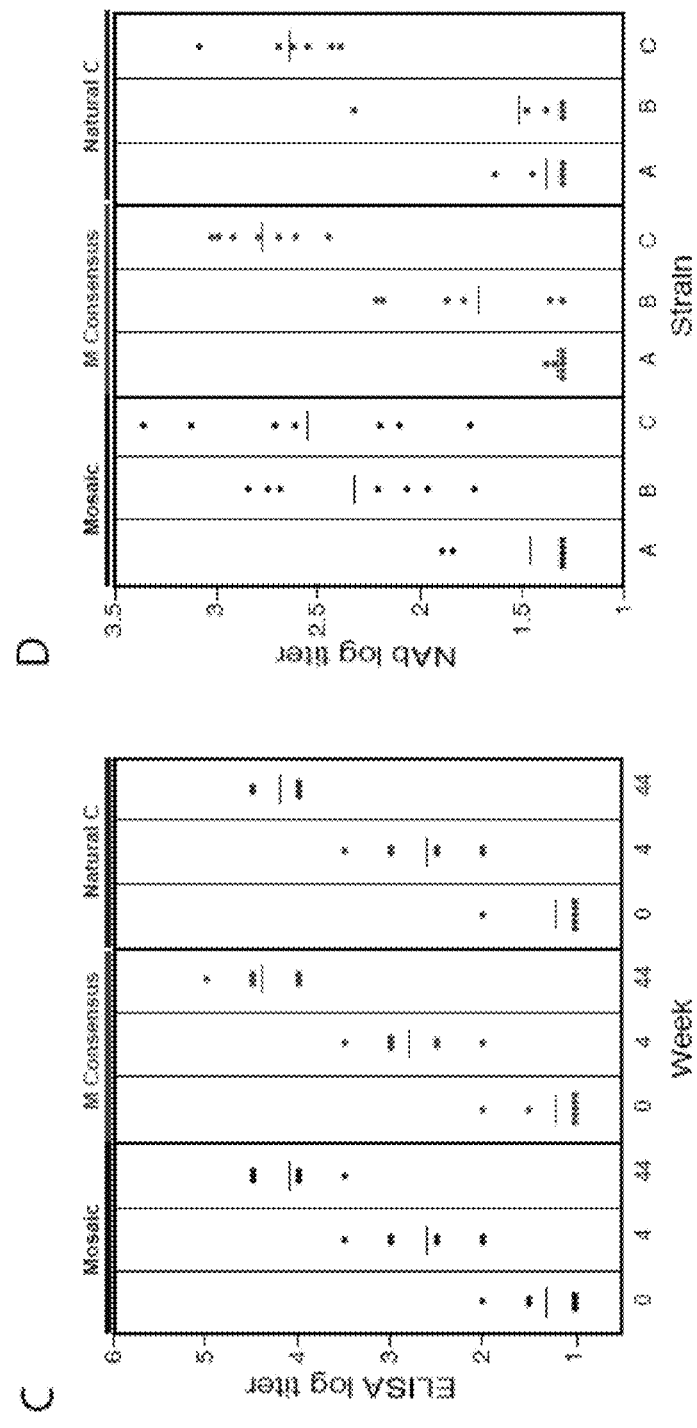

FIG. 26A-D are graphs showing the cellular and humoral immune responses following the boost immunization. Shown are the magnitude (FIG. 26A) and breadth (FIG. 26B) of individual T lymphocyte responses at week 4 post-prime (left side of each panel) and at week 44 post-boost (right side of each panel) for each monkey. Monkeys were primed at week 0 with rAd26 vectors and were boosted at week 40 with rAd5HVR48 vectors expressing mosaic, M consensus, or optimal natural clade C HIV-1 Gag, Pol, and Env antigens. Individual monkeys are depicted on the x axis. In FIG. 26A, red denotes CD8+ T lymphocyte responses, blue denotes CD4+ T lymphocyte responses, lines depict responses observed at both timepoints, and dots depict responses observed at only one timepoint. In FIG. 26B, different shades of each color reflect responses to the different antigens (Gag, Pol, Env). FIG. 26C is a graph showing the Env-specific ELISA endpoint titers at weeks 0, 4, and 44. FIG. 26D is a graph showing the neutralizing antibody (NAb) titers to the tier 1 clade A (DJ263.8), clade B (SF162.LS), and clade C (MW965.26) viruses at week 44. NAb titers to murine leukemia virus as a negative control were <20 for all samples.

Figure 27:
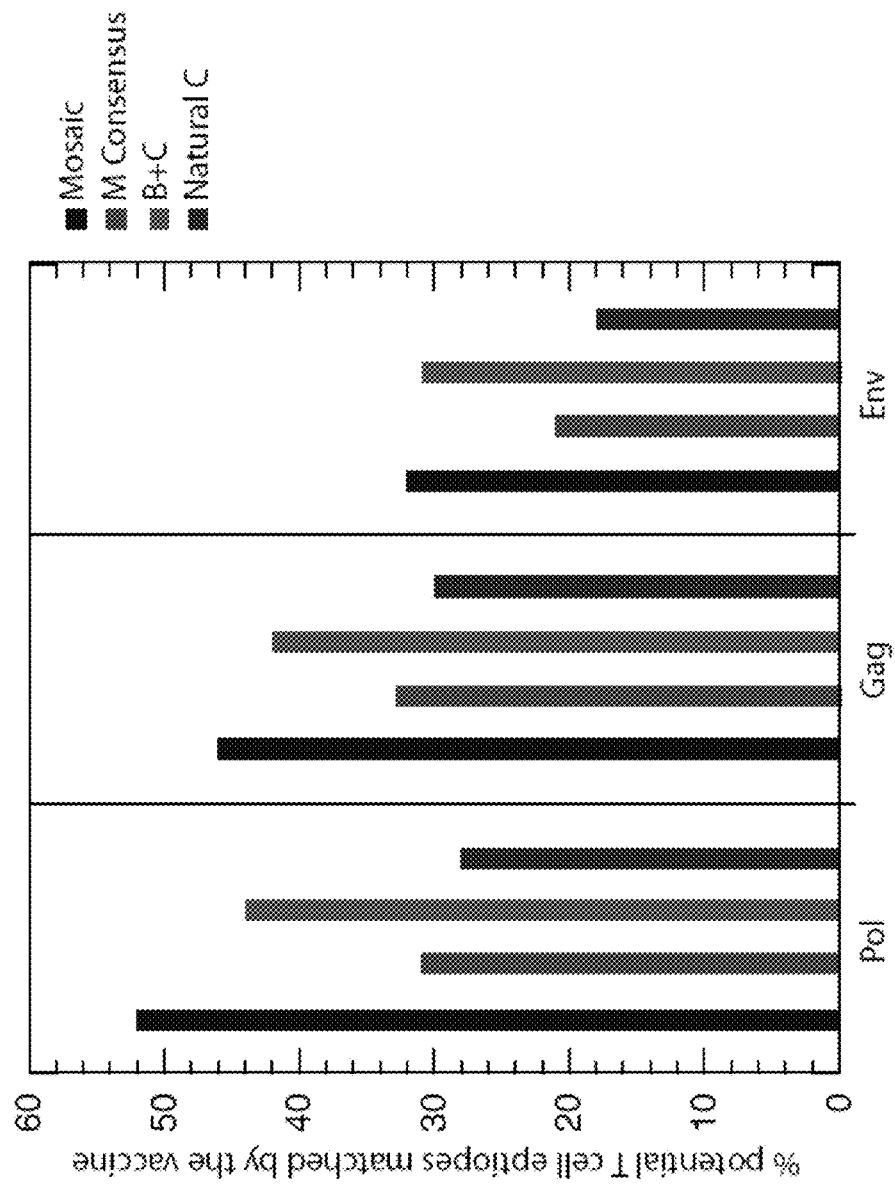

FIG. 27 is a graph showing the theoretical coverage of PTE peptides by the various vaccine antigens. Percentage of 9 amino acid PTE peptides that are covered by the mosaic (blue), M consensus (green), clade B+clade C (purple), or optimal natural clade C (red) HIV-1 Gag, Pol, and Env antigens are shown.

DETAILED DESCRIPTION OF THE INVENTION

The invention features optimized viral polypeptides that are computationally derived from naturally-occurring viral gene products. The optimized viral polypeptides of the invention allow for an increased breadth and depth of virus-specific immunity (e.g., cellular immunity, such as T cell-based immune responses) following immunization of a subject (e.g., a human) with one or more optimized viral polypeptides of the invention or vaccines (e.g., a vector) that incorporate one or more optimized viral polypeptides of the invention. The invention provides vaccines that can be administered to a subject (e.g., a human) infected with or at risk of becoming infected with a viral infection. The vaccines of the invention incorporate at least two distinct optimized viral polypeptides for each corresponding viral gene product represented. The incorporation of at least two distinct optimized viral polypeptides allows for increased coverage and representation of immunogenic epitopes in the vaccine, which the inventors have found results in an increase in the total number of virus-specific immune responses following vaccination of a subject. The present invention also provides methods of administering and manufacturing vaccines, vectors, and optimized viral polypeptides that to a subject (e.g., a human). The compositions, methods, and kits described herein can substantially increase the diversity, breadth, and/or depth of the virus-specific cellular immune responses by providing at least two distinct optimized viral polypeptides.

Optimized Viral Polypeptides of the Invention

The present invention provides for polyvalent (e.g., 2-valent) vaccines that incorporate computationally-optimized viral polypeptides that correspond to and are derived from viral gene products that naturally circulate. Polyvalent mosaic proteins are assembled from natural sequences by in silico recombination and optimized to provide maximal coverage of potential T cell epitopes (PTEs) for a given valency. Mosaic antigens are full-length proteins that are designed to preserve natural antigen expression and processing.

The inventors have discovered that immunization with two distinct optimized viral polypeptides corresponding to and derived from a single viral gene product (i.e., a 2-valent vaccine) elicits a substantially higher number of cellular immune responses (e.g., T cell responses) than conventional monovalent or polyvalent vaccines that incorporate naturally-occurring polypeptides derived from the same viral gene product (e.g., sequences based on clinical isolates), or a consensus sequence of such naturally-occurring polypeptides derived from the same viral gene product. Accordingly, a vaccine that incorporates computationally-optimized viral polypeptides, the sequences of which provide maximum coverage of non-rare short stretches of circulating viral sequences, can increase the breadth and depth of the immune response.

A genetic algorithm is used to create sets of optimized viral polypeptides as "mosaic" blends of fragments of an arbitrary set of naturally-occurring viral gene product sequences provided as inputs. This genetic algorithm strategy uses unaligned protein sequences from a general viral population as an input data set, and thus has the virtue of being "alignment independent." It creates artificial optimized viral polypeptides that resemble viral proteins found in nature, but are not naturally-occurring. The genetic algorithm can be adjusted to optimize viral polypeptides of different lengths, depending on the intended target or desired immune response. As most T cell epitopes are nine amino acids in length, the genetic algorithm utilized to design the optimized viral polypeptides of the invention was based on optimizing each consecutive 9-mer amino acid sequence of a given viral gene product (e.g., HIV-1 Gag). In accordance with this approach, 9-mers (for example) that do not exist in nature or that are very rare can be excluded—this is an improvement relative to consensus sequence-based vaccine strategies since the latter can contain some 9-mers (for example) that occur rarely or not at all in nature. The definition of fitness used for the genetic algorithm is that the most "fit" polyvalent cocktail is the combination of input viral sequences that gives the best coverage (highest fraction of perfect matches) of all of the 9 mers in the population and is subject to the constraint that no 9 mer is absent or rare in the population. The genetic algorithm used to generate the optimized viral polypeptides of the invention is further described in International Patent Application Publication WO 2007/024941, herein incorporated by reference.

In one embodiment, the invention provides polyvalent (e.g., 2-valent) HIV-1 vaccines that incorporate single optimized HIV-1 polypeptides (e.g., the polypeptides set forth in SEQ ID NOS:1-29). In another embodiment, the invention features a polyvalent vaccine that incorporates two or more optimized HIV-1 polypeptides. In each case, the optimized HIV-1 polypeptides are based on all HIV-1 variants in global circulation, known as the HIV-1 Main (M) group. The inventors have generated a set of optimized HIV-1 polypeptides (SEQ ID NOS:1-29) that augment the breadth and depth of cellular immunity based on group M mosaic genes that utilize only two variants per gene (e.g., two polypeptide sequences each for Gag, Pol, Env, Nef, Tat, Rev, Vif, Vpr, and Vpu). We have obtained the novel and surprising result in Rhesus macaques that the use of these optimized HIV-1 polypeptides in a polyvalent (e.g., 2-valent) HIV-1 group M vaccine elicits a significantly greater breadth and depth of HIV-1-specific cellular immune responses when compared with two other leading vaccine antigen strategies (M consensus antigens and optimal natural clade C antigens).

The invention provides for the fusion of optimized viral polypeptides that correspond to different viral gene products. The genetic algorithm described above can be used to generate fused polypeptides for use in a vaccine of the invention. For example, the optimized HIV-1 polypeptide fusions of Gag/Nef (SEQ ID NOS:19-20), Gag/Pol (SEQ ID NOS:21-27), and Gag/Pol/Nef (SEQ ID NOS:28-29) can be incorporated into a vector of the invention for administration to a subject (e.g., a human) infected with or at risk of being infected with HIV-1. The vaccines of the invention (whether in polypeptide or nucleic acid form) can also include one or more of the non-"mosaic" polypeptides (or sequences encoding them, respectively), such as, e.g., the optimal clade C sequences (SEQ ID NOS: 30-36) or the consensus sequences (SEQ ID NOS: 37-39).

The optimized viral polypeptides disclosed in this invention can be prepared conventionally by chemical synthesis techniques, such as described by Merrifield, *J. Amer. Chem. Soc.* 85:2149 (1963) (see also, e.g., Stemmer et al., 164 *Gene* 49 (1995)). For example, the vaccines can be readily prepared using solid phase peptide synthesis (SPPS). Automated solid phase synthesis can be performed using any one of a number of well known, commercially available automated synthesizers, such as the Applied Biosystems ABI 433A peptide synthesizer. Alternatively, the optimized viral polypeptides of the invention can be recombinantly produced by transfecting or transducing a cell or organism with a nucleic acid or vector (e.g., a viral vector, such an adenovirus) that allows for the intracellular expression of the optimized viral polypeptide. Nucleic acids and vectors that encode the nucleotide sequence of optimized viral polypeptides of the invention can be synthesized by well-known recombinant DNA techniques, including those described herein.

Vaccines of the Invention

The invention also features vaccines that can be administered to a patient infected with or at risk of becoming infected with a virus (e.g., HIV-1). A vaccine of the invention contains at least one of the optimized viral polypeptides of the invention, as discussed herein. The vaccine of the invention can be a nucleic acid encoding the nucleotide sequence of two or more optimized viral polypeptides of the invention (e.g., the immunogenic component of a recombinant (e.g., subunit) or whole-organism (e.g., whole-virus) viral vector). Nucleic acids include vectors (e.g., viral vectors, such as adenoviruses) that incorporate the nucleotide sequence of two or more optimized viral polypeptides of the invention. The optimized viral polypeptides of the invention, as well as vaccines, nucleic acids, and vectors that incorporate optimized viral polypeptides, can be recombinantly expressed in a cell or organism, or can be directly administered to subject (e.g., a human) infected with, or at risk of becoming infected with, a virus.

Vectors of the Invention

The invention also features vectors encoding the nucleotide sequences (e.g., DNA or RNA) of one or more optimized viral polypeptides of the invention. The vector can be a carrier (e.g., a liposome), a plasmid, a cosmid, a yeast artificial chromosome, or a virus that includes a nucleotide sequence encoding one or more optimized viral polypeptides of the invention. The vector can include additional nucleic acid sequences from several sources.

Vectors encoding one or more optimized viral polypeptides of the invention can be constructed using any recombinant molecular biology technique known in the art. The vector, upon transfection or transduction of a target cell or organism, can be extrachromosomal or it can be integrated into the host cell chromosome. The nucleic acid component of a vector can be in single or multiple copy number per target cell, and can be linear, circular, or concatamerized.

Vectors of the invention can also include internal ribosome entry site (IRES) sequences to allow for the expression of multiple peptide or polypeptide chains from a single nucleic acid transcript. For example, a vector of the invention can encode one or more optimized viral polypeptides of the invention as well as another polypeptides (e.g., a detectable label, such as green fluorescent protein (GFP)).

Vectors of the invention further include gene expression elements that facilitate the expression of optimized viral polypeptides of the invention. Gene expression elements useful for the expression of an vector encoding an optimized viral polypeptide of the invention include, but are not limited to (a) regulatory sequences, such as viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Also included are plasmid origins of replication, antibiotic resistance or selection genes, multiple cloning sites (e.g., restriction enzyme cleavage loci), and other viral gene sequences (e.g., sequences encoding viral structural, functional, or regulatory elements, such as the HIV long terminal repeat (LTR)).

Vectors of the invention can also include optimized viral polypeptides of the invention that have been optimized for expression in humans, such as, e.g., any one of SEQ ID NOS:11, 14-18, and 23.

Vectors of the invention can also be engineered to include a multiple cloning site (MCS) having the following enzyme cleavage sites: XbaI-EcoRI-Kozak-Start . . . Stop-BamHI-NheI; and the following sequence: TCTAGA GAATTC GCCACC [ATG gene TAA TGA] GGATCC GCTAGC. Vectors having this MCS can be used with optimized viral polypeptides having no internal XbaI, EcoRI, BamHI, NheI sites and no stretches of 6 or more C's or G's.

In Vivo Administration

The invention features methods for the in vivo administration of one or more vaccines of the invention (e.g., a vector encoding two or more optimized viral polypeptides of the invention) to a subject (e.g., a human) to facilitate the expression of two or more optimized viral polypeptides of the invention. Upon administering the vaccine to the subject, one or more optimized viral polypeptides of the invention will be expressed that can elicit protective or therapeutic immune responses (e.g., cellular or humoral immune responses) directed against the viral immunogens.

Several types of vectors can be employed to deliver a nucleotide sequence encoding one or more optimized viral polypeptides of the invention directly to a subject (e.g., a human). Vectors of the invention include viruses, naked DNA, oligonucleotides, cationic lipids (e.g., liposomes), cationic polymers (e.g., polysomes), virosomes, and dendrimers. The present invention provides for the ex vivo transfection or transduction of cells (e.g., blood cells) followed by administration of these cells back into the donor subject to allow for the expression of optimized viral polypeptides of the invention that have immunogenic properties. Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells and hematopoietic stem cells (HSC), can be isolated and transfected or transduced with an vector encoding one or more optimized viral polypeptides of the invention, and administered to a subject according to the methods of the invention.

The method of transfection or transduction used to express an optimized viral vector of the invention has a strong influence on the strength and longevity of protein expression in the transfected or transduced cell, and subsequently, in the subject receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Ex Vivo Transfection and Transduction

The invention also features methods for the ex vivo transfection and transduction of cells (e.g., blood cells, such as lymphocytes), followed by administration of these cells to a subject (e.g., a human). In one embodiment, the cells are autologous to the treated subject. Cells can be transfected or transduced ex vivo with one or more vectors encoding the nucleotide sequence of one or more optimized viral polypeptides of the invention to allow for the temporal or permanent expression of the optimized viral polypeptides in the treated subject. Upon administering these modified cells to the subject, one or more optimized viral vectors of the invention will be expressed that can elicit protective or therapeutic immune responses (e.g., cellular or humoral immune responses) directed against the viral immunogens.

Several types of vectors can be employed to deliver a nucleotide sequence encoding one or more optimized viral polypeptides of the invention to a cell (e.g., a blood cell, such as a lymphocyte). Vectors of the invention include viruses, naked DNA, oligonucleotides, cationic lipids (e.g., liposomes), cationic polymers (e.g., polysomes), virosomes, and dendrimers. The present invention provides for the ex vivo transfection or transduction of cells (e.g., blood cells) followed by administration of these cells back into the donor subject to allow for the expression of optimized viral polypeptides of the invention that have immunogenic properties. Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells and hematopoietic stem cells (HSC), can be isolated and transfected or transduced with an vector encoding one or more optimized viral polypeptides of the invention, and administered to a subject according to the methods of the invention.

The method of transfection or transduction used to express an optimized viral vector of the invention has a strong influence on the strength and longevity of protein expression in the transfected or transduced cell, and subsequently, in the subject receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Viral Vectors

Viral vectors encoding the nucleotide sequence of one or more optimized viral polypeptides of the invention can be used as a vaccine of the invention. For example, the nucleotide sequence of one or more optimized viral polypeptides of the invention can be inserted recombinantly into that of a natural or modified (e.g., attenuated) viral genome suitable for the transduction of a subject (e.g., in vivo administration) or cells isolated from a subject (e.g., for ex vivo transduction followed by administration of the cells back to the subject). Additional modifications can be made to the virus to improve infectivity or tropism (e.g., pseudotyping), reduce or eliminate replicative competency, or reduce immunogencity of the viral components (e.g., all components not related to the immunogenic vaccine agent). A vector of the invention can be expressed by the transduced cell and secreted into the extracellular space or remain with the expressing cell (e.g., as an intracellular molecule or displayed on the cell surface). Chimeric or pseudotyped viral vectors can also be used to transduce a cell to allow for expression of one or more optimized viral polypeptides of the invention. Exemplary vectors are described below.

Adenoviruses

Recombinant adenoviruses offer several significant advantages for use as vectors for the expression of one or more optimized viral polypeptides of the invention. The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid encoding an optimized viral polypeptide of the invention) can be prolonged by using cell or tissue-specific promoters. Other improvements in the molecular engineering of the adenoviral vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Acad. Sci. USA* 91:6196 (1994) and Kochanek et al., *Proc. Natl. Acad. Sci. USA* 93:5731 (1996), each herein incorporated by reference).

The rare serotype and chimeric adenoviral vectors disclosed in International Patent Application Publications WO 2006/040330 and WO 2007/104792, each incorporated by reference herein, are particularly useful as vectors of the invention. For example, recombinant adenoviruses rAd26, rAd34, rAd35, rAd48, and rAd5HVR48 can encode one or more optimized viral polypeptides of the invention. One or more recombinant viral vectors encoding optimized viral polypeptides of the invention can be administered to a subject to treat or prevent a viral infection.

Adeno-Associated Viruses (AAV)

Adeno-associated viruses (rAAV), derived from non-pathogenic parvoviruses, can also be used to express optimized viral polypeptides of the invention as these vectors evoke almost no anti-vector cellular immune response, and produce transgene expression lasting months in most experimental systems.

Retroviruses

Retroviruses are useful for the expression of optimized viral polypeptides of the invention. Unlike adenoviruses, the retroviral genome is based in RNA. When a retrovirus infects a cell, it will introduce its RNA together with several enzymes into the cell. The viral RNA molecules from the retrovirus will produce a double-stranded DNA copy, called a provirus, through a process called reverse transcription. Following transport into the cell nucleus, the proviral DNA is integrated in a host cell chromosome, permanently altering the genome of the transduced cell and any progeny cells that may derive from this cell. The ability to permanently introduce a gene into a cell or organism is the defining characteristic of retroviruses used for gene therapy. Retroviruses include lentiviruses, a family of viruses including human immunodeficiency virus (HIV) that includes several accessory proteins to facilitate viral infection and proviral integration. Current, "third-generation," lentiviral vectors feature total replication incompetence, broad tropism, and increased gene transfer capacity for mammalian cells (see, e.g., Mangeat and Trono, *Human Gene Therapy* 16(8):913 (2005) and Wiznerowicz and Trono, *Trends Biotechnol.* 23(1):42 (2005), each herein incorporated by reference).

Other Viral Vectors

Besides adenoviral and retroviral vectors, other viral vectors and techniques are known in the art that can be used to express optimized viral polypeptides of the invention in a cell (e.g., a blood cell, such as a lymphocyte) or subject (e.g., a human). Theses viruses include Poxviruses (e.g., vaccinia virus and modified vaccinia virus Ankara or (MVA); see, e.g., U.S. Pat. Nos. 4,603,112 and 5,762,938, each incorporated by reference herein), Herpesviruses, Togaviruses (e.g., Venezuelan Equine Encephalitis virus; see, e.g., U.S. Pat. No. 5,643,576, incorporated by reference herein), Picornaviruses (e.g., poliovirus; see, e.g., U.S. Pat. No. 5,639,649, incorporated by reference herein), Baculoviruses, and others described by Wattanapitayakul and Bauer (*Biomed. Pharmacother.* 54:487 (2000), incorporated by reference herein).

Other Expression Vectors: Naked DNA and Oligonucleotides

Naked DNA or oligonucleotides encoding one or more optimized viral polypeptides of the invention can also be used to express these polypeptides in a cell (e.g., a blood cell, such as a lymphocyte) or subject (e.g., a human). See, e.g., Cohen, *Science* 259:1691-1692 (1993); Fynan et al., *Proc. Natl. Acad. Sci. USA,* 90: 11478 (1993); and Wolff et al., *BioTechniques* 11: 474485 (1991), each herein incorporated by reference. This is the simplest method of non-viral transfection. Efficient methods for delivery of naked DNA exist such as electroporation and the use of a "gene gun," which shoots DNA-coated gold particles into a cell using high pressure gas and carrier particles (e.g., gold).

Lipoplexes and Polyplexes

To improve the delivery of an nucleic acid encoding an optimized viral polypeptide of the invention into a cell or subject, lipoplexes (e.g., liposomes) and polyplexes can be used to protect the vector DNA from undesirable degradation during the transfection process. Plasmid DNA can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively-charged DNA. Also as a result of their charge they interact with the cell membrane, endocytosis of the lipoplex occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Exemplary cationic lipids and polymers that can be used in combination with a nucleic acid encoding an optimized viral polypeptide of the invention to form lipoplexes, or polyplexes include, but are not limited to, polyethylenimine, lipofectin, lipofectamine, polylysine, chitosan, trimethylchitosan, and alginate.

Hybrid Methods

Several hybrid methods of gene transfer combine two or more techniques. Virosomes, for example, combine lipoplexes (e.g., liposomes) with an inactivated virus. This approach has been shown to result in more efficient gene transfer in respiratory epithelial cells than either viral or liposomal methods alone. Other methods involve mixing other viral vectors with cationic lipids or hybridising viruses. Each of these methods can be used to facilitate transfer of an nucleic acid encoding optimized viral polypeptides of the invention into a cell (e.g., a blood cell, such as a lymphocyte) or subject (e.g., a human).

Dendrimers

Dendrimers may be also be used to transfer an nucleic acid encoding an optimized viral polypeptide of the invention into a cell (e.g., a blood cell, such as a lymphocyte) or subject (e.g., a human). A dendrimer is a highly branched macromolecule with a spherical shape. The surface of the particle may be functionalized in many ways, and many of the properties of the resulting construct are determined by its surface. In particular it is possible to construct a cationic dendrimer (i.e. one with a positive surface charge). When in the presence of genetic material such as DNA or RNA, charge complimentarity leads to a temporary association of the nucleic acid with the cationic dendrimer. On reaching its destination the dendrimer-nucleic acid complex is then taken into the cell via endocytosis.

In Vivo Administration

The invention also features in vivo methods for immunizing a subject (e.g., a human) with a vaccine of the invention. In one embodiment, one or more vaccines of the invention can be directly administered to a subject to elicit a protective or therapeutic immune response (e.g., a cellular or humoral immune response) against a virus (e.g., HIV-1). Alternatively, a vector encoding one or more optimized viral polypeptides of the invention, as described above, can be directly administered to a subject to prevent or treat a viral infection. A vector (e.g., a viral vector) that efficiently transfects or transduces one or more cells in vivo can elicit a broad, durable, and potent immune response in the treated subject. Upon transfer of the nucleic acid component of the expression vector into a host cell (e.g., a blood cell, such as a lymphocyte), the host cell produces and displays or secretes the vaccine of the invention, which then serves to activate components of the immune system such as antigen-presenting cells (APCs), T cells, and B cells, resulting in the establishment of immunity.

Pharmaceutical Compositions

The invention features the vaccines, vectors, and optimized viral polypeptides of the invention in combination with one or more pharmaceutically acceptable excipients, diluents, buffers, or other acceptable carriers. The formulation of a vaccine, vector, or optimized viral polypeptides will employ or allow expression of an effective amount of the optimized viral polypeptide immunogen. That is, there will be included an amount of antigen which will cause the treated subject (e.g., a human) to produce a specific and sufficient immunological response so as to impart protection to the subject from subsequent exposure to a virus (e.g., HIV-1) or to treat an existing viral infection. For example, a formulation of a vaccine of the invention can allow for the expression of an amount of antigen which will cause the subject to produce a broad and specific cellular immune response. A subject treated with a vaccine, vector, or optimized viral polypeptide of the invention can also produce anti-viral antibodies (e.g., neutralizing antibodies) which can confer a protective or therapeutic benefit to the subject. A vaccine, vector, or optimized viral polypeptide of the invention can be directly administered to a subject, either alone or in combination with any pharmaceutically acceptable carrier, salt or adjuvant known in the art.

Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, ($18^{th}$ edition), ed. A. Gennaro, 1990, Mack Publishing Company, Easton, Pa.

Pharmaceutical formulations of a prophylactically or therapeutically effective amount of a vaccine, vector, or optimized viral polypeptide of the invention can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration. The concentration of a vaccine, vector, or optimized viral polypeptide of the invention in the formulation can vary from about 0.1-100 wt. %.

Formulations for parenteral administration of compositions containing a vaccine, vector, or optimized viral polypeptide of the invention include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for compositions containing a vaccine, vector, or optimized viral polypeptide of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

Compositions containing vaccine, vector, or optimized viral polypeptide of the invention for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the peptide being administered, the time of administration, the route of administration, the nature of the formulation, the rate of excretion, the nature of the subject's conditions, and the age, weight, health, and gender of the patient. In addition, the severity of the condition treated by the vaccine, vector, or optimized viral polypeptide will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise prophylactically or therapeutically effective dosage can be determined by the attending clinician in consideration of the above-identified factors.

The amount of a vaccine, vector, or optimized viral polypeptide of the invention present in each dose given to a patient is selected with regard to consideration of the patient's age, weight, sex, general physical condition and the like. The amount of a vaccine, vector, or optimized viral polypeptide required to induce an immune response (e.g., a cellular immune response) or produce an exogenous effect in the patient without significant adverse side effects varies depending upon the pharmaceutical composition employed and the optional presence of an adjuvant. Initial doses can be optionally followed by repeated boosts, where desirable. The method can involve chronically administering the vaccine, vector, or optimized viral polypeptide of the invention. For therapeutic use or prophylactic use, repeated dosages of the immunizing vaccine, vector, or optimized viral polypeptide can be desirable, such as a yearly booster or a booster at other intervals. The dosage administered will, of course, vary depending upon known factors such as the pharmacodynamic characteristics of the particular vaccine, vector, or optimized viral polypeptide, and its mode and route of administration; age, health, and weight of the recipient; nature and extent of symptoms, kind of concurrent treatment, frequency of treatment, and the effect desired. A vaccine, vector, or optimized viral polypeptide of the invention can be administered in chronic treatments for subjects at risk of acute infection due to needle sticks or maternal infection. A dosage frequency for such "acute" infections may range from daily dosages to once or twice a week i.v. or i.m., for a duration of about 6 weeks. The vaccine, vector, or optimized viral polypeptide can also be employed in chronic treatments for infected patients, or patients with advanced infection with a virus (e.g., HIV-1). In infected patients, the frequency of chronic administration can range from daily dosages to once or twice a week i.v. or i.m., and may depend upon the half-life of immunogen present in the vaccine, vector, or optimized viral polypeptide of the invention.

Adjuvants

A vaccine of the invention used to vaccinate a mammal (e.g., a human) in need thereof against a virus can be administered concurrent with or in series with one or more pharmaceutically acceptable adjuvants to increase the immunogenicity of the vaccine. Adjuvants approved for human use include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1, 2-dipalmitoyl-s-gly-cero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

Kits

The invention provides kits that include a pharmaceutical composition containing a vaccine, vector, or optimized viral polypeptide of the invention, and a pharmaceutically-acceptable carrier, in a therapeutically effective amount for preventing or treating a viral infection. The kits include instructions to allow a clinician (e.g., a physician or nurse) to administer the composition contained therein.

Preferably, the kits include multiple packages of the single-dose pharmaceutical composition(s) containing an effective amount of a vaccine, vector, or optimized viral polypeptide of the invention. Optionally, instruments or devices necessary for administering the pharmaceutical composition(s) may be included in the kits. For instance, a kit of this invention may provide one or more pre-filled syringes containing an effective amount of a vaccine, vector, or optimized viral polypeptide of the invention. Furthermore, the kits may also include additional components such as instructions or administration schedules for a patient infected with or at risk of being infected with a virus to use the pharmaceutical composition(s) containing a vaccine, vector, or optimized viral polypeptide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The present invention is illustrated by the following examples, which are in no way intended to be limiting of the invention.

Example 1

The mosaic antigen Gag, Pol, Nef, and Env sequences (SEQ ID NOS:1-8) were constructed using the genetic algorithm discussed above. These sequences were then modified to make them practical for vaccine development by eliminating cleavage/fusion activity in Env (SEQ ID NOS:9-11), eliminating catalytic activity in Pol (SEQ ID NOS:12-14), eliminating myristylation sites in Nef (SEQ ID NOS:16-18), and constructing fusion constructs including GagNef, GagPol, or GagPolNef (SEQ ID NOS:19-29). The comparator optimal natural clade C genes are also depicted (SEQ ID NOS:30-36).

Example 2

Twenty rhesus monkeys were immunized with $3 \times 10^{10}$ vp rAd26 vectors expressing Gag, Pol, and Env genes from M consensus (Group 1), 2-valent M mosaic (Group 2), or optimal natural clade C (Group 3) sequences. The M consensus sequences represent synthetic sequences that represent the single best "average" of circulating viruses worldwide. The 2-valent M mosaic sequences are described above. The optimal natural clade C sequences are naturally occurring sequences from actual clade C HIV-1 viruses that are the most "consensus-like" in character. Cellular immune breadth was assessed by evaluating the number of responding peptides from the global potential T cell epitope (PTE) peptide set. The PTE peptides represent >85% of global HIV-1 sequences and are freely available from the NIH.

The results show that the novel 2-valent M mosaic sequences dramatically outperformed these other two leading antigen concepts. As shown in Table 1, the 2-valent M mosaic antigens elicited significantly increased breadth of Gag-specific, Env-specific, Pol-specific, and total T lymphocyte responses as compared with M consensus antigens and optimal natural clade C antigens. (Mean represents the average # epitopes in each group of monkeys; SEM represents the standard error of the mean).

TABLE 1

Mosaic HIV-1 Gag/Pol/Env Antigens Expand Breadth Against Global PTE Peptides in Rhesus Monkeys

|  | Group I: M Consensus | | Group II: 2-valent M Mosaic | | Group III: Natural Clade C | |
| --- | --- | --- | --- | --- | --- | --- |
| Breadth | Mean | SEM | Mean | SEM | Mean | SEM |
| Gag | 2.0 | 0.4 | 7.7 | 0.9 | 2.2 | 0.5 |
| Env | 2.0 | 0.4 | 4.0 | 0.6 | 1.6 | 0.5 |
| Pol | 2.7 | 0.5 | 8.1 | 1.4 | 2.4 | 0.5 |
| Total | 6.7 | 0.7 | 19.9 | 1.9 | 6.1 | 1.1 |

Example 3

Macaque monkeys were immunized IM with $3 \times 10^{10}$ vp rAd26 vectors expressing Gag, Pol, and Env genes from M consensus (Group 1; n=7), 2-valent M mosaic (Group 2; n=7), or optimal natural clade C (Group 3; n=6) sequences described in Example 2. Cellular immune breadth was assessed by evaluating the number of responding peptides from the global potential T cell epitope (PTE) peptide set.

As a readout, we assessed the CD4/CD8 IFNγ Elispot responses to pooled PTE peptides (magnitude). The epitopes were comprehensively mapped using 15 mer PTE peptides to assess the number of positives (positives were defined as 55 spot forming cells (SFC) per $10^6$ PBMC and 4× background). Pooled sets of overlapping peptides spanning 5 Gag proteins were also tested to compare responses to a set of complete proteins.

The results show that the 2-valent M mosaic sequences dramatically outperformed the other two leading antigen concepts (Mcon and OptC).

Example 4

We used modeling to validate our observation that T cell responses increase as a result of the mosaic vaccine. We fit Poisson regression models that predicted the number of reactive peptides as a function of vaccine, polypeptide, and T cell type and then did a stepwise elimination of interactions. We observed that, although the mosaic vaccine produced a highly significant enhancement in the number of positive PTE responses, it did so more-or-less uniformly across all polyproteins and T-cell types. Thus, one may predict the number of peptides having a positive effect in an animal by combining contributions that depend, separately, on the type of T-cell, the polypeptide, and the vaccine the animal received.

These models also included random effects to account for animal-to-animal variation. This is a precaution designed to make for more credible p-values, by properly apportioning the predictive power of the model.

We observed the following effects:

a) There are many more CD8 responses than CD4 responses, by a factor of 4.37, $p<2\times10^{-16}$;

b) There are fewer responses in gp160 than in gag or pol, by a factor of 0.54, p=0.000830, and no significant difference between gag and pol (even when normalized by sequence length as pol is twice as long as Gag and so has more opportunity to react); and c) The mosaic vaccine generates significantly more positive responses than Mcon (by a factor of 3.6, $p=6.26\times10^{-11}$) while OptC generates fewer, though the Mcon-OptC difference is not significant.

Example 5

If one considers just the minimal number of responses elicited by a vaccine and detected by PTE peptides, so that all peptide that overlap by >8 amino acids regardless of variation are counted just 1 time, the mosaic vaccines still generate a greater number of responses to distinct regions.

For CD8, counting each overlapping peptide set just once:
Statistical Summary:
Mos2>Mcon~OptC (Mcon shows a trend for more response than OptC)
Wilcoxon p-value for Mos2 compared to Mcon: p-value=0.0009992
Wilcoxon p-value for Mcon compared to Optimal C: p-value=0.2351

Summary of the Groups:

| Vaccine  | Min. | 1stQu. | Median | Mean | 3rdQu. | Max. |
|----------|------|--------|--------|------|--------|------|
| Mos2.cd8 | 7    | 7.5    | 8      | 9.4  | 11     | 14   |
| Mcon.cd8 | 0    | 3      | 3      | 3.3  | 4      | 6    |
| OptC.cd8 | 0    | 1      | 1.5    | 2    | 4.25   | 5    |

For CD4, counting each overlapping peptide set just once (there is very little overlap in CD4, so this is almost the same as the first count).
Statistical Summary:
Mos2>>Mcon~OptC (Mcon shows a trend for more response than OptC)
Wilcoxon p-value for Mos2 compared to Mcon: p-value=0.00198
Wilcoxon p-value for Mcon compared to Optimal C, 0.099
Summary of the Groups:

| Vaccine  | Min. | 1stQu. | Median | Mean | 3rdQu. | Max. |
|----------|------|--------|--------|------|--------|------|
| Mos2.cd4 | 2    | 2.5    | 3      | 3.4  | 4.5    | 5    |
| Mcon.cd4 | 0    | 1      | 1      | 1.3  | 2      | 2    |
| OptC.cd4 | 0    | 0      | 0.5    | 0.67 | 1      | 2    |

Example 6

Poisson Regression Counting Each Overlapping Peptide Set Just Once

Using overlapping PTE peptides, we determined the following, which are in broad agreement with the results discussed in Example 4 above, where each positive PTE response counted separately:

a) There are many more CD8 responses than CD4 responses, by a factor of about 2.8, $p \approx 1 \times 10^{-7}$;

b) The mosaic vaccine generates significantly more positive responses than Mcon (by a factor of 2.84, $p \approx 4.3 \times 10^{-7}$), while OptC generates fewer, though the Mcon-OptC difference is not significant; and c) There are more responses to Pol than to Gag and more to Gag than gp160, but only the Pol-gp160 difference, a factor of about 2, was significant, p<0.001.

Example 7

The following table is a tally of the total responses to Gag, Pol, and Env responses to the three vaccines in the 7 animals vaccinated with 2 Mosaic (Mos2) or Mcon, and the 6 animals vaccinated with the Optimal Natural C clade (OptC):

|      | CD8 |     |     | CD4 |     |     |
|------|-----|-----|-----|-----|-----|-----|
|      | Env | Gag | Pol | Env | Gag | Pol |
| 2Mos | 13  | 20  | 33  | 3   | 10  | 11  |
| ConM | 8   | 7   | 8   | 2   | 3   | 4   |
| OptC | 4   | 5   | 5   | 1   | 2   | 1   |

The OptC vaccine yielded an average response across all monkeys that was slightly less than the CD8+ T cell response per protein. The Mcon vaccine exhibited ~1 response per protein. Only with Mos2 do we observe a difference in the proteins, where Env typically has fewer responses than either Gag or Pol.

Each of the proteins in the Mos2 vaccine elicited many responses and contributed to the overall response. The relative length of the consensus proteins after the modifications to inactivate pol and the deletion of the cleavage and fusion domain in Env was: 671 amino acids of Env, 851 of Pol, 498 of Gag (1.35:1.7:1).
Summary
Breadth: The 2 mosaic vaccines elicit T cell responses that are capable of recognizing many more epitope-regions than the M consensus or a single optimal natural strain.
Depth: The diversity of the PTE peptides recognized suggests both forms in the 2 mosaics are eliciting different T cell responses to the variant peptides, increasing the cross-reactive potential.

Example 8

Mosaic HIV-1 vaccines of the invention expand the breadth and depth of cellular immune responses in Rhesus monkeys. We constructed mosaic HIV-1 Gag, Pol, and Env antigens that optimized PTE coverage of HIV-1 M group sequences, which include all major HIV-1 clades and recombinant lineages in the Los Alamos HIV-1 sequence database. A 2-valent mosaic strategy was utilized to balance the competing issues of theoretical coverage and practical utility. 2-valent mosaic HIV-1 Gag, Pol, and Env antigens substantially expanded the breadth and magnitude (depth) of epitope-specific CD8+ and CD4+ T lymphocyte responses in rhesus monkeys, relative to the immune response observed using consensus and natural sequence HIV-1 antigens in rhesus monkeys.

We immunized 27 outbred rhesus monkeys with a single injection of recombinant adenovirus serotype 26 (rAd26) vectors expressing the following antigens: (i) 2-valent mosaic (N=7), (ii) M consensus (N=7), (iii) 2-valent combined clade B and clade C(N=7), or (iv) optimal natural clade C(N=6) HIV-1 Gag, Pol, and Env antigens. A total dose of $3 \times 10^{10}$ viral particles of rAd26 vectors expressing these antigens was administered once i.m. to each animal. The optimal clade C antigens were the natural strain sequences selected to provide maximal PTE coverage of clade C sequences in the Los Alamos HIV-1 sequence database (discussed in the Materials and Methods below). We assessed the breadth and magnitude (depth) of vaccine-elicited HIV-1-specific T lymphocyte responses by IFN-γ ELISPOT assays at week 4 following immunization utilizing pools and subpools of peptides that included all PTEs found in at least 15% of HIV-1 M group sequences. All individual peptide responses were resolved, and cell-depleted IFN-γ ELISPOT assays were performed to determine if reactive peptides represented CD8+ or CD4+ T lymphocyte epitopes.

Figure 1:
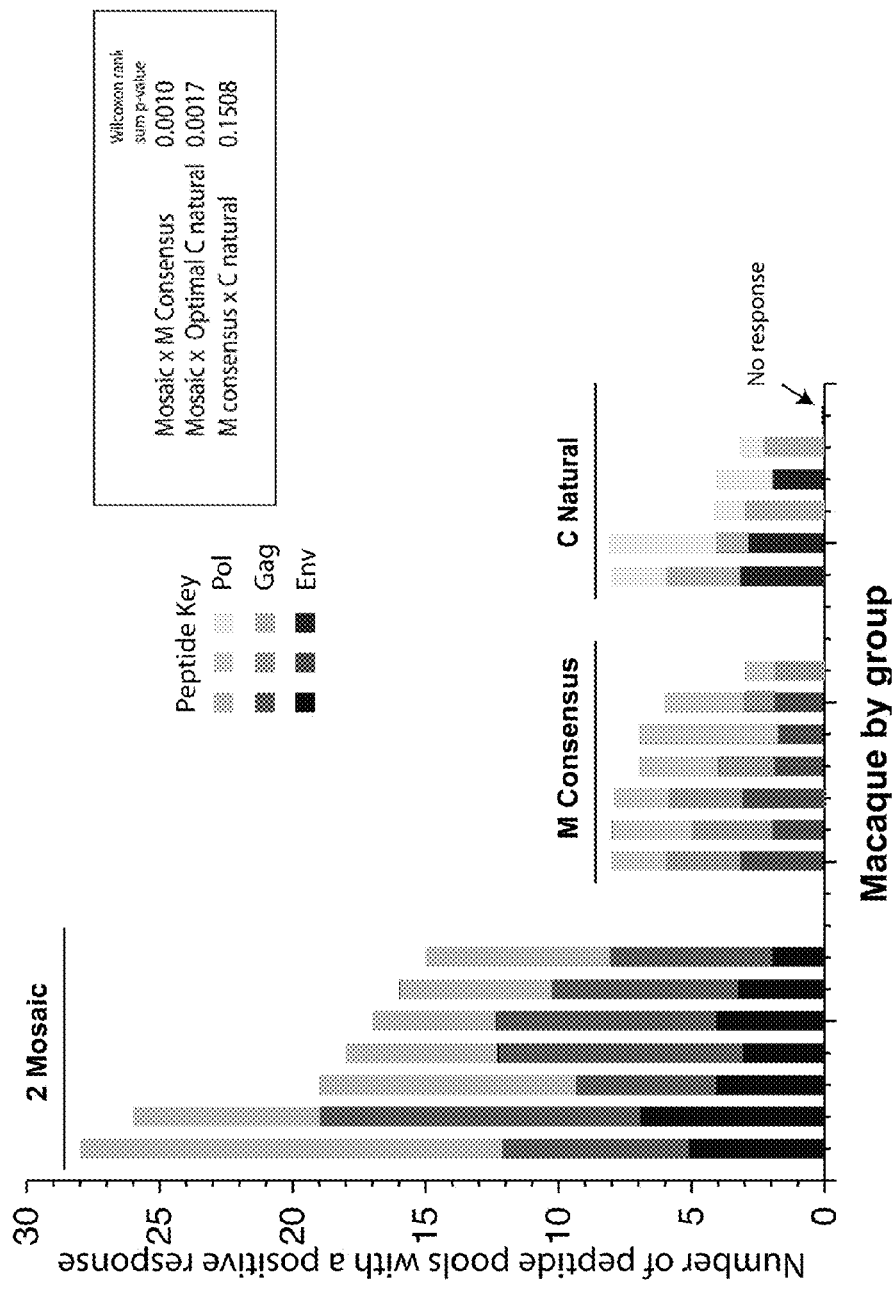
FIG. 1 is a chart that illustrates the expanded breadth of computationally-optimized HIV-1 Gag, Pol, and Env viral polypeptides against global potential T-cell epitopes (PTE) peptides in Rhesus mac HIV-1 M group in the peptide reagents used to assess vaccines. Inevitably, there is a lot of overlap in PTE peptides, but because of the algorithm, overlap is usually an overlap with some variation.
Figure 2:
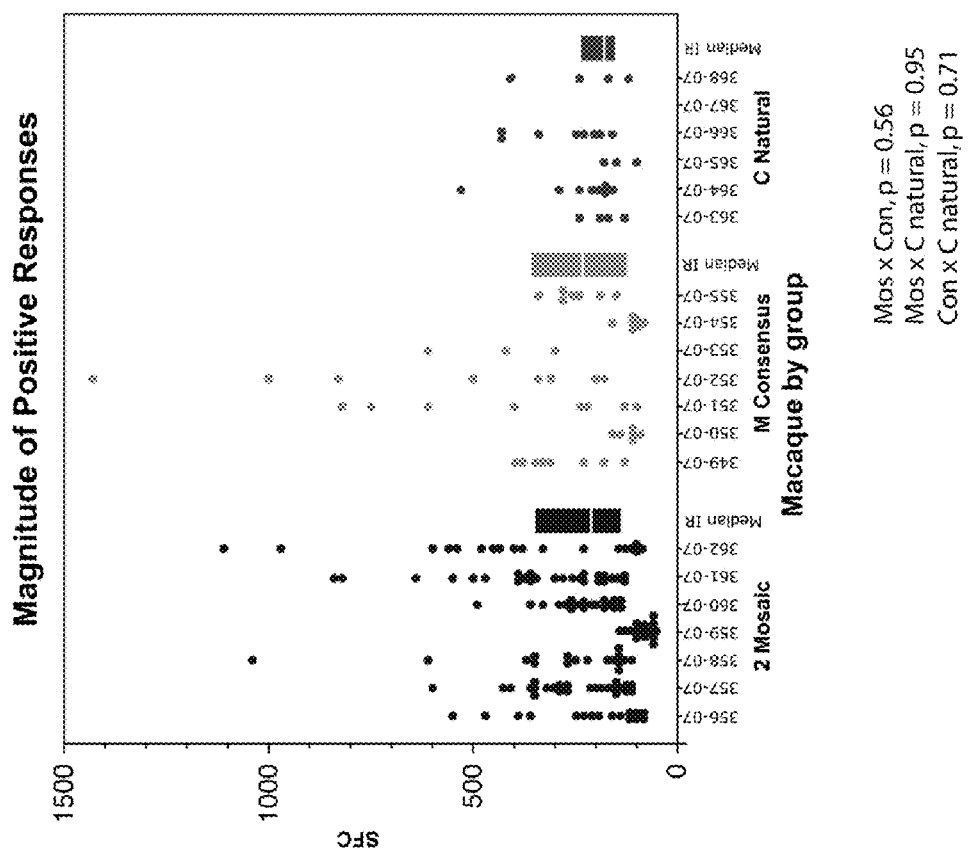
Figure 3:
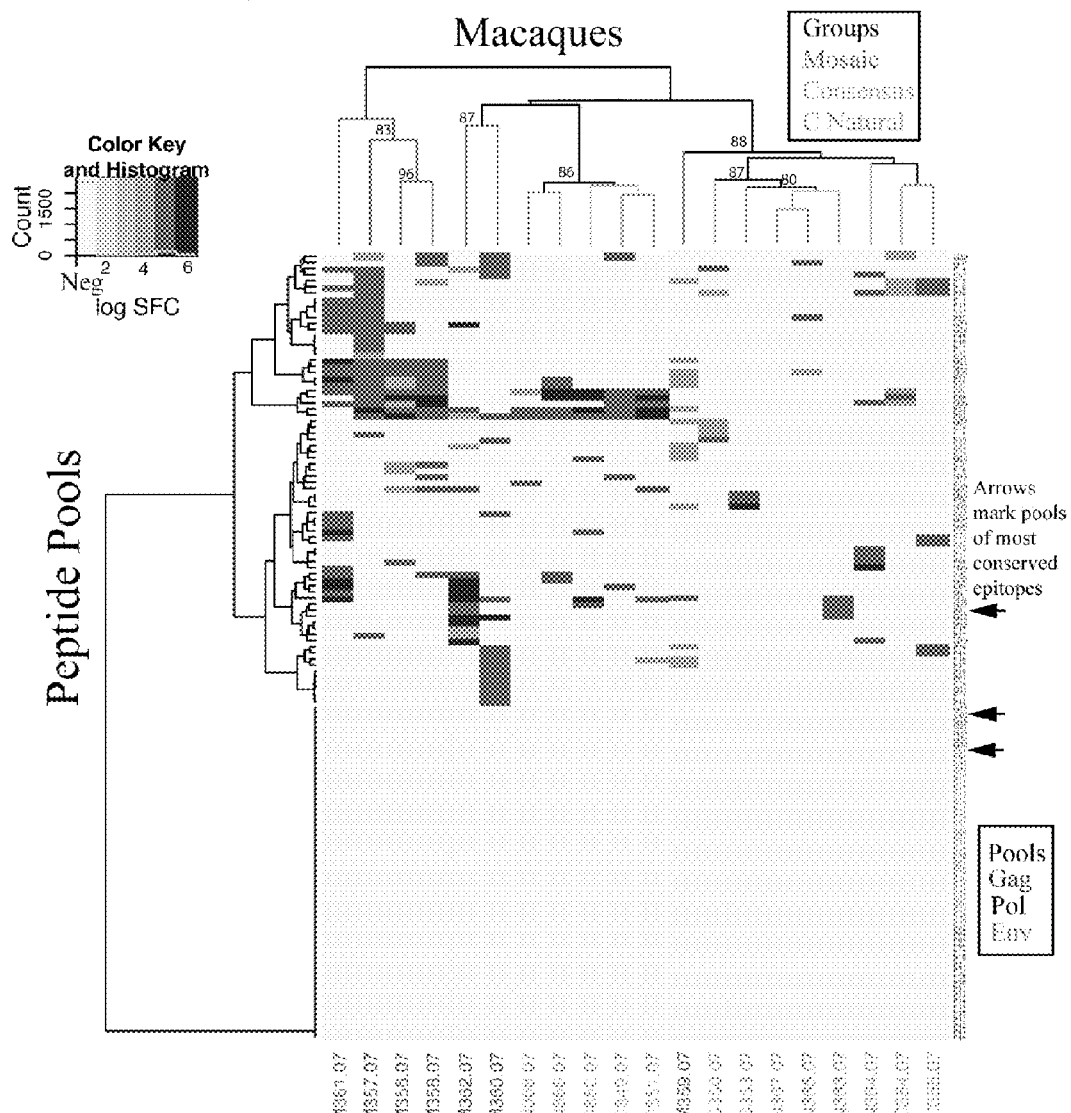
Figure 4:
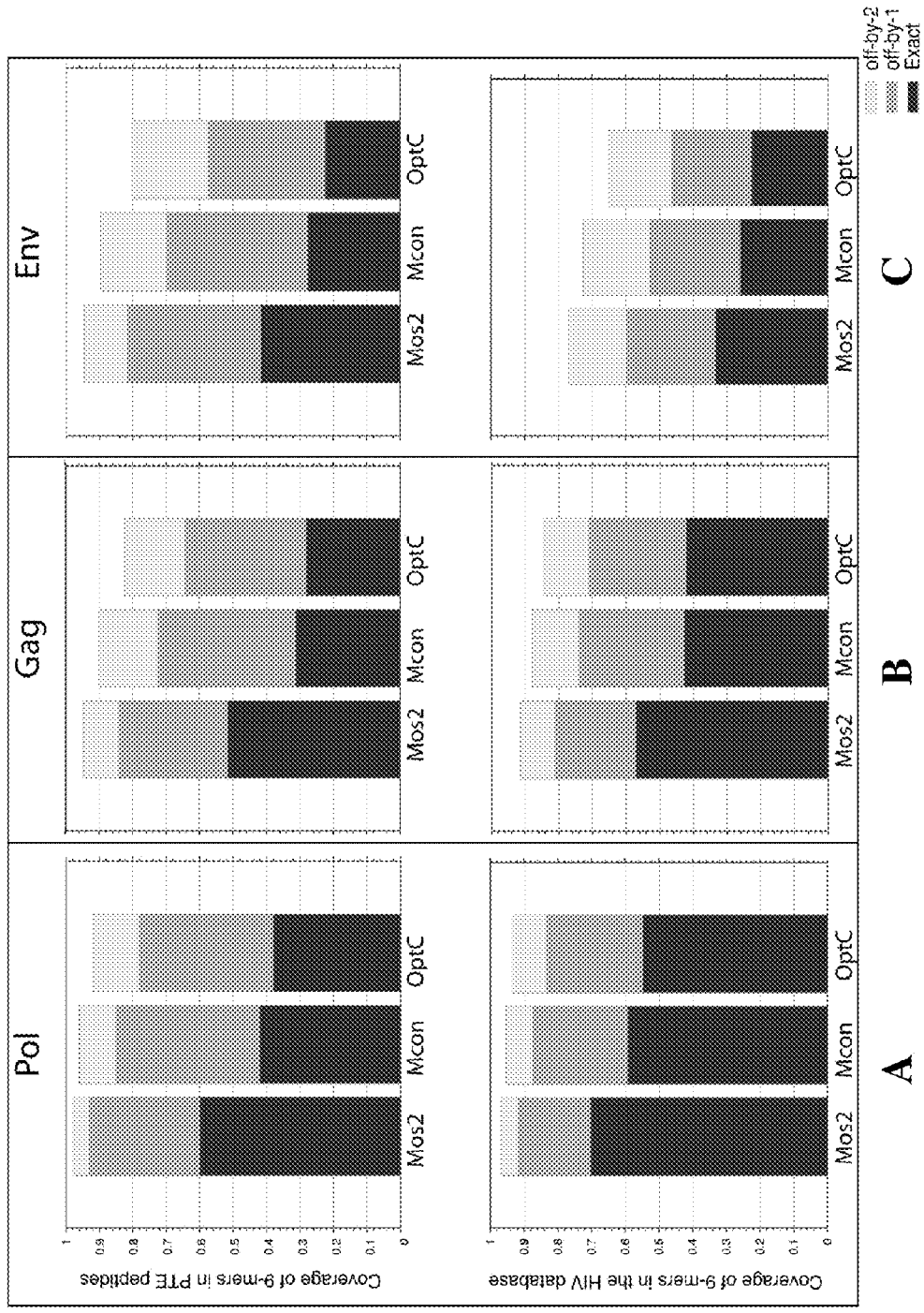
Figure 5:
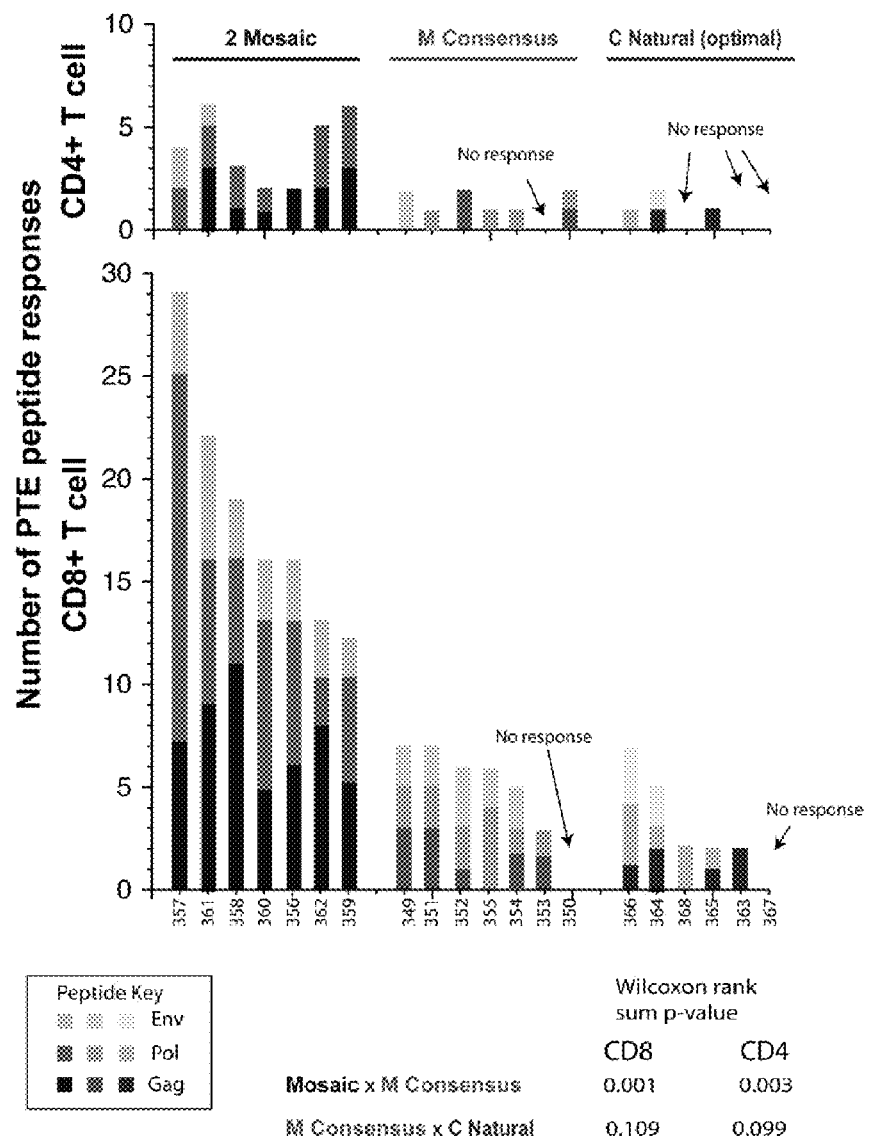
Figure 7:
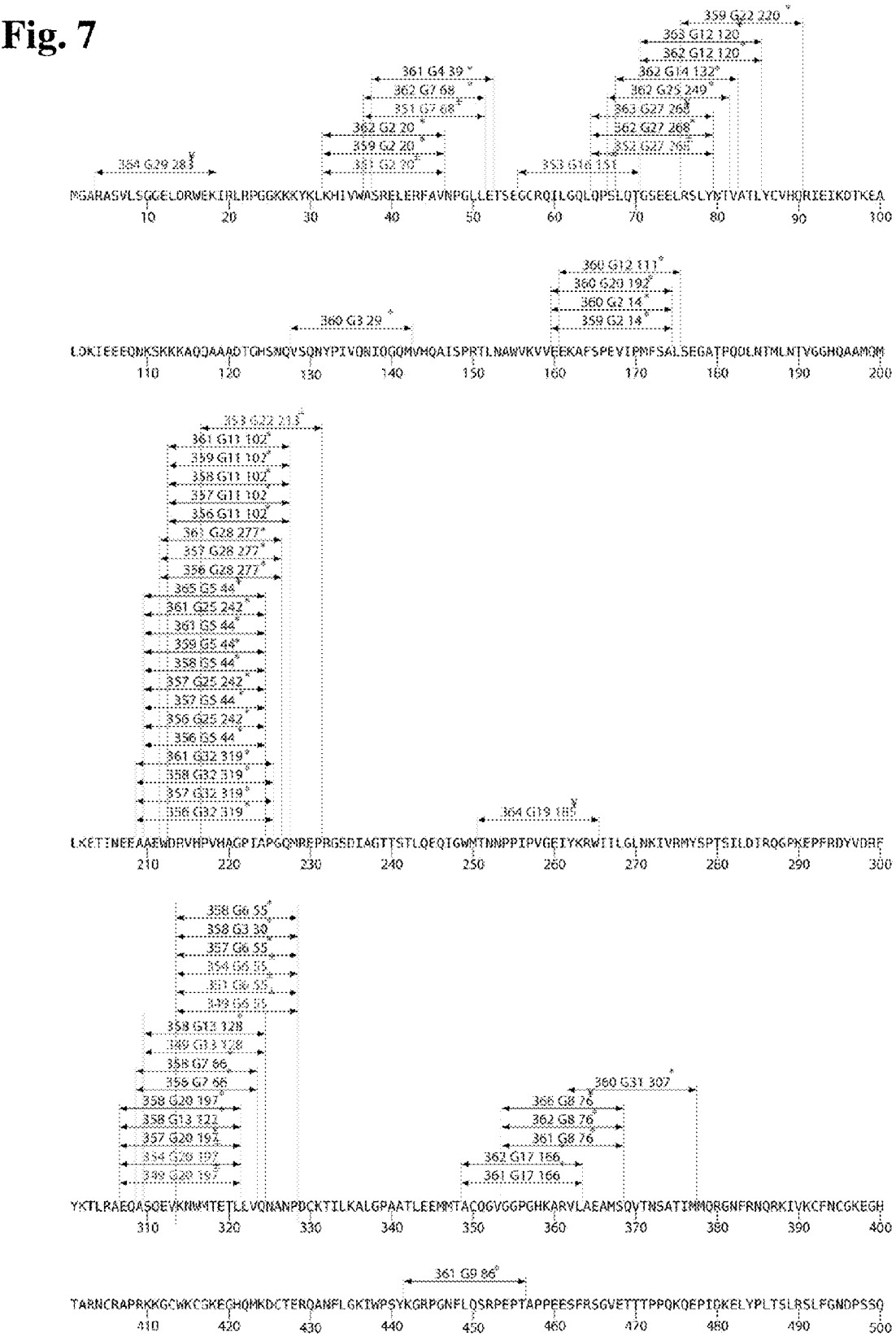
FIG. 7 discloses SEQ ID NO: 42.
Figure 8:
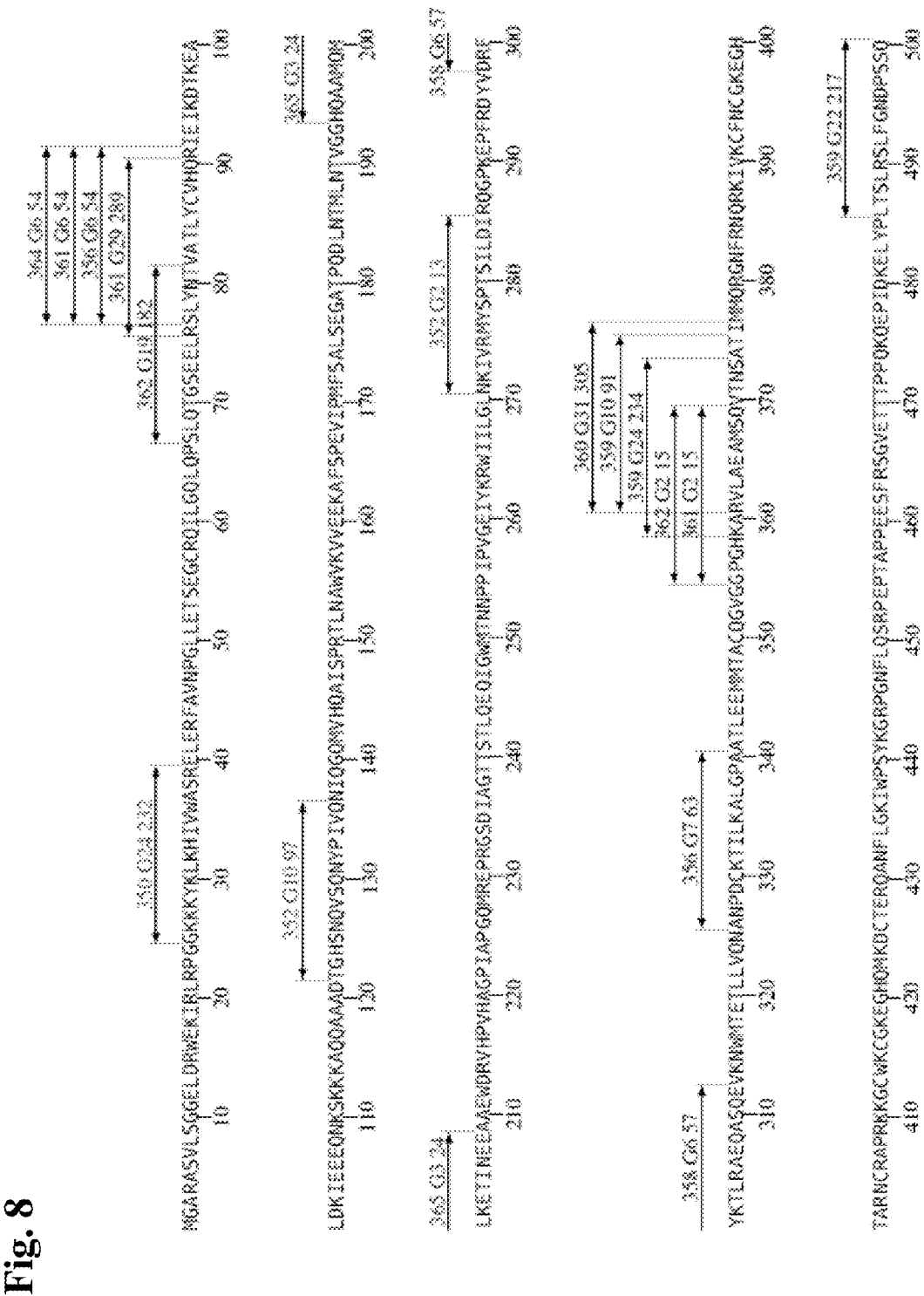
FIG. 8 is a schematic summarizing the mapping of CD4+ T cell Gag PTE peptides that are recognized by T cells from each of the animals studied.
Figure 12:
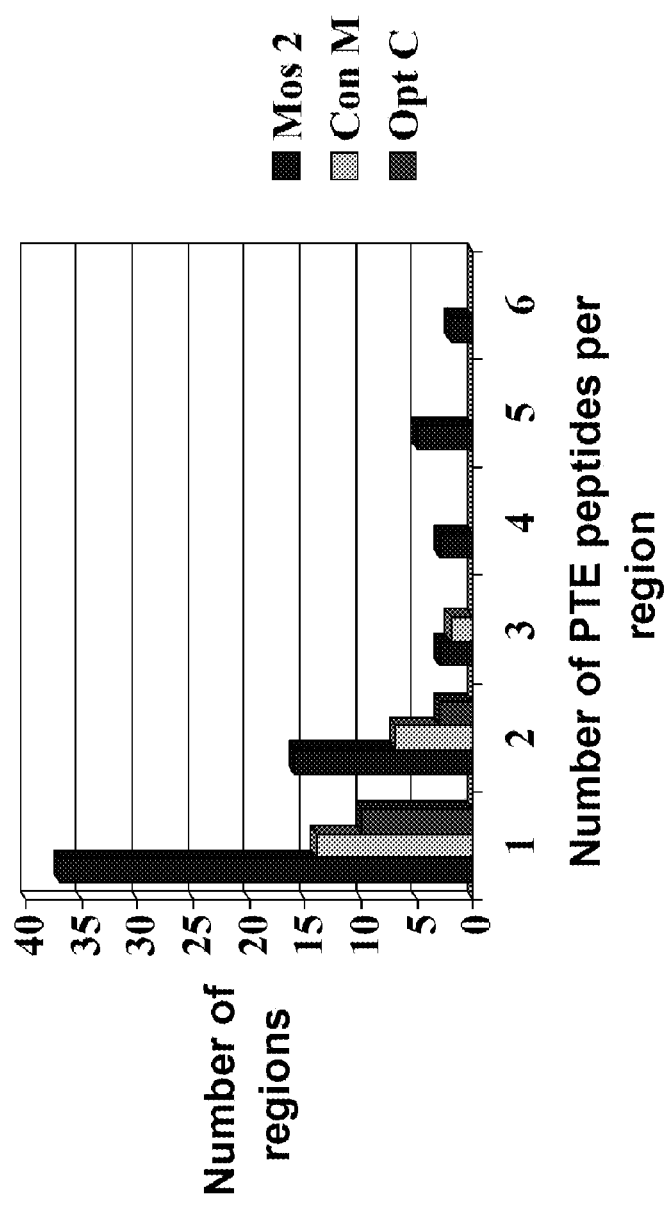
FIG. 12 is a graph showing the number of overlapping variable PTE peptides that span regions targeted by vaccine elicited T cells.
Figure 13:
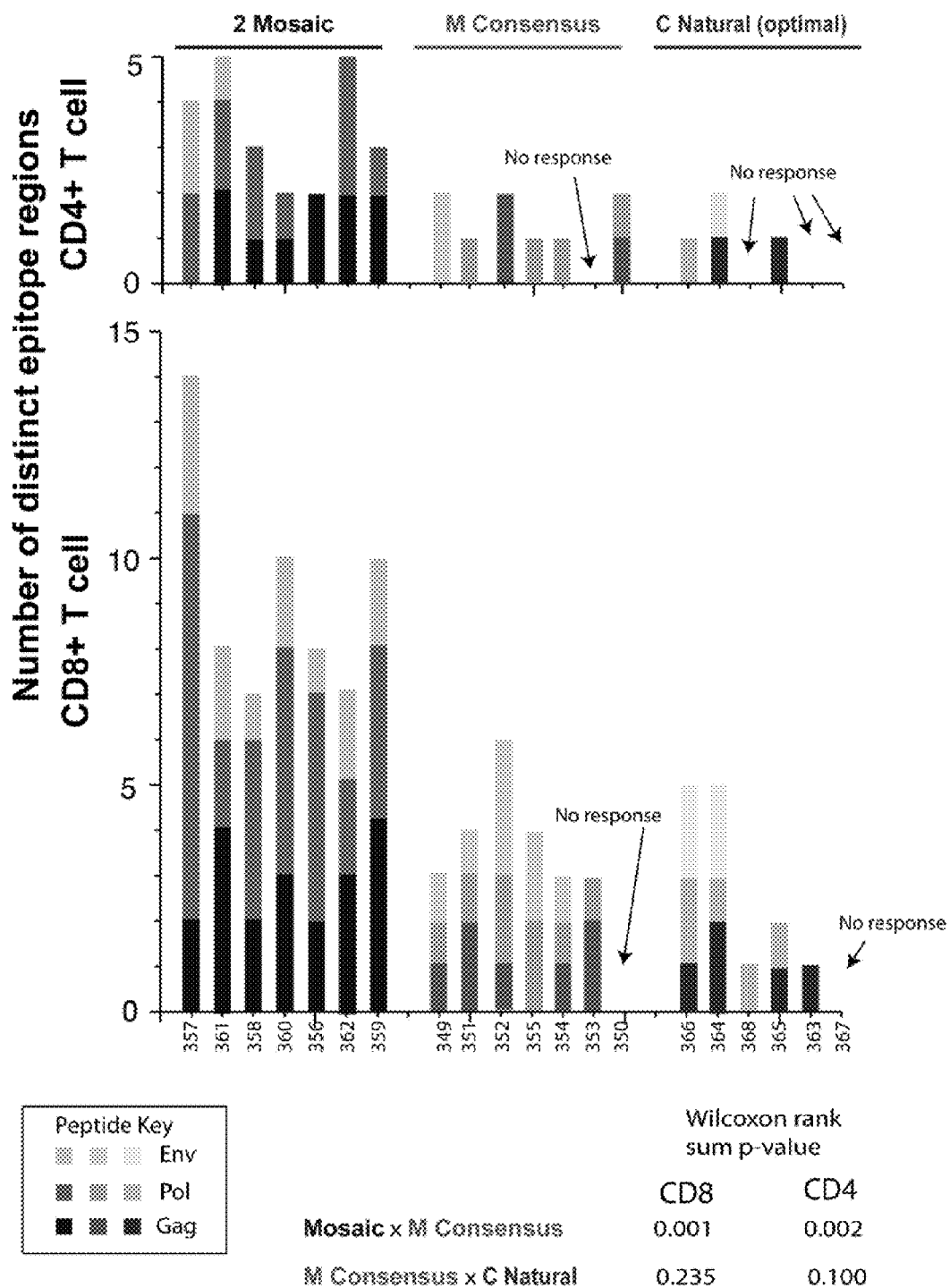
FIG. 13 is graph showing that the 2 mosaic antigen vaccine yields more T cell responses, relative to the Mcon and OptC vaccines, to regions that contain one or more overlapping PTE peptides.
Figure 15:
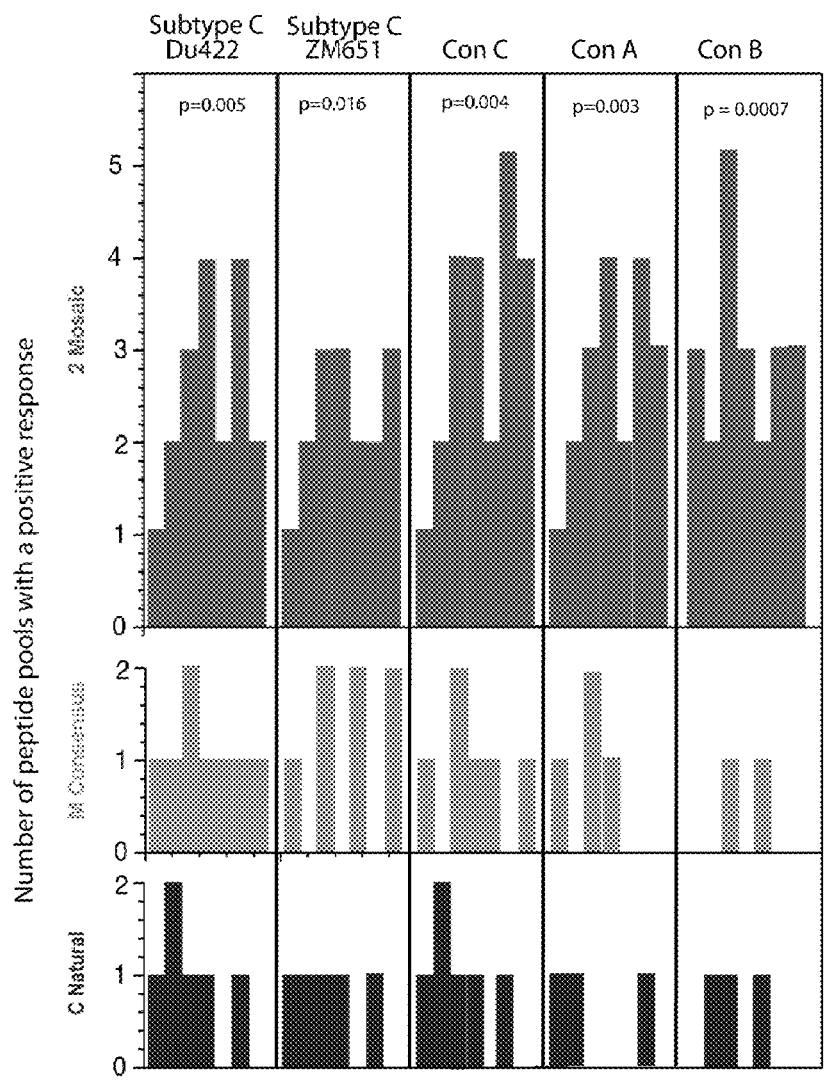
FIG. 15 is a graph showing that the mosaic vaccines can elicit more responses that cross-react with C clade natural proteins than can a C clade natural vaccine: GAG pooled peptides representing 5 proteins. Animals vaccinated with the M group consensus or the optimal coverage C clade natural protein had 0-2 responses to the peptides derived from these proteins, while the Mosaic vaccinated animals could respond to 1-5 peptide pools. The Mosaic vaccine elicits more responses to each of the proteins tested than either M con or the optimal C. T cell responses elicited by mosaic vaccines also recognized more pooled peptide sets spanning actual Gag proteins. 10-12 Subpools=10×15mer peptides (except 96ZM Gag, which is 5×20mer peptides).
Figure 16:
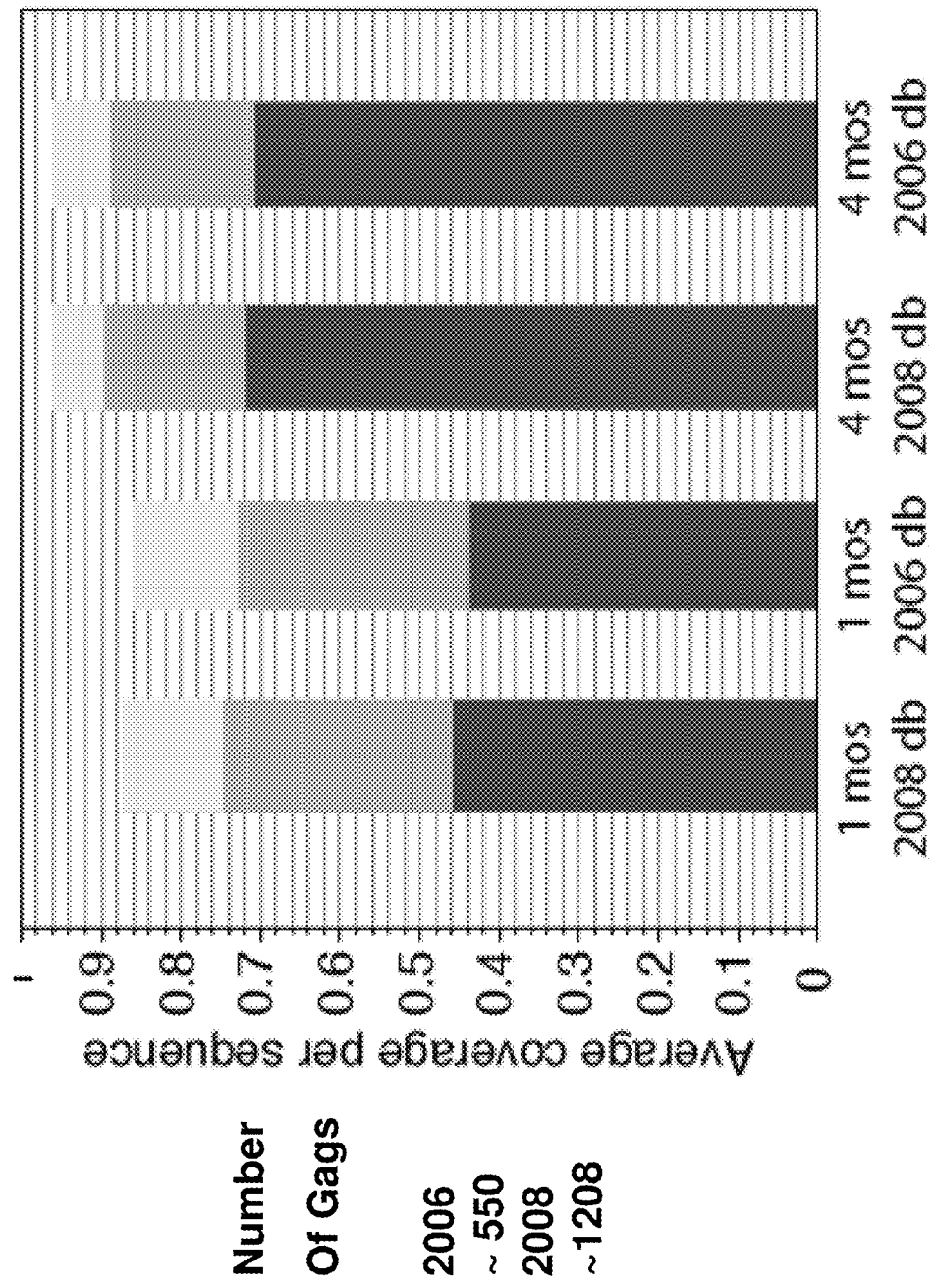
FIG. 16 is a graph showing that the mosaic design is robust to changes in viral polypeptides over time (e.g., Gag M).
Figure 17:
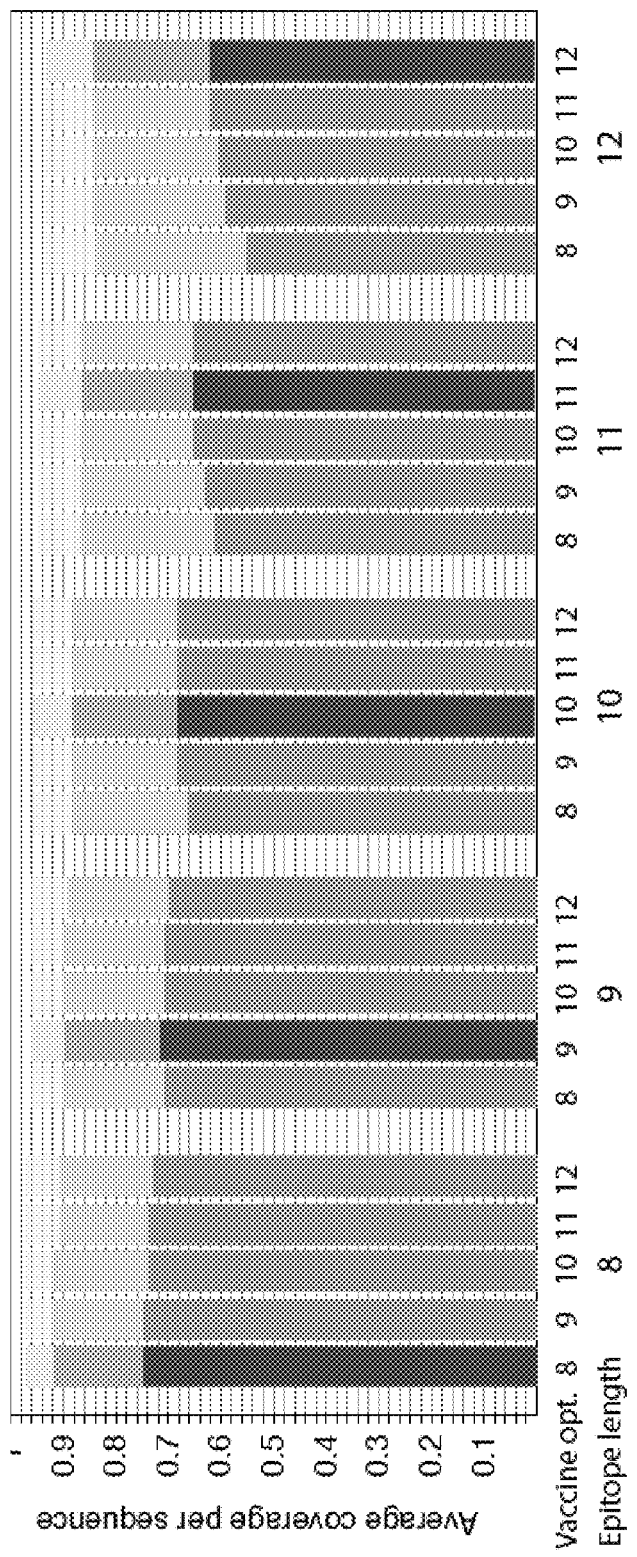
FIG. 17 is a graph showing that coverage using 9-mer optimization is robust over near (e.g., 8-12 mers) optimization lengths (Gag is shown).
Figure 18:
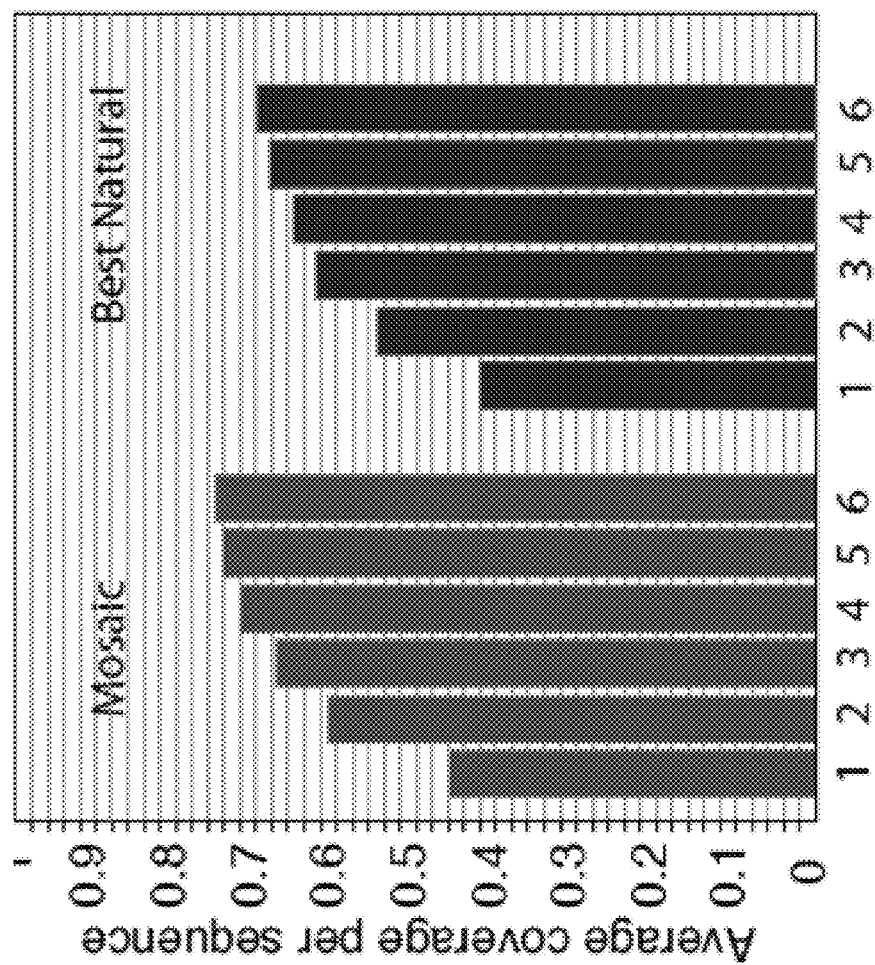
FIG. 18 is a graph showing that an increase in the number of variants increases coverage, but has only diminishing returns (Gag is shown).
Figure 19:
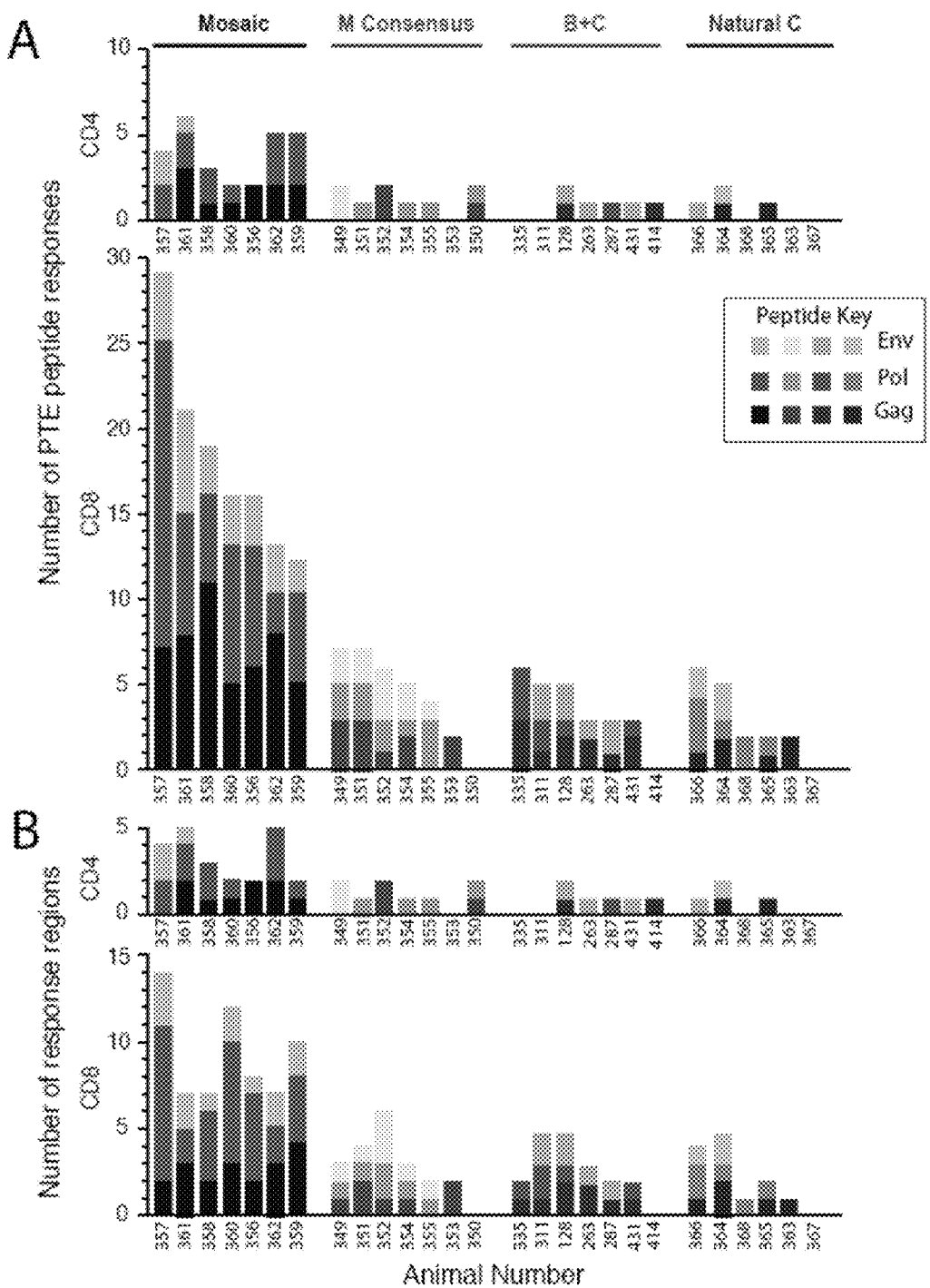
FIGS. 19A-19B are graphs showing the breadth and magnitude of epitope-specific T lymphocyte responses to PTE peptides.
Figure 20A:
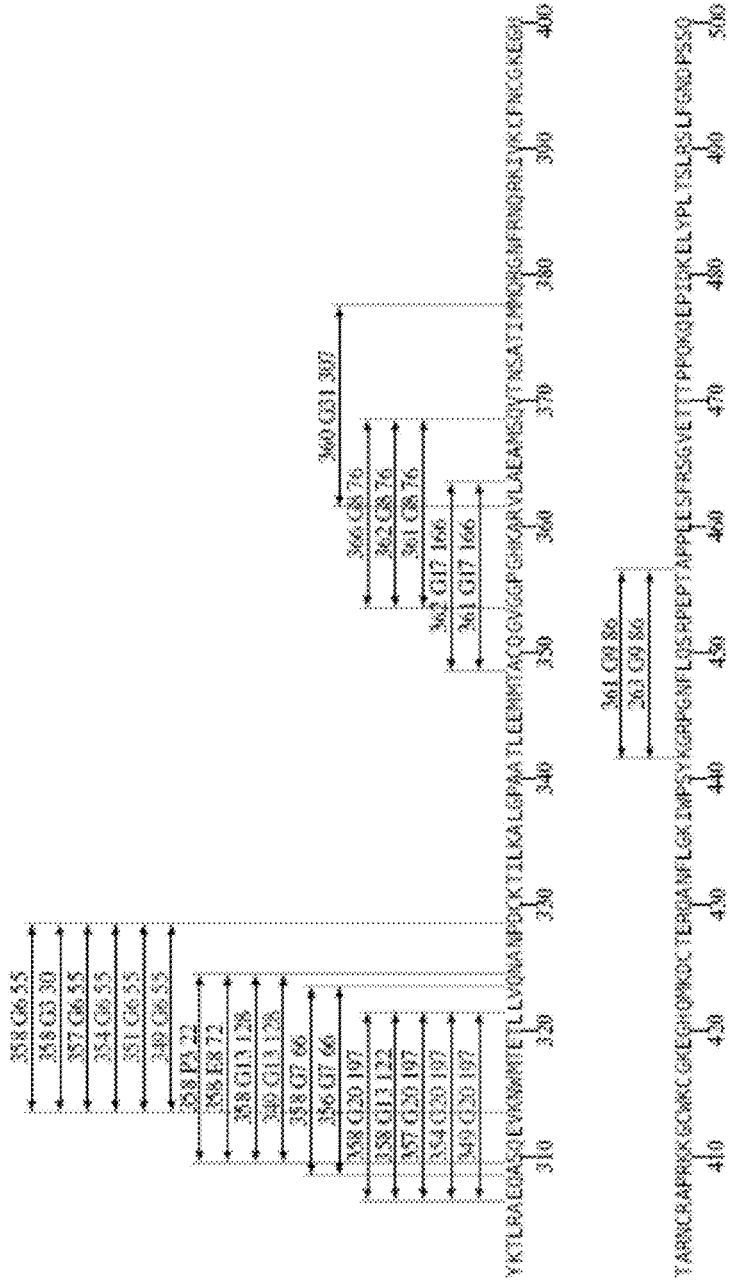
FIGS. 20A-20C show a schematic showing CD8+ T lymphocyte responses to PTE peptides at week 4 following immunization mapped on HIV-1 Gag (FIG. 20A) (SEQ ID NO: 118), Pol (FIG. 20B) (SEQ ID NO: 119), and Env (FIG. 20C) (SEQ ID NO: 120) protein sequences. Colors denote monkeys that received the mosaic (blue), M consensus (green), clade B+clade C (purple), or optimal natural clade C (red) HIV-1 Gag, Pol, and Env antigens. For each epitope, the monkey number, antigen (G, Gag; P, Pol; E, Env), subpool number, and individual PTE peptide number are indicated.
Figure 20B:
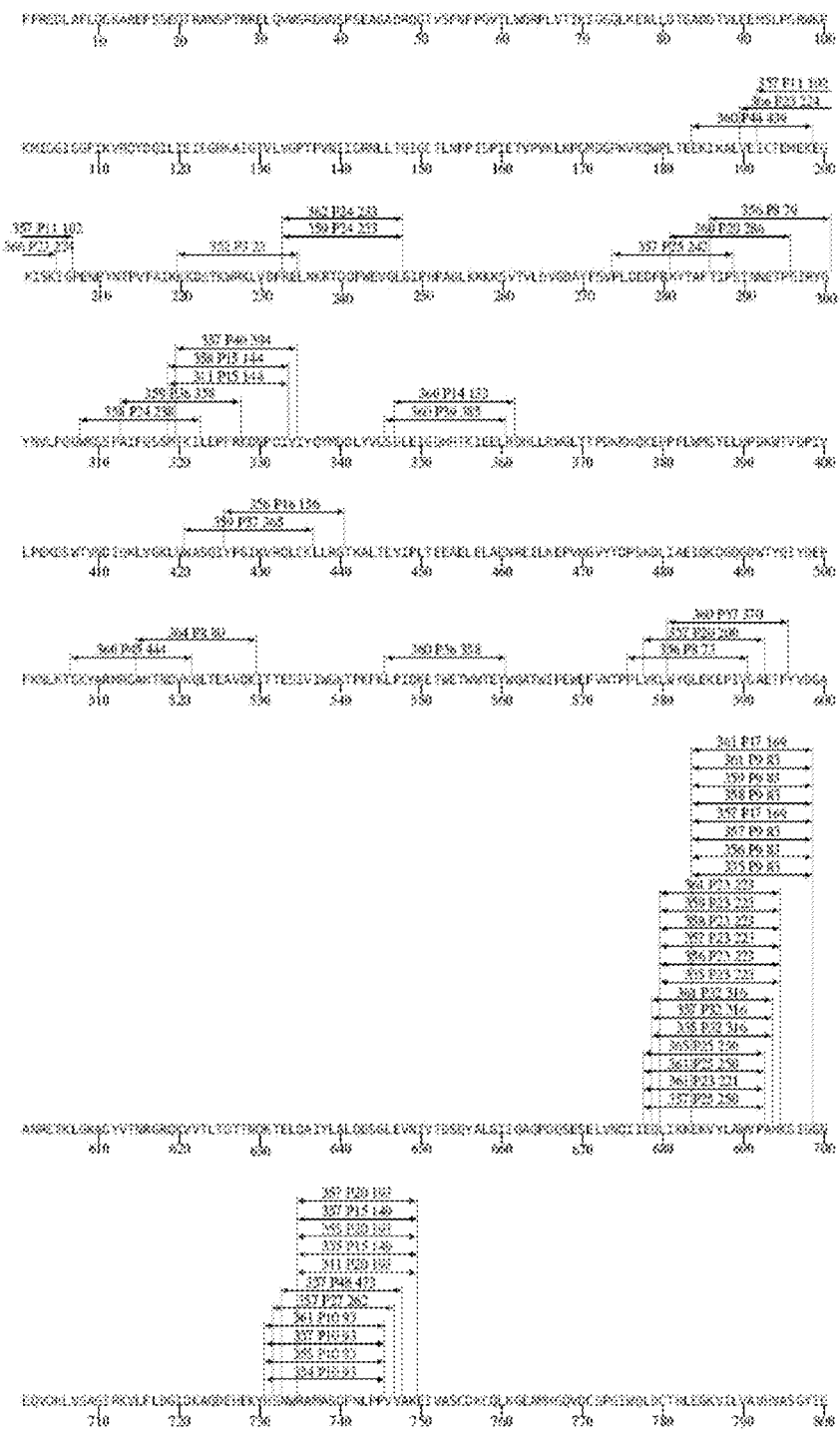
Figure 20B:
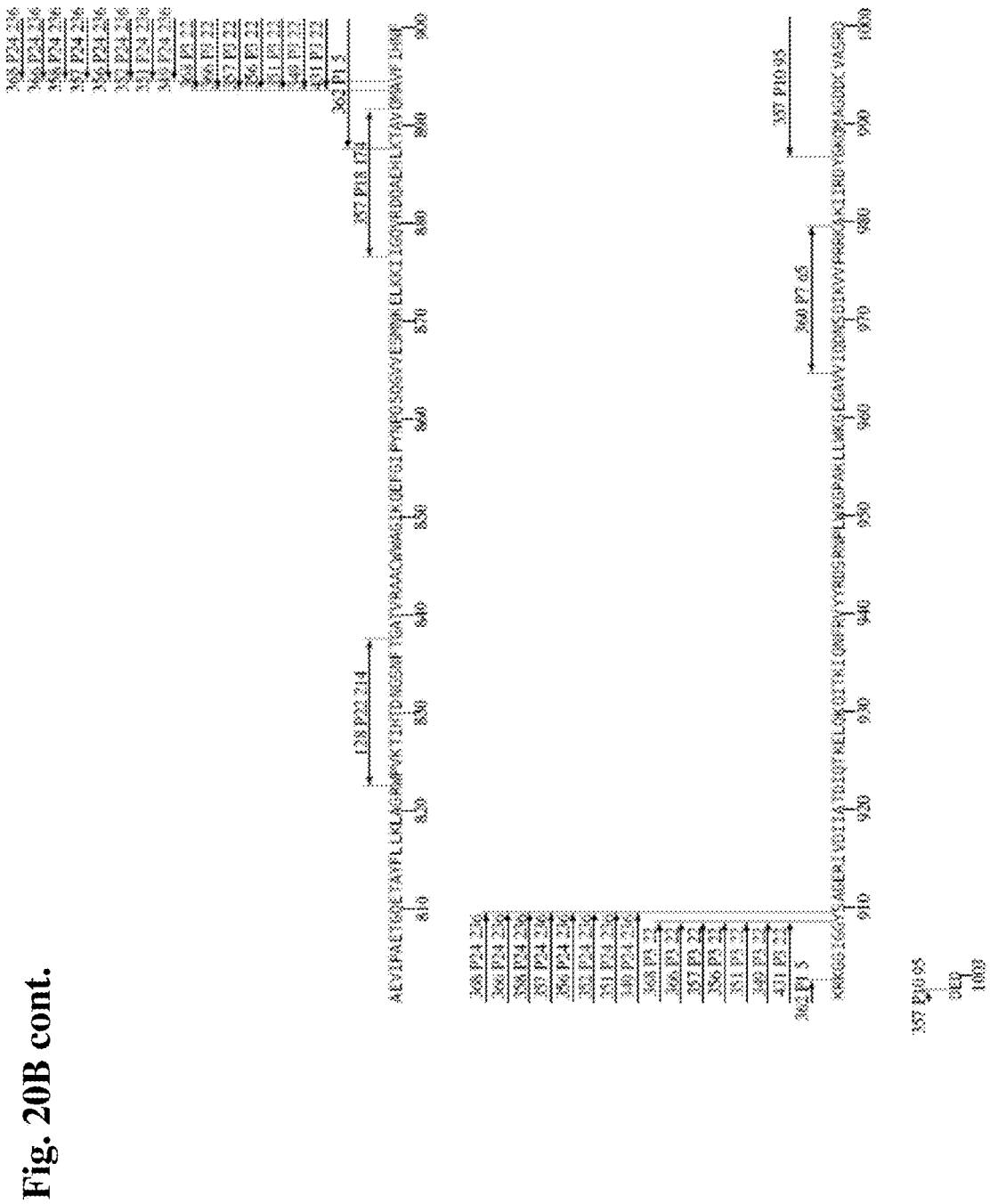
Figure 20C:
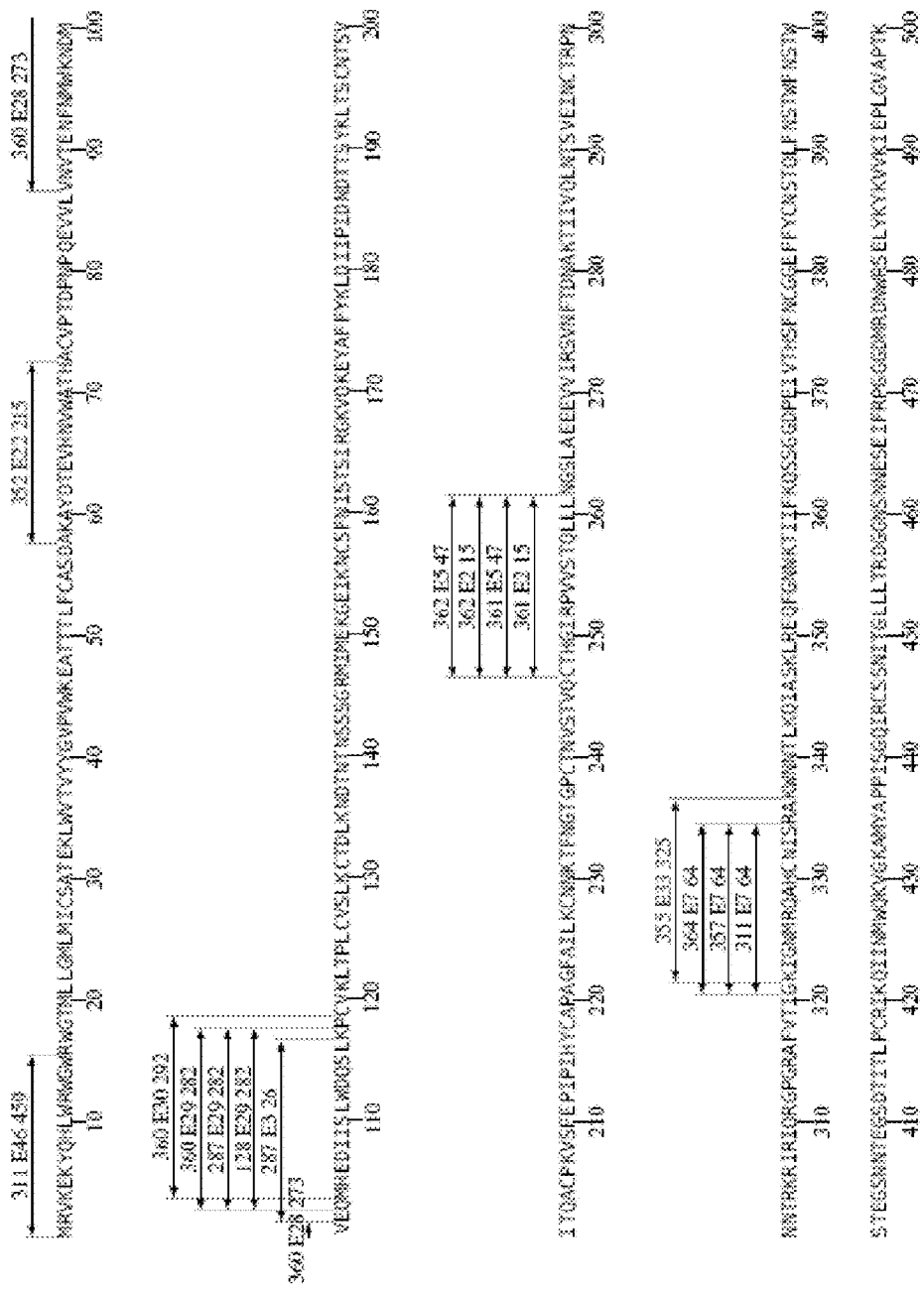
Figure 20C:
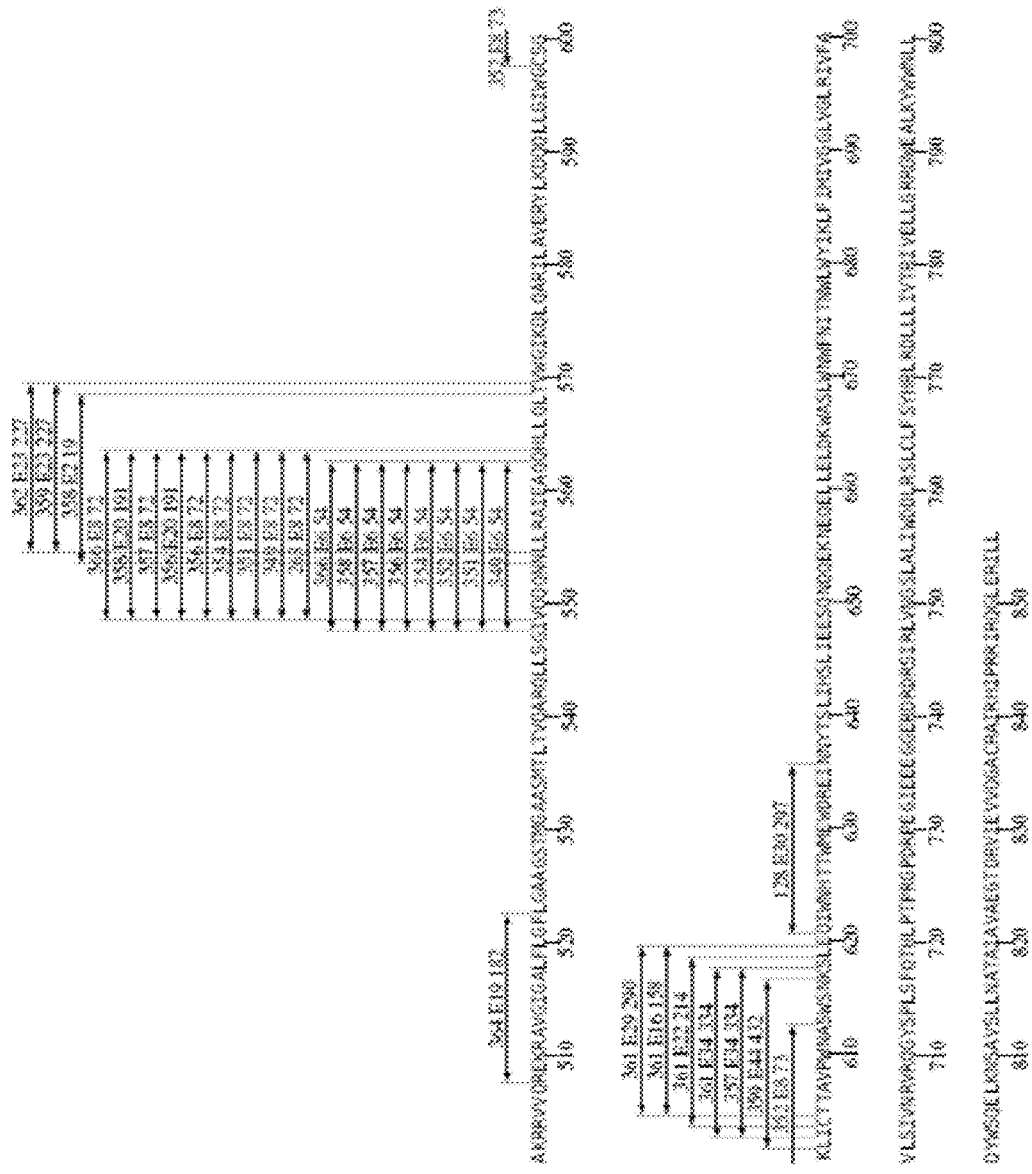

The total number of Gag-, Pol-, and Env-specific cellular immune responses to PTE peptides elicited by the mosaic antigens was 3.8-fold higher than the number of responses induced by the consensus or natural sequence antigens (FIG. 19A; P=1×10-11, comparing the mosaic with the consensus antigens, the next highest group, based on a Poisson regression model). There were 4.4-fold more CD8+ than CD4+ T lymphocyte responses (P<10-11) and fewer responses to Env than to Gag or Pol (P<0.0007). The median number of CD8+ T lymphocyte responses was highest for the mosaic vaccine, followed by the consensus, the combined B+C, and the natural clade C vaccines (medians of 16, 5, 3, and 2 responses per animal in each group, respectively). Although there were fewer CD4+ T lymphocyte responses overall, the same relative pattern emerged with the highest number of CD4+ T lymphocyte responses to the mosaic vaccine, followed by the consensus, the combined B+C, and the natural clade C vaccines (medians of 4, 1, 1, and 0.5 responses per animal in each group, respectively). The numbers of CD8+ and CD4+ T lymphocyte responses elicited by the consensus, the combined B+C, and the natural clade C vaccines were not statistically distinguishable.

PTE peptides include multiple overlapping sequences that reflect naturally occurring HIV-1 sequence polymorphisms, and thus the PTE peptide responses encompass both the recognition of a particular epitope (breadth) and the cross-recognition of variants of that epitope (depth). We performed a conservative analysis of breadth by assessing the number of reactive epitopic regions per monkey in which all reactive PTE peptides that overlapped by 8 or more amino acids were counted as one event. In this conservative analysis, we still observed that the mosaic antigens elicited 3.1-fold increased numbers of Gag, Pol, and Env reactive epitopic regions as compared with the consensus antigens or natural sequence antigens (FIG. 19B; P=1.6×10-7, Poisson regression). Epitopic regions exhibited some clustering across animals, as evidenced by regions of high epitope density (FIGS. 20A-20C and FIGS. 21A-21C). Complete alignments of all positive peptides organized by response regions are shown in FIG. 22.

These data show that the mosaic antigens substantially increased the breadth of cellular immune responses as compared with M consensus and natural clade C antigens. The 2-valent mosaic antigens also proved superior to the 2-valent combination of clade B and clade C antigens (FIGS. 19A and 19B), indicating that the enhanced breadth was due to the mosaic sequence design and did not simply reflect the use of two distinct antigenic sequences per protein. To determine if the increased breadth induced by mosaic antigens compromised the potency of the responses, we assessed the magnitude of all individual CD8+ and CD4+ T lymphocyte responses. The magnitude of these responses proved comparable among all groups (FIG. 23; P=0.58 and P=0.99, respectively, two-sided Kolmogorov-Smirnov tests). Thus, mosaic antigens expanded cellular immune breadth without compromising the magnitude of individual epitope-specific responses, indicating that antigenic competition and immunodominance constraints did not limit the immunogenicity of the mosaic antigens in this study.

We next characterized the depth of the cellular immune responses elicited by the various vaccine regimens. We defined depth as the number of simultaneously elicited variant PTE peptides for a particular epitopic region. Inducing responses to multiple common epitope variants may increase immunologic coverage of infecting virus sequences, block common escape routes in vivo, or force the virus down tertiary escape routes that incur high fitness costs. The consensus and natural sequence antigens elicited responses that were characterized by a high degree of sequence identity between the vaccine sequences and the reactive PTE peptides, as exemplified by the responses in monkey 366 that received the natural clade C antigens (FIG. 24A; see also FIG. 22). In contrast, the mosaic antigens elicited responses that were characterized by multiple reactive PTE peptides in particular epitopic regions. These peptides represented common variants and often reflected the polymorphisms contained in the mosaic vaccine sequences, as exemplified by the responses in monkey 361 (FIG. 24B; see also FIG. 22). A summary of all epitope-specific responses in these animals demonstrates that the mosaic antigens increased the frequency of cellular immune responses to peptides with two or more targeted variants as compared with the consensus or natural sequence antigens (FIG. 24C; P=0.001, Wilcoxon rank-sum test comparing the mosaic with the consensus antigens, the next highest group).

To complement the analysis utilizing PTE peptides, we also assessed the breadth of cellular immune responses in the vaccinated monkeys with traditional overlapping peptides covering 5 different Gag sequences: clade C DU422, clade C ZM651, consensus C, consensus A, and consensus B. Cellular immune breadth was determined by assessing reactivity to subpools of 10 overlapping peptides spanning each Gag sequence. The mosaic antigens elicited greater breadth of T lymphocyte responses as compared with the consensus or natural sequence antigens against all Gag sequences that were tested (FIG. 25; P=1×10$^{-7}$, binomial regression). Thus, the mosaic antigens augmented cellular immune breadth not only to PTE peptides but also to actual Gag peptides from clades A, B, and C. The mosaic antigens even proved superior to the optimal natural clade C antigens for inducing responses against clade C Gag peptides. Moreover, the mosaic antigens elicited comparable responses to Gag peptides from multiple clades, whereas the natural clade C antigens exhibited diminished responses to clade A and clade B Gag peptides (FIG. 25).

To assess the durability of these observations, we boosted the monkeys that received the mosaic, consensus, and optimal natural clade C antigens at week 40 with a total dose of 3×10$^{10}$ viral particles of the heterologous vector rAd5HVR48 expressing HIV-1 Gag, Pol, and Env antigens that matched the sequences utilized in the initial immunization. Cellular immune breadth was determined by assessing reactivity to subpools of 10 PTE peptides at week 4 (post-prime) and at week 44 (post-boost). The majority of CD8+ and CD4+ T lymphocyte responses that were observed after the priming immunization expanded following the boost (FIG. 26A, red and blue lines), and a number of new responses were also detected (FIG. 26A, red and blue dots). At week 44, the magnitude of individual cellular immune responses proved comparable among groups (FIG. 26A). The number of subpool responses elicited by the mosaic antigens (median 27 responses per animal), however, remained substantially higher than the number of subpool responses induced by the consensus antigens (median 11 responses per animal) or the optimal natural clade C antigens (median 10 responses per animal) following the boost immunization (FIG. 26B). Both before and after the boost, there were more responses per animal elicited by the mosaic vaccine than by the consensus or natural clade C vaccines (P<0.001, Wilcoxon rank-sum tests for all pairwise comparisons).

We also measured Env-specific humoral immune responses following the boost immunization by ELISAs (FIG. 26C) and luciferase-based pseudovirus neutralization assays (FIG. 26D). All groups exhibited comparable ELISA titers to clade C gp140 and comparable neutralizing antibody (NAb) responses to the tier 1 clade C virus MW965.26. The mosaic antigens elicited slightly higher Nab responses to the tier 1 clade B virus SF162.LS as compared with the consensus or natural clade C antigens (P=0.02, Wilcoxon rank-sum test), although we did not detect any NAb responses to tier 2 viruses in any group.

Our data demonstrate that mosaic HIV-1 Gag, Pol, and Env antigens augmented both the breadth and depth of epitope-specific cellular immune responses as compared with consensus or natural sequence antigens in rhesus monkeys, in good agreement with theoretical predictions (FIG. 27). The striking results with mosaic antigens in this study may have reflected the fact that rAd26 vectors are particularly efficient at eliciting CD8+ T lymphocyte responses as well as the fact that mosaic antigens appear particularly effective at augmenting CD8+ T lymphocyte breadth (FIGS. 19A and 19B). We also observed enhanced CD4+ T lymphocyte breadth with mosaic antigens, although there were substantially lower numbers of these responses.

The breadth of Gag-specific cellular immune responses has been shown to be critical for SIV control in rhesus monkeys and for HIV-1 control in humans. Moreover, in the phase 2b STEP study, the rAd5-based HIV-1 vaccine candidate expressing natural clade B Gag, Pol, and Nef antigens elicited only a limited breadth of HIV-1-specific cellular immune responses, and no vaccine benefit was observed. Vaccinees in the STEP study developed a median of only 2-3 epitope-specific T lymphocyte responses, including a median of only 1 epitope-specific response to Gag, and this very narrow breadth of cellular immune responses likely provided insufficient immunologic coverage of the diversity of infecting viruses. Viral escape from CD8+ T lymphocytes has also been reported to occur rapidly during acute HIV-1 infection, and thus vaccine-elicited cellular immune responses against common epitope variants may also prove critical. Taken together, these studies emphasize the need to develop HIV-1 vaccine strategies that augment cellular immune breadth and depth.

Since we evaluated mosaic HIV-1 antigens in the present study, we were unable to assess the protective efficacy of these vaccine regimens against SIV challenges. However, we have previously reported that the breadth of SIV-specific cellular immune responses elicited by rAd vectors correlated with protective efficacy against SIV challenges in rhesus monkeys (Liu et al., Nature 457:87, 2009). We have also shown that cellular immune responses against variant epitopes can block SIV mutational evolution in rhesus monkeys in vivo (Barouch et al., Nat. Immunol. 6:247, 2005), suggesting the biologic relevance of expanding cellular immune depth. Modeling the protective efficacy of mosaic vaccines against SIV challenges in nonhuman primates has intrinsic limitations, since the observed diversity of SIV and HIV-1 M group sequences differs substantially and is influenced by different underlying biology. For example, CD8+ T lymphocyte selection pressure in natural hosts such as sooty mangabees appears substantially less than that in humans. Thus, the further evaluation of mosaic antigens as candidate HIV-1 vaccines can be benefited by clinical trials.

In summary, we demonstrate that 2-valent mosaic HIV-1 Gag, Pol, and Env antigens substantially expanded cellular immune breadth and depth in rhesus monkeys. These findings have major implications for HIV-1 vaccine development, since global virus diversity and viral escape from cellular immune responses represent critical hurdles in the development of a T cell-based HIV-1 vaccine. A 2-valent cocktail of mosaic antigens is also practical and potentially feasible for clinical development. Increasing the valency of mosaic antigens may further improve coverage. Finally, the mosaic antigen strategy is generalizable and could be utilized for other genetically diverse pathogens in addition to HIV-1.

Materials and Methods

Antigen design and vector production. 2-valent mosaic Gag, Pol, and Env antigens were constructed to provide optimal coverage of HIV-1 M group sequences in the Los Alamos HIV-1 sequence database essentially as described (1, 2). Optimal natural clade C antigens were selected to be the sequences that provide optimal PTE coverage of clade C sequences in the Los Alamos HIV-1 sequence database (C.IN.-0.70177 Gag, C.ZA.04.04ZASK208B1 Pol, C.SN.90.90SE 364 Env). Clade B antigens were selected to be near-consensus or consensus sequences (B.CAM-1 Gag, B.IIIB Pol, B.Con Env) and were used to complement the optimal clade C antigens for the 2-valent clade B+C vaccine approach. Pol antigens contained RT and IN without PR and included point mutations to eliminate catalytic activity as described (Priddy et al., Clinical infectious diseases 46:1769, 2008). Env gp140 antigens contained point mutations to eliminate cleavage and fusion activity. Vaccine sequences are depicted in FIG. 27. Recombinant, replication-incompetent adenovirus serotype 26 (rAd26) and hexon-chimeric rAd5HVR48 vectors expressing these antigens were grown in PER.55K cells and purified by double CsC1 gradient sedimentation essentially as described (Abbink et al., J. Virol. 81:4654, 2007, and Roberts et al., Nature 441:239, 2006).

Animals and immunizations. 27 outbred rhesus monkeys that did not express the MHC class I allele Mamu-A*01 were housed at New England Primate Research Center (NEPRC), Southborough, Mass. Immunizations involved $3 \times 10^{10}$ viral particles rAd26 or rAd5HVR48 vectors expressing mosaic, M consensus, clade B+clade C, or optimal natural clade C HIV-1 Gag, Pol, and Env antigens delivered as 1 ml injections i.m. in both quadriceps muscles at weeks 0 and 40. All animal studies were approved by our Institutional Animal Care and Use Committees (IACUC).

IFN-γ ELISPOT assays. HIV-1-specific cellular immune responses in vaccinated monkeys were assessed by interferon-γ (IFN-γ) ELISPOT assays essentially as described (Roberts et al., Nature 441:239, 2006, and Liu et al., Nature 457:87, 2009). HIV-1 Gag, Pol, and Env potential T cell epitope (PTE) peptides that included all PTEs found in at least 15% of HIV-1 M group sequences as well as HIV-1 Gag peptides from clade C DU422, clade C ZM651, consensus C, consensus A, and consensus B strains were obtained from the NIH AIDS Research and Reference Reagent Program. 96-well multiscreen plates (Millipore) were coated overnight with 100 of 10 µg/ml anti-human IFN-γ (BD Biosciences) in endotoxin-free Dulbecco's PBS (D-PBS). The plates were then washed three times with D-PBS containing 0.25% Tween-20 (D-PBS/Tween), blocked for 2 h with D-PBS containing 5% FBS at 37° C., washed three times with D-PBS/Tween, rinsed with RPMI 1640 containing 10% FBS to remove the Tween-20, and incubated with 2 µg/ml each peptide and $2 \times 10^5$ PBMC in triplicate in 100 µl reaction volumes. Following an 18 h incubation at 37° C., the plates were washed nine times with PBS/Tween and once with distilled water. The plates were then incubated with 2 µg/ml biotinylated anti-human IFN-γ (BD Biosciences) for 2 h at room temperature, washed six times with PBS/Tween, and incubated for 2 h with a 1:500 dilution of streptavidin-alkaline phosphatase (Southern Biotechnology Associates). Following five washes with PBS/Tween and one with PBS, the plates were developed with nitro blue tetrazolium/5-bromo-4-chloro-3-indolyl-phosphate chromogen (Pierce), stopped by washing with tap water, air dried, and read using an ELISPOT reader (Cellular Technology Ltd). Spot-forming cells (SFC) per $10^6$ PBMC were calculated. Media backgrounds were typically <15 SFC per $10^6$ PBMC. Positive responses were defined as >55 SFC per $10^6$ PBMC and >4-fold background.

Epitope mapping. Comprehensive CD8+ and CD4+ T lymphocyte epitope mapping was performed utilizing Gag, Pol, and Env PTE peptides that were obtained from the NIH AIDS Research and Reference Reagent Program. IFN-γ ELISPOT assays were conducted at week 4 following immunization initially with complete peptide pools as well as with subpools containing 10 PTE peptides. All peptide subpools with positive responses were deconvoluted, and epitopes were confirmed with individual 15 amino acid PTE peptides. Cell-depleted IFN-γ ELISPOT assays were then performed to determine if reactive peptides represented CD8+ or CD4+ T lymphocyte epitopes. Partial epitope mapping utilizing PTE subpools was also performed 4 weeks following the boost immunization at week 44. All borderline responses were retested and only considered positive if confirmed. Partial epitope mapping utilizing subpools containing 10 overlapping Gag peptides was also performed to assess breadth to HIV-1 Gag from various clades.

Humoral immune assays. Env-specific humoral immune responses were evaluated by direct ELISAs utilizing HIV-1 clade C Env gp140 and luciferase-based pseudovirus neutralization assays essentially as described (Montefiori, *Evaluating neutralizing antibodies against HIV, SIV and SHIV in luciferase reporter gene assays. Current Protocols in Immunology*, Coligan, Kruisbeek, Margulies, Shevach, Strober, and Coico, Ed. (John Wiley & Sons, 2004, pp. 1-15).

Statistical analyses. All statistical analyses were done using the package R (Team, *Foundation for Statisical Computing*, Vienna, Austria, 2009). To analyze the breadth of cellular immune responses to mapped PTE peptides (FIG. 19A), we fit Poisson regression models that predicted the number of reactive peptides as a function of vaccine group, antigen (Gag, Pol, Env), and lymphocyte subpopulation (CD4, CD8). Our models included random effects to accommodate animal-to-animal variation and were fit with the lme4 library (Pinheiro, Springer, N.Y. (2000)) of the package R. The data fit the models well (dispersion parameter 1.0), and there were no significant interactions among the three explanatory factors. For example, the 3.8-fold enhancement in the number of PTE peptides recognized by monkeys that received the mosaic antigens as compared to those that received the consensus or natural sequence antigens (FIG. 19A) applied equally to PTEs from Gag, Pol, and Env and held for responses by CD8+ as well as CD4+ T lymphocytes. The analysis of the number of reactive epitopic regions (FIG. 19B) also included Poisson regression models with random effects and again fit well (dispersion parameter 0.87) without any significant interactions. Comparisons of the magnitude of CD8+ and CD4+ T lymphocyte responses (FIG. 23) were performed utilizing 2-sided Kolmogorov-Smirnov tests. Non-parametric tests to compare the breadth and depth of responses per monkey between different vaccines were also performed (FIGS. 19A and 24C). We initially employed Kruskal-Wallis tests to determine if there was a difference among the 4 vaccine groups. In each case this was highly significant, and we then assessed all pairwise comparisons between the 4 vaccine groups using Wilcoxon rank-sum tests. In each of these comparisons, the mosaic vaccine elicited significantly more responses per monkey than the other 3 vaccines. To analyze the breadth of responses to HIV-1 Gag from various clades (FIG. 25), we fit the data to binomial regression models. These models used the vaccine group as an explanatory variable and included random effects to account for animal-to-animal and strain-to-strain variation. The data were slightly underdispersed, but the animals that received the mosaic vaccine still elicited a significantly larger number of responses. PTE coverage assessment was performed using tools available at the Los Alamos HIV-1 sequence database.

SEQUENCE APPENDIX

I. 2-VALENT M MOSAIC ENV GP160, GAG, POL, NEF SEQUENCES

MOSAIC ENV1 GP160 (AA SEQUENCE)

SEQ ID NO: 1
MRVTGIRKNYQHLWRWGTMLLGILMICSAAGKLWVTVYYGVPVWKEATTT
LFCASDAKAYDTEVHNVWATHACVPTDPNPQEVVLENVTENFNMWKNNMV
EQMHEDIISLWDQSLKPCVKLTPLCVTLNCTDDVRNVTNNATNTNSSWGE
PMEKGEIKNCSFNITTSIRNKVQKQYALFYKLDVVPIDNDSNNTNYRLIS

SEQUENCE APPENDIX

CNTSVITQACPKVSFEPIPIHYCAPAGFAILKCNDKKFNGTGPCTNVSTV
QCTHGIRPVVSTQLLLNGSLAEEEVVIRSENFTNNAKTIMVQLNVSVEIN
CTRPNNNTRKSIHIGPGRAFYTAGDIIGDIRQAHCNISRANWNNTLRQIV
EKLGKQFGNNKTIVFNHSSGGDPEIVMHSFNCGGEFFYCNSTKLFNSTWT
WNNSTWNNTKRSNDTEEHITLPCRIKQIINMWQEVGKAMYAPPIRGQIRC
SSNITGLLLTRDGGNDTSGTEIFRPGGGDMRDNWRSELYKYKVVKIEPLG
VAPTKAKRRVVQREKRAVGIGAVFLGFLGAAGSTMGAASMTLTVQARLLL
SGIVQQQNNLLRAIEAQQHLLQLTVWGIKQLQARVLAVERYLKDQQLLGI
WGCSGKLICTTTVPWNASWSNKSLDKIWNNMTWMEWEREINNYTSLIYTL
IEESQNQQEKNEQELLELDKWASLWNWFDISNWLWYIKIFIMIVGGLVGL
RIVFAVLSIVNRVRQGYSPLSFQTRLPAPRGPDRPEGIEEEGGERDRDRS
VRLVDGFLVLIWDDLQSLCLFSYHRLRDLLLIVELLGRRGWEALKYWWNL
LQYWSQELKNSAISLLNATAVAVAEGTDRVIEALQRACRAILHIPRRIRQ
GLERLLL

MOSAIC ENV2 GP160 (AA SEQUENCE)

SEQ ID NO: 2
MRVRGIQRNWPQWWIWGILGFWMIIICRVMGNLWVTVYYGVPVWKEAKTT
LFCASDAKAYEKEVHNVWATHACVPTDPNPQEMVLENVTENFNMWKNDMV
DQMHEDIIRLWDQSLKPCVKLTPLCVTLECRNVRNVSSNGTYNIIHNETY
KEMKNCSFNATTVVEDRKQKVHALFYRLDIVPLDENNSSEKSSENSSEYY
RLINCNTSAITQACPKVSFDPIPIHYCAPAGYAILKCNNKTFNGTGPCNN
VSTVQCTHGIKPVVSTQLLLNGSLAEEEIIRSENLTNNAKTIIVHLNET
VNITCTRPNNNTRKSIRIGPGQTFYATGDIIGDIRQAHCNLSRDGWNKTL
QGVKKKLAEHFPNKTINFTSSSGGDLEITTHSFNCRGEFFYCNTSGLFNG
TYMPNGTNSNSSSNITLPCRIKQIINMWQEVGRAMYAPPIAGNITCRSNI
TGLLLTRDGGSNNGVPNDTETFRPGGGDMRNNWRSELYKYKVVEVKPLGV
APTEAKRRVVEREKRAVGIGAVFLGILGAAGSTMGAASITLTVQARQLLS
GIVQQQSNLLRAIEAQQHMLQLTVWGIKQLQTRVLAIERYLQDQQLLGLW
GCSGKLICTTAVPWNTSWSNKSQTDIWDNMTWMQWDKEIGNYTGEIYRLL
EESQNQQEKNEKDLLALDSWKNLWNWFDITNWLWYIKIFIMIVGGLIGLR
IILGVLSIVRRVRQGYSPLSFQTLTPNPRGLDRLGRIEEEGGEQRDRSI
RLVNGFLALAWDDLRSLCLFSYHQLRDFILIVARAVELLGRSSLRGLQRG
WEALKYLGNLVQYWGLELKKGAISLLDTIAIAVAEGTDRIIELIQSICRA
IRNIPRRIRQGFEASLL

MOSAIC GAG1 (AA SEQUENCE)

SEQ ID NO: 3
MGARASVLSGGELDRWEKIRLRPGGKKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGPIAPGQMREPRGSDIAGTTSTLQEQIGWM
TNNPPIPVGEIYKRWIILGLNKIVRMYSPVSILDIRQGPKEPFRDYVDRF
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ

MOSAIC GAG2 (AA SEQUENCE)

SEQ ID NO: 4
MGARASILRGGKLDKWEKIRLRPGGKKHYMLKHLVWASRELERFALNPGL
LETSEGCKQIIKQLQPALQTGTEELRSLFNTVATLYCVHAEIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN
PPIPVGDIYKRWIILGLNKIVRMYSPTSILDIKQGPKEPFRDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQ

MOSAIC POL1 (AA SEQUENCE)

SEQ ID NO: 5
FFRENLAFQQGEAREFPSEQTRANSPTSRELQVRGDNPHSEAGAERQGTL
NFPQITLWQRPLVSIKVGGQIREALLDTGADDTVLEDINLPGKWKPKMIG
GIGGFIKVRQYDQILIEICGKKAIGTVLVGPTPVNIIGRNMLTQLGCTLN
FPISPIETVPVKLKPGMDGPRVKQWPLTEEKIKALTAICEEMEKEGKITK
IGPENPYNTPVFAIKKKDSTKWRKLVDFRELNKRTQDFWEVQLGIPHPAG
LKKKKSVTVLDVGDAYFSVPLDEGFRKYTAFTIPSTNNETPGIRYQYNVL
PQGWKGSPAIFQCSMTRILEPFRAKNPEIVIYQYMDDLYVGSDLEIGQHR
AKIEELREHLLKWGFTTPDKKHQKEPPFLWMGYELHPDKWTVQPIQLPEK
DSWTVNDIQKLVGKLNWASQIYPGIKVRQLCKLLRGAKALTDIVPLTEEA
ELELAENREILKEPVHGVYYDPSKDLIAEIQKQGHDQWTYQIYQEPFKNL
KTGKYAKMRTAHTNDVKQLTEAVQKIAMESIVIWGKTPKFRLPIQKETWE
TWWTDYWQATWIPEWEFVNTPPLVKLWYQLEKDPIAGVETFYVDGAANRE
TKLGKAGYVTDRGRQKIVSLTETTNQKTELQAIYLALQDSGSEVNIVTDS

SEQUENCE APPENDIX

QYALGIIQAQPDKSESELVNQIIEQLIKKERVYLSWVPAHKGIGGNEQVD
KLVSSGIRKVLFLDGIDKAQEEHEKYHSNWRAMASDFNLPPVVAKEIVAS
CDQCQLKGEAMHGQVDCSPGIWQLDCTHLEGKIILVAVHVASGYIEAVI
PAETGQETAYFILKLAGRWPVKVIHTDNGSNFTSAAVKAACWWAGIQQEF
GIPYNPQSQGVVESMNKELKKIIGQVRDQAEHLKTAVQMAVFIHNFKRKG
GIGGYSAGERIIDIIATDIQTKELQKQIIKIQNFRVYYRDSRDPIWKGPA
KLLWKGEGAVVIQDNSDIKVVPRRKVKIIKDYGKQMAGADCVAGRQDED

MOSAIC POL2 (AA SEQUENCE)
SEQ ID NO: 6
FFRENLAFPQGKAREFSSEQTRANSPTRRELQVWGRDNNSLSEAGADRQG
TVSFSFSPQITLWQRPLVTIKIGGQLKEALLDTGADDTVLEEMNLPGRWKP
KMIGGIGGFIKVRQYDQIPIEICGHKAIGTVLVGPTPVNIIGRNLLTQIG
CTLNFPISPIETVPVKLKPGMDGPKVKQWPLTEEKIKALVEICTEMEKEG
KISKIGPENPYNTPIFAIKKKDSTKWRKLVDFRELNKRTQDFWEVQLGIP
HPAGLKKKKSVTVLDVGDAYFSVPLDEDFRKYTAFTIPSINNETPGIRYQ
YNVLPQGWKGSPAIFQSSMTKILEPFRKQNPDIVIYQYMDDLYVGSDLEI
GQHRTKIEELRQHLLRWGFTTPDKKHQKEPPFLWMGYELHPDKWTVQPIV
LPEKDSWTVNDIQKLVGKLNWASQIYAGIKVKQLCKLLRGTKALTEVVPL
TEEAELELAENREILKEPVHGVYYDPSKDLIAEIQKQGQGQWTYQIYQEP
FKNLKTGKYARMRGAHTNDVKQLTEAVQKIATESIVIWGKTPKFKLPIQK
ETWEAWWTEYWQATWIPEWEFVNTPPLVKLWYQLEKEPIVGAETFYVDGA
ANRETKLGKAGYVTDRGRQKVVSLTDTTNQKTELQAIHLALQDSGLEVNI
VTDSQYALGIIQAQPDKSESELVSQIIEQLIKKEKVYLAWVPAHKGIGGN
EQVDKLVSRGIRKVLFLDGIDKAQEEHEKYHSNWRAMASEFNLPPIVAKE
IVASCDKCQLKGEAIHGQVDCSPGIWQLDCTHLEGKVILVAVHVASGYIE
AEVIPAETGQETAYFLLKLAGRWPVKTIHTDNGSNFTSATVKAACWWAGI
KQEFGIPYNPQSQGVVESINKELKKIIGQVRDQAEHLKTAVQMAVFIHNF
KRKGGIGEYSAGERIVDIIASDIQTKELQKQITKIQNFRVYYRDSRDPLW
KGPAKLLWKGEGAVVIQDNSDIKVVPRRKAKIIRDYGKQMAGDDCVASRQ
DED

MOSAIC NEF1 (AA SEQUENCE)
SEQ ID NO: 7
MGGKWSKSSVVGWPAIRERMRRAEPAADGVGAVSRDLEKHGAITSSNTAA
NNADCAWLEAQEEEEVGFPVRPQVFLRPMTYKGALDLSHFLKEKGGLEGL
IYSQKRQDILDLWVYHTQGYFPDWQNYTPGPGIRYPLTFGWCFKLVPVEP
EKIEEANEGENNSLLHPMSQHGMDDPEKEVLMWKFDSRLAFHHMARELHP
EYYKDC

MOSAIC NEF2 (AA SEQUENCE)
SEQ ID NO: 8
MGGKWSKSSIVGWPAVRERIRRAEPAAEGVGAASQDLDKYGALTSSNTAA
TNADCAWLEAQEDEEVGFPVKPQVPLRPMTYKAAFDLSFFLKEKGGLDGL
IYSKKRQEILDLWVYNTQGFFPDWQNYTPGPGVRYPLTFGWCFKLVPVDP
REVEEANKGENNCLLHPMNLHGMDDPEREVLVWRFDSRLAFHHMAREKHP
EYYKNC

II. 2-VALENT MMOSAIC ENV GP140 SEQUENCES
(CLEAVAGE/FUSION-DEFECTIVE)

MOSAIC ENV1 GP140 (AA SEQUENCE)
SEQ ID NO: 9
MRVTGIRKNYQHLRWGTMLLGILMICSAAGKLWVTVYYGVPVWKEATTT
LFCASDAKAYDTEVHNVWATHACVPTDPNPQEVVLENVTENFNMWKNNMV
EQMHEDIISLWDQSLKPCVKLTPLCVTLNCTDDVRNVTNNATNTNSSWGE
PMEKGEIKNCSFNITTSIRNKVQKQYAFFKLDIVPIDNDSNNTNYRLIS
CNTSVITQACPKVSFEPIPIHYCAPAGFAILKCNDKKFNGTGPCTNVSTV
QCTHGIRPVVSTQLLLNGSLAEEEVVIRSENFTNNAKTIMVQLNVSVEIN
CTRPNNNTRKSIHIGPGRAFYTAGDIIGDIRQAHCNISRANWNNTLRQIV
EKLGKQFGNNKTIVFNHSSGGDPEIVMHSFNCGGEFFYCNSTKLFNSTWT
WNNSTWNNTKRSNDTEEHITLPCRIKQIINMWQEVGKAMYAPPIRGQIRC
SSNITGLLLTRDGGNDTSGTEIFRPGGGDMRDNWRSELYKYKVVKIEPLG
VAPTKAKRRVVSEKSAVGIGAVFLGFLGAAGSTMGAASMTLVQARLLL
SGIVQQQNNLLRAIEAQQHLLQLTVWGIKQLQARVLAVERYLKDQQLLGI
WGCSGKLICTTTVPWNASWSNKSLDKIWNNMTWMEWEREINNYTSLIYTL
IEESQNQQEKNEQELLELDKWASLWNWFDISNWLW

MOSAIC ENV2 GP140 (AA SEQUENCE)
SEQ ID NO: 10
MRVRGIQRNWPQWWIWGILGFWMIICRVMGNLWVTVYYGVPVWKEATTT
LFCASDAKAYEKEVHNVWATHACVPTDPNPQEMVLENVTENFNMWKNDMV
DQMHEDIIRLWDQSLKPCVKLTPLCVTLECRNVRNVSSNGTYNIIHNETY
KEMKNCSFNATTVVEDRKQKVHALFYRLDIVPLDENNSSEKSSENSSEYY
RLINCNTSAITQACPKVSFDPIPIHYCAPAGYAILKCNNKTENGTGPCNN
VSTVQCTHGIKPVVSTQLLLNGSLAEEEIIRSENLTNNAKTIIVHLNET
VNITCTRPNNNTRKSIRIGPGQTFYATGDIIGDIRQAHCNLSRDGWNKTL

QGVKKKLAEHFPNKTINFTSSSGGDLEITTHSENCRGEFFYCNTSGLFNG
TYMPNGTNSNSSSNITLPCRIKQIINMWQEVGRAMYAPPIAGNITCRSNI
TGLLLTRDGGSNNGVPNDTETFRPGGGDMRNNWRSELYKYKVVEVKPLGV
APTEAKRRVVSEKSAVGIGAVFLGILGAAGSTMGAASITLTVQARQLLS
GIVQQQSNLLRAIEAQQHMLQLTVWGIKQLQTRVLAIERYLQDQQLLGLW
GCSGKLICTTAVPWNTSWSNKSQTDIWDNMTWMQWDKEIGNYTGEIYRLL
EESQNQQEKNEKDLLALDSWKNLWNWFDITNWLW

MOS3 ENV GP140 (AA SEQUENCE)
678 AA
SEQ ID NO: 11
MRVKGIRKNYQHLWKWGTMLLGLMLICSAAEQLWVTVYYGVPVWRDAETT
LFCASDAKAYEREVHNIWATHACVPTDPNPQEIVLENVTEEFNMWKNDMV
EQMHTDIISLWDESLKPCVKLAPLCVTLNCTNANLNCTNDNCNRTVDKMR
EEIKNCSFNMTTELRDKKQKVYALFYKLDIVPIEKNSSEYRLINCNTSTI
TQACPKVTFEPIPIHYCTPAGFAILKCKDKKFNGTGPCKNVSTVQCTHGI
KPVISTQLLLNGSLAEGEIIIRSENITNNAKTIIVQLNESVVINCTRPGN
NTRKSVRIGPGQAFYATGEIIGDIRQAYCNISRAKWNNTLKQIVTKLKEQ
FKNKTIVFNQSSGGDPEITTHSFNCGGEFFYCNTTQLFNSTWNSNSTWND
TTGSVTEGNDTITLPCRIKQIVNMWQRVGQAMYAPPIEGNITCKSNITGL
LLVRDGGNINRTNETFRPGGGNMKDNWRSELYKYKVVEIKPLGVAPTRAK
RRVVSEKSAVGLGAVFLGFLGTAGSTMGAASLTLTVQARQVLSGIVQQQ
SNLLKAIEAQQHLLKLTVWGIKQLQARILAVERYLRDQQLLGIWGCSGKL
ICTTNVPWNSSWSNKSQEEIWNNMTWMQWDREISNYTDTIYRLLEDSQNQ
QEKNEQDLLALDKWASLWNWFSITNWLW

III. 2-VALENT M MOSAIC POL SEQUENCES (EXTENSIVELY
INACTIVATED, PR-DELETED, 9 A INACTIVATION
MUTATIONS TO ELIMINATE CATALYTIC ACTIVITY)

MOSAIC POL1 (AA SEQUENCE)
SEQ ID NO: 12
MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKSVTVLAVGDAYFSVPLDEGFRKYTAFTIPSTNNETPGIRYQNV
LPQGWKGSPAIFQSCMTRILEPFRKQNPEIVIYQYMAALYVGSDLEIGQH
RAKIEELREHLLKWGFTTPDKKHQKEPPFLWMGYELHPDKWTVQPIQLPE
KDSWTVNDIQKLVGKLNWASQIYPGIKVRQLCKLLRGAKALTDIVPLTEE
AELELAENREILKEPVHGVYYDPSKDLIAEIQKQGHDQWTYQIYQEPFKN
LKTGKYAKMRTAHTNDVKQLTEAVQKIAMESIVIWGKTPKFRLPIQKETW
ETWWTDYWQAIPEWEFVNTPPLVKLWYQLEKDPIAGVETFYVAGAANR
ETKLGKAGYVTDRGRQKIVSLTETTNQKTALQAIYLALQDSGSEVNIVTA
SQYALGIIQAQPDKSESELVNQIIEQLIKKERVYLSWVPAHKGIGGNEQV
DKLVSSGIRKVLFLDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKVIHTANGSNFTSAAVKAACWWAGIQQE
FGIPYNPQSQGVVASMNKELKKIIGQVRDQAEHLKTAVQMAVFIHNFKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED

MOSAIC POL2 (AA SEQUENCE)
SEQ ID NO: 13
MAPISPIETVPVKLKPGMDGPKVKQWPLTEEKIKALVEICTEMEKEGKIS
KIGPENPYNTPIFAIKKKDSTKWRKLVDFRELNKRTQDFWEVQLGIPHPA
GLKKKKSVTVLAVGDAYFSVPLDEDERKYTAFTIPSINNETPGIRYQNV
LPQGWKGSPAIFQSSMTKILEPFRKQNPDIVIYQYMAALYVGSDLEIGQH
RTKIEELRQHLLRWGFTTPDKKHQKEPPFLWMGYELHPDKWTVQPIVLPE
KDSWTVNDIQKLVGKLNWASQIYAGIKVKQLCKLLRGTKALTEVVPLTEE
AELELAENREILKEPVHGVYYDPSKDLIAEIQKQGQGQWTYQIYQEPFKN
LKTGKYARMRGAHTNDVKQLTEAVQKIATESIVIWGKTPKFKLPIQKETW
EAWWTEYWQATWIPEWEFVNTPPLVKLWYQLEKEPIVGAETFYVAGAANR
ETKLGKAGYVTDRGRQKVVSLTDTTNQKTALQAIHLALQDSGLEVNIVTA
SQYALGIIQAQPDKSESELVSQIIEQLIKKEKVYLAWVPAHKGIGGNEQV
DKLVSRGIRKVLFLDGIDKAQEEHEKYHSNWRAMASEFNLPPIVAKEIVA
SCDKCQLKGEAIHGQVDCSPGIWQLACTHLEGKVILVAVHVASGYIEAEV
IPAETGQETAYFLLKLAGRWPVKTIHTANGSNFTSATVKAACWWAGIKQE
FGIPYNPQSQGVVASINKELKKIIGQVRDQAEHLKTAVQMAVEIHNFKRK
GGIGEYSAGERIVDIIASDIQTKELQKQITKIQNFRVYYRDSRDPLWKGP
AKLLWKGEGAVVIQDNSDIKVVPRRKAKIIRDYGKQMAGDDCVASRQDED

MOS3 POL V3 (AA SEQUENCE)
851 AA
SEQ ID NO: 14
MAPISPIDTVPVTLKPGMDGPKIKQWPLTEEKIKALTEICTEMEKEGKIS
RIGPENPYNTPVFAIKKKNSTRWRKLVDFRELNKKTQDFWEVQLGIPHPA
GLKKKRSVTVLAVGDAYFSVPLDKDFRKYTAFTIPSVNNETPGVRYQYNV
LPQGWKGSPAIFQSCMTKILEPFRAQNPEIVIYQYVAALYVGSDLEIEQH

SEQUENCE APPENDIX

RTKIEELRAHLLSWGFTTPDKKHQREPPFLWMGYELHPDRWTVQPIELPE
KESWTVNDIQKLVGKLNWASQIYPGIKVKQLCRLLRGAKALTEVIPLTKE
AELELAENREILREPVHGVYYDPSKDLVAEIQKQGQDQWTYQIYQEPYKN
LKTGKYARKRSAHTNDVRQLTEAVQKIALESIVIWGKIPKFRLPIQRETW
ETWWTEYWQATWIPDWEFVNTPPLVKLWYQLEKEPIAGAETFYVAGASNR
ETKIGKAGYVTDKGRQKVVSLTETTNQKAALQAIQLALQDSGPEVNIVTA
SQYVLGIIQAQPDRSESELVNQIIEELIKKEKVYLSWVPAHKGIGGNEQV
DKLVSAGIRKILFLDGIDKAQEEHERYHSNWRTMASDFNLPPIVAKEIVA
NCDKCQLKGEAMHGQVDCSPGMWQLACTHLEGKIIIVAVHVASGYMEAEV
IPAETGQET

SEQUENCE APPENDIX

```
ATWIPEWEFVNTPPLVKLWYQLEKEPIVGAETFYVAGAANRETKLGKAGY
VTDRGRQKVVSLTDTTNQKTALQAIHLALQDSGLEVNIVTASQYALGIIQ
AQPDKSESELVSQIIEQLIKKEKVYLAWVPAHKGIGGNEQVDKLVSRGIR
KVLFLDGIDKAQEEHEKYHSNWRAMASEFNLPPIVAKEIVASCDKCQLKG
EAIHGQVDCSPGIWQLACTHLEGKVILVAVHVASGYIEAEVIPAETGQET
AYFLLKLAGRWPVKTIHTANGSNFTSATVKAACWWAGIKQEFGIPYNPQS
QGVVASINKELKKIIGQVRDQAEHLKTAVQMAVFIHNFKRKGGIGEYSAG
ERIVDIIASDIQTKELQKQITKIQNFRVYYRDSRDPLWKGPAKLLWKEG
AVVIQDNSDIKVVPRRKAKIIRDYGKQMAGDDCVASRQDED

MOS3 GAG-POL V3 (AA SEQUENCES)
1359 aa-GAG-POL FUSION WITH COMPLETE GAG
AND MODIFIED POL
                                    SEQ ID NO: 23
MGARASVLSGGKLDAWEKIRLRPGGKKKYKLKHIVWASRELDRFALNPGL
LETAEGCQQIIEQLQPALQTGSEELKSLYNTVAVLYCVHQRIDVKDTKEA
LDKIEEIQNKSKQKTQQAAADTGSSSKVSQNYPIVQNAQGQMVHQALSPR
TLNAWVKVVEEKGFNPEVIPMFSALAEGATPQDLNMMLNIVGGHQAAMQI
LKDTINEEAADWDRLHPVHAGPIPPGQMREPRGSDIAGTTSTPQEQIGWM
TSNPPVPVGEIYKRWIIMGLNKIVRMYSPVSILDIKQGPKESFRDYVDRE
TKVLRAEQATQEVKNWMTETLLIQNANPDCKSILRALGPGASLEEMMTAC
QGVGGPSHKARILAEAMSQANNTNIMMQRGNFKGQKRIKCFNCGKEGHLA
RNCRAPRKRGCWKCGREGHQMKDCNERQANFLGKIWPSSKGRPGNFPQSR
PEPTAPLEPTAPPAEPTAPPAESFGFGEEITPSPKQEQKDREPLTSLKSL
FGSDPLLQMAPISPIDTVPVTLKPGMDGPKIKQWPLTEEKIKALTEICTE
MEKEGKISRIGPENYNTPVFAIKKKNSTRWRKLVDFRELNKKTQDFWEV
QLGIPHPAGLKKKRSVTVLAVGDAYFSVPLDKDFRKYTAFTIPSVNNETP
GVRYQYNVLPQGWKGSPAIFQCSMTKILEPFRAQNPEIVIYQYVAALYVG
SDLEIEQHRTKIEELRAHLLSWGFTTPDKKHQREPPFLWMGYELHPDRWT
VQPIELPEKESWTVNDIQKLVGKLNWASQIYPGIKVQLCRLLRGAKALT
EVIPLTKEAELELAENREILREPVHGVYYDPSKDLVAEIQKQGQDQWTYQ
IYQEPYKNLKTGKYARKRSAHTNDVRQLTEAVQKIALESIVIWGKIPKFR
LPIQRETWETWWTEYWQATWIPDWEFVNTPPLVKLWYQLEKEPIAGAETF
YVAGASNRETKIGKAGYVTDKGRQKVVSLTETTNQKAALQAIQLALQDSG
PEVNIVTASQYVLGIIQAQPDRSESELVNQIIEELIKKEKVYLSWVPAHK
GIGGNEQVDKLVSAGIRKILFLDGIDKAQEEHERYHSNWRTMASDFNLPP
IVAKEIVANCDKCQLKGEAMHGQVDCSPGMWQLACTHLEGKIIIVAVHVA
SGYMEAEVIPAETGQETAYYILKLAGRWPVKVVHTANGSNFTSTTVKAAC
WWANVTQEFGIPYNPQSQGVIASMNKELKKIIGQVREQAEHLKTAVQMAV
LIHNFKRRGGIGGYSAGERIVDIIATDIQTRELQKQIIKIQNFRVYFRDS
RDPVWKGPAKLLWKGEGAVVIQDNSEIKVVPRRKVKIIRDYGKQMAGDDC
VAGRQDEDQ

VIII. 2-VALENT M MOSAIC GAGPOL FUSION SEQUENCES
(VERSION 4; POL MINIMALLY INACTIVATED, COMPLETE
PR-RT-IN)

MOSAIC GAGPOL1 V4 (AA SEQUENCE)
                                    SEQ ID NO: 24
MGARASVLSGGELDRWEKIRLRPGGKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGPIAPGQMREPRGSDIAGTTSTLQEQIGWM
TNNPPIPVGEIYKRWIILGLNKIVRMYSPVSILDIRQGPKEPERDYVDRE
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ
RENLAFQQGEAREFPSEQTRANSPTSRELQVRGDNPHSEAGAERQGTLNF
PQITLWQRPLVSIKVGGQIREALLATGADDTVLEEMNLPGKWKPKMIGGI
GGFIKVGQYDQILEICGKKAIGTVLVGPTPVNIIGRNMLTQLGCTLNFP
ISPIETVPVKLKPGMDGPRVKQWPLTEEKIKALTAICEEMEKEGKITKIG
PENPYNTPVFAIKKKDSTKWRKLVDFRELNKRTQDFWEVQLGIPHPAGLK
KKKSVTVLDVGDAYFSVPLDEGFRKYTAFTIPSTNNETPGIRYQYNVLPQ
GWKGSPAIFQCSMTRILEPFRAKNPEIVIYQYMDHLYVGSDLEIGQHRAK
IEELREHLLKWGFTTPDKKHQKEPPFLWMGYELHPDKWTVQPIQLEKDS
WTVNDIQKLVGKLNWASQIYPGIKVRQLCKLLRGAKALTDIVPLTEEAEL
ELAENREILKEPVHGVYYDPSKDLIAEIQKQGHDQWTYQIYQEPFKNLKT
GKYAKMRTAHTNDVKQLTEAVQKIAMESIVIWGKTPKERLPIQKETWETW
WTDYWQATWIPEWEEVNTPPLVKLWYQLEKDPIAGVETFYVDGAANRETK
LGKAGYVTDRGRQKIVSLTETTNQKTELQAIYLALQDSGSEVNIVTDSQY
ALGIIQAQPDKSESELVNQIIEQLIKKERVYLSWVPAHKGIGGNEQVDKL
VSSGIRKVLFLDGIDKAQEEHEKYHSNWRAMASDFNLPPVVAKEIVASCD
QCQLKGEAMHGQVDCSPGIWQLACTHLEGKIILVAVHVASGYIEAEVIPA
ETGQETAYFILKLAGRWPVKIVHTDNGSNFTSAAVKAACWWAGIQQEFGI
PYNPQSQGVVESMNKELKKIIGQVRDQAEHLKTAVQMAVFIHNFKRKGGI
GGYSAGERIIDIIATDIQTKELQKQIIIKQNFRVYYRDSRDPIWKGPAKL
LWKGEGAVVIQDNSDIKVVPRRKVKIIKDYGKQMAGADCVAGRQDED

MOSAIC GAGPOL2 V4 (AA SEQUENCE)
                                    SEQ ID NO: 25
MGARASILRGGKLDKWEKIRLRPGGKKHYMLKHLVWASRELERFALNPGL
LETSEGCKQIIKQLQPALQTGTEELRSLFNTVATLYCVHAEIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN
PPIPVGDIYKRWIILGLNKIVRMYSPTSILDIKQGPKEPFRDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQRENLAFPQG
KAREFSSEQTRANSPTRRELQVWGRDNNSLSEAGADRQGTVSFSFPQITL
WQRPLVTIKIGGQLKEALLATGADDTVLEEMNLPGRWKPKMIGGIGGFIK
VGQYDQIPIEICGHKAIGTVLVGPTPVNIIGRNLLTQIGCTLNFPISPIE
TVPVKLKPGMDGPKVKQWPLTEEKIKALVEICTEMEKEGKISKIGPENPY
NTPIFAIKKKDSTKWRKLVDFRELNKRTQDFWEVQLGIPHPAGLKKKKSV
TVLDVGDAYESVPLDEDFRKYTAFTIPSINNETPGIRYQYNVLPQGWKGS
PAIFQSSMTKILEPERKQNPDIVIYQYMDHLYVGSDLEIGQHRTKIEELR
QHLLRWGFTTPDKKHQKEPPFLWMGYELHPDKWTVQPIVLPEKDSWTVND
IQKLVGKLNWASQIYGLKCKLLRGTKALTEVVPLTEEAELELAEN
REILKEPVHGVYYDPSKDLIAEIQKQGQGQWTYQIYQEPFKNLKTGKYAR
MRGAHTNDVKQLTEAVQKIATESIVIWGKTPKFKLPIQKETWEAWWTEYW
QATWIPEWEFVNTPPLVKLWYQLEKEPIVGAETFYVDGAANRETKLGKAG
YVTDRGRQKVVSLTDTTNQKTELQAIHLALQDSGLEVNIVTDSQYALGII
QAQPDKSESELVSQIIEQLIKKEKVYLAWVPAHKGIGGNEQVDKLVSRGI
RKVLFLDGIDKAQEEHEKYHSNWRAMASEFNLPPIVAKEIVASCDKCQLK
GEAIHGQVDCSPGIWQLACTHLEGKVILVAVHVASGYIEAEVIPAETGQE
TAYFLLKLAGRWPVKTIHTDNGSNFTSATVKAACWWAGIKQEFGIPYNPQ
SQGVVESINKELKKIIGQVRDQAEHLKTAVQMAVFIHNFKRKGGIGEYSA
GERIVDIIASDIQTKELQKQITKIQNFRVYYRDSRDPLWKGPAKLLWKGE
GAVVIQDNSDIKVVPRRKAKIIRDYGKQMAGDDCVASRQDED

IX. 2-VALENT M MOSAIC GAGPOL FUSION SEQUENCES
(VERSION 5; POL MINIMALLY INACTIVATED,
PR-DELETED)

MOSAIC GAGPOL1 V5 (AA SEQUENCE)
                                    SEQ ID NO: 26
MGARASVLSGGELDRWEKIRLRPGGKKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGFIAPGQMREPRGSDIAGTTSTLQEQIGWM
TNNPPIPVGEIYKRWIILGLNKIVRMYSPVSILDIRQGPKEPFRDYVDRF
YKTLRAEQASQDVKNWMTETLLVQNANPDCTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESERFGEETTIPSQKQEPIDKEMYPLASLKSLFGNDPSSQ
MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKSVTVLDVGDAYFSVPLDEGFRKYTAFTIPSTNNETPGIRYQYNV
LPQGWKGSPAIFQCSMTRILEPFRAKNPEIVIYQYMDHLYVGSDLEIGQH
RAKIEELREHLLKWGFTTPDKKHQKEPPFLWMGYELHPDKWTVQPIQLPE
KDSWTVNDIQKLVGKLNWASQIYPGIKVRQLCKLLRGAKALTDIVPLTEE
AELELAENREILKEPVHGVYYDPSKDLIAEIQKQGHDQWTYQIYQEPFKN
LKTGKYAKMRTAHTNDVKQLTEAVQKIAMESIVIWGKTPKERLPIQKETW
ETWWTDYWQATWIPEWEEVNTPPLVKLWYQLEKDPIAGVETFYVDGAANR
ETKLGKAGYVTDRGRQKIVSLTETTNQKTELQAIYLALQDSGSEVNIVTD
SQYALGIIQAQPDKSESELVNQIIEQLIKKERVYLSWVPAHKGIGGNEQV
DKLVSSGIRKVLELDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKIVHTDNGSNFTSAAVKAACWWAGIQQE
FGIPYNPQSQGVVESMNKELKKIIGQVRDQAEHLKTAVQMAVFIHNFKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED

MOSAIC GAGPOL2 V5 (AA SEQUENCE)
                                    SEQ ID NO: 27
MGARASILRGGKLDKWEKIRLRPGGKKHYMLKHLVWASRELERFALNPGL
LETSEGCKQIIKQLQPALQIGTEELRSLFNIVATLYCVHAEIEVRDTKEA
LDKIEEEQNKSQQKTQQAKEADGKVSQNYPIVQNLQGQMVHQPISPRILN
AWVKVIEEKAFSPEVIPMFTALSEGATPQDLNTMLNTVGGHQAAMQMLKD
TINEEAAEWDRLHPVHAGPVAPGQMREPRGSDIAGITSNLQEQIAWMTSN
```

SEQUENCE APPENDIX

PPIPVGDIYKRWIILGLNKIVRMYSPTSILDIKQGPKEPFRDYVDRFFKT
LRAEQATQDVKNWMTDILLVQNANPDCKTILRALGPGATLEEMMTACQGV
GGPSHKARVLAEAMSQINSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLISLRSLFGSDPLSQMAPISPIET
VPVKLKPGMDGPKVKQWPLTEEKIKALVEICTEMEKEGKISKIGPENPYN
TPIFAIKKKDSTKWRKLVDFRELNKRTINFWEVQLGIPHPAGLKKKKSVI
VLDVGDAYFSVPLDEDFRKYTAFTIPSINNETPGIRYQYNVLPQGWKGSP
AIFQSSMTKILEPFRKQNPDIVIYQYMDHLYVGSDLEIGQHRTKIEELRQ
HLLRWGFTTPDKKHQKEPPFLWMGYELHPDKWTVQPIVLPEKDSWTVNDI
QKLVGKLNWASQIYAGIKVKQLCKLLRGTKALTEVVPLTEEAELELAENR
EILKEPVHGVYYDPSKDLIAEIQKGQGQGWTYQIYQEPFKNLKTGKYARM
RGAHTNDVKQLTEAVQKIATESIVIWGKTPKFKLPIQKETWEAWWTEYWQ
ATWIPEWEFVNTPPLVKLWYQLEKEPIVGAEIFYVDGAANRETKLGKAGY
VTDRGRQKVVSLIDTTNQKTELQAIHLALQDSGLEVNIVIDSQYALGIIQ
AQPDKSESELVSQIIEQLIKKEKVYLAWVPAHKGIGGNEQVDKLVSRGIR
KVLFLDGIDKAQEEHEKYHSNWRAMASEFNLPPIVAKEIVASCDKCQLKG
EAIHGQVDCSPGIWQLACTHLEGKVILVAVHVASGYIEAEVIPAETGQET
AYFLLKLAGRWPVKTIHTDNGSNFTSATVKAACWWAGIKQEFGIPYNPQS
QGVVESINKELKKIIGQVRDQAEHLKIAVQMAVFIHNFKRKGGIGEYSAG
ERIVDIIASDIQTKELQKQIIKIQNFRVYYRDSRDPLWKGPAKLLWKGEG
AVVIQDNSDIKVVPRRKAKIIRDYGKQMAGDDCVASRQDED

X. 2-VALENT M MOSAIC GAGPOLNEF FUSION
SEQUENCES (POL EXTENSIVELY INACTIVATED,
PR-DELETED)

MOSAIC GAGPOLNEF1 (AA SEQUENCE)
SEQ ID NO: 28
MGARASVLSGGELDRWEKIRLRPGGKKKYRLKHIVWASRELERFAVNPGL
LETESEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
ILNAWVKVVEEKAFSPEVIPMFSALSEGATPQDLNTMLNTVGGHQAAMQM
LKETINEEAAEWDRVHPVHAGPIAPGQMREPRGSDIAGITSTLQEQIGWM
TNNPPIPVGEIYKRWIILGLNKIVRMYSPVSILDIRQGPKEPFRDYVDRE
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ
MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKKSVTVLAVGDAYFSVPLDEGFRKYTAFTIPSTNNETPGIRYQYNV
LPQGWKGSPAIFQCSMTRILEPFRAKNPEIVIYQYMMAALYVGSDLEIGQH
RAKIEELREHLLKWGETTPDKKHQKEPPFLWMGYELHPDKWTVQPIQLPE
KDSWTVNDIQKLVGKLNWASQIYPGIKVRQLCKLLRGAKALTDIVPLTEE
AELELAENREILKEPVHGVYYDPSKDLIAEIQKGQGHDQWTYQIYQEPFKN
LKTGKYAKMRTAHTNDVKQLTEAVQKIAMESIVIWGKTPKFRLPIQKETW
ETWWTDYWQATWIPEWEEVNTPPLVKLWYQLEKDPIAGVETFYVAGAANR
ETKLGKAGYVTDRGRQKIVSLTETTNQKTALQAIYALQDSGSEVNIVTA
SQYALGIIQAQPKSESELVNQIIEQLIKKERVYLSWVPAHKGIGGDNEQV
DKLVSSGIRKVLFLDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKTIHTANGSNFTSATVKAACWWAGIQQE
FGIPYNPQSQGVVASMNKELKKIIGQVRDQAEHLKTAVQMAVFIHNFKRK
GGIGGYSAGERIIDDIIATDIQTKELQKQIIKIQNFRVYYRDSRDPIWKGP
AKLLWKGEGAVVIQDNSDIKVVPRRKVKIIKDYGKQMAGADCVAGRQDED
MAGKWSKSSVVGWPAIRERMRRAEPAADGVGAVSRDLEKHGAITSSNTAA
NNDADCAWLEAQEEEVGFPVRPQVPLRPMTYKGALDLSHFLKEKGGLEGL
IYSQKRQDILDLWVYHTQGYFPDWQNYTPGPGIRYPLTEGWCFKLVPVEP
EKIEEANEGENNSLLHPMSQHGMDDPEKEVLMWKFDSRLAFHHMARELHP
EYYKDC

MOSAIC GAGPOLNEF2 (AA SEQUENCE)
SEQ ID NO: 29
MGARASILRGGKLDKWEKIRLRPGGKKHYMLKHLVWASRELERFALNPGL
LETESGCKQILKQLQPALQTGTEELRSLENTVATLYCVHAGIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN
PPIPVGDIYKRWIILGLNKIVRMYSPTSILDIKQGPKEPERDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQMAPISPIET
VPVKLKPGMDGPKVKQWPLTEEKIKALVEICTEMEKEGKISKIGPENPYN
TPIFAIKKKDSTKWRKLVDFRELNKRTQDFWEVQLGIPHPAGLKKKKSVT
VLAVGDAYFSVPLDEDFRKYTAFTIPSINNETPGIRYQYNVLPQGWKGSP

AIFQSSMTKILEPFRKQNPDIVIYQYMAALYVGSDLEIGQHRTKIEELRQ
HLLRWGFTTPDKKHQKEPPFLWMGYELHPDKWTVQPIVLPEKDSWTVNDI
QKLVGKLNWASQIYAGIKVKQLCKLLRGTKALTEVVPLTEEAELELAENR
EILKEPVHGVYYDPSKDLIAEIQKGQGQGWTYQIYQEPFKNLKTGKYARM
RGAHTNDVKQLTEAVQKIATESIVIWGKTPKFKLPIQKETWEAWWTEYWQ
ATWIPEWEFVNTPPLVKLWYQLEKEPIVGAETFYVAGAANRETKLGKAGY
VTDRGRQKVVSLTDTTNQKTALQAIHLALQDSGLEVNIVTASQYALGIIQ
AQPDKSESELVSQIIEQLIKKEKVYLAWVPAHKGIGGNEQVDKLVSRGIR
KVLFLDGIDKAQEEHEKYHSNWRAMASEFNLPPIVAKEIVASCDKCQLKG
EATHGQVDCSPGIWQLACTHLEGKVILVAVHVASGYIEAEVIPAETGQET
AYFLLKLAGRWPVKTIHTANGSNFTSATVKAACWWAGIKQEFGIPYNPQS
QGVVASINKELKKIIGQVRDQAEHLKTAVQMAVFIHNFKRKGGIGEYSAG
ERIVDIIASDIQTKELQKQITKIQNFRVYYRDSRDPLWKGPAKLLWKGEG
AVVIQDNSDIKVVPRRKAKIIRDYGKQMAGDDCVASRQDEDMAGKWSKSS
IVGWPAVRERIRRAEPAAEGVGAASQDLDKYGALTSSNTAATNADCAWLE
AQEDEEVGFPVKPQVPLRPMTYKAAFDLSFFLKEKGGLDGLIYSKKRQEI
LDLWVYNTQGFFPDWQNYTPGPGVRYPLTFGWCFKLVPVDPREVEEANKG
ENNCLLHPMNLHGMDDPEREVLVWRFDSRLAFHHMAREKHPEYYKNC

XI. OPTIMAL CLADE C ENV GP160, GAG, POL, NEF
SEQUENCES

OPTIMAL CLADE C ENV GP160(

SEQUENCE APPENDIX

GIGGYSAGERIIDIIATDIQTKELQKQIIKIQNFRVYYRDSRDPIWKGPA
KLLWKGEGAVVIQDNSDIKVVPRRKVKIIKDYGKQMAGADCVAGRQDED

OPTIMAL CLADE CNE F (ZA00.1170MB) (AA SEQUENCE)
SEQ ID NO: 33
MGGKWSKSSIVGWPDVRERMRRTEPAAEGVGAASQDLDKYGALTSSNTTH
NNADCAWLEAQEEGEVGFPVRPQVPLRPMTYKGAFDLSFFLKEKGGLDGL
IYSKKRQEILDLWVYHTQGFFPDWQNYTPGPGVRYPLTFGWCFKLVPVDP
REVEEANKGENNCLLHPMSLHGMEDEEREVLKWEFDSSLARRHLARELHP
EYYKDC

XII. OPTIMAL CLADE C ENV GP140 SEQUENCE
(CLEAVAGE/FUSION-DEFECTIVE)

OPTIMAL CLADE C ENV GP140 (SN90.90.SE364)
(AA SEQUENCE)
SEQ ID NO: 34
MRVTGMLRNCQPWWIWGILGFWMLLIYNVGGNLWVTVYYGVPVWKEATTL
LFCASDAKAYEKEVHNVWATHACVPTDPNPQEMVLENVTEYFNMWKNDMV
DQMHEDIISLWDQSLKPCVKLTPLCVTLNCRNVTTSNNATSNDNPNGEIK
NCSFNITTELRDKRRNEYALFYRLDIVPLSGSKNSSNSSEYRLINCNTSA
ITQACPKVSFDPIPIHYCAPAGYAILKCNNKTFNGTGPCNNVSTVQCTHG
IKPVVSTQLLLNGSLAEGEIIIRSENLTNNAKTIIVHLNESIEIVCARPN
NNTRKSMRIGPGQTFYATGDIIGDIRQAHCNISGNWNATLEKVKGKLQEH
FPGKNISFEPSSGGDLEITTHSFNCRGEFFYCDTSKLFNGTTHTANSSIT
IQCRIKQIINMWQGVGRAIYAPPIAGNITCKSNITGLLLTRDGGTLNNDT
EKFRPGGGDMRDNWRSELYKYKVVEIKPLGIAPTKAKRRVVESEKSAVGI
GAVFLGFLGAAGSTMGAASITLTVQARQLLSGIVQQQSNLLRAIEAQQHM
LQLTVWGIKQLQTRVLAIERYLKDQQLLGIWGCSGKIICTTAVPWNTSWS
NKSLEDIWDNMTWMQWDREINNYTSIIYSLLEESQNQQEKNEKDLLALDS
WNNLWNWFNITKWLW

XIII. OPTIMAL CLADE C POL SEQUENCE (EXTENSIVELY
INACTIVATED, PR-DELETED)

OPTIMAL CLADE C POL (ZA.04.04ZASK208B1)
(AA SEQUENCE)

SEQ ID NO: 35

MAPISPIETVPVKLKPGMDGPKIKQWPLTEEKIKALMAICEEMEKEGKIT
KIGPENPYNTPIFAIKKKDSTKWRKLVDFRELNKRTQDFWEVQLGIPHPA
GLKKKKSVTVLAVGDAYFSVPLDESFRKYTAFTIPSINNETPGIRYQYNV
LPQGWKGSPAIFQSSMTKILEPFRAKNPEIVIYQYMAALYVGSDLEIGQH
RAKIEELREHLLRWGFTTPDKKHQKEPPFLWMGYELHPDKWTVQPIQLPE
KDSWTVNDIQKLVGKLNWASQIYSGIKVRQLCKLLRGAKALTDIVPLTEE
AELELAENREILKEPVHGVYYDPSKDLIAEIQKQGYDQWTYQIYQEPFKN
LKTGKYAKMRTAHTNDVKQLTEAVQKIALESIVIWGKTPKFRLPIQKETW
EIWWTDYWQATWIPEWEFVNTPPLVKLWYQLEKEPIAGAETFYVAGAANR
ETKIGKAGYVTDKGRQKIVTLTETTNQKTALQAIQLALQDSGSEVNIVTA
SQYALGIIQAQPDKSESELVNQIIEQLINKERVYLSWVPAHKGIGGNEQV
DKLVSSGIRKVLFLDGIDKAQEEHEKYHSNWRAMASEFNLPPVVAKEIVA
SCDKCQLKGEAIHGQVDCSPGIWQLACTHLEGKVILVAVHVASGYMEAEV
IPAETGQETAYYILKLAGRWPVKVIHTANGSNFTSAAVKAACWWAGIQQE
FGIPYNPQSQGVVASMNKELKKIIGQVRDQAEHLKTAVQMAVFIHNFKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED

XIV. OPTIMAL CLADE C GAGNEF FUSION SEQUENCE

OPTIMAL CLADE C GAGNEF (IN.70177-ZA00.1170MB)
(AA SEQUENCE)

SEQ ID NO: 36

MGARASILRGGKLDKWEKIRLRPGGKKHYMLKHLVWASRELERFALNPGL
LETSEGCKQILKQLQPALQTGTEELRSLYNTVATLYCVHAGIEVRDTKEA
LDKIEEEQNKGQQKTQQAKGADGKVSQNYPIVQNLQGQMVHQAISPRTLN
AWVKVIEEKAFSPEVIPMFTALSEGATPQDLNTMLNTVGGHQAAMQMLKD
TINEEAAEWDRLHPVHAGPIAPGQMREPRGSDIAGTTSTLQEQIAWMTNN
PPVPVGDIYKRWIILGLNKIVRMYSPVSILDIKQGPKEPFRDYVDRFFKT
LRAEQATQDVKNWMTDTLLVQNANPDCKTILRALGPGATLEEMMTACQGV
GGPSHKARVLAEAMSQTGSTIMMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQELKDREPLTSLKSLFGSDPLSQAGKWSKSSI
VGWPDVRERMRRTEPAAEGVGAASQDLDKYGALTSSNTTHNNADCAWLEA
QEEGEVGFPVRPQVPLRPMTYKGAFDLSFFLKEKGGLDGLIYSKKRQEIL
DLWVYHTQGFFPDWQNYTPGPGVRYPLTFGWCFKLVPVDPREVEEANKGE
NNCLLHPMSLHGMEDEEREVLKWEFDSSLARRHLARELHPEYYKDC

SEQUENCE APPENDIX

XV. CONSENSUS SEQUENCES

M CONSENSUS ENV

SEQ ID NO: 37

MRVRGIQRNCQHLWRWGTLILGMLMICSAAENLWVTVYYGVPVWKEANTT
LFCASDAKAYDTEVHNVWATHACVPTDPNPQEIVLENVTENFNMWKNNMV
EQMHEDIISLWDQSLKPCVKLTPLCVTLNCTNVNVTNTTNNTEEKGEIKN
CSFNITTEIRDKKQKVYALFYRLDVVPIDDNNNNSSNYRLINCNTSAITQ
ACPKVSFEPIPIHYCAPAGFAILKCNDKKENGTGPCKNVSTVQCTHGIKP
VVSTQLLLNGSLAEEEIIIRSENITNNAKTIIVQLNESVEINCTRPNNNT
RKSIRIGPGQAFYATGDIIGDIRQAHCNISGTKWNKTLQQVAKKLREHFN
NKTIIFKPSSGGDLEITTHSFNCRGEFFYCNTSGLFNSTWIGNGTKNNNN
TNDTITLPCRIKQIINMWQGVGQAMYAPPIEGKITCKSNITGLLLTRDGG
NNNTNETEIFRPGGGDMRDNWRSELYKYKVVKIEPLGVAPTKAKRRVVES
EKSAVGIGAVFLGELGAAGSTMGAASITLTVQARQLLSGIVQQQSNLLRA
IEAQQHLLQLTVWGIKQLQARVLAVERYLKDQQLLGIWGCSGKLICTTTV
PWNSSWSNKSQDEIWDNMTWMEWEREINNYTDIIYSLIEESQNQQEKNEQ
ELLALDKWASLWNWFDITNWLW

M CONSENSUS GAG

SEQ ID NO: 38

MGARASVLSGGKLDAWEKIRLRPGGKKKYRLKHLVWASRELERFALNPGL
LETSEGCKQIIGQLQPALQTGSEELRSLYNTVATLYCVHQRIEVKDTKEA
LEKIEEEQNKSQQKTQQAAADKGNSSKVSQNYPIVQNLQGQMVHQAISPR
TLNAWVKVIEEKAFSPEVIPMFSALSEGATPQDLNTMLNTVGGHQAAMQM
LKDTINEEAAEWDRLHPVHAGPIPPGQMREPRGSDIAGTTSTLQEQIAWM
TSNPPIPVGEIYKRWIILGLNKIVRMYSPVSILDIRQGPKEPERDYVDRF
EKTLRAEQATQDVKNWMTDTLLVQNANPDCKTILKALGPGATLEEMMTAC
QGVGGPGHKARVLAEAMSQVTNAAIMMQRGNFKGQRRIIKCFNCGKEGHI
ARNCRAPRKKGCWKCGKEGHQMKDCTERQANFLGKIWPSNKGRPGNFLQS
RPEPTAPPAESFGFGEEITPSPKQEPKDKEPPLTSLKSLFGNDPLSQ

M CONSENSUS POL

SEQ ID NO: 39

MAPISPIETVPVKLKPGMDGPKVKQWPLTEEKIKALTEICTEMEKEGKIS
KIGPENPYNTPIFAIKKKIDSTKWRKLVDFRELNKRTUFWEVQLGIPHPA
GLKKKKSVTVLDVGDAYFSVPLDEDFRKYTAFTIPSINNETPGIRYQYNV
LPQGWKGSPAIFQSSMTKILEPFRTQNPEIVIYQYMDHLYVGSDLEIGQH
RAKIEELREHLLRWGFTTPDKKHQKEPPFLWMGYELHPDKWTVQPIQLPE
KDSWTVNDIQKLVGKLNWASQIYPGIKVKQLCKLLRGAKALTDIVPLTEE
AELELAENREILKEPVHGVYYDPSKDLIAEIQKQGQDQWTYQIYQEPFKN
LKTGKYAKMRSAHTNDVKQLTEAVQKIATESIVIWGKTPKFRLPIQKETW
ETWWTEYWQATWIPEWEFVNTPPLVKLWYQLEKEPIAGAETFYVDGAANR
ETKLGKAGYVTDRGRQKVVSLTETTNQKTELQAIHLALQDSGSEVNIVTD
SQYALGIIQAQPDKSESELVNQIIEQLIKKEKVYLSWVPAHKGIGGNEQV
DKLVSTGIRKVLFLDGIDKAQEEHEKYHSNWRAMASDFNLPPIVAKEIVA
SCDKCQLKGEAMHGQVDCSPGIWQLACTHLEGKIILVAVHVASGYIEAEV
IPAETGQETAYFILKLAGRWPVKVIHTDNGSNFTSAAVKAACWWAGIQQE
FGIPYNPQSQGVVESMNKELKKIIGQVRDQAEHLKTAVQMAVFIHNFKRK
GGIGGYSAGERIIDIIATDIQTKELQKQITKIQNFRVYYRDSRDPIWKGP
AKLLWKGEGAVVIQDNSDIKVVPRRKAKIIRDYGKQMAGDDCVAGRQDED

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. An immunogenic composition comprising at least two distinct optimized viral polypeptides, wherein said optimized viral polypeptides correspond to the same viral gene product, wherein the viral gene product is selected from the group consisting of gag, pol, and env, and wherein the at least two distinct optimized gag polypeptides are selected from any one or more of the groups:
(a) SEQ ID NO: 3 and 4, (b) SEQ ID NO: 3, and 15 (c) SEQ ID NO: 4 and 15;

wherein the at least two distinct optimized pol polypeptides are selected from any one or more of the groups:
(a) SEQ ID NO: 12 and 13, (b) SEQ ID NO: 12 and 14, (c) SEQ ID NO: 13 and 14; and wherein the at least two distinct optimized env polypeptides are selected from any one or more of the groups:
(a) SEQ ID NO: 9 and 10, (b) SEQ ID NO: 9 and 11, (c) SEQ ID NO: 10 and 11.

2. The immunogenic composition of claim 1, wherein said mammal is a human.

3. The immunogenic composition of claim 1, wherein said immunogenic composition elicits a cellular immune response against said viral gene product.

4. The immunogenic composition of claim 1, wherein said at least two optimized gag viral polypeptides comprise an amino acid sequence having the sequences set forth in each of SEQ ID NO:3 and 4.

5. The immunogenic composition of claim 1, wherein said at least two optimized pol viral polypeptides comprise an amino acid sequence having the sequences set forth in each of SEQ ID NO:12 and 13.

6. The immunogenic composition of claim 4 further comprising at least two optimized pol viral polypeptides, wherein said polypeptides comprise an amino acid sequence having the sequences set forth in each of SEQ ID NO:12 and 13.

7. The immunogenic composition of claim 6 further comprising at least two optimized env viral polypeptides, wherein said polypeptides comprise an amino acid sequence having the sequences set forth in each of SEQ ID NO:9 and 10.

8. The immunogenic composition of claim 1, wherein said at least two distinct optimized viral polypeptides are encoded in a viral vector selected from the group consisting of adenovirus serotype 26 (Ad26), adenovirus serotype 34 (Ad34), adenovirus serotype 35 (Ad35), adenovirus serotype 48 (Ad48), er adenovirus serotype 5 HVR48 (Ad5HVR48), poxvirus, and modified vaccinia virus Ankara (MVA).

9. A method for inducing an HIV-1-specific immune response in a mammal comprising administering to said mammal the immunogenic composition of claim 1.

10. A method of manufacturing the immunogenic composition of claim 1 comprising synthesizing said optimized viral polypeptides and combining said optimized viral polypeptides with a pharmaceutically acceptable carrier.

11. A kit comprising:
a) the immunogenic composition of claim 1;
b) a pharmaceutically acceptable carrier, excipient, or diluent;
c) instructions for the use thereof; and, optionally,
d) an adjuvant.

12. The immunogenic composition of claim 8, wherein said vector is the Ad26 vector.

13. The immunogenic composition of claim 8, wherein said vector is the MVA vector.

14. The immunogenic composition of claim 1 admixed with a pharmaceutically acceptable carrier, excipient, or diluent.

15. The immunogenic composition of claim 1, wherein said at least two optimized env viral polypeptides comprise an amino acid sequence having the sequences set forth in each of SEQ ID NO:9 and 11.

16. A method for inducing an HIV-1-specific immune response in a mammal comprising administering to said mammal the immunogenic composition of claim 8.

17. The method of claim 16, wherein said vector is the Ad26 vector.

18. The method of claim 16, wherein said vector is the MVA vector.

19. A polypeptide comprising the amino acid sequence of SEQ ID NO: 9.

20. A method for inducing an HIV-1-specific immune response in a mammal comprising administering to said mammal the immunogenic composition of claim 19.

21. The method of claim 20, wherein the mammal is a human.

22. The method of claim 21, wherein said composition comprises a pharmaceutically acceptable carrier, excipient, or diluent.

23. The method of claim 16, wherein said mammal is a human.

* * * * *

UNITED STATES PATENT AND TRADEMARK OFFICE
CERTIFICATE OF CORRECTION

| | | Page 1 of 1 |
|---|---|---|
| PATENT NO. | : 9,017,691 B2 | |
| APPLICATION NO. | : 13/130018 | |
| DATED | : April 28, 2015 | |
| INVENTOR(S) | : Dan H. Barouch et al. | |

It is certified that error appears in the above-identified patent and that said Letters Patent is hereby corrected as shown below:

Specification

Column 1, lines 18-20, under STATEMENT OF FEDERALLY FUNDED RESEARCH, replace:

"This research has been sponsored in part by NIH grant numbers U19-AI066305 and U19-AI078526. The government has certain rights to the invention."

with

--This invention was made with government support under grants AI066305 and AI078526 awarded by NIH. The government has certain rights in the invention.--

Signed and Sealed this
Twelfth Day of April, 2016

Michelle K. Lee
*Director of the United States Patent and Trademark Office*